(12) United States Patent
Priestley et al.

(10) Patent No.: US 8,222,453 B2
(45) Date of Patent: Jul. 17, 2012

(54) BENZAMIDE FACTOR VIIA INHIBITORS USEFUL AS ANTICOAGULANTS

(75) Inventors: Eldon Scott Priestley, Yardley, PA (US); Xiaojun Zhang, Furlong, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 573 days.

(21) Appl. No.: 12/303,571

(22) PCT Filed: Jun. 7, 2007

(86) PCT No.: PCT/US2007/070566
§ 371 (c)(1),
(2), (4) Date: Aug. 11, 2009

(87) PCT Pub. No.: WO2007/146719
PCT Pub. Date: Dec. 21, 2007

(65) Prior Publication Data
US 2010/0227894 A1     Sep. 9, 2010

Related U.S. Application Data

(60) Provisional application No. 60/811,995, filed on Jun. 8, 2006.

(51) Int. Cl.
C07C 233/00 (2006.01)
C07C 235/00 (2006.01)
C07C 237/00 (2006.01)
C07C 239/00 (2006.01)
A01N 37/18 (2006.01)
A01N 43/64 (2006.01)
A61K 31/165 (2006.01)
A61K 31/41 (2006.01)

(52) U.S. Cl. ........ 564/161; 564/163; 514/617; 514/619; 514/359

(58) Field of Classification Search ................. 564/161, 564/163; 514/617, 619, 359
See application file for complete search history.

(56) References Cited

U.S. PATENT DOCUMENTS

| | | | |
|---|---|---|---|
| 5,023,236 A | 6/1991 | Edgington et al. | |
| 5,556,886 A * | 9/1996 | Van Daele et al. | 514/646 |
| 5,843,442 A | 12/1998 | Soule et al. | |
| 5,866,542 A | 2/1999 | Vlasuk et al. | |
| 6,140,353 A | 10/2000 | Ackermann et al. | |
| 6,642,252 B2 | 11/2003 | Bisacchi et al. | |
| 6,906,192 B2 | 6/2005 | Zhao et al. | |
| 7,122,559 B2 | 10/2006 | Glunz et al. | |
| 7,144,895 B2 | 12/2006 | Bisacchi et al. | |
| 7,456,195 B2 | 11/2008 | Zhang et al. | |
| 2006/0166997 A1 | 7/2006 | Zhang et al. | |
| 2006/0211720 A1 | 9/2006 | Glunz et al. | |

FOREIGN PATENT DOCUMENTS

WO WO2004/072102 8/2004
WO WO2007/103996 9/2007

OTHER PUBLICATIONS

Arnold, C. Shane et al., "The antithrombotic and anti-inflammatory effects of BCX-3607, a small molecule tissue factor/factor VIIa inhibitor", Thrombosis Research, vol. 117, pp. 343-349 (2006).
Carson, S.D. et al., "The role of tissue factor in the production of thrombin", Blood Coagulation and Fibrinolysis, vol. 4, pp. 281-292 (1993).
Frédérick, R. et al., "Modulators of the Coagulation Cascade: Focus and Recent Advances in Inhibitors of Tissue Factor, Factor VIIa and their Complex", Current Medicinal Chemistry, vol. 12, pp. 397-417 (2005).
Giesen, P. et al., "Blood-borne tissue factor: Another view of thrombosis", PNAS, vol. 96, pp. 2311-2315 (1999).
Girard, T. et al., "The role of tissue factor/factor VIIa in the pathophysiology of acute thrombotic formation", Current Opinion in Pharmacology, vol. 1, pp. 159-163 (2001).
Himber, J. et al., "Inhibition of tissue factor limits the growth of venous thrombus in the rabbit", J. of Thrombosis and Haemostasis, vol. 1, pp. 889-895 (2003).
Hirsh, J. et al., "New anticoagulants", Blood, vol. 105, pp. 453-463 (2005).
Hoffman, M., "A cell-based model of coagulation and the role of factor VIIa", Blood Reviews, vol. 17, pp. S1-S5 (2003).
Lazarus, R. et al., "Inhibitors of Tissue Factor•Factor VIIa for Anticoagulant Therapy", Current Medicinal Chemistry, vol. 11, pp. 2275-2290 (2004).
Lee, A. et al., "Dose-Response Study of Recombinant Factor VIIa/Tissue Factor Inhibitor Recombinant Nematode Anticoagulant Protein c2 in Prevention of Postoperative Venous Thromboembolism in Patients Undergoing Total Knee Replacement", Circulation, vol. 104, pp. 74078 (2001).
Moons, A. et al., "Recombinant Nematode Anticoagulant Protein c2, an Inhibitor of the Tissue Factor/Factor VIIa Complex, in Patients Undergoing Elective Coronary Angioplasty", J. of the American College of Cardiology, vol. 41(12), pp. 2147-2153 (2003).

(Continued)

Primary Examiner — Sreeni Padmanabhan
Assistant Examiner — Kendra D Carter
(74) Attorney, Agent, or Firm — Jing G. Sun

(57) ABSTRACT

The present invention provides novel benzamide derivatives of Formula (I):

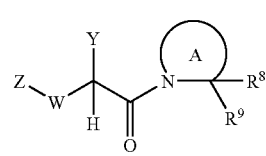

(I)

or a stereoisomer, tautomer, pharmaceutically acceptable salt, solvate, or prodrug thereof, wherein the variables A, W, Y, Z, $R^8$, and $R^9$ are as defined herein. These compounds are selective inhibitors of factor VIIa which can be used as medicaments.

17 Claims, No Drawings

OTHER PUBLICATIONS

Morrissey, J.H., "Tissue factor: in at the start . . . and the finish?", J. of Thrombosis and Haemostasis, vol. 1, pp. 878-880 (2003).

Morrissey, J.H. et al., "Quantitation of Activated Factor VII Levels in Plasma Using a Tissue Factor Mutant Selectively Deficient in Promoting Factor VII Activation", Blood, vol. 81, pp. 734-744 (1993).

Suleymanov, O. et al., "Pharmacological Interruption of Acute Thrombus Formation with Minimal Hemorrhagic Complications by a Small Molecule Tissue Factor/Factor VIIa Inhibitor: Comparison to Factor Xa and Thrombin Inhibition in a Nonhuman Primate Thrombosis Model", The Journal of Pharmacology and Experimental Therapeutics, vol. 306(3), pp. 1115-1121 (2003).

Szalony, J. et al., "Administration of a small molecule tissue factor/Factor VIIa inhibitor in a non-human primate thrombosis model of venous thrombosis: effects on thrombus formation and bleeding time", Thrombosis Research, vol. 112, pp. 167-174 (2003).

Szalony, J. et al., "pharmacological Intervention at Disparate Sites in the Coagulation Cascade: Comparison of Anti-thrombotic Efficacy vs. Bleeding Propensity in a Rat Model of Acute Arterial Thrombosis", J. of Thrombosis and Thrombolysis, vol. 14(2), pp. 113-121 (2002).

Young, W. et al., "Factor VIIa inhibitors: Chemical optimization, preclinical pharmacokinetics, pharmacodynamics, and efficacy in an arterial baboon thrombosis model", Bioorganic & Medicinal Chemistry Letters, vol. 16, pp. 2037-2041 (2006).

* cited by examiner

BENZAMIDE FACTOR VIIA INHIBITORS USEFUL AS ANTICOAGULANTS

CROSS-REFERENCE TO RELATED APPLICATIONS

This application is a 371 application of PCT/US2007/070566 filed Jun. 7, 2007, which claims priority benefit of U.S. provisional application Ser. No. 60/811,995, filed Jun. 8, 2006, which is incorporated by reference herein.

FIELD OF THE INVENTION

The present invention provides novel benzamide derivatives, and analogues thereof, which are selective inhibitors of the serine protease blood coagulation factor VIIa. This invention also relates to pharmaceutical compositions comprising these compounds and methods of using the same.

BACKGROUND OF THE INVENTION

Factor VII is a plasma serine protease involved in the initiation of the coagulation cascade. It is present in human blood at a concentration of approximately 500 ng/mL, with about 1% of the total amount in the proteolytically active form Factor VIIa (Morrissey, J. H. et al. *Blood* 1993, 81, 734-744). Factor VIIa binds with high affinity to its cofactor, tissue factor, in the presence of calcium ions to form a complex with significantly enhanced proteolytic activity (Carson, S. D. and Brozna, J. P. *Blood Coag. Fibrinol.* 1993, 4, 281-292). Tissue factor is normally expressed in cells surrounding the vasculature and within the vessel wall, and is exposed to factor VIIa in blood by vessel injury or atherosclerotic plaque rupture. Once formed, the tissue factor/factor VIIa complex initiates blood coagulation by proteolytic cleavage of factor X to factor Xa, factor IX to factor IXa and autoactivation of additional factor VII to VIIa. Factor Xa, generated either directly by tissue factor/factor VIIa or indirectly through action of factor IXa, catalyzes the conversion of prothrombin to thrombin. Thrombin coverts fibrinogen to fibrin, which polymerizes to form the structural framework of a blood clot, and activates platelets, which are a key cellular component of coagulation (Hoffman, M. *Blood Reviews* 2003, 17, S1-S5). In addition, there is evidence that tissue factor is present in blood, likely in an encrypted form that is de-encrypted during clot formation. (Giesen, P. L. A. et al. *Proc. Natl. Acad. Sci.* 1999, 96, 2311-2315; Himber, J. et al. *J. Thromb. Haemost.* 2003, 1, 889-895). The tissue factor/factor VIIa complex derived from blood borne tissue factor may play an important role in propagation of the coagulation cascade (clot growth) and in thrombus formation in the absence of vessel wall injury (i.e., stasis induced deep vein thrombosis or sepsis). The source of blood borne tissue factor is an area of active research (Morrissey, J. H. *J. Thromb. Haemost.* 2003, 1, 878-880).

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsh, J. et al. *Blood* 2005, 105, 453-463).

Because of its key role in the coagulation cascade, researchers have postulated that inhibition of factor VIIa could be used to treat or prevent thrombotic or thromboembolic disease. (Girard, T. J.; Nicholson, N. S. *Curr. Opin. Pharmacol.* 2001, 1, 159-163; Lazarus, R. A., et al. *Curr. Med. Chem.* 2004, 11, 2275-2290; Frederick, R. et al. *Curr. Med. Chem.* 2005, 12, 397-417.) Several studies have confirmed that various biological and small molecule inhibitors of factor VIIa have in vivo antithrombotic efficacy with a low bleeding liability. For instance, it has been demonstrated that a biological factor VIIa inhibitor XK1, comprising a hybrid of Factor X light chain and tissue factor pathway inhibitor first kunitz domain, prevents thrombus formation in a rat model of arterial thrombosis, with no change in bleeding time or total blood loss (Szalony, J. A. et al. *J. Thrombosis and Thrombolysis* 2002, 14, 113-121). In addition, small molecule active site directed factor VIIa inhibitors have demonstrated antithrombotic efficacy in animal models of arterial thrombosis (Suleymanov, O., et al. *J Pharmacology and Experimental Therapeutics* 2003, 306, 1115-1121; Young, W. B., et al. *Bioorg. Med. Chem. Lett.* 2006, 16, 2037-2041) and venous thrombosis (Szalony, J. A., et al. Thrombosis Research 2003, 112, 167-174; Arnold, C. S., et al. *Thrombosis Research* 2006, 117, 343-349), with little impact on bleeding time or blood loss. Moreover, the biological factor VIIa inhibitor recombinant nematode anticoagulant protein c2 (rNAPc2) is currently under clinical investigation for treatment of acute coronary syndromes. Results of initial clinical trials demonstrate that rNAPc2 reduces systemic thrombin generation in patients undergoing coronary angioplasty (Moons, A. H. M. *J. Am. Coll. Cardiol.* 2003, 41, 2147-2153) and that it prevents deep vein thrombosis in patients undergoing total knee replacement (Lee, A., et al. *Circulation* 2001, 104, 74-78).

Work has accordingly been performed to identify and optimize factor VIIa inhibitors. For example, U.S. Pat. No. 5,866,542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

While a number of factor VIIa inhibitors have been discussed in the art, improved inhibitors, especially non-peptide inhibitors, for the treatment of thromboembolic disorders are always desirable. The present invention discloses benzamides and analogues thereof as inhibitors of coagulation factor VIIa, which, as such, are useful in the treatment of thromboembolic disorders.

In addition, it is also desirable to find new compounds with improved pharmacological characteristics compared with known factor VIIa inhibitors. For example, it is preferred to find new compounds with improved factor VIIa inhibitory activity and improved selectivity for factor VIIa versus other serine proteases. Also, it is preferred to find new compounds with improved activity in in vitro clotting assays, such as the prothrombin time (PT) assay. (For a description of the PT assay see, Goodnight, S. H.; Hathaway, W. E. Screening Tests of Hemostasis. *Disorders of Thrombosis and Hemostasis: a clinical guide*, $2^{nd}$ edition, McGraw-Hill: New York, 2001 pp. 41-51). It is also desirable and preferable to find compounds with advantageous and improved characteristics in one or more of the following categories, which are given as examples and are not intended to be limiting: (a) pharmacokinetic properties, including oral bioavailability; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects; and (h) factors that improve manufacturing costs or feasibility.

SUMMARY OF THE INVENTION

The present invention provides benzamide derivatives, and analogues thereof, which are useful as selective inhibitors of factor VIIa, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or a stereoisomer, tautomer, pharmaceutically acceptable salt, solvate, or prodrug thereof.

The present invention also provides a method for modulation of the coagulation cascade comprising administering to a patient in need of such treatment a therapeutically effective amount of at least one of the compounds of the present invention or a stereoisomer, tautomer, pharmaceutically acceptable salt, solvate, or prodrug thereof.

The present invention also provides a method for treating a thrombotic or thromboembolic disorder comprising administering to a patient in need of such treatment a therapeutically effective amount of at least one of the compounds of the present invention or a stereoisomer, tautomer, pharmaceutically acceptable salt, solvate, or prodrug thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of a thrombotic or thromboembolic disorder.

These and other features of the invention will be set forth in the expanded form as the disclosure continues.

DETAILED DESCRIPTION OF THE INVENTION

In a first aspect, the present invention provides, inter alia, a compound of Formula (I):

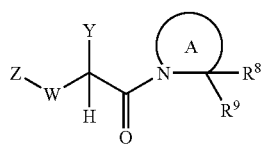
(I)

or a stereoisomer, tautomer, pharmaceutically acceptable salt, solvate, or prodrug thereof, wherein:

ring A is a 4- to 8-membered heterocycle comprising: the nitrogen atom shown in the ring, carbon atoms and 0-1 additional heteroatom selected from N, $NR^c$, O, and $S(O)_p$, 0-1 carbonyl, and 0-2 double bonds, wherein said heterocycle is substituted with 0-2 $R^7$;

Z is

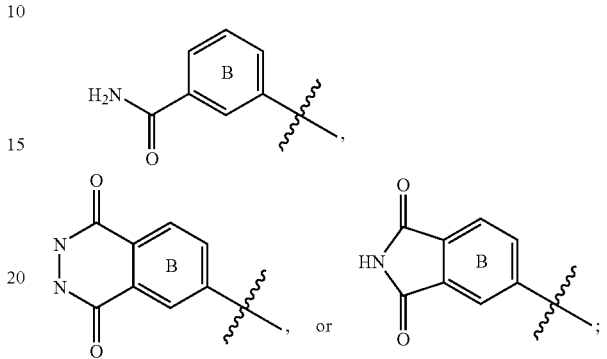

ring B is phenyl substituted with 0-3 $R^6$ or pyridyl substituted with 0-3 $R^6$;

W is NH or O;

Y is:

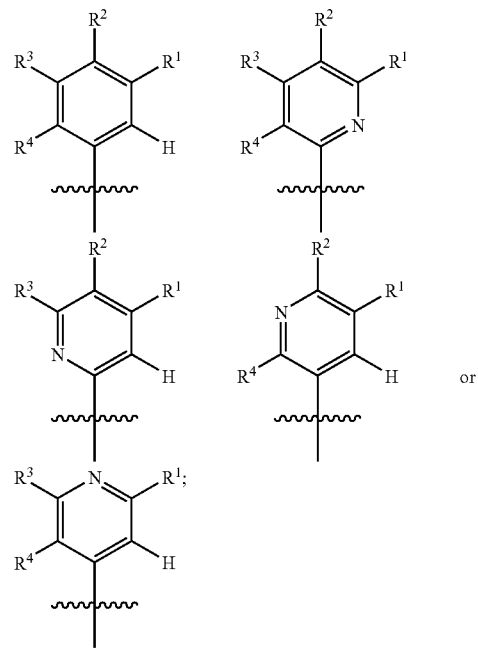

$R^1$ is, independently at each occurrence, H, F, Cl, Br, I, $C_{1-5}$ alkyl substituted with 0-1 OH, $C_{1-5}$ haloalkyl, $C_{2-5}$ alkenyl, $C_{2-5}$ alkynyl, —O—$C_{1-5}$ alkyl, —O—$C_{1-5}$ haloalkyl, —S—$C_{1-5}$ alkyl, or $C_{3-6}$ cycloalkyl;

$R^2$ and $R^3$ are, independently at each occurrence, H, F, Cl, Br, I, $OR^a$, $SR^a$, $OCF_3$, $OCHF_2$, $OCH_2F$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle is substituted with 0-3 $R^f$;

$R^4$ is, independently at each occurrence, H, F, Cl, Br, I, $OR^a$, $SR^a$, $OCF_3$, CN, $NO_2$, $-NR^bR^c$, $-C(O)R^a$, $-CO_2R^a$, $-NR^dC(O)R^a$, $-C(O)NR^cR^d$, $-NR^cC(O)OR^a$, $-NR^cC(O)NR^cR^d$, $-SO_2NR^cR^d$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each occurrence, F, Cl, Br, I, CN, OH, $CF_3$, $C_{1-4}$ alkyl, $C_{1-4}$ haloalkyl, or $C_{1-4}$ alkoxy;

$R^7$ is, independently at each occurrence, $OR^a$, F, Cl, Br, I, CN, $NO_2$, $-OCF_3$, $-NR^bR^c$, $-C(O)R^a$, $-CO_2R^a$, $-NR^dC(O)R^a$, $-C(O)NR^cR^d$, $-SO_2NR^cR^d$, $-NR^cSO_2R^i$, $-SO_2NHC(O)R^a$, $-C(O)NHSO_2R^a$, $-NR^cSO_2CF_3$, $-SO_2CF_3$, $-S(O)_pR^i$, $-(CF_2)_rCF_3$, tetrazole, $-(CH_2)_r$-phenyl substituted with 0-3 $R^f$, or a $-(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

$R^8$ is H, CN, $-CO_2R^a$, $-C(O)NR^cR^d$, tetrazolyl, or $C_{1-4}$ alkyl substituted with 0-2 $R^{8a}$;

$R^{8a}$ is, independently at each occurrence, =O, $OR^a$, F, Cl, Br, I, CN, $NO_2$, $-OCF_3$, $-NR^bR^c$, $-C(O)R^a$, $-CO_2R^a$, $-OC(O)R^a$, $-OC(O)NR^cR^d$, $-NR^dC(O)R^a$, $-C(O)NR^cR^d$, $-NR^cC(O)NR^cR^d$, $-NR^cC(O)OR^a$, $-SO_2NR^cR^d$, $-NR^cSO_2R^i$, $-NR^cSO_2NR^cR^d$, $-SO_2NHC(O)R^a$, $-C(O)NHSO_2R^a$, $-NR^cSO_2CF_3$, $-SO_2CF_3$, $-S(O)_pR^i$, $-(CF_2)_rCF_3$, tetrazole, $C_{3-6}$ cycloalkyl substituted with 0-3 $R^f$, phenyl substituted with 0-3 $R^f$, or 5- to 6-membered heterocycle comprising: carbon atoms and 1-4 heteroatoms selected from N, $NR^c$, O, and $S(O)_p$, wherein said heterocycle is substituted with 0-3 $R^f$;

$R^9$ is phenyl or pyridyl substituted with 1-3 $R^{10}$;

$R^{10}$ is independently at each occurrence, F, Cl, Br, I, $-(CH_2)_r-OR^a$, $-(CH_2)_r-SR^a$, $OCF_3$, $SCF_3$, CN, $NO_2$, $-(CH_2)_r-NR^bR^c$, $-C(O)R^a$, $-(CH_2)_r-CO_2R^a$, $-(CH_2)_r-NR^cCO_2R^a$, $-NR^dC(O)R^a$, $-(CH_2)_r-C(O)NR^cR^d$, $-NR^cC(O)NR^cR^d$, $-SO_2NR^cR^d$, $-OSO_2NR^cR^d$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $-(CH_2)_r-C_{3-10}$ carbocycle substituted with 0-3 $R^f$, or $-(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^a$ is, independently at each occurrence, H, $C_{1-6}$ alkyl substituted with 0-4 $R^h$, $-(CH_2)_r-C_{3-7}$ carbocycle substituted with 0-4 $R^f$, or $-(CH_2)_r$-5- to 10-membered heterocycle comprising: carbon atoms and 1-4 heteroatoms selected from N, $NR^g$, O, and $S(O)_p$, wherein said heterocycle is substituted with 0-4 $R^f$;

$R^b$ is, independently at each occurrence, H, $C_{1-6}$ alkyl, $-(CH_2)_n$-phenyl, $(C_{1-6}$ alkyl$)C(O)-$, $(C_{3-6}$ cycloalkyl$)-C_{0-4}$ alkyl-$C(O)-$, $(C_{6-10}$ aryl$)-(C_{0-4}$ alkyl$)-C(O)-$, (5- to 10-membered heteroaryl$)-C_{0-4}$ alkyl-$C(O)-$, $(C_{1-6}$ alkyl$)$-$NHC(O)-$, $(C_{1-6}$ alkyl$)_2$-$NHC(O)-$, $(C_{6-10}$ aryl$)-C_{0-4}$ alkyl-$NHC(O)-$, (5- to 10-membered heteroaryl$)-C_{0-4}$ alkyl-$NHC(O)-$, $(C_{1-6}$ alkyl$)$-$SO_2-$, $(C_{6-10}$ aryl$)-C_{0-4}$ alkyl-$SO_2-$, or (5- to 10-membered heteroaryl$)-C_{0-4}$ alkyl-$SO_2-$, wherein said phenyl, aryl and heteroaryl are substituted with 0-2 $R^f$;

$R^c$ is, independently at each occurrence, H, $C_{1-6}$ alkyl substituted with 0-3 $R^h$, $-(CH_2)_n-C_{3-7}$ cycloalkyl substituted with 0-3 $R^h$, or $-(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each occurrence, H, $C_{1-6}$ alkyl, $-(CH_2)_r-C_{3-10}$ carbocycle substituted with 0-3 $R^f$, or a $-(CH_2)_r$-5- to 12-membered heterocycle comprising: carbon atoms and 1-4 heteroatoms selected from N, $NR^g$, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^e$ is, independently at each occurrence, =O, $OR^a$, F, Cl, Br, I, CN, $NO_2$, $-SR^a$, $-OCF_3$, $-NR^bR^c$, $-C(O)R^a$, $-CO_2R^a$, $-NR^dC(O)R^a$, $-C(O)NR^cR^d$, $-OC(O)R^a$, $-NR^dC(O)OR^a$, $-NR^dC(O)NR^cR^d$, $-OC(O)NR^cR^d$, $-SO_2NR^cR^d$, $-NC(O)OR^a$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{3-10}$ carbocycle substituted with 0-3 $R^f$, or a 5- to 12-membered heterocycle comprising: carbon atoms and 1-4 heteroatoms selected from N, $NR^g$, O, and $S(O)_p$, wherein said heterocycle is substituted with 0-3 $R^f$;

$R^f$ is, independently at each occurrence, =O, $OR^g$, F, Cl, Br, I, CN, $NO_2$, $-SR^g$, $-OCF_3$, $-NR^cR^c$, $-C(O)R^g$, $-CO_2R^g$, $-NR^cC(O)R^g$, $-C(O)NR^cR^c$, $-OC(O)R^g$, $-NR^cC(O)OR^g$, $-NR^cC(O)NR^cR^c$, $-OC(O)NR^cR^c$, $-SO_2NR^cR^c$, $-NR^cSO_2NR^cR^c$, $-NR^cSO_2R^i$, $-NR^cSO_2CF_3$, $-SO_2CF_3$, $-S(O)_pR^i$, $-(CF_2)_rCF_3$, $C_{1-6}$ alkyl, $C_{2-6}$ alkenyl, $C_{2-6}$ alkynyl, $C_{3-10}$ carbocycle substituted with 0-3 $R^h$, or a 5- to 12-membered heterocycle comprising: carbon atoms and 1-4 heteroatoms selected from N, $NR^g$, O, and $S(O)_p$, and substituted with 0-3 $R^h$;

$R^g$ is, independently at each occurrence, H, $C_{1-6}$ alkyl, or $-(CH_2)_n$-phenyl;

$R^h$ is, independently at each occurrence, =O, $-(CH_2)_rOR^g$, F, Cl, Br, I, CN, $NO_2$, $-OCF_3$, $-NR^gR^g$, $-C(O)R^g$, $-CO_2R^g$, $-NR^gC(O)R^g$, $-C(O)NR^gR^g$, $-SO_2NR^gR^g$, $-NR^gSO_2NR^gR^g$, $-NR^gSO_2-C_{1-4}$ alkyl, $-NR^gSO_2CF_3$, $-NR^gSO_2$-phenyl, $-SO_2CF_3$, $-S(O)_p-C_{1-4}$ alkyl, $-S(O)_p$-phenyl, $-(CF_2)_rCF_3$, $C_{1-6}$ alkyl, $C_{2-6}$ alkenyl, $C_{2-6}$ alkynyl, $(C_{1-6}$ alkyl$)C(O)-$, $(C_{3-6}$ cycloalkyl$)-C_{0-4}$ alkyl-$C(O)-$, $(C_{6-10}$ aryl$)-(C_{0-4}$ alkyl$)-C(O)-$, (5-10 membered heteroaryl$)-C_{0-4}$ alkyl-$C(O)-$, $(C_{1-6}$ alkyl$)$-$NHC(O)-$, $(C_{1-6}$ alkyl$)_2$-$NHC(O)-$, $(C_{6-10}$ aryl$)-C_{0-4}$ alkyl-$NHC(O)-$, (5-10 membered heteroaryl$)-C_{0-4}$ alkyl-$NHC(O)-$, $(C_{1-6}$ alkyl$)$-$SO_2-$, $(C_{6-10}$ aryl$)-C_{0-4}$ alkyl-$SO_2-$, (5-10 membered heteroaryl$)-C_{0-4}$ alkyl-$SO_2-$, $-(CH_2)_r-C_{3-10}$ carbocycle, or a —(CH$_2$)$_r$-5- to 12-membered heterocycle comprising: carbon atoms and 1-4 heteroatoms selected from N, NR$^g$, O, and S(O)$_p$;

R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^h$;

n, at each occurrence, is selected from 0, 1, 2, 3, and 4;

p, at each occurrence, is selected from 0, 1, and 2; and r, at each occurrence, is selected from 0, 1, 2, 3, and 4.

In a second aspect, the present invention includes the compounds of Formula (I) or a stereoisomer, tautomer, pharmaceutically acceptable salt, solvate, or prodrug thereof, wherein:

ring A is a 5- or 6-membered heterocycle comprising: the nitrogen atom shown in the ring, carbon atoms and 0-1 additional heteroatom selected from N, NR$^c$, O, and S(O)$_p$, wherein said heterocycle is substituted with 0-2 R$^7$;

Z is

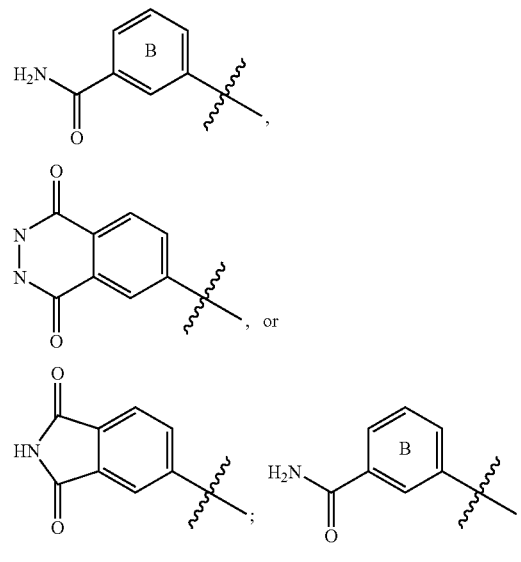

is,

-continued

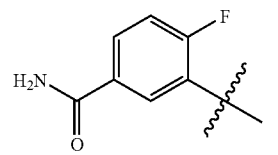

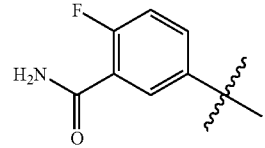

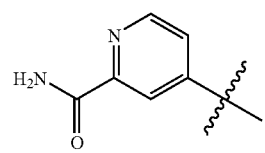

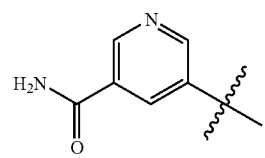

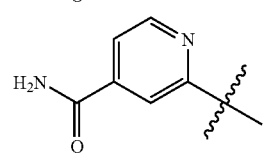

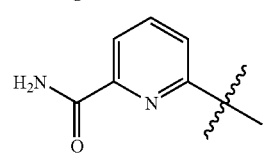

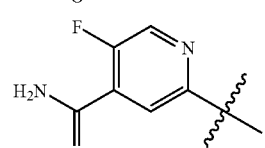

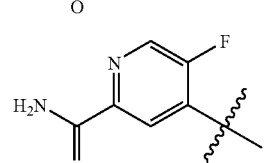

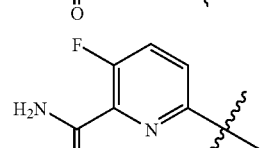

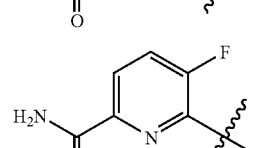

-continued

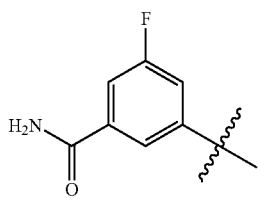
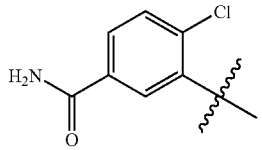
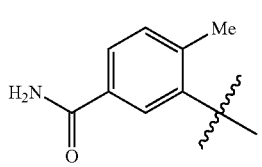
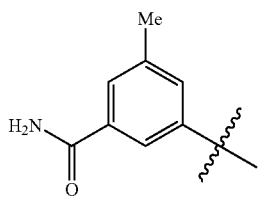

or

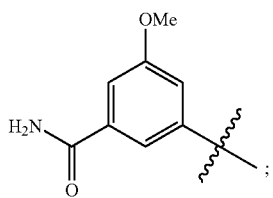

wherein each phenyl and pyridyl is substituted with 0-1 $R^6$; and $R^1$ is, independently at each occurrence, H, F, Cl, Br, $C_{1-3}$ alkyl substituted with 0-1 OH, $C_{1-3}$ haloalkyl, $C_{2-3}$ alkenyl, $C_{2-3}$ alkynyl, —O—$C_{1-3}$ alkyl, or $C_{3-5}$ cycloalkyl.

In a third embodiment, the present invention includes a compound of Formula (II):

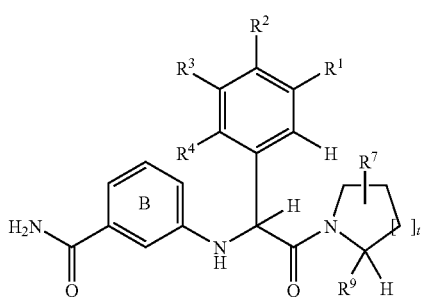

(II)

or a stereoisomer, tautomer, pharmaceutically acceptable salt, solvate, or prodrug thereof, wherein:

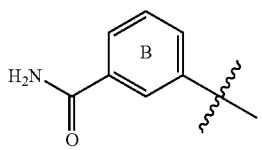

is:

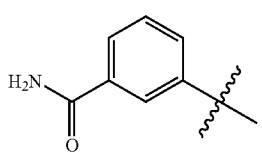 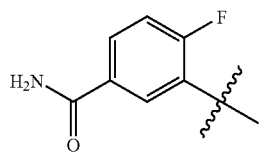
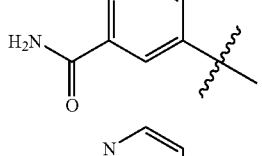
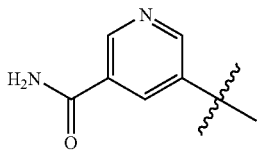

wherein each phenyl and pyridyl is substituted with 0-1 $R^6$;

$R^1$ is H, F, Cl, Br, $C_{1-2}$ alkyl substituted with 0-1 OH, $C_{1-2}$ haloalkyl, $C_{2-3}$ alkenyl, $C_{2-3}$ alkynyl, —O—$C_{1-2}$ alkyl, or $C_{3-5}$ cycloalkyl;

$R^2$ and $R^3$ are, independently at each occurrence, H, F, Cl, Br, I, $OR^a$, $SR^a$, $OCF_3$, $OCHF_2$, $OCH_2F$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

$R^4$ is, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each occurrence, F, Cl, OH, $CF_3$, $C_{1-2}$ alkyl, or $C_{1-2}$ alkoxy;

$R^7$ is, independently at each occurrence, $OR^a$, F, Cl, Br, I, CN, $NO_2$, $-OCF_3$, $-NR^bR^c$, $-C(O)R^a$, $-CO_2R^a$, $-NR^dC(O)R^a$, $-C(O)NR^cR^d$, $-SO_2NR^cR^d$, $-NR^cSO_2R^i$, $-SO_2NHC(O)R^a$, $-C(O)NHSO_2R^a$, $-NR^cSO_2CF_3$, $-SO_2CF_3$, $-S(O)_pR^i$, $-(CF_2)_rCF_3$, tetrazole, $-(CH_2)_r$-phenyl substituted with 0-3 $R^f$, or a $-(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

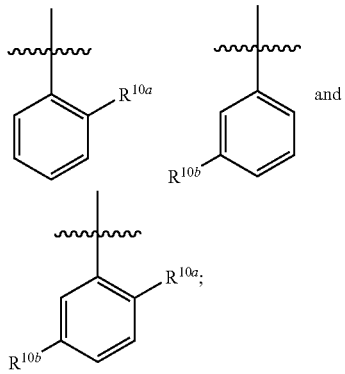

$R^9$ is selected from:

$R^{10a}$ and $R^{10b}$ are, independently at each occurrence, H, F, Cl, Br, I, $-(CH_2)_r-OR^a$, $-(CH_2)_r-SR^a$, $OCF_3$, $SCF_3$, CN, $NO_2$, $-(CH_2)_r-NR^bR^c$, $-C(O)R^a$, $-(CH_2)_r-CO_2R^a$, $-(CH_2)_r-NR^cCO_2R^a$, $-NR^dC(O)R^a$, $-(CH_2)_r-C(O)NR^cR^d$, $-NR^cC(O)NR^cR^d$, $-SO_2NR^cR^d$, $-OSO_2NR^cR^d$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $-(CH_2)_r-C_{3-10}$ carbocycle substituted with 0-3 $R^f$, or $-(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^a$ is, independently at each occurrence, H, $C_{1-6}$ alkyl substituted with 0-4 $R^h$, $-(CH_2)_r-C_{3-7}$ carbocycle substituted with 0-4 $R^f$, or $-(CH_2)_r$-5- to 10-membered heterocycle comprising: carbon atoms and 1-4 heteroatoms selected from N, $NR^g$, O, and $S(O)_p$, wherein said heterocycle is substituted with 0-4 $R^f$;

$R^b$ is, independently at each occurrence, H, $C_{1-6}$ alkyl, $-(CH_2)_n$-phenyl, $(C_{1-6}$ alkyl$)C(O)-$, $(C_{3-6}$ cycloalkyl$)-C_{0-4}$ alkyl-$C(O)-$, $(C_{6-10}$ aryl$)-(C_{0-4}$ alkyl$)-C(O)-$, (5- to 10-membered heteroaryl)-$C_{0-4}$ alkyl-$C(O)-$, $(C_{1-6}$ alkyl)-$NHC(O)-$, $(C_{1-6}$ alkyl$)_2$-$NHC(O)-$, $(C_{6-10}$ aryl$)-C_{0-4}$ alkyl-$NHC(O)-$, (5- to 10-membered heteroaryl)-$C_{0-4}$ alkyl-$NHC(O)-$, $(C_{1-6}$ alkyl)-$SO_2-$, $(C_{6-10}$ aryl$)-C_{0-4}$ alkyl-$SO_2-$, or (5- to 10-membered heteroaryl)-$C_{0-4}$ alkyl-$SO_2-$, wherein said phenyl, aryl and heteroaryl are substituted with 0-2 $R^f$;

$R^c$ is, independently at each occurrence, H, $C_{1-6}$ alkyl substituted with 0-3 $R^h$, $-(CH_2)_n-C_{3-7}$ cycloalkyl substituted with 0-3 $R^h$, or $-(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each occurrence, H, $C_{1-6}$ alkyl, $-(CH_2)_r-C_{3-10}$ carbocycle substituted with 0-3 $R^f$, or a $-(CH_2)_r$-5- to 12-membered heterocycle comprising: carbon atoms and 1-4 heteroatoms selected from N, $NR^g$, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^e$ is, independently at each occurrence, =O, $OR^a$, F, Cl, Br, I, CN, $NO_2$, $-SR^a$, $-OCF_3$, $-NR^bR^c$, $-C(O)R^a$, $-CO_2R^a$, $-NR^dC(O)R^a$, $-C(O)NR^cR^d$, $-OC(O)R^a$, $-NR^dC(O)OR^a$, $-NR^dC(O)NR^cR^d$, $-OC(O)NR^cR^d$, $-SO_2NR^cR^d$, $-NC(O)OR^a$, $-NR^cSO_2NR^cR^d$, $-NR^cSO_2R^i$, $-NR^cSO_2CF_3$, $-SO_2CF_3$, $-S(O)_pR^i$, $-(CF_2)_rCF_3$, $C_{3-10}$ carbocycle substituted with 0-3 $R^f$, or a 5- to 12-membered heterocycle comprising: carbon atoms and 1-4 heteroatoms selected from N, $NR^g$, O, and $S(O)_p$, wherein said heterocycle is substituted with 0-3 $R^f$;

$R^f$ is, independently at each occurrence, =O, $OR^g$, F, Cl, Br, I, CN, $NO_2$, $-SR^g$, $-OCF_3$, $-NR^cR^c$, $-C(O)R^g$, $-CO_2R^g$, $-NR^cC(O)R^g$, $-C(O)NR^cR^c$, $-OC(O)R^g$, $-NR^cC(O)OR^g$, $-NR^cC(O)NR^cR^c$, $-OC(O)NR^cR^c$, $-SO_2NR^cR^c$, $-NR^cSO_2NR^cR^c$, $-NR^cSO_2R^i$, $-NR^cSO_2CF_3$, $-SO_2CF_3$, $-S(O)_pR^i$, $-(CF_2)_rCF_3$, $C_{1-6}$ alkyl, $C_{2-6}$ alkenyl, $C_{2-6}$ alkynyl, $C_{3-10}$ carbocycle substituted with 0-3 $R^h$, or a 5- to 12-membered heterocycle comprising: carbon atoms and 1-4 heteroatoms selected from N, $NR^g$, O, and $S(O)_p$, and substituted with 0-3 $R^h$;

$R^g$ is, independently at each occurrence, H, $C_{1-6}$ alkyl, or $-(CH_2)_n$-phenyl;

$R^h$ is, independently at each occurrence, =O, $-(CH_2)_rOR^g$, F, Cl, Br, I, CN, $NO_2$, $-OCF_3$, $-NR^gR^g$, $-C(O)R^g$, $-CO_2R^g$, $-NR^gC(O)R^g$, $-C(O)NR^gR^g$, $-SO_2NR^gR^g$, $-NR^gSO_2NR^gR^g$, $-NR^gSO_2-C_{1-4}$ alkyl, $-NR^gSO_2CF_3$, $-NR^gSO_2$-phenyl, $-SO_2CF_3$, $-S(O)_p-C_{1-4}$ alkyl, $-S(O)_p$-phenyl, $-(CF_2)_rCF_3$, $C_{1-6}$ alkyl, $C_{2-6}$ alkenyl, $C_{2-6}$ alkynyl, $(C_{1-6}$ alkyl$)C(O)-$, $(C_{3-6}$ cycloalkyl$)-C_{0-4}$ alkyl-$C(O)-$, $(C_{6-10}$ aryl$)-(C_{0-4}$ alkyl$)-C(O)-$, (5-10 membered heteroaryl)-$C_{0-4}$ alkyl-$C(O)-$, $(C_{1-6}$ alkyl$)-NHC(O)-$, $(C_{1-6}$ alkyl$)_2$-$NHC(O)-$, $(C_{6-10}$ aryl$)-C_{0-4}$ alkyl-$NHC(O)-$, (5-10 membered heteroaryl)-$C_{0-4}$ alkyl-$NHC(O)-$, $(C_{1-6}$ alkyl)-$SO_2-$, $(C_{6-10}$ aryl$)-C_{0-4}$ alkyl-$SO_2-$, (5-10 membered heteroaryl)-$C_{0-4}$ alkyl-$SO_2-$, $-(CH_2)_r-C_{3-10}$ carbocycle, or a $-(CH_2)_r$-5- to 12-membered heterocycle comprising: carbon atoms and 1-4 heteroatoms selected from N, $NR^g$, O, and $S(O)_p$;

$R^i$ is, independently at each occurrence, H, $C_{1-6}$ alkyl substituted with 0-3 $R^h$, $C_{3-6}$ cycloalkyl substituted with 0-3 $R^h$, $-(CH_2)_p$-phenyl substituted with 0-3 $R^h$, $-(CH_2)_r$-5- to 10-membered heterocycle comprising: carbon atoms and 1-4 heteroatoms selected from N, $NR^g$, O, and $S(O)_p$, wherein said heterocycle is substituted with 0-3 $R^h$;

n, at each occurrence, is selected from 0, 1, 2, 3, and 4;

p, at each occurrence, is selected from 0, 1, and 2;

r, at each occurrence, is selected from 0, 1, 2, 3, and 4; and t is selected from 1 and 2.

In a fourth embodiment, the present invention includes a compound of Formula (II) or a stereoisomer, tautomer, pharmaceutically acceptable salt, solvate, or prodrug thereof, wherein:

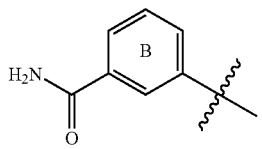

is:

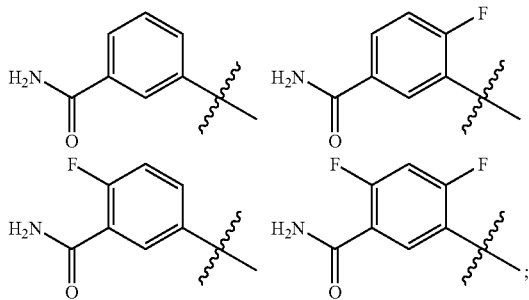

R¹ is, Cl, Br, Me, Et, vinyl, 2-propenyl, ethynyl, —CH(OH)Me, OMe, OEt, cyclopropyl, —OCHF$_2$, or —OCF$_2$CHF$_2$;

R² and R³ are, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$, C$_{3-6}$ cycloalkyl substituted with 0-3 R$^f$, phenyl substituted with 0-3 R$^f$, or a 5- to 6-membered heterocycle comprising: carbon atoms and 1-4 heteroatoms selected from N, NR$^c$, O, and S(O)$_p$, wherein said heterocycle are substituted with 0-3 R$^f$;

R⁴ is, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, C$_{3-6}$ cycloalkyl substituted with 0-3 R$^f$, phenyl substituted with 0-3 R$^f$, or a 5- to 6-membered heterocycle comprising: carbon atoms and 1-4 heteroatoms selected from N, NR$^c$, O, and S(O)$_p$, wherein said heterocycle are substituted with 0-3 R$^f$;

R$^a$ is, independently at each occurrence, H, C$_{1-6}$ alkyl substituted with 0-2 R$^h$, —(CH$_2$)$_r$—C$_{3-6}$ cycloalkyl substituted with 0-2 R$^f$, —(CH$_2$)$_r$-phenyl substituted with 0-3 R$^f$, or —(CH$_2$)$_r$-5- to 6-membered heterocycle comprising: carbon atoms and 1-4 heteroatoms selected from N, NR$^g$, O, and S(O)$_p$, wherein said heterocycle is substituted with 0-3 R$^f$;

R$^b$ is, independently at each occurrence, H, C$_{1-6}$ alkyl, —(CH$_2$)$_n$-phenyl, (C$_{1-6}$ alkyl)C(O)—, (C$_{3-6}$ cycloalkyl)-C$_{0-4}$ alkyl-C(O)—, phenyl-(C$_{0-4}$ alkyl)-C(O)—, (5- to 6-membered heteroaryl)-C$_{0-4}$ alkyl-C(O)—, (C$_{1-6}$ alkyl)-NHC(O)—, (C$_{1-6}$ alkyl)$_2$-NHC(O)—, phenyl-C$_{0-4}$ alkyl-NHC(O)—, (5- to 6-membered heteroaryl)-C$_{0-4}$ alkyl-NHC(O)—, (C$_{1-6}$ alkyl)-SO$_2$—, phenyl-C$_{0-4}$ alkyl-SO$_2$—, or (5- to 6-membered heteroaryl)-C$_{0-4}$ alkyl-SO$_2$—, wherein said phenyl and heteroaryl are substituted with 0-2 R$^f$;

R$^c$ is, independently at each occurrence, H, C$_{1-6}$ alkyl substituted with 0-3 R$^h$, —(CH$_2$)$_n$—C$_{3-6}$ cycloalkyl substituted with 0-2 R$^h$, or —(CH$_2$)$_n$-phenyl substituted with 0-3 R$^h$;

R$^d$ is, independently at each occurrence, H, C$_{1-6}$ alkyl, —(CH$_2$)$_n$—C$_{3-6}$ cycloalkyl substituted with 0-2 R$^f$, —(CH$_2$)$_r$-phenyl substituted with 0-3 R$^f$, or a —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^f$;

R$^e$ is, independently at each occurrence, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{3-6}$ cycloalkyl substituted with 0-2 R$^f$, phenyl substituted with 0-3 R$^f$, or a 5- to 10-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-6}$ cycloalkyl substituted with 0-2 R$^f$, phenyl substituted with 0-3 R$^f$, or a 5- to 10-membered heterocycle comprising: carbon atoms and 1-4 heteroatoms selected from N, NR$^g$, O, and S(O)$_p$, and substituted with 0-3 R$^h$;

R$^h$ is, independently at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, C$_{3-6}$ cycloalkyl, phenyl, or a —(CH$_2$)$_r$-5- to 10-membered heterocycle comprising: carbon atoms and 1-4 heteroatoms selected from N, NR$^g$, O, and S(O)$_p$; and R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 6-membered heterocycle comprising: carbon atoms and 1-4 heteroatoms selected from N, NR$^g$, O, and S(O)$_p$, wherein said heterocycle is substituted with 0-3 R$^h$.

In a fifth embodiment, the present invention includes a compound of Formula (III):

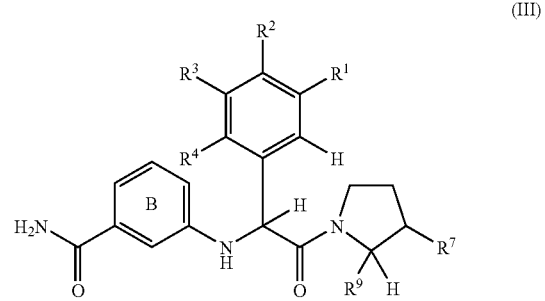

or a stereoisomer, tautomer, pharmaceutically acceptable salt, solvate, or prodrug thereof, wherein:

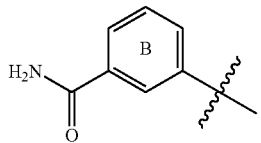

is:

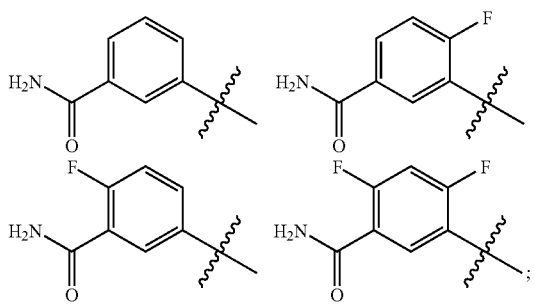

$R^1$ is Cl, Br, Me, Et, vinyl, 2-propenyl, ethynyl, —CH(OH)Me, OMe, OEt, cyclopropyl, —OCHF$_2$, or —OCF$_2$CHF$_2$;
$R^2$ is H, F, Cl, $C_{1-4}$ alkyl, $C_{1-4}$ alkoxy, or —OCHF$_2$;
$R^3$ is H, $C_{1-4}$ alkyl, or $C_{1-4}$ alkoxy;
$R^4$ is H or F;
$R^7$ is H, CO$_2$H, CO$_2$Me, CO$_2$Et, or CONMe$_2$;
$R^9$ is:

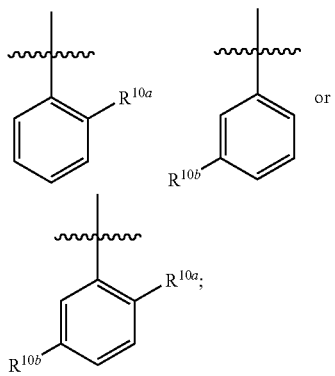

$R^{10a}$ is, independently at each occurrence, H, —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$-(4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, 1-piperidyl, 4-morpholinyl, 3,5-diethyl-1H-pyrazol-1-yl, NO$_2$, or —B(OH)$_2$; and
$R^{10b}$ is, independently at each occurrence, H, CONH$_2$, NH$_2$, NHMe, NHEt, NMe$_2$, —NHCOH, —NHCOMe, —NHCOEt, —NHCOPr, —NHCO(i-Pr), —NHCO(i-Bu), —NHCO-cyclopropyl, —N(Me)COMe, —NHCO$_2$Me, —NHCO$_2$Et, —NHCONH$_2$, —NHCONHMe, —NH-CONMe$_2$, —NHCON(Me)Et, —NHCON(Me)(i-Pr), —NHCO-(1-azetidinyl), —NHCO-(1-pyrrolidinyl), or —NHCO-(3-thiazolidinyl).

In a sixth embodiment, the present invention includes a compound of Formula (III) or a stereoisomer, tautomer, pharmaceutically acceptable salt, solvate, or prodrug thereof, wherein:
$R^1$ is Cl, Me, Et, OMe, or OEt;
$R^2$ is F, Cl, OMe or O(i-Pr);
$R^3$ is H;
$R^4$ is H or F;
$R^7$ is H, CO$_2$H, CO$_2$Me, or CO$_2$Et;
$R^9$ is:

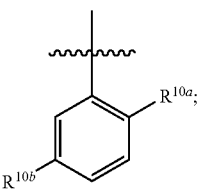

$R^{10a}$ is, independently at each occurrence, H, —SO$_2$—C$_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—C$_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, 4-morpholinyl, or 3,5-diethyl-1H-pyrazol-1-yl; and
$R^{10b}$ is, independently at each occurrence, H, OH, NH$_2$, —NHCOH, —NHCOMe, —NHCOEt, —NHCO$_2$Me, —NHCO$_2$Et, —NHCONHMe, —NHCONH$_2$, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —OSO$_2$NH$_2$, —NHSO$_2$NH$_2$, —NHSO$_2$Me, —SO$_2$NH$_2$, or NO$_2$.

In a seventh embodiment, the present invention includes a compound of Formula (III) or a stereoisomer, tautomer, pharmaceutically acceptable salt, solvate, or prodrug thereof, wherein:
$R^7$ is H;
$R^{10a}$ is, independently at each occurrence, —SO$_2$—C$_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—C$_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, 4-morpholinyl, or 3,5-diethyl-1H-pyrazol-1-yl; and
$R^{10b}$ is, independently at each occurrence, OH, NH$_2$, —NHCOH, —NHCOMe, —NHCOEt, —NHCO$_2$Me, —NHCO$_2$Et, —NHCONHMe, —NHCONMe$_2$, —NHCON(Me)Et, —NHCON(Me)(i-Pr), —NHCO-(1-azetidinyl), —NHCO-(1-pyrrolidinyl), —NHCO-(3-thiazolidinyl), —NHCONH$_2$, —OSO$_2$NH$_2$, —NHSO$_2$NH$_2$, —NHSO$_2$Me, or —SO$_2$NH$_2$.

In an eighth embodiment, the present invention includes a compound of Formula (III) or a stereoisomer, tautomer, pharmaceutically acceptable salt, solvate, or prodrug thereof, wherein:
$R^7$ is CO$_2$H, CO$_2$Me, or CO$_2$Et;
$R^{10a}$ is, independently at each occurrence, —SO$_2$—C$_{1-4}$ alkyl, —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$NH—C$_{1-4}$ alkyl, —SO$_2$NH-cyclopropyl, —SO$_2$NMe$_2$, CONMe$_2$, CO(1-pyrrolidinyl), CO(1-piperidinyl), 1-piperidyl, or 4-morpholinyl, or 3,5-diethyl-1H-pyrazol-1-yl; and $R^{10b}$ is H.

In a ninth embodiment, the present invention includes a compound of Formula (III) or a stereoisomer, tautomer, pharmaceutically acceptable salt, solvate, or prodrug thereof, wherein:

$R^7$ is $CO_2H$, $CO_2Me$, or $CO_2Et$;

$R^{10a}$ is, independently at each occurrence, $-SO_2-C_{1-4}$ alkyl, $-SO_2$-cyclopropyl, $-SO_2$-cyclobutyl, $-SO_2$-cyclopentyl, $-SO_2Ph$, $-SO_2$-(1-pyrrolidinyl), $-SO_2$-(1-piperidyl), $-SO_2$-(1-azepanyl), $-SO_2NH-C_{1-4}$ alkyl, $-SO_2NH$-cyclopropyl, $-SO_2NMe_2$, $CONMe_2$, CO(1-pyrrolidinyl), CO(1-piperidinyl), 1-piperidyl, 4-morpholinyl, or 3,5-diethyl-1H-pyrazol-1-yl; and $R^{10b}$ is, independently at each occurrence, OH, $NH_2$, $-NHCOH$, $-NHCOMe$, $-NHCOEt$, $-NHCO_2Me$, $-NHCO_2Et$, $-NHCONHMe$, $-NHCONMe_2$, $-NHCON(Me)Et$, $-NHCON(Me)(i-Pr)$, $-NHCO$-(1-azetidinyl), $-NHCO$-(1-pyrrolidinyl), $-NHCO$-(3-thiazolidinyl), $-NHCONH_2$, $-OSO_2NH_2$, $-NHSO_2NH_2$, $-NHSO_2Me$, or $-SO_2NH_2$.

In a tenth embodiment, the present invention includes a compound of Formula (III) or a stereoisomer, tautomer, pharmaceutically acceptable salt, solvate, or prodrug thereof, wherein:

$R^7$ is $CO_2H$, $CO_2Me$, or $CO_2Et$;

$R^{10a}$ is H;

$R^{10b}$ is, independently at each occurrence, OH, $NH_2$, $-NHCOH$, $-NHCOMe$, $-NHCOEt$, $-NHCO_2Me$, $-NHCO_2Et$, $-NHCONHMe$, $-NHCONMe_2$, $-NHCON(Me)Et$, $-NHCON(Me)(i-Pr)$, $-NHCO$-(1-azetidinyl), $-NHCO$-(1-pyrrolidinyl), $-NHCO$-(3-thiazolidinyl), $-NHCONH_2$, $-OSO_2NH_2$, $-NHSO_2NH_2$, $-NHSO_2Me$, or $-SO_2NH_2$.

In an eleventh embodiment, the present invention includes a compound of Formula (IIIa):

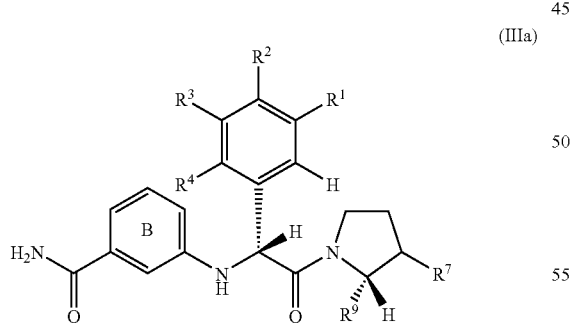

(IIIa)

wherein: ring B, $R^1$, $R^2$, $R^3$, $R^4$, $R^7$ and $R^9$ are the same as defined in the fifth embodiment.

In a twelfth aspect, the present invention provides a compound selected from the exemplified examples or a stereoisomer, tautomer, pharmaceutically acceptable salt, solvate, or prodrug thereof.

In another embodiment the present invention provides a compound wherein:

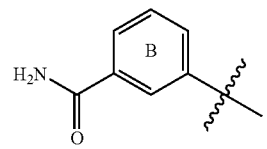

is:

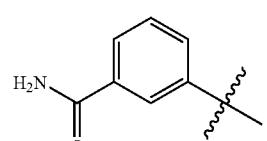

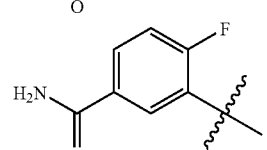

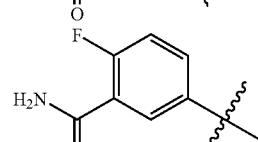

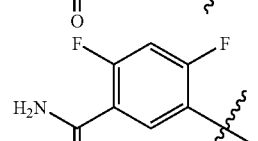

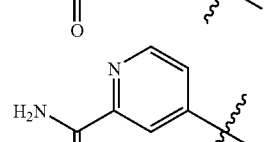

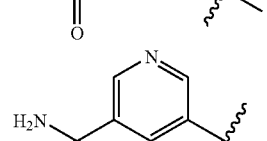

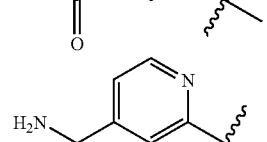

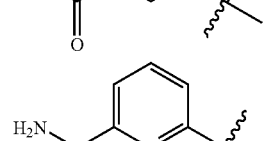

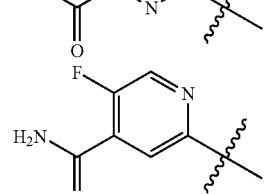

-continued

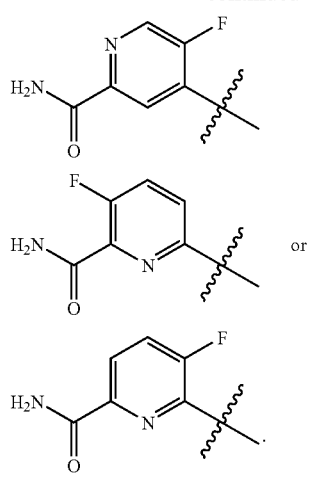

In another embodiment the present invention provides a compound
wherein:

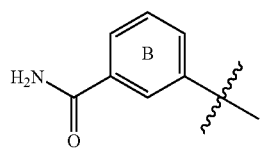

is:

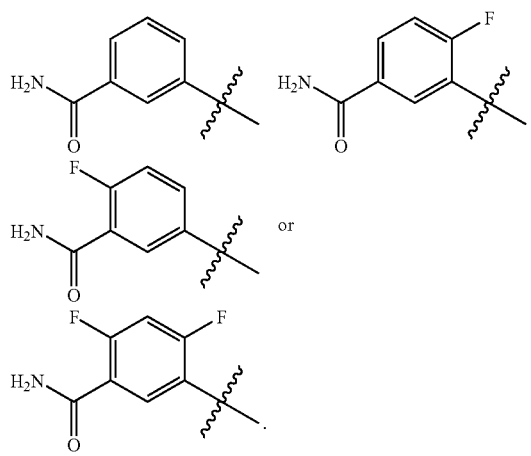

In another embodiment the present invention provides a compound wherein: $R^9$ is:

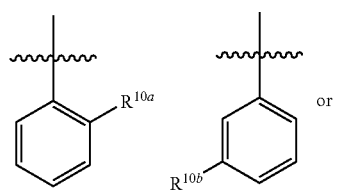

or

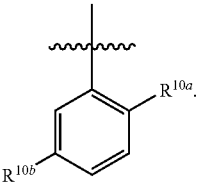

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment the present invention provides a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof.

In another embodiment, the present invention provides a novel process for making a compound of the present invention or a stereoisomer, tautomer, pharmaceutically acceptable salt, solvate or prodrug thereof.

In another embodiment, the present invention provides a novel intermediate for making a compound of the present invention or a stereoisomer, tautomer, pharmaceutically acceptable salt, solvate or prodrug thereof.

In another embodiment the present invention provides a method for modulation of the coagulation cascade comprising administering to a patient in need of such treatment a therapeutically effective amount of at least one of the compounds of the present invention or a stereoisomer, tautomer, pharmaceutically acceptable salt, solvate, or prodrug thereof.

In another embodiment the present invention provides a method for treating thrombotic or thromboembolic disorders comprising: administering to a patient in need of such treatment a therapeutically effective amount of at least one of the compounds of the present invention or a stereoisomer, tautomer, pharmaceutically acceptable salt, solvate, or prodrug thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method of treating a patient in need of thromboembolic disorder treatment, comprising: administering a compound of the present invention or a stereoisomer, tautomer, pharmaceutically acceptable salt, solvate, or prodrug thereof in an amount effective to treat a thromboembolic disorder.

In another embodiment, the present invention provides a method, comprising: administering a compound of the present invention or a stereoisomer, tautomer, pharmaceutically acceptable salt, solvate, or prodrug thereof in an amount effective to treat a thrombotic or thromboembolic disorder.

In another embodiment, the present invention provides a pharmaceutical composition further comprising at least one additional therapeutic agent selected from one or more of potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents, lipid profile therapies, and agents that mimic ischemic preconditioning and/or myocardial stunning, or a combination thereof.

In another embodiment, the present invention provides a pharmaceutical composition wherein the additional therapeutic agent(s) is an antihypertensive agent selected from ACE inhibitors, AT-1 receptor antagonists, beta-adrenergic receptor antagonists, ETA receptor antagonists, dual ETA/AT-1 receptor antagonists, and vasopeptidase inhibitors, an antiarrythmic agent selected from IKur inhibitors, an anticoagulant agent selected from thrombin inhibitors, antithrombin-III activators, heparin co-factor II activators, other factor VIIa inhibitors, plasminogen activator inhibitor (PAI-1) antagonists, thrombin activatable fibrinolysis inhibitor (TAFI) inhibitors, plasma kallikrein inhibitors, factor IXa inhibitors, factor Xa inhibitors, and factor XIa inhibitors, or an antiplatelet agent selected from GPIIb/IIIa blockers, protease activated receptor (PAR-1) antagonists, phosphodiesterase-III inhibitors, $P2Y_1$ receptor antagonists, $P2Y_{12}$ receptor antagonists, thromboxane receptor antagonists, cyclooxygense-1 inhibitors, and aspirin, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, tlcopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent selected from clopidogrel and aspirin, or a combination thereof.

In a preferred embodiment, the present invention provides a pharmaceutical composition, wherein the additional therapeutic agent is the anti-platelet agent clopidogrel.

In another embodiment, the present invention provides a compound of the present invention for use in therapy.

In another embodiment, the present invention provides a compound of the present invention for use in therapy for treating a thrombotic and thromboembolic disorder.

In another embodiment, the present invention also provides the use of a compound of the present invention for the manufacture of a medicament for the treatment of a thrombotic or thromboembolic disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a thrombotic or thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, (enantiomeric and diastereomeric) racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→>O) derivative. In cases wherein there are quarternary carbon atoms on compounds of the present invention, these may be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^f$, then said group may optionally be substituted with up to three $R^f$ groups and $R^f$ at each occurrence is selected independently from the definition of $R^f$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. Branched cycloalkyl groups such as 1-methylcyclopropyl and 2-methylcyclopropyl are included in the definition of "cycloalkyl".

"Alkoxy" or "alkyloxy" represents an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S-, pentafluoroethyl-S-, and the like.

As used herein, "carbocycle" is intended to mean any stable 3, 4, 5, 6, 7, or 8-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl. When the term "carbocycle" is used, it is intended to include "aryl".

As used herein, the term "bicyclic carbocycle" or "bicyclic carbocyclic group" is intended to mean a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_{1-6}$-10 aryl" or "aromatic residue", is intended to mean an aromatic moiety containing, if specified, the specified number of carbon atoms; for example phenyl or naphthyl. Unless otherwise specified, "aryl", "$C_{6-10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3, 4, 5, 6, or 7-membered monocyclic or polycyclic or 7, 8, 9, 10, 11, 12, 13, or 14-membered polycyclic heterocyclic ring which is saturated, partially unsaturated or fully unsaturated, and which consists of carbon atoms and 1, 2, 3 or 4 heteroatoms independently selected from the group consisting of N, O and S; and including any polycyclic group in which any of the above-defined heterocyclic rings is fused to a benzene ring.

The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted.

Also included are fused ring and spiro compounds containing, for example, the above carbocycles or heterocycles.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, sulfate, and the like.

When a dotted ring is used within a ring structure, this indicates that the ring structure may be saturated, partially saturated or unsaturated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

Isotopically labeled compounds of the present invention, i.e., wherein one or more of the atoms described are replaced by an isotope of that atom (e.g., C replaced by $^{13}C$ or by $^{14}C$; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);
b) *A Textbook of Drug Design and Development*, edited by Krosgaard-Larsen and H. Bundgaard, Chapter 5, "Design and Application of Prodrugs," by H. Bundgaard, at pp. 113-191 (1991);
c) H. Bundgaard, *Advanced Drug Delivery Reviews*, Vol. 8, p. 1-38 (1992);
d) H. Bundgaard, et al., *Journal of Pharmaceutical Sciences*, Vol. 77, p. 285 (1988); and
e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and insoluble solvates. Exemplary solvates include hydrates, ethanolates, methanolates, isopropanolates and the like. Methods of solvation are generally known in the art.

As used herein, the term "patient" encompasses all mammalian species.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

"Therapeutically effective amount" is intended to include an amount of a compound of the present invention that is effective when administered alone or in combination with other active ingredients to inhibit factor VIIa or to treat the disorders listed herein. When applied to a combination, the term refers to combined amounts of the active ingredients that result in the therapeutic effect, whether administered in combination, serially or simultaneously. The combination of compounds is preferably a synergistic combination. Synergy, as described, for example, by Chou and Talalay, *Adv. Enzyme Regul.* 1984, 22, 27-55, occurs when the effect (in this case, e.g., prevention of thrombosis) of the compounds when administered in combination is greater than the additive effect of the compounds when administered alone as a single agent. In general, a synergistic effect is most clearly demonstrated at sub-optimal concentrations of the compounds. Synergy can be in terms of increased antithrombotic effect, lower toxicity, or some other beneficial effect of the combination compared with the individual components.

The term "pharmaceutical composition" means a composition comprising a compound of the invention in combination with at least one additional pharmaceutical acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th ed., 1990, which is incorporated herein by reference in its entirety.

Abbreviations used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "atm" for atmosphere, "psi" for pounds per square inch, "RT" for retention time, "sat" or "sat'd" for saturated, "MW" for molecular weight, "MS" for mass spectrometry, "ESI" for electrospray ionization mass spectroscopy, "HR" for high resolution, "LCMS" for liquid chromatography mass spectrometry, "HPLC" for high pressure liquid chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" or "TLC" for thin layer chromatography, and "α", "β", "R", "S", "E", and "Z" are stereochemical designations familiar to one skilled in the art.

AcOH or HOAc is acetic acid,
AIBN is 2,2'-azo-bis-isobutyronitrile,
$BH_3.SMe_2$ is borane-dimethyl sulfide complex,
$BH_3.THF$ is borane-tetrahydrofuran complex, BINAP is 2,2'-bis(diphenylphosphino)-1,1'-binaphthalene,
Bn is benzyl,
Boc is tert-butyl oxycarbonyl,
BOP is benzotriazol-1-yloxy-tris(dimethylamino)phosphonium hexafluorophosphate,
Bu is butyl,
iBu or i-Bu is isobutyl,
t-Bu is tert-butyl,
Cbz is carbonylbenzyloxy,
CbzSerOtBu is (S)-2-tert-butoxycarbonylamino-3-hydroxy-propionic acid tert-butyl ester,
CDI is 1,1'-carbonyldiimidazole,
$CH_2Cl_2$ is dichloromethane,
$CH_3CN$ is acetonitrile,
Davis oxaziridine is 2-benzenesulfonyl-3-phenyl-oxaziridine,
DABCO is 1,4-diazabicyclo[2.2.2]octane,
DBU is 1,8-diazabicyclo[5.4.0]undec-7-ene,
DCE is 1,2-dichloroethane,
DEAD is diethyl azodicarboxylate,
DIBAL is diisobutylaluminum,
DIBAH is diisobutylaluminum hydride,
DIC is 1,3-diisopropylcarbodiimide,
DIEA or DIPEA is N,N-diisopropylethyl amine,
DMA is N,N-dimethylacetamide,
DMAP is dimethylaminopyridine,
DME is dimethyl ether,
DMF is dimethylformamide,
DMPU is 1,3-dimethyl-3,4,5,6-tetrahydro-2(1H)-pyrimidone,
DMSO is dimethyl sulfoxide,
DPPA is diphenylphosphoryl azide,
EDCI or EDC is 1-(3-dimethylaminopropyl)-3-ethylcarbodiimide hydrochloride,
Et is ethyl,
EtOH is ethanol,
EtOAc is ethyl acetate,
$Et_2O$ is diethyl ether,
HATU is O-(7-azabenzotriazol-1-yl)-N,N,N',N'-tetramethyluronium,
HBTU is O-benzotriazol-1-yl-N,N,N',N'-tetramethyluronium hexafluorophosphate,
HCl is hydrochloric acid,
HOAt or HOAT is 1-hydroxy-7-azabenzotriazole,
HOBt or HOBT is 1-hydroxybenzotriaole,
$H_3PO_4$ is phosphoric acid,
$K_2CO_3$ is potassium carbonate,
LAH is lithium aluminum hydride
LDA is lithium diisopropylamide,
LiHMDS is bis(trimethylsilyl)amide,
LiOH is lithium hydroxide,
mCPBA or MCPBA is meta-chloroperbenzoic acid,
Me is methyl,
MeOH is methanol,
$MgSO_4$ is magnesium sulfate,
$MnO_2$ is manganese dioxide,
MoOPH is oxodiperoxymolybdenum(pyridine)(hexamethylphosphoric triamide),
MsCl is methanesulfonyl chloride,
Na is sodium,
NaH is sodium hydride,
$NaHCO_3$ is sodium bicarbonate,
$NaHSO_3$ is sodium thiosulfate,
NaOAc is sodium acetate,
NaOH is sodium hydroxide,
$Na_2SO_4$ is sodium sulfate,
NBS is N-bromosuccinimide,
NCS is N-chlorosuccinimide,
Ni is nickel,
OAc is acetate,
Pd/C is palladium on carbon,
$Pd(PPh_3)_4$ is tetraks (triphenylphosphine) palladium,
Ph is phenyl,
Pr is propyl,
iPr or i-Pr is isopropyl,
i-PrOH or IPA is isopropanol,
PyBroP or Py-BroP is bromotripyrrolidinophosphonium hexafluorophosphate,
Selectfluor™ is [1(chloromethyl)-4-fluoro-1,4-diazoniabicyclo[2,2,2]octanebis(tetrafluoroborate)],
TBAF is tetrabutylammoniumfluoride,
TBAI is tetrabutylammonium iodide,
tBME is tert-butyl methyl ether,
TEA is triethylamine,
TFA is trifluoroacetic acid,
TFAA is trifluoroacetic anhydride,
THF is tetrahydrofuran.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3nd Edition, 1999). All references cited herein are hereby incorporated in their entirety herein by reference.

Compounds having the general Formula (I):

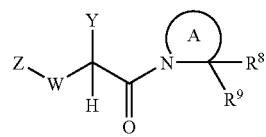

wherein A, W, Y, Z, $R^8$, and $R^9$ are each as defined above, can be prepared by coupling an acid of Formula (Ia):

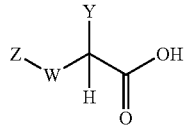
(Ia)

with an amine of Formula (Ib):

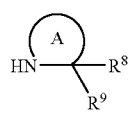
(Ib)

under conditions suitable for forming an amide bond between the acid and the amine. Coupling conditions can be found in Bodanszky, "Principles of Peptide Synthesis, Second Edition" Springer Verlag Ed, Berlin (1993). Coupling reagents include CDI, DIC, and EDCI. Optionally, an intermediate activated ester can be prepared by adding one equivalent of 1-hydroxybenzotriazole or 1-hydroxy-7-azabenzotriazole. Other coupling reagents include HATU, HBTU, and Py-Brop which are usually reacted in the presence of one equivalent of a tertiary base such as DIEA or TEA. Protection and deprotection of functional groups may be required before or after the amide formation step to afford a compound of Formula (I).

The intermediate acid of Formula (Ia) can be prepared in several different ways. For example, it can be prepared according to the steps described in Scheme 1. Thus, amines 1 (prepared following the methods shown in later Schemes and in the Examples) react with phenyl or pyridyl acetate derivatives 2 (Y is substituted phenyl or pyridyl) under basic conditions to give 3. X is a leaving group such as Cl, Br, $OSO_2Me$ or $OSO_2CF_3$ and P is a protecting group such as methyl or benzyl. Deprotection of P in 3 by hydrolysis or hydrogenation gives acid intermediates Ia.

Scheme 1

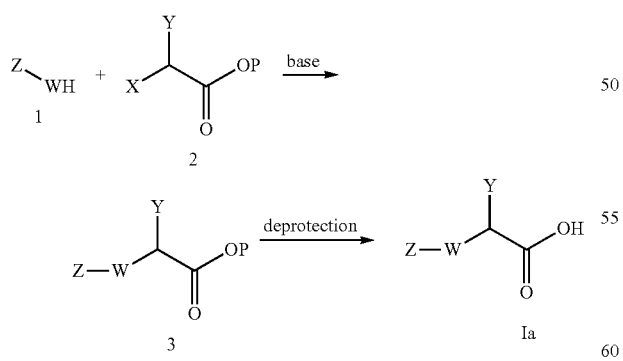

W = NH, O
Y = substituted phenyl or pyridyl

Acids Ia with Y as substituted phenyl and W as NH can be prepared by a Petasis boronic acid Mannich reaction (*J. Am. Chem. Soc.* 1997, 119, 445-446) shown in Scheme 2. Amines 1 react with phenyl boronic acid derivatives 4 and glyoxylic acid 5 in a suitable solvent such as 1,2-dichloroethane and toluene or acetonitrile and DMF to give the acids 6 directly. Many phenyl boronic acid derivatives are commercial available. They can also be prepared by methods known in the art.

Scheme 2

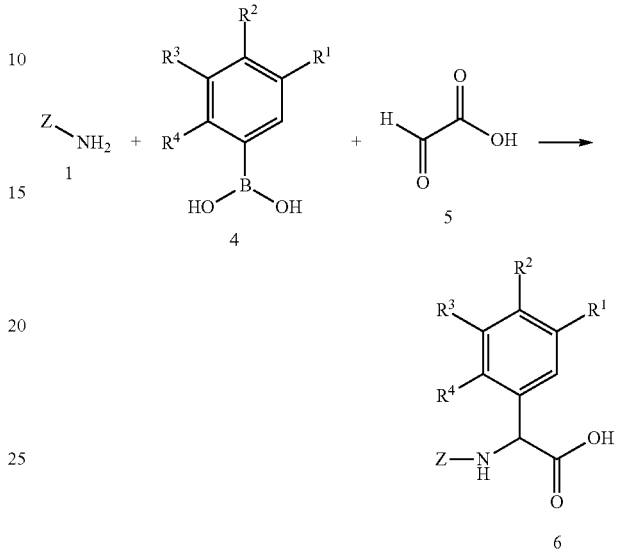

Acids 6 can also be prepared by reductive amination (*Tetrahedron*, 1996, 52, 9777-9784) of α-keto acids 7 with amines 1 as shown in Scheme 3.

Scheme 3

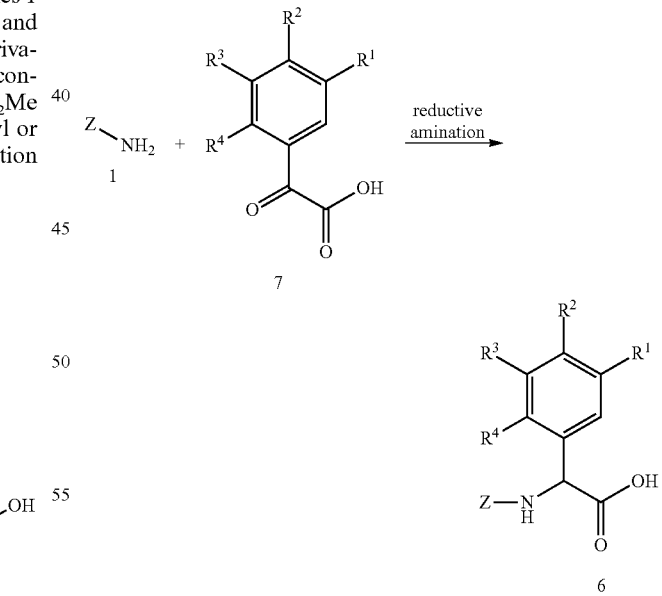

Alternatively to Schemes 2 and 3, as exemplified in Scheme 4, acids 6 can be prepared from amino-esters 9. Amino-esters 9 can be accessed through a Strecker type synthesis, by condensation of aldehydes 8 with trimethylsilyl-cyanide in presence of ammonia, followed by treatment with hydrochloric acid in MeOH. Compounds 9 can be converted to 11 via coupling with aryl halides or sulfonates 10 by methods known in the art (Huang, X. et al. *J. Am. Chem. Soc.* 2003, 125, 6653-6655). For example, amino-esters 9 may be coupled to aryl halides 10 in the presence of a palladium catalyst, an appropriate ligand, for example, BINAP, and a base such as cesium carbonate to provide esters 11. Hydrolysis of 11 under controlled condition gives 6.

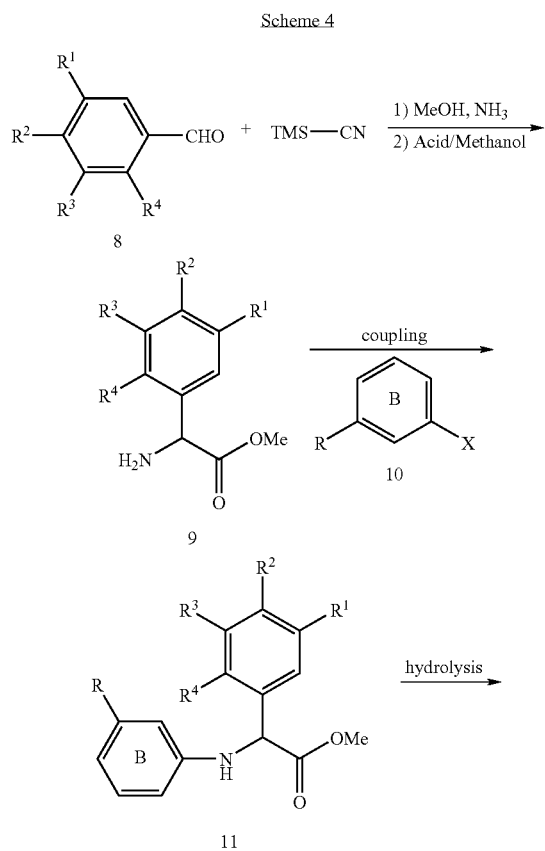

Amines of Formula (Ib) may be prepared in different ways depending on the ring size and substituents. A general method to prepare N-heterocycles of formula Ib may be via palladium catalyzed coupling of lactam-derived ketene aminal with aryl boronic acids, as shown in Scheme 5. Thus, treatment of properly protected lactam 12 with base such as LDA at low temperature and trapping the enolate with diphenylphosphoryl chloride gives the ketene aminal diphenylphosphate 13. Diphenylphosphate 13 undergoes palladium catalyzed coupling with arylboronic acid 14 to give the coupled intermediate 15. Hydrogenation of the double bond in 15 and removal of the protecting group in 16 should give rise to α-aryl substituted N-heterocycle 17. The sequences described in scheme 5 are particularly useful for preparation of 5-, 6-, 7- and 8-membered N-heterocycles.

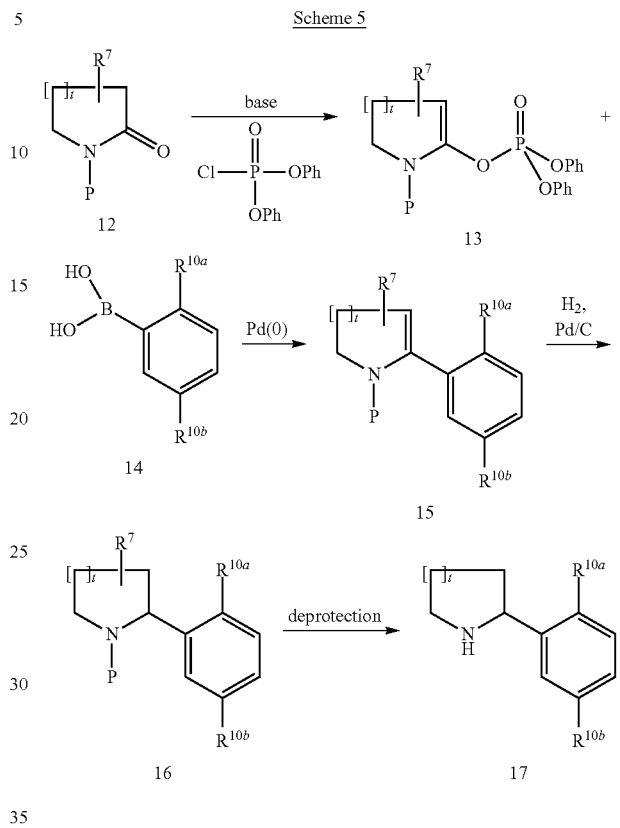

Scheme 6 illustrate another general method to prepare N-heterocycles of Formula (Ib), particularly for the preparation of α-aryl substituted pyrrolidine and piperidine. Condensation of benzylamine 18 with diphenylketone gives Shiff base 19. Treatment of the Schiff base 19 with 1.0 equivalent of base such as LDA and mono-alkylation with a dielectrophile 20 gives intermediate amine 21 after acid hydrolysis. Intramolecular cyclization of 21 in the presence of base such as $K_2CO_3$ should give rise to α-aryl substituted N-heterocycle 22.

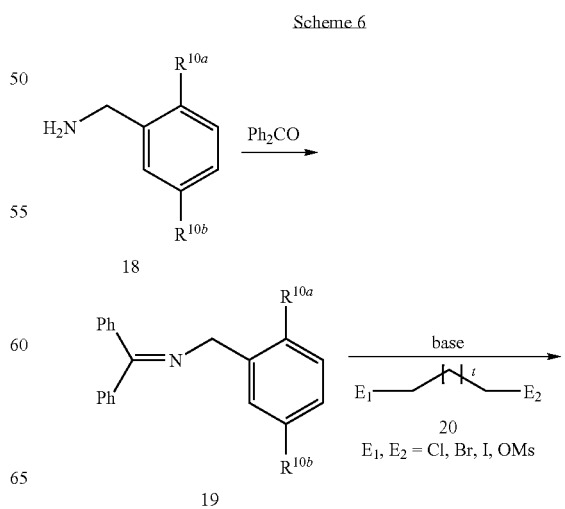

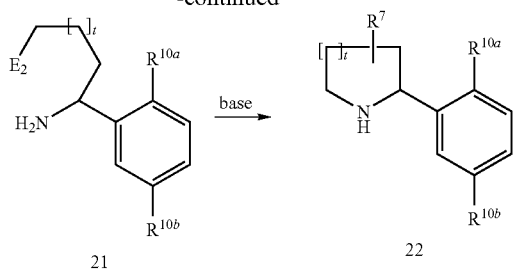

Functionalized phenylpyrrolidines can be prepared by the procedures described in Schemes 7-11. In Scheme 7, palladium catalyzed coupling of Boc protected 2-pyrrole boronic acid 23 with substituted phenyl halide 24 (X=Br or I) gives α-aryl pyrrole 25. Aryl pyrrole 25 can be hydrogenated with a catalyst such as Pt/C, PtO$_2$/C and Pd(OH)$_2$/C in a solvent such as MeOH to Boc-protected aryl pyrrolidine 26. At this stage, the $R^{10a}$ and $R^{10b}$ groups can be manipulated to the desired functional groups. Treatment of the Boc protected 2-aryl pyrrolidine 26 with acid such as HCl in dioxane or TFA gives the pyrrolidine 27.

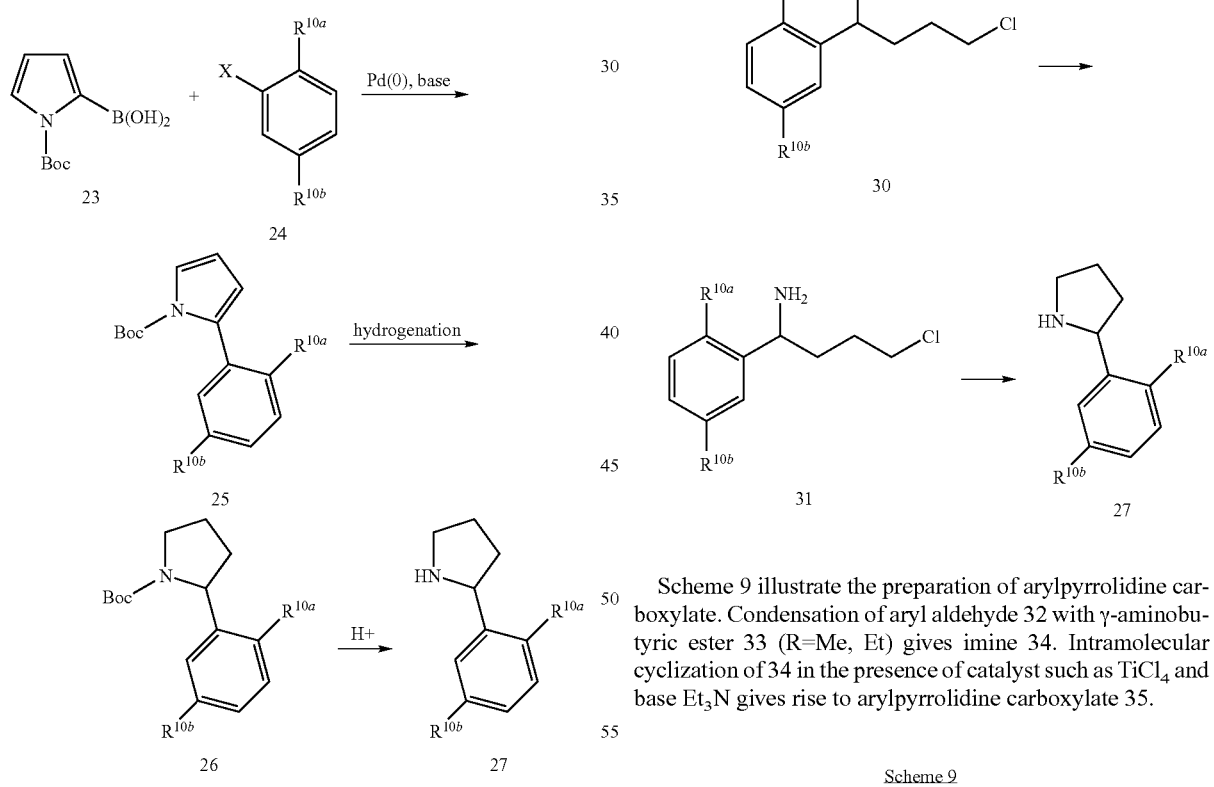

In Scheme 8, reduction of chloro ketone 28 gives hydroxy chlorides 29. Hydroxy chloride 29 can be converted to azides 30, e.g. by the action of DPPA/DBU. Reduction of the azides with PPh$_3$ to amines 31, followed by base-promoted intramolecular cyclization gives the functionalized phenylpyrrolidines 27. It is known that the reduction of the aryl ketones like 28 can be achieved enantioselectively with chiral boranes, e.g. B-chlorodiisopinocamphenyl borane (Dip-Cl, Brown, H. C. et al, *Tetrahedron Lett.* 1994, 35, 2141-2144). It is possible that both enantiomers of 27 can be prepared with the proper choice of chiral borane reagent.

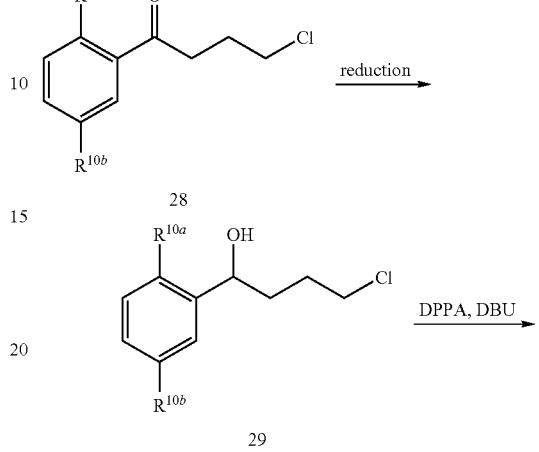

Scheme 9 illustrate the preparation of arylpyrrolidine carboxylate. Condensation of aryl aldehyde 32 with γ-aminobutyric ester 33 (R=Me, Et) gives imine 34. Intramolecular cyclization of 34 in the presence of catalyst such as TiCl$_4$ and base Et$_3$N gives rise to arylpyrrolidine carboxylate 35.

Scheme 9

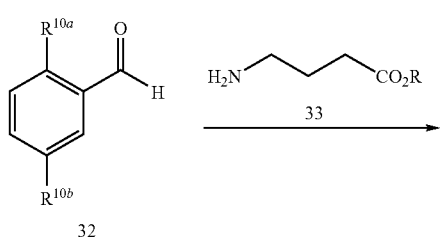

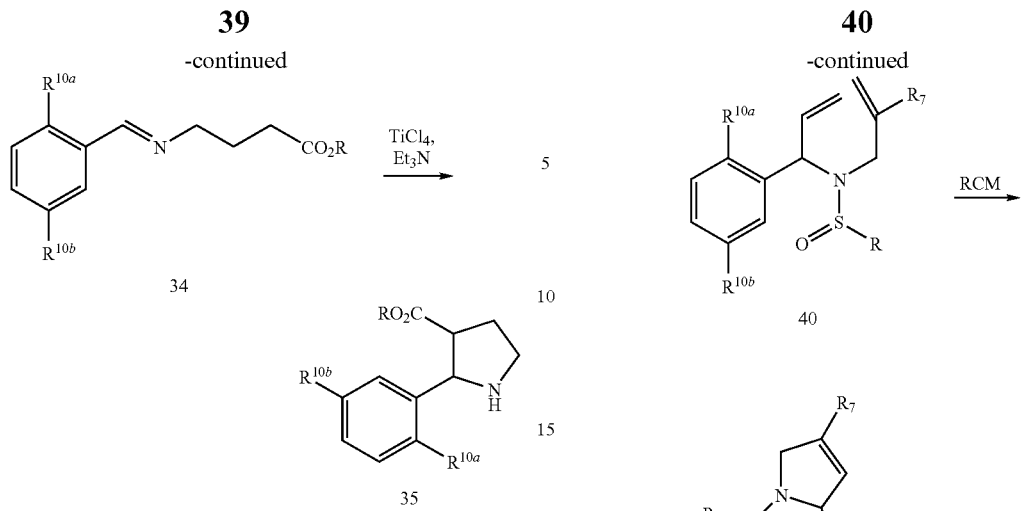

Scheme 10 illustrates a ring closing metathesis (RCM) route to functionalized phenylpyrrolidine derivative 43. Condensation of aldehyde 32 with sulfinamide 36 (racemic or chiral, R is tert-butyl or p-tolyl) in the presence of titanium tetraethoxide gives activated imine 37. Sulfinimine 37 is then treated with vinyl Grignard reagent to give intermediate 38. High diastereoselectivity towards 38 may be achieved with a chiral sulfinamide 36 and with a proper choice of reaction condition. N-allylation of 38 with a substituted allylbromide 39 gives a diene intermediate 40 which can undergo ring closing metathesis (RCM) to give dihydropyrrole 41. Sulfinamide in 41 can be removed under acidic condition and the dihydropyrrole re-protected with a more common protecting group, e.g. a Boc to intermediate 42. Hydrogenation and deprotection of 42 gives rise to functionalized phenylpyrrolidine 43.

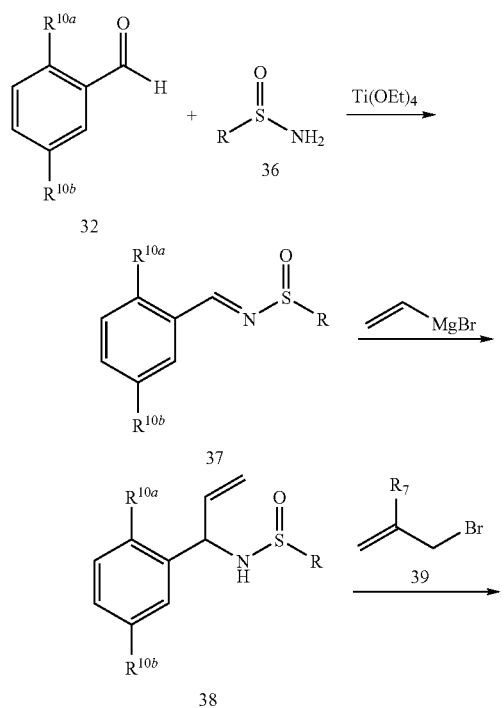

Scheme 11 illustrate a variation of scheme 10 using RCM to the synthesis of phenylpyrrolidine derivative 50 from Baylis-Hillman adduct 46. Thus three component condensation of aldehyde 32, sulfonamide 44 (R is tert-butyl or p-tolyl) and acrylate or vinyl ketone 45 in the presence of a base, e.g. DABCO, gives Baylis-Hillman adduct 46. N-allylation of 46 with allylbromide gives a diene intermediate 47 which can undergo ring closing metathesis (RCM) to give dihydropyrrole 48. Sulfonamide in 48 can be removed and the dihydropyrrole re-protected with a more common protecting group, e.g. a Boc to intermediate 49. Hydrogenation and deprotection of 49 gives rise to functionalized phenylpyrrolidine 50.

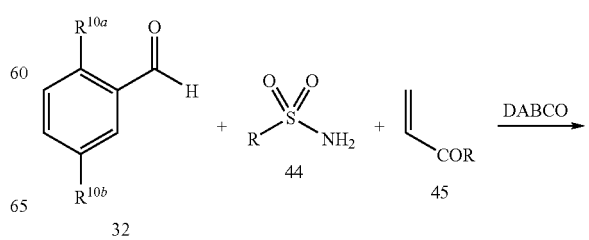

-continued

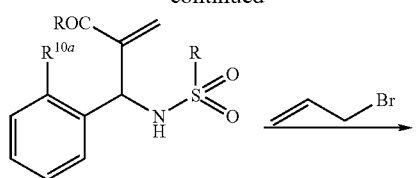
46

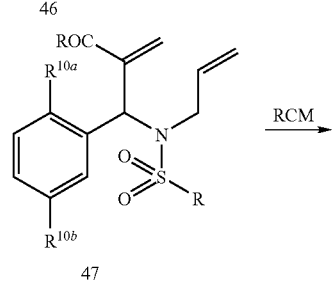
47

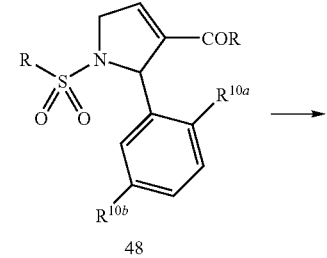
48

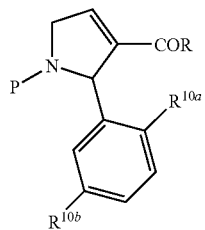 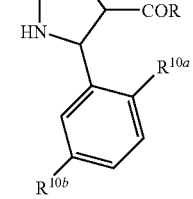
49    50

(R = Me, OMe)

The compound of the instant invention herein described may have asymmetric centers. For example, the chiral carbon atoms in Formula (I) as indicated below, exist in either as S or R configuration.

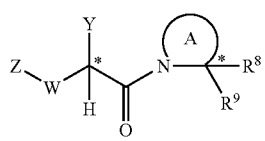
(I)

Thus, the stereoisomeric configurations of each compound of the present invention are considered part of the invention. For example, but not limited to therein, in compounds of Formula (III), the following four stereoisomeric configurations are possible:

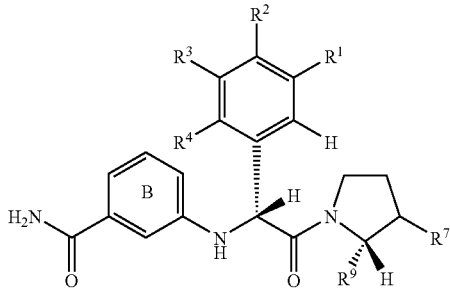
isomer-1

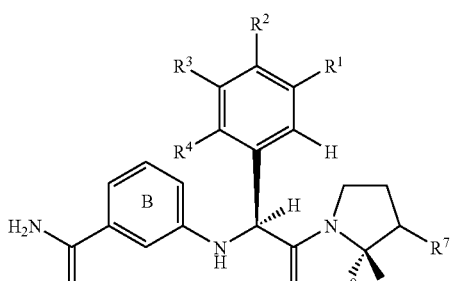
isomer-2

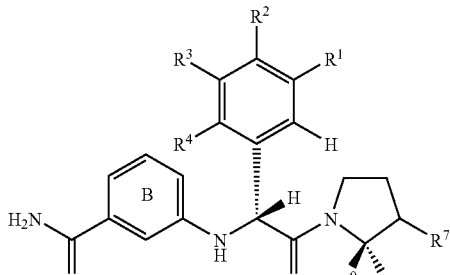
isomer-3

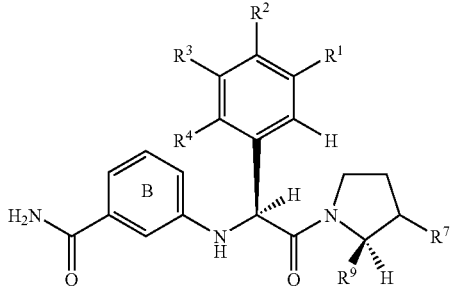
isomer-4

They are collectively, as well as individually, considered part of the invention. In a preferred stereoisomeric embodiment the present invention provides for a stereoisomeric configuration of isomer-1 for all embodiments of Formula (I), (II) or (III), or tautomer, pharmaceutically acceptable salt, solvate, or prodrug form thereof.

In the following experimental procedures, solution ratios express a volume relationship, unless stated otherwise. NMR chemical shifts (δ) are reported in parts per million.

Products were analyzed by reverse phase analytical HPLC carried out on a Shimadzu Analytical HPLC system running DiscoveryVP software using Method A: Phenomenex Luna C18 column (4.6×50 mm or 4.6×75 mm) eluted at 4 mL/min with a 4 or 8 min gradient from 100% A to 100% B (A: 10% methanol, 89.9% water, 0.1% TFA; B: 10% water, 89.9% methanol, 0.1% TFA, UV 220 nm), or Method B: Phenomenex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm). Purification of intermediates and final products was carried out via either normal or reverse phase chromatography. Normal phase chromatography was carried out on an ISCO CombiFlash™ System using pre-packed $SiO_2$ cartridges eluted with gradients of hexanes and ethyl acetate. Reverse phase preparative HPLC was carried out using a Shimadzu Preparative HPLC system running DiscoveryVP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: Phenomenex AXIA Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: Phenomenex Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: Phenomenex Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). LCMS chromatograms were obtained on a Shimadzu HPLC system running DiscoveryVP software, coupled with a Waters ZQ mass spectrometer running MassLynx version 3.5 software using the same columns and conditions as utilized for analytical described above.

EXAMPLES

The following Examples have been prepared, isolated and characterized using the methods disclosed herein. The following Examples demonstrate a partial scope of the invention and are not meant to be limiting of the scope of the invention.

General Coupling Procedure

Most of the final compounds described in the Examples were made according to the following general coupling scheme:

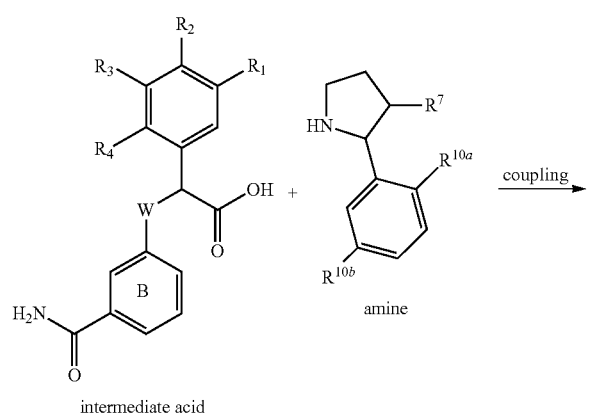

intermediate acid

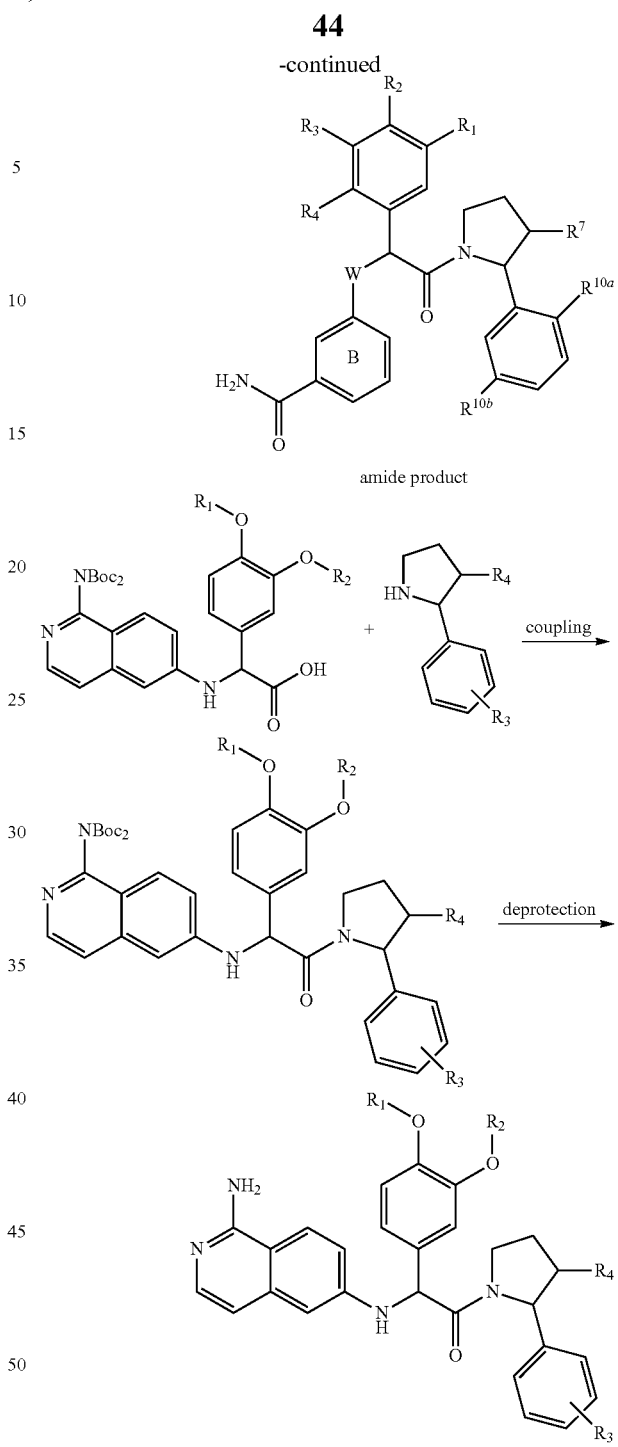

A mixture of intermediate acid (1 eq, preparation given in examples), amine (1.2-1.75 eq, preparation given in examples), EDCI (1.5-2.5 eq), HOAT (0.4-1.0 eq), DIEA (0-5 eq) in $CH_2Cl_2$ (0.01M) or $CH_2Cl_2$/DMF (0.03 M, 10:1) was stirred at rt for 4 h to overnight. The reaction product was concentrated and purified via preparative HPLC (MeOH/$H_2O$/TFA or $CH_3CN$/$H_2O$/TFA) to provide the desired amide. When the amine used was enantiomerically pure, the coupling gave a mixture of two diastereoisomers which were separated in chirally pure fractions by prep HPLC. In each case of examples where diastereomers were obtained, the more effective FVIIa inhibitor is listed first. In some cases, the less active diastereomer is actually inactive vs FVIIa, and is included to enable accurate identification of the more active diastereomer through comparison of spectroscopic data.

Example 1

Methyl 3-((R)-1-((R)-2-(3-carbamoylphenylamino)-2-(3,4-dimethoxyphenyl)acetyl)pyrrolidin-2-yl)-4-(isopropylsulfonyl)phenylcarbamate

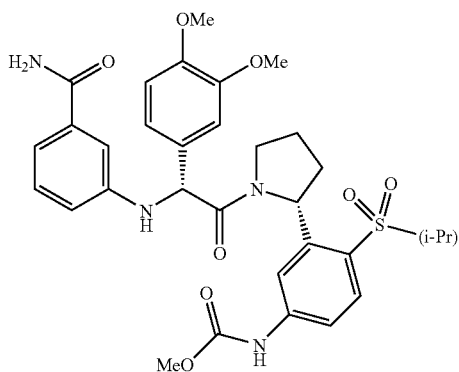

1A: 2-(3-Carbamoylphenylamino)-2-(3,4-dimethoxyphenyl)acetic acid

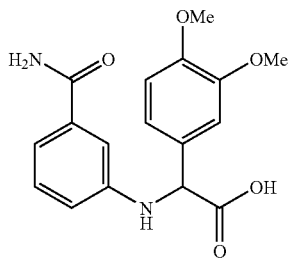

A mixture of 3-aminobenzamide (204 mg, 1.5 mmol), 3,4-dimethoxyphenylboronic acid (273 mg, 1.5 mmol) and glyoxylic acid monohydrate (138 mg, 1.5 mmol) in acetonitrile (8.0 mL) and DMF (0.8 mL) was heated at 55° C. for 4.0 h and then stirred at rt for 18 h. The precipitate formed was collected by filtration and washed with ethyl acetate to give 1A (390 mg, 78% yield) after drying. $^1$H NMR (400 MHz, DMSO-$d_6$) δ ppm 7.03-7.19 (m, 5H) 6.91 (d, J=9.0 Hz, 1H) 6.81 (d, J=8.00 Hz, 1H) 5.05 (s, 1H) 3.83 (s, 3H) 3.72 (s, 3H). LC-MS 331 (M+H).

1B: (2-Bromo-4-nitrophenyl)(isopropyl)sulfane

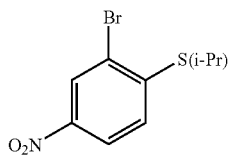

To 3-bromo-4-fluoronitrobenzene (5.0 g, 22.7 mmol) and 2-thiopropane (2.3 mL, 24.9 mmol) in DMF (15 mL) was added potassium carbonate (3.44 g, 24.9 mmol). The reaction was heated to 50° C. overnight. After cooling, the crude reaction mixture was filtered over Celite® and washed with ethyl acetate. The combined filtrate and washings were concentrated. The residue was redissolved in ethyl acetate and washed with water (3×) and then dried over sodium sulfate. Some of the yellow solid (2.53 g) precipitated. The filtrate was concentrated and purified by flash column chromatography to give 3.65 g of 1B (98% total yield). $^1$H NMR (400 MHz, CDCl$_3$) δ ppm 1.41 (d, J=6.60 Hz, 6H) 3.69 (m, 1H) 7.50 (d, J=8.80 Hz, 1H) 8.15 (dd, J=8.80, 2.45 Hz, 1H) 8.35 (d, J=2.45 Hz, 1H).

1C: 2-Bromo-1-(isopropylsulfonyl)-4-nitrobenzene

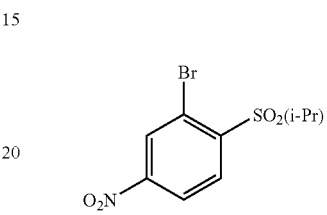

To 1B (1.6 g, 5.8 mmol) in methanol (7 mL) was added Oxone® (10.7 g, 17.4 mmol) in water (10 mL). The reaction was stirred at rt overnight. The reaction was quenched with 5% NaHSO$_3$ and then neutralized with 1 M NaOH. The organic solvent was evaporated and the aqueous layer was extracted with dichloromethane (3×). The combined extracts were washed with brine and dried over sodium sulfate. The solvent was removed and the crude residue was purified by flash column chromatography to give 1.35 g of 1C (76% yield). $^1$H NMR (400 MHz, Methanol-$d_4$) δ ppm 1.25 (d, J=6.85 Hz, 6H) 3.92 (m, 1H) 8.30 (d, J=8.56 Hz, 1H) 8.39 (m, 1H) 8.64 (d, J=1.96 Hz, 1H).

1D: tert-Butyl 2-(2-(isopropylsulfonyl)-5-nitrophenyl)-1H-pyrrole-1-carboxylate

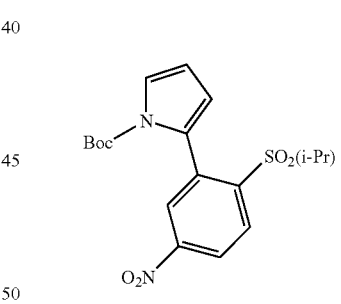

To a mixture of 1C (3.0 g, 9.7 mmol), 1-(tert-butoxycarbonyl)-1H-pyrrol-2-ylboronic acid (2.5 g, 11.7 mmol, prepared according to the procedure in *Synthesis,* 1991, 613-615.) and sodium carbonate (19.5 mL, 2M, 38.9 mmol) in 1,2-dimethoxyethane (100 mL, flushed and degassed (3×) with nitrogen) was added Pd(PPh$_3$)$_4$ (2.2 g, 1.9 mmol) under nitrogen. The reaction was heated to 95° C. for 3 h. The catalyst was filtered over Celite® and washed with ethyl acetate. The organic layer was washed with water, brine and then dried over sodium sulfate. The solvent was removed and the crude residue was purified by flash column chromatography to give 3.68 g of 1D (96% yield). $^1$H NMR (400 MHz, Methanol-$d_4$) δ ppm 1.01 (d, J=6.85 Hz, 3H) 1.15 (d, J=6.85 Hz, 3H) 1.20 (d, J=7.83 Hz, 9H) 3.00 (m, 1H) 6.29 (m, 2H) 7.41 (dd, J=3.18, 1.71 Hz, 1H) 8.20 (d, J=2.20 Hz, 1H) 8.25 (d, J=8.56 Hz, 1H), 8.41 (dd, J=8.68 Hz, 2.32 Hz, 1H).

1E: tert-Butyl 2-(5-amino-2-(isopropylsulfonyl)phenyl)pyrrolidine-1-carboxylate

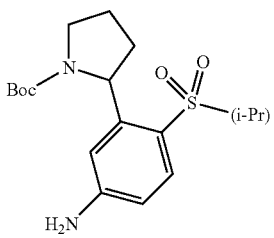

To platinum oxide (0.5 g) was added 1D in ethanol and hydrogen chloride (0.45 mL) under nitrogen. The reaction was placed under hydrogen (40 psi). After 1.5 h the reaction was half done, additional platinum oxide (200 mg) was added and reaction was stirred under hydrogen (40 psi) for 2 h. The catalyst was filtered over Celite® and washed with ethanol. The filtrate was neutralized with diethylamine. The solvent was evaporated and the crude residue was redissolved in dichloromethane. The organic layer was washed with water, brine and dried over sodium sulfate. The solvent was removed and the crude product was purified by flash column chromatography to give a white solid 1E (1.6 g, 88%). $^1$H NMR (400 MHz, Methanol-$d_4$) δ ppm 1.24 (m, 15H) 1.84 (m, 3H) 2.37 (m, 1H) 3.15 (m, 1H) 3.62 (m, 2H) 5.28 (s, 1H) 6.53 (d, J=19.56 Hz, 2H) 7.50 (d, J=8.56 Hz, 1H).

1F: (R)-tert-Butyl 2-(5-amino-2-(isopropylsulfonyl)phenyl)pyrrolidine-1-carboxylate

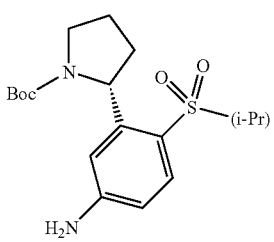

Racemate 1E was separated using a preparative HPLC equipped with a Chiralpak® AD column (5 cm×50 cm, 20μ). The separation was performed using an isocratic method of 15% isopropanol/heptane with 0.1% diethylamine for 100 min with a flow rate of 50 mL/min. The first peak is 1F: $^1$H NMR (400 MHz, Methanol-$d_4$) δ ppm 1.20 (m, 15H) 1.83 (s, 3H) 2.44 (s, 1H) 3.26 (m, 1H) 3.64 (m, 2H) 5.29 (s, 1H) 6.57 (m, 2H) 7.52 (s, 1H).

1G: (R)-Methyl (4-(isopropylsulfonyl)-3-(pyrrolidin-2-yl)phenyl)carbamate hydrochloride

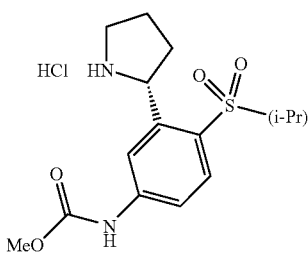

To 1F (0.1 g, 0.27 mmol) in pyridine (1 mL) at 0° C. was added methyl chloroformate (57 (μL, 0.54 mmol). After 2.0 h of stirring at rt the reaction was acidified with 1M HCl to pH 3-4. The product was extracted with ethyl acetate and was washed with brine and dried over sodium sulfate. After evaporation of the solvent, the crude product was redissolved in ethyl acetate (1.5 mL) and hydrogen chloride (2 mL, 4M in dioxane) was added. The reaction was stirred for 3 h at rt. The solvent was removed and placed on the lyophilizer to give 0.15 g white solid 1G. $^1$H NMR (400 MHz, Methanol-$d_4$) δ ppm 1.25 (t, J=7.09 Hz, 3H) 1.37 (d, J=6.85 Hz, 3 H) 2.13-2.31 (m, 1H) 2.31-2.47 (m, 2H) 2.47-2.63 (m, 1H) 3.36-3.56 (m, 3H) 3.73-3.91 (m, 3H) 5.43 (t, J=7.70 Hz, 1H) 7.66 (dd, J=8.80, 2.20 Hz, 1H) 7.97 (d, J=8.80 Hz, 1H) 8.11 (d, J=1.96 Hz, 1H).

1H: Example 1

Example 1 was prepared according to the general coupling condition using 1A and 1G. $^1$H NMR (400 MHz, Methanol-$d_4$) δ ppm 1.16 (d, J=6.59 Hz, 3 H) 1.41 (d, J=7.03 Hz, 3H) 1.69 (dd, J=12.30, 5.71 Hz, 1H) 1.97-2.09 (m, 2H) 2.46 (dd, J=12.96, 7.69 Hz, 1H) 3.63 (s, 3H) 3.69 (s, 3H) 3.82 (s, 3H) 3.92-3.99 (m, 1H) 4.01-4.07 (m, 1H) 5.41 (s, 1H) 5.66 (dd, J=8.13, 5.05 Hz, 1H) 6.82 (s, 1 H) 6.86 (d, J=8.79 Hz, 2H) 6.98 (d, J=8.79 Hz, 1H) 7.08 (s, 1H) 7.20-7.30 (m, 2 H) 7.34-7.41 (m, 2H) 7.74 (d, J=8.79 Hz, 1H); LC-MS 639 (M+H).

Example 2

Diastereoisomer of Example 1

Methyl 3-((R)-1-((S)-2-(3-carbamoylphenylamino)-2-(3,4-dimethoxyphenyl)acetyl)pyrrolidin-2-yl)-4-(isopropylsulfonyl)phenylcarbamate

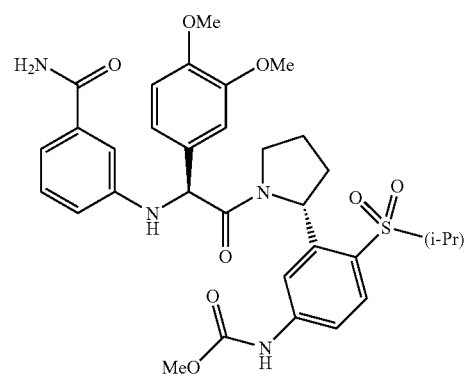

Example 2 was obtained as a diastereomer of Example 1 during its HPLC purification. $^1$H NMR (400 MHz, Methanol-$d_4$) δ ppm 1.00-1.25 (m, 3H) 1.28-1.60 (m, 3H) 1.58-2.50 (m, 4H) 3.66-3.90 (m, 9H) 4.03-4.38 (m, 1H) 5.42 (s, 1H) 5.59 (dd, J=8.35, 4.39 Hz, 1H) 6.17-6.64 (m, 1H) 6.60-8.09 (m, 9H); LC-MS 639 (M+H).

Example 3

Methyl 3-((R)-1-((R)-2-(5-carbamoyl-2-chlorophenylamino)-2-(3,4-dimethoxyphenyl)acetyl)pyrrolidin-2-yl)-4-(isopropylsulfonyl)phenylcarbamate

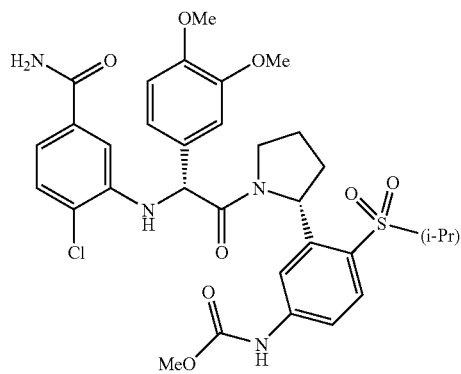

3A: 2-(5-Carbamoyl-2-chlorophenylamino)-2-(3,4-dimethoxyphenyl)acetic acid

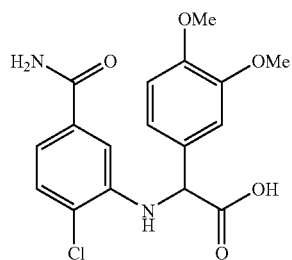

A mixture of 3-amino-4-chlorobenzamide (170 mg, 1.0 mmol), 3,4-dimethoxyphenylboronic acid (182 mg, 1.0 mmol) and glyoxylic acid monohydrate (92 mg, 1.0 mmol) in methylene chloride (4.0 mL) and DMF (0.3 mL) was heated at 65° C. for 3.0 h and then stirred at rt for 18 h. The precipitate formed was collected by filtration and washed with methylene chloride to give 3A (200 mg, 57% yield) after drying. $^1$H NMR (400 MHz, Methanol-$d_4$) δ ppm 3.80 (s, 3H) 3.81 (s, 3H) 5.17 (s, 1 H) 6.92 (d, J=8.35 Hz, 1H) 7.04 (s, 1H) 7.04-7.11 (m, 3H) 7.33 (d, J=7.91 Hz, 1 H); LC-MS 365 (M+H).

3B: Example 3

Example 3 was prepared according to the general coupling condition using 3A and 1G. $^1$H NMR (400 MHz, Methanol-$d_4$) δ ppm 1.13-1.19 (d, J=8.0 Hz, 3H) 1.40 (d, J=7.03 Hz, 3H) 1.61 (dt, J=12.74, 6.37 Hz, 1H) 1.94-2.01 (m, 2 H) 2.36-2.46 (m, 1H) 3.56 (dt, J=10.11, 7.03 Hz, 1H) 3.66 (s, 3H) 3.68-3.72 (s, 3 H) 3.76-3.79 (s, 3H) 3.79-3.87 (m, 1H) 4.02 (dt, J=10.11, 6.59 Hz, 1H) 5.35 (s, 1H) 5.59 (dd, J=7.91, 5.71 Hz, 1H) 6.54 (d, J=2.20 Hz, 1H) 6.78-6.87 (m, 2H) 6.93-7.00 (m, 2H) 7.24-7.29 (m, 2H) 7.49 (dd, J=8.79, 2.20 Hz, 1H) 7.56 (s, 1H) 7.75 (d, J=8.79 Hz, 1H); LC-MS 673 (M+H).

Example 4

Diastereoisomer of Example 3

Methyl 3-((R)-1-((S)-2-(5-carbamoyl-2-chlorophenylamino)-2-(3,4-dimethoxyphenyl)acetyl)pyrrolidin-2-yl)-4-(isopropylsulfonyl)phenylcarbamate

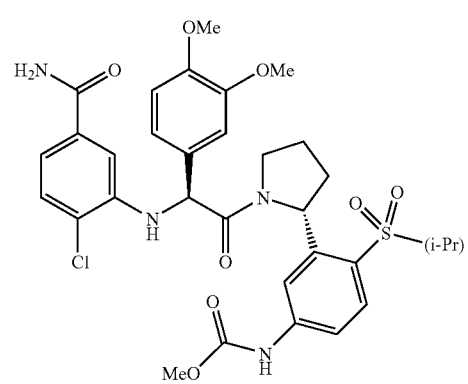

Example 4 was obtained as a diastereomer of Example 3 during its HPLC purification. $^1$H NMR (400 MHz, Methanol-$d_4$) δ 1.05 (d, J=6.81 Hz, 3H) 1.34 (d, J=6.59 Hz, 3H) 1.63-1.71 (m, 1H) 1.73-1.82 (m, 1H) 2.20-2.29 (m, 1H) 3.50 (ddd, J=10.33, 7.47, 7.25 Hz, 1H) 3.63-3.71 (m, 4H) 3.76-3.79 (m, 4H) 5.41 (s, 1H) 5.49 (dd, J=8.35, 4.39 Hz, 1H) 6.25 (s, 1H) 6.92-7.04 (m, 4H) 7.07 (d, J=2.20 Hz, 1H) 7.17 (d, J=2.20 Hz, 1H) 7.27 (d, J=7.91 Hz, 2H) 7.75 (d, J=8.79 Hz, 1H) 7.86 (dd, J=8.79, 2.20 Hz, 1H) 8.77 (s, 1H); LC-MS 673 (M+H).

Example 5

Methyl 3-((R)-1-((R)-2-(5-carbamoyl-2-methylphenylamino)-2-(3,4-dimethoxyphenyl)acetyl)pyrrolidin-2-yl)-4-(isopropylsulfonyl)phenylcarbamate

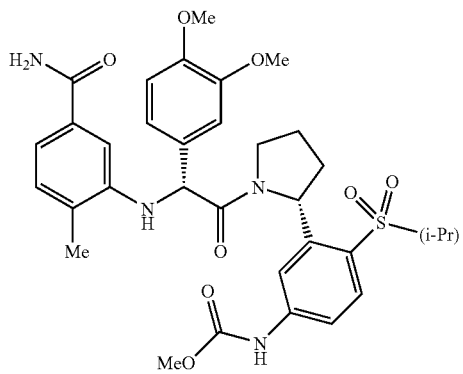

5A: 2-(5-Carbamoyl-2-methylphenylamino)-2-(3,4-dimethoxyphenyl)acetic acid

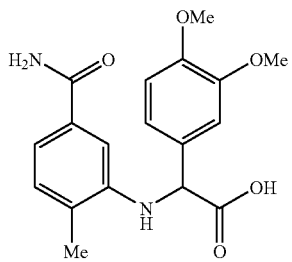

A mixture of 3-amino-4-methylbenzamide (75 mg, 0.5 mmol), 3,4-dimethoxyphenylboronic acid (91 mg, 0.5 mmol) and glyoxylic acid monohydrate (46 mg, 0.5 mmol) in acetonitrile (2.0 mL) and DMF (0.2 mL) was heated at 100° C. for 20 min in a microwave reactor. After removal of solvent, the crude was triturated with methylene chloride. The precipitate formed was collected by filtration and washed with methylene chloride to give 5A after drying. $^1$H NMR (400 MHz, Methanol-$d_4$) δ ppm 3.79 (s, 3H) 3.81 (s, 3H) 5.15 (s, 1H) 6.91 (d, J=8.35 Hz, 1H) 6.95 (s, 1H) 7.05-7.14 (m, 4H); LC-MS 345 (M+H).

5B: Example 5

Example 5 was prepared according to the general coupling condition using 5A and 1G. $^1$H NMR (400 MHz, Methanol-$d_4$) δ ppm 1.17 (d, J=6.59 Hz, 3H) 1.39 (d, J=7.03 Hz, 3H) 1.61 (dd, J=12.74, 5.71 Hz, 1H) 1.95-2.02 (m, 2H) 2.41 (dd, J=13.18, 7.47 Hz, 1H) 3.53-3.60 (m, 1H) 3.67 (d, J=5.27 Hz, 6H) 3.77-3.80 (m, 3H) 4.02 (dd, J=6.59, 3.52 Hz, 1H) 5.35 (s, 1H) 5.61 (dd, J=7.91, 5.27 Hz, 1H) 6.59 (d, J=2.20 Hz, 1H) 6.81-6.88 (m, 2H) 6.95 (s, 1H) 7.00-7.10 (m, 2H) 7.18 (s, 1H) 7.50 (dd, J=8.57, 1.98 Hz, 1H) 7.60 (s, 1H) 7.76 (d, J=8.79 Hz, 1H); LC-MS 653 (M+H).

Example 6

Diastereoisomer of Example 5

Methyl 3-((R)-1-((S)-2-(5-carbamoyl-2-methylphenylamino)-2-(3,4-dimethoxyphenyl)acetyl)pyrrolidin-2-yl)-4-(isopropylsulfonyl)phenylcarbamate

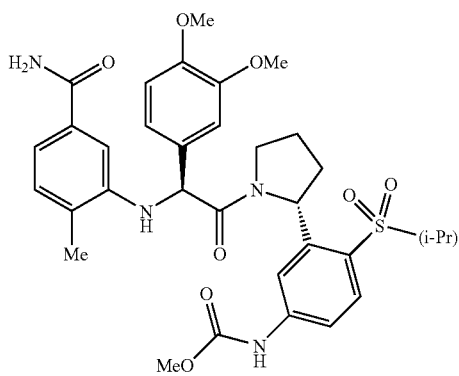

Example 6 was obtained as a diastereomer of Example 5 during its HPLC purification. $^1$H NMR (400 MHz, Methanol-$d_4$) δ ppm 1.04 (d, J=6.59 Hz, 3 H) 1.34 (d, J=7.03 Hz, 3H) 1.62-1.73 (m, 1H) 1.73-1.83 (m, 1H) 1.99-2.08 (m, 4 H) 2.21-2.31 (m, 1H) 3.50-3.58 (m, 1H) 3.63-3.70 (m, 2H) 3.71-3.73 (m, 3H) 3.79 (s, 6H) 4.11 (s, 1H) 5.39 (s, 1H) 5.51 (dd, J=8.35, 4.39 Hz, 1H) 6.22 (s, 1H) 6.90-6.97 (m, 1H) 6.97-7.08 (m, 5H) 7.18 (d, J=2.20 Hz, 2H) 7.74 (d, J=8.79 Hz, 1H) 7.93 (dd, J=8.79, 2.20 Hz, 1H) 9.04 (s, 1H); LC-MS 653 (M+H).

Example 7

Methyl 3-((R)-1-((R)-2-(3-carbamoylphenylamino)-2-(4-fluoro-3-methoxyphenyl)acetyl)pyrrolidin-2-yl)-4-(isopropylsulfonyl)phenylcarbamate

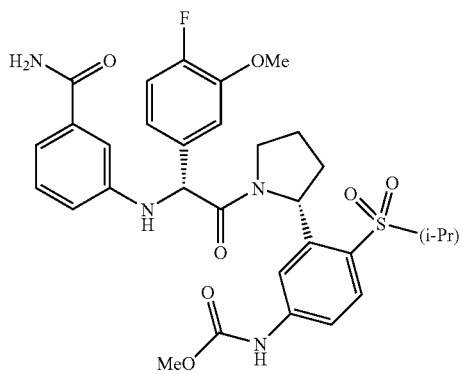

7A: 5-Bromo-2-fluorophenol

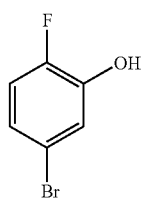

To a solution of 2,2,6,6-tetramethyl piperidine (5.6 mL, 33.2 mmol) in THF at −20° C. was added n-BuLi (1.6 M in hexanes, 18.8 mL, 30 mmol). The mixture was stirred at −20° C. for 10 min before it was cooled to −78° C. 1-Bromo-4-fluorobenzene (2.95 mL, 27 mmol) was added over 10 min and the mixture was stirred at −78° C. for 2.0 h before trimethyl borate (6.0 mL, 54 mmol) was added. The mixture was stirred at −78° C. for 30 min and then at rt for 2.0 h. After it was cooled back to 0° C., glacial acetic acid (4.86 mL, 81 mmol) was added and stirred for 30 min, followed by addition of 30% $H_2O_2$ (4.86 mL, 81 mmol). The mixture was stirred at rt for 24 h, quenched by addition of $MnO_2$ (40 mg). After stirring at rt for 30 min, the cloudy solution was filtered through a pad of wet Celite® and extracted with EtOAc. The EtOAc layer was washed with aqueous $NaHSO_3$, brine and dried over $Na_2SO_4$. The crude residue was purified by flash column chromatography (EtOAc:hexanes=1:5) to give 4.4 g (85%) of 7A as a liquid. $^1$H NMR (400 MHz, $CDCl_3$) δ ppm 5.39 (s, 1H) 6.90-6.98 (m, 2H) 7.14 (dd, J=8.13, 1.98 Hz, 1H).

7B: 4-Bromo-2-methoxy-1-fluorobenzene

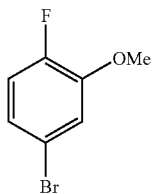

To a solution of 7A (3.3 g, 17.3 mmol) and K₂CO₃ (4.78 g, 34.6 mmol) in DMF (20 mL) was added methyl iodide (1.46 mL, 23.4 mmol) at rt. The mixture was heated at 40° C. for 2.0 h. After cooling to rt, it was diluted with diethyl ether, washed with water and brine, dried over MgSO₄. The crude residue was purified by flash column chromatography (EtOAc:hexanes=1:6) to give 2.74 g (77%) of 7B as a viscous oil. $^1$H NMR (400 MHz, CDCl₃) δ ppm 3.89 (s, 3H), 6.95-7.00 (m, 3H).

7C: 3-Methoxy-4-fluorophenylboronic acid

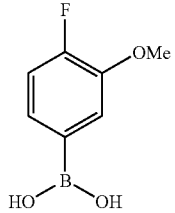

To a solution of 7B (2.7 g, 13.1 mmol) in THF (25 mL) at −78° C. was added n-BuLi (1.6 M in hexanes, 11.0 mL, 17.7 mmol). The mixture was stirred at −78° C. for 40 min before trimethyl borate (2.7 mL, 24.3 mmol) was added. The reaction was left stirring from −78° C. to rt over 18 h. It was quenched with 1.0 N HCl (40 mL), extracted with EtOAc, washed with brine and dried over Na₂SO₄. After evaporation of the solvent, the crude solid product was triturated with EtOAc/hexanes (1:4). After filtration, 7C (0.75 g, 35% yield) was collected as a white solid. $^1$H NMR (400 MHz, Methanol-d₄) δ ppm 3.86 (s, 3H) 7.03-7.45 (m, 3H).

7D: 2-(3-Carbamoylphenylamino)-2-(4-fluoro-3-methoxyphenyl)acetic acid

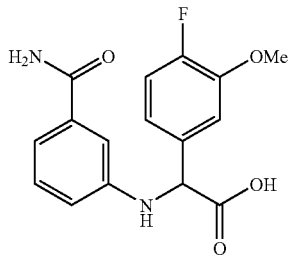

A mixture of 3-aminobenzamide (136 mg, 1.0 mmol), 7C (170 mg, 1.0 mmol) and glyoxylic acid monohydrate (92 mg, 1.0 mmol) in acetonitrile (5.0 mL) and DMF (1.2 mL) was heated at 55° C. for 2.0 h and then stirred at rt for 18 h. After removal of solvent, the crude was purified by silica gel column chromatography eluting with gradient methanol in methylene chloride to give 7D as a solid (190 mg, 60% yield). $^1$H NMR (400 MHz, Methanol-d₄) δ ppm 3.85 (s, 3H) 5.11 (s, 1H) 6.79 (d, J=7.03 Hz, 1H) 7.04-7.15 (m, 5H) 7.27 (dd, J=8.35, 1.76 Hz, 1H); LC-MS 319 (M+H).

7E: Example 7

Example 7 was prepared according to the general coupling condition using 7D and 1G. $^1$H NMR (400 MHz, Methanol-d₄) δ ppm 1.15 (d, J=6.59 Hz, 3H) 1.41 (d, J=6.59 Hz, 3H) 1.69 (d, J=7.47 Hz, 1H) 2.05 (ddd, J=12.19, 6.04, 5.93 Hz, 2H) 2.43-2.53 (m, 1H) 3.62 (dd, J=7.03, 3.08 Hz, 1H) 3.66 (s, 3H) 3.70 (s, 3H) 3.91-3.97 (m, 2H) 4.09 (d, J=10.11 Hz, 1H) 5.44 (s, 1H) 5.65 (dd, J=7.91, 5.27 Hz, 1H) 6.95 (td, J=4.50, 2.42 Hz, 3H) 7.01-7.09 (m, 1H) 7.12-7.18 (m, 2H) 7.24 (t, J=8.13 Hz, 1H) 7.27-7.32 (m, 2H) 7.73 (d, J=8.79 Hz, 1H) 9.50 (s, 1H); LC-MS 627 (M+H).

Example 8

Diastereoisomer of Example 7

Methyl 3-((R)-1-((S)-2-(3-carbamoylphenylamino)-2-(4-fluoro-3-methoxyphenyl)acetyl)pyrrolidin-2-yl)-4-(isopropylsulfonyl)phenylcarbamate

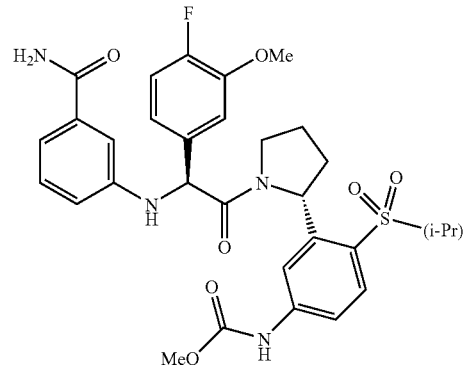

Example 8 was obtained as a diastereomer of Example 7 during its HPLC purification. $^1$H NMR (400 MHz, Methanol-d₄) δ ppm 1.08 (d, J=7.03 Hz, 3 H) 1.39 (d, J=7.03 Hz, 3H) 1.71-2.3 (m, 4H) 3.54-3.65 (m, 1H) 3.67-3.91 (m, 8H) 4.13-4.22 (m, 1H) 5.43-5.51 (s, 1H) 5.59 (dd, J=8.35, 3.95 Hz, 1H) 6.87 (dd, J=7.91, 1.76 Hz, 1H) 7.04-7.08 (m, 1H) 7.10-7.16 (m, 2H) 7.18-7.27 (m, 2H) 7.29-7.33 (m, 1H) 7.50 (dd, J=8.35, 2.20 Hz, 1H) 7.63 (d, J=1.76 Hz, 1H) 7.71-7.82 (m, 1H); LC-MS 627 (M+H).

Example 9

Methyl 3-((R)-1-((R)-2-(3-carbamoylphenylamino)-2-(3-ethoxy-4-fluorophenyl)acetyl)pyrrolidin-2-yl)-4-(isopropylsulfonyl)phenylcarbamate

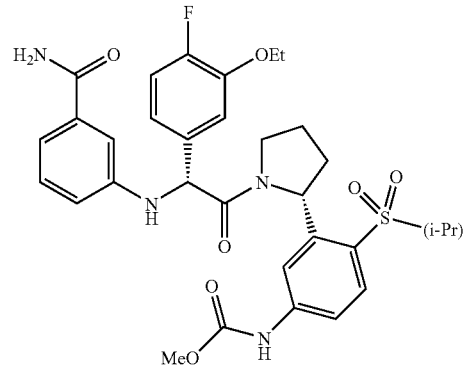

9A: 4-Bromo-2-ethoxy-1-fluorobenzene

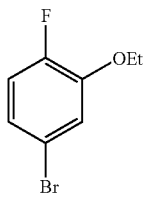

To a solution of 7A (4.4 g, 23 mmol) and K$_2$CO$_3$ (6.4 g, 46 mmol) in DMF (30 mL) was added ethyl iodide (2.49 mL, 31 mmol) at rt. The mixture was heated at 50° C. for 2.0 h. After cooling to rt, it was diluted with ether, washed with water and brine, dried over MgSO$_4$. The crude residue was purified by flash column chromatography (EtOAc:hexanes=1:5) to give 3.86 g (77%) of 9A as viscous oil. $^1$H NMR (400 MHz, CDCl$_3$) δ ppm 1.47 (m, 3H) 4.00 (m, 2H) 6.96-7.08 (m, 3H).

9B: 3-Ethoxy-4-fluorophenylboronic acid

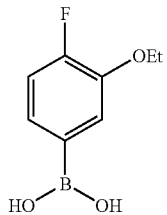

To a solution of 9A (3.86 g, 17.6 mmol) in THF (60 mL) at −78° C. was added n-BuLi (1.6 M in hexanes, 14.3 mL, 22.8 mmol). The mixture was stirred at −78° C. for 40 min before trimethyl borate (3.63 mL, 33 mmol) was added. The reaction was left stirring from −78° C. to rt over 4 h. It was quenched with 1.0 N HCl (40 mL), extracted with EtOAc, washed with brine and dried over Na$_2$SO$_4$. After evaporation of the solvent, the crude solid product was triturated with EtOAc/hexanes (1:4). After filtration, 9B (2.2 g, 69% yield) was collected as a white solid. $^1$H NMR (400 MHz, CDCl$_3$) δ ppm 1.42 (t, J=7.03 Hz, 3H) 4.11 (q, J=7.03 Hz, 2H) 7.03 (dd, J=11.42, 8.35 Hz, 1H) 7.18-7.29 (m, 2H) 7.35 (d, J=7.91 Hz, 1H).

9C: 2-(3-Carbamoylphenylamino)-2-(3-ethoxy-4-fluorophenyl)acetic acid

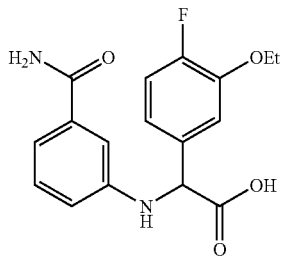

A mixture of 3-aminobenzamide (68 mg, 0.5 mmol), 9B (92 mg, 0.5 mmol) and glyoxylic acid monohydrate (46 mg, 0.5 mmol) in acetonitrile (3.0 mL) and DMF (0.8 mL) was heated at 55° C. for 18 h. After removal of solvent, the crude was purified by silica gel column chromatography eluting with gradient methanol in methylene chloride to give 9C as a solid (100 mg, 60% yield). $^1$H NMR (400 MHz, Methanol-d$_4$) δ ppm 1.25 (t, J=6.81 Hz, 3H) 3.96 (m, 2H) 5.03 (s, 1H) 6.70 (d, J=7.91 Hz, 1H) 6.96-7.08 (m, 5H) 7.15 (dd, J=8.35, 1.76 Hz, 1H); LC-MS 333 (M+H).

9D: Example 9

Example 9 was prepared according to the general coupling condition using 9C and 1G. $^1$H NMR (400 MHz, Methanol-d$_4$) δ ppm 1.13 (d, J=7.03 Hz, 3 H) 1.32 (t, J=7.03 Hz, 3H) 1.41 (d, J=7.03 Hz, 3H) 1.69 (dd, J=12.74, 5.27 Hz, 1H) 1.99-2.10 (m, 2H) 2.48 (dd, J=13.18, 7.91 Hz, 1H) 3.62 (dd, J=7.03, 3.08 Hz, 1H) 3.71 (s, 3H) 3.74-3.81 (m, 1H) 3.87-3.98 (m, 2H) 4.09 (dd, J=6.59, 3.52 Hz, 1H) 5.42 (s, 1H) 5.65 (dd, J=7.91, 5.27 Hz, 1H) 6.89-6.98 (m, 3H) 7.01-7.08 (m, 1H) 7.13-7.18 (m, 2H) 7.23 (t, J=7.91 Hz, 1H) 7.26-7.30 (m, 2H) 7.73 (d, J=9.23 Hz, 1H) 9.51 (s, 1H); LC-MS 641 (M+H).

Example 10

Diastereoisomer of Example 9

Methyl 3-((R)-1-((S)-2-(3-carbamoylphenylamino)-2-(3-ethoxy-4-fluorophenyl)acetyl)pyrrolidin-2-yl)-4-(isopropylsulfonyl)phenylcarbamate

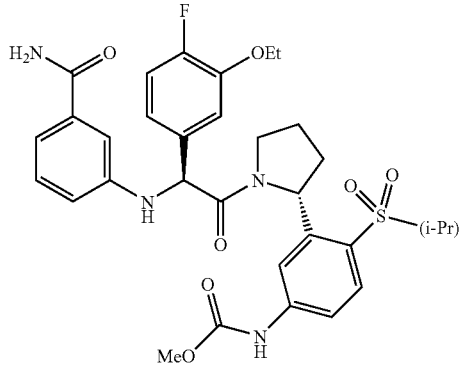

Example 10 was obtained as a diastereomer of Example 9 during its HPLC purification. $^1$H NMR (400 MHz, Methanol-d$_4$) δ ppm 1.10 (d, J=7.03 Hz, 3 H) 1.36-1.41 (m, 6H) 1.76 (m, 1H) 1.90 (m, 1H) 2.12 (m, 1H) 2.36 (m, 1H) 3.57-3.67 (m, 1H) 3.79 (s, 3H) 4.05-4.14 (m, 1H) 4.18 (s, 1H) 5.40-5.46 (s, 1H) 5.58 (dd, J=8.13, 4.17 Hz, 1H) 6.82 (d, J=7.91 Hz, 1H) 7.03-7.07 (m, 1H) 7.09-7.19 (m, 3H) 7.21-7.29 (m, 2H) 7.52 (dd, J=8.79, 2.20 Hz, 1H) 7.63 (d, J=1.76 Hz, 1H) 7.73-7.79 (m, 1H) 9.62 (s, 1H); LC-MS 641 (M+H).

Example 11

Methyl 3-((R)-1-((R)-2-(3-carbamoylphenylamino)-2-(3-ethoxy-4-isopropoxyphenyl)acetyl)pyrrolidin-2-yl)-4-(isopropylsulfonyl)phenylcarbamate

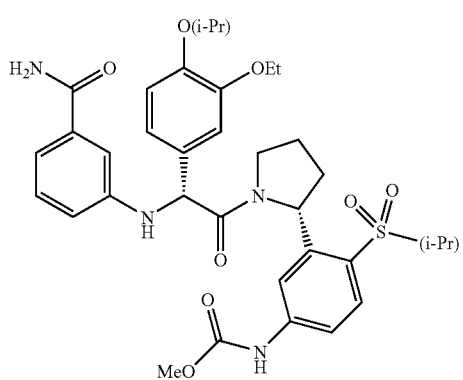

11A: 2-(3-Carbamoylphenylamino)-2-(3-ethoxy-4-isopropoxyphenyl)acetic acid

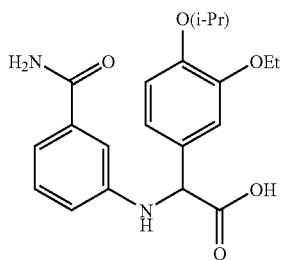

11A was prepared in a procedure similar to that of 1A using 3-aminobenzamide, 3-ethoxy-4-isopropoxyphenylboronic acid and glyoxylic acid monohydrate. Yield: 80%. $^1$H NMR (400 MHz, CDCl$_3$) δ ppm 1.16 (d, J=6.15 Hz, 6 H) 1.25 (t, J=7.03 Hz, 3H) 3.88-3.97 (m, 2H) 4.32-4.45 (m, 1H) 4.93 (s, 1H) 6.64-6.69 (m, 1H) 6.80 (d, J=8.35 Hz, 1H) 6.92 (dd, J=8.35, 2.20 Hz, 1H) 6.95-7.07 (m, 4H). LCMS: 373 (M+1).

11B: Example 11

Example 11 was prepared according to the general coupling condition using 11A and 1G. $^1$H NMR (400 MHz, Methanol-d$_4$) δ ppm 1.04 (d, J=6.59 Hz, 3H) 1.16-1.22 (m, 9H) 1.29 (d, J=7.03 Hz, 3H) 1.53-1.65 (m, 1H) 1.84-2.05 (m, 2 H) 2.27-2.43 (m, 1H) 3.49-3.56 (m, 1H) 3.61 (s, 3H) 3.63-3.89 (m, 3H) 3.91-4.00 (m, 1H) 4.37-4.48 (m, 1H) 5.25 (s, 1H) 5.55 (dd, J=8.13, 5.05 Hz, 1H) 6.68-6.78 (m, 3H) 6.81 (d, J=9.23 Hz, 1H) 7.05-7.21 (m, 5H) 7.63 (d, J=8.35 Hz, 1H). LCMS: 681 (M+1).

Example 12

Diastereoisomer of Example 11

Methyl 3-((R)-1-((S)-2-(3-carbamoylphenylamino)-2-(3-ethoxy-4-isopropoxyphenyl)acetyl)pyrrolidin-2-yl)-4-(isopropylsulfonyl)phenylcarbamate

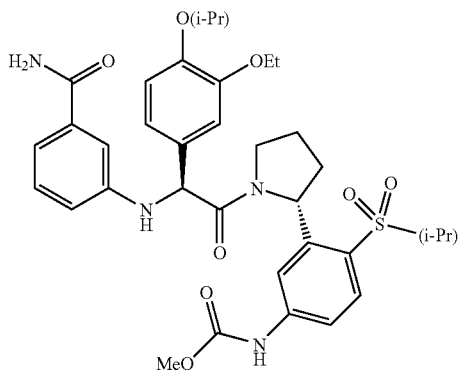

Example 12 was obtained as a diastereomer of Example 11 during its HPLC purification. $^1$H NMR (400 MHz, Methanol-d$_4$) δ ppm 1.01 (d, J=6.59 Hz, 3 H) 1.19 (d, J=6.15 Hz, 6H) 1.25-1.31 (m, 6H) 1.59-1.71 (m, 1H) 1.70-1.84 (m, 1 H) 1.98-2.11 (m, 1H) 2.18-2.31 (m, 1H) 3.44-3.53 (m, 1H) 3.63-3.68 (m, 1H) 3.69 (s, 3H) 3.90-3.99 (m, 2H) 4.04-4.10 (m, 1H) 4.38-4.49 (m, 1H) 5.27 (s, 1 H) 5.47 (dd, J=8.35, 3.95 Hz, 1H) 6.73 (d, J=7.91 Hz, 1H) 6.85-6.94 (m, 2H) 6.99 (d, J=1.76 Hz, 1H) 7.00-7.10 (m, 2H) 7.14 (s, 1H) 7.43 (dd, J=8.79, 2.20 Hz, 1H) 7.52 (d, J=2.20 Hz, 1H) 7.65 (d, J=8.79 Hz, 1H), LCMS: 681 (M+1).

Example 13

Methyl 3-((R)-1-((R)-2-(3-carbamoyl-4-fluorophenylamino)-2-(3,4-dimethoxyphenyl)acetyl)pyrrolidin-2-yl)-4-(isopropylsulfonyl)phenylcarbamate

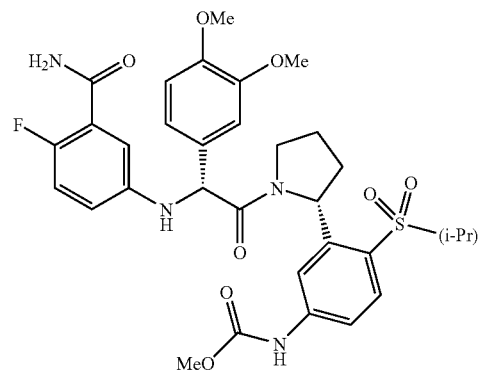

13A: 2-(3-Carbamoyl-4-fluorophenylamino)-2-(3,4-dimethoxyphenyl)acetic acid

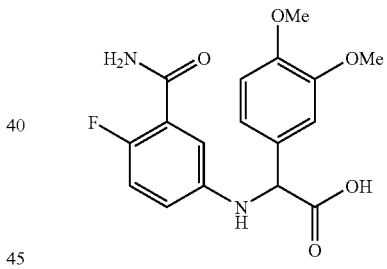

A mixture of 3-amino-6-fluorobenzamide (85 mg, 0.5 mmol), 3,4-dimethoxyphenylboronic acid (91 mg, 0.5 mmol) and glyoxylic acid monohydrate (46 mg, 0.5 mmol) in acetonitrile (2.0 mL) and DMF (0.2 mL) was heated at 100° C. for 20 min. in a microwave reactor. After removal of solvent, the crude was triturated with methylene chloride. The precipitate formed was collected by filtration and washed with methylene chloride to give 13A after drying, yield: 46%. $^1$H NMR (400 MHz, Methanol-d$_4$) δ ppm 3.81 (s, 3H) 3.82 (s, 3H) 4.92 (s, 1H) 6.83-6.89 (m, 1 H) 6.93 (d, J=8.35 Hz, 1H) 6.96-7.02 (m, 1H) 7.03-7.07 (m, 1H) 7.10 (d, J=1.76 Hz, 1H) 7.15 (dd, J=5.93, 2.86 Hz, 1H), LCMS: 349 (M+1).

13B: Example 13

Example 13 was prepared according to the general coupling condition using 13A and 1G. $^1$H NMR (400 MHz, Methanol-d$_4$) δ ppm 1.16 (d, J=6.59 Hz, 3 H) 1.42 (d, J=6.59 Hz, 3H) 1.64-1.76 (m, 1H) 1.97-2.15 (m, 2H) 2.37-2.58 (m, 1 H) 3.62-3.66 (m, 1H) 3.66 (s, 3H) 3.69 (s, 3H) 3.83 (s, 3H) 3.91-3.99 (m, 1H) 4.04-4.12 (m, 1H) 5.33 (s, 1H) 5.66 (dd, J=8.13, 5.05 Hz, 1H) 6.84 (s, 1H) 6.88-6.95 (m, 3H) 6.98-7.07 (m, 2H) 7.19-7.25 (m, 2H) 7.74 (d, J=8.35 Hz, 1H), LCMS: 657 (M+1).

Example 14

Diastereoisomer of Example 13

Methyl 3-((R)-1-((S)-2-(3-carbamoyl-4-fluorophenylamino)-2-(3,4-dimethoxyphenyl)acetyl)pyrrolidin-2-yl)-4-(isopropylsulfonyl)phenylcarbamate

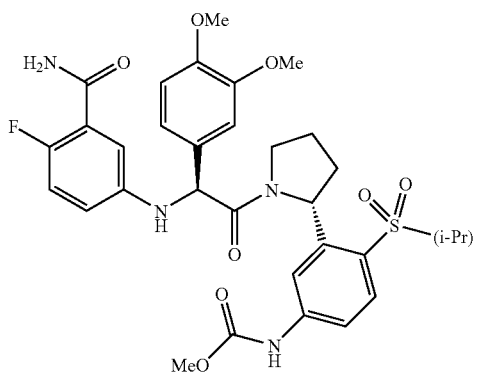

Example 14 was obtained as a diastereomer of Example 13 during its HPLC purification. $^1$H NMR (400 MHz, Methanol-d$_4$) δ ppm 1.12 (d, J=6.59 Hz, 3 H) 1.39 (d, J=7.03 Hz, 3H) 1.69-1.80 (m, 1H) 1.81-1.93 (m, 1H) 2.07-2.21 (m, 1H) 2.27-2.45 (m, 1H) 3.57-3.65 (m, 1H) 3.75-3.79 (m, 1H) 3.80 (s, 3H) 3.83 (s, 3H) 3.84 (s, 3H) 4.13-4.23 (m, 1H) 5.35 (s, 1H) 5.57 (dd, J=8.35, 4.39 Hz, 1H) 6.79 (dd, J=7.91, 4.39 Hz, 1H) 6.85-6.92 (m, 1H) 6.99 (d, 1H) 7.05 (dd, J=8.13, 1.98 Hz, 1H) 7.11 (s, 1H) 7.18 (dd, J=5.71, 3.08 Hz, 1H) 7.56-7.62 (m, 2H) 7.77 (d, J=8.79 Hz, 1H), LCMS 657 (M+1).

Example 15

Methyl 3-((R)-1-((R)-2-(3,4-dimethoxyphenyl)-2-(1,4-dioxo-1,2,3,4-tetrahydrophthalazin-6-ylamino)acetyl)pyrrolidin-2-yl)-4-(isopropylsulfonyl)phenylcarbamate

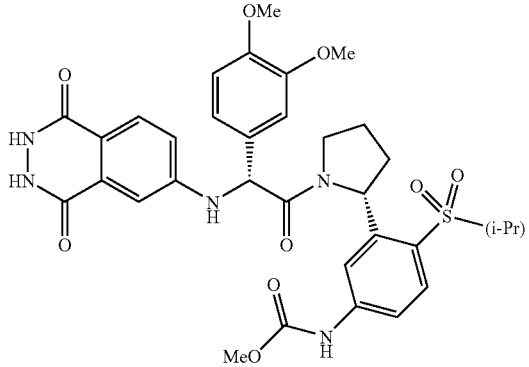

15A: 2-(3,4-Dimethoxyphenyl)-2-(1,4-dioxo-1,2,3,4-tetrahydrophthalazin-6-ylamino)acetic acid

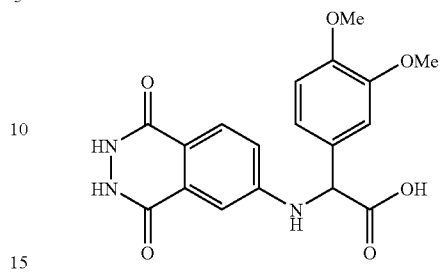

15A was prepared in a procedure similar to that of 13A using 6-amino-2,3-dihydrophthalazine-1,4-dione, 3,4-dimethoxyphenylboronic acid and glyoxylic acid monohydrate. Yield: 95%. $^1$H NMR (400 MHz, DMSO-d$_6$) δ ppm 3.73 (s, 3H) 3.74 (s, 3H) 5.15 (d, J=7.03 Hz, 1H) 6.95 (d, 1H) 7.01-7.06 (m, 1H) 7.13 (d, J=2.20 Hz, 1H) 7.25 (d, J=7.03 Hz, 2H) 7.74 (s, 1H), LCMS: 344 (M+1).

15B: Example 15

Example 15 was prepared according to the general coupling condition using 15A and 1G. $^1$H NMR (400 MHz, Methanol-d$_4$) δ ppm 1.13 (d, J=6.59 Hz, 3 H) 1.39 (d, J=7.03 Hz, 3H) 1.65-1.79 (m, 1H) 2.02-2.17 (m, 2H) 2.43-2.58 (m, 1H) 3.69 (s, 3H) 3.70 (s, 3H) 3.71-3.80 (m, 1H) 3.84 (s, 3H) 3.89-3.99 (m, 1H) 4.15-4.25 (m, 1H) 5.43 (s, 1H) 5.68 (dd, J=8.35, 4.83 Hz, 1H) 6.89-6.94 (m, 2H) 6.98-7.04 (m, 2H) 7.13 (d, J=2.20 Hz, 1H) 7.17 (dd, J=8.79, 2.64 Hz, 1H) 7.22 (dd, J=8.79, 2.20 Hz, 1H) 7.73 (d, J=8.35 Hz, 1H) 7.89 (d, J=8.79 Hz, 1H), LCMS: 680 (M+1).

Example 16

Diastereoisomer of Example 15

Methyl 3-((R)-1-((S)-2-(3,4-dimethoxyphenyl)-2-(1,4-dioxo-1,2,3,4-tetrahydrophthalazin-6-ylamino)acetyl)pyrrolidin-2-yl)-4-(isopropylsulfonyl)phenylcarbamate

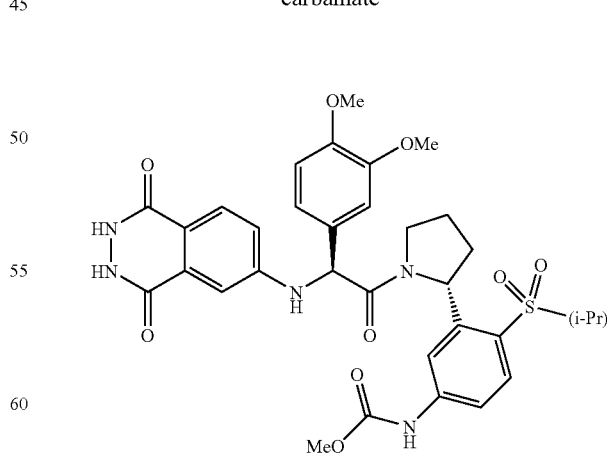

Example 16 was obtained as a diastereomer of Example 15 during its HPLC purification. $^1$H NMR (400 MHz, Methanol-d$_4$) δ ppm 1.06 (d, J=6.59 Hz, 3 H) 1.36 (d, J=7.03 Hz, 3H) 1.72-1.83 (m, 1H) 1.83-1.97 (m, 1H) 2.10-2.23 (m, 1 H)

2.31-2.46 (m, 1H) 3.62-3.78 (m, 2H) 3.81 (s, 3H) 3.85 (s, 3H) 3.85-3.85 (m, 3H) 4.24-4.35 (m, 1H) 5.46 (s, 1H) 5.58 (dd, J=8.13, 4.61 Hz, 1H) 7.02 (d, J=8.35 Hz, 1H) 7.12 (dd, J=8.13, 1.98 Hz, 2H) 7.17 (d, J=2.20 Hz, 1H) 7.22 (d, J=2.20 Hz, 1H) 7.60 (s, 1H) 7.69 (d, J=7.91 Hz, 2H) 7.75-7.78 (m, 1H), LCMS: 680 (M+1).

Example 17

Methyl 3-((R)-1-((R)-2-(3,4-dimethoxyphenyl)-2-(1,3-dioxoisoindolin-5-ylamino)acetyl)pyrrolidin-2-yl)-4-(isopropylsulfonyl)phenylcarbamate

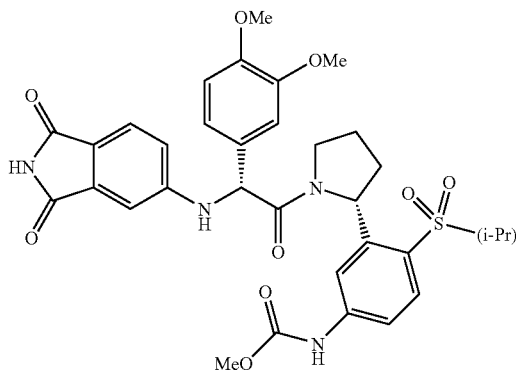

17A: 2-(3,4-Dimethoxyphenyl)-2-(1,3-dioxoisoindolin-5-ylamino)acetic acid

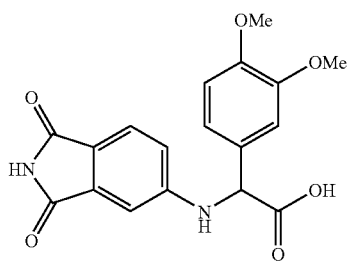

17A was prepared in a procedure similar to that of 13A using 5-iminoisoindoline-1,3-dione, 3,4-dimethoxyphenylboronic acid and glyoxylic acid monohydrate. Yield: 88%. $^1$H NMR (400 MHz, Methanol-$d_4$) δ ppm 3.82 (s, 3H) 3.83 (s, 3H) 5.17 (s, 1H) 6.90 (dd, J=8.35, 2.20 Hz, 1H) 6.95 (d, J=7.91 Hz, 1H) 6.99 (d, J=2.20 Hz, 1H) 7.07-7.10 (m, 1H) 7.13 (d, J=2.20 Hz, 1H) 7.50 (d, J=8.35 Hz, 1H), LCMS: 366 (M+1).

17B: Example 17

Example 17 was prepared according to the general coupling condition using 17A and 1G. $^1$H NMR (400 MHz, Methanol-$d_4$) δ ppm 1.12 (d, J=6.59 Hz, 3 H) 1.39 (d, J=7.03 Hz, 3H) 1.65-1.76 (m, 1H) 2.01-2.16 (m, 2H) 2.44-2.57 (m, 1 H) 3.66-3.76 (m, 1H) 3.67 (s, 3H) 3.70 (s, 3H) 3.84 (s, 3H) 3.89-3.97 (m, 1H) 4.10-4.21 (m, 1H) 5.42 (s, 1H) 5.67 (dd, J=7.91, 4.83 Hz, 1H) 6.86-6.92 (m, 3H) 6.96-7.03 (m, 3H) 7.21 (dd, J=8.35, 2.20 Hz, 1H) 7.48 (d, J=8.35 Hz, 1H) 7.72 (d, J=8.79 Hz, 1H), LCMS: 665 (M+1).

Example 18

Diastereoisomer of Example 17

Methyl 3-((R)-1-((S)-2-(3,4-dimethoxyphenyl)-2-(1,3-dioxoisoindolin-5-ylamino)acetyl)pyrrolidin-2-yl)-4-(isopropylsulfonyl)phenylcarbamate

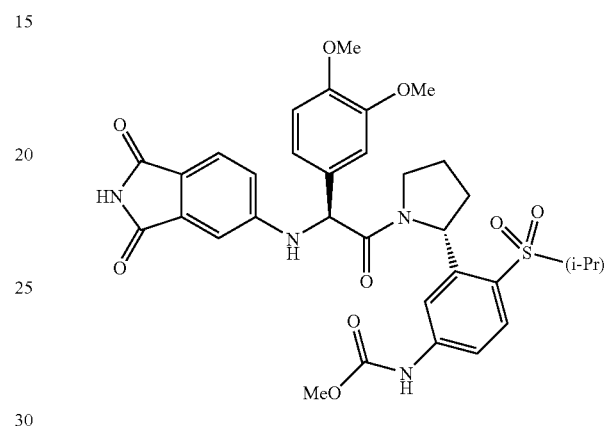

Example 18 was obtained as a diastereomer of Example 17 during its HPLC purification. $^1$H NMR (400 MHz, Methanol-$d_4$) δ ppm 1.10 (d, J=6.59 Hz, 3 H) 1.39 (d, J=7.03 Hz, 3H) 1.72-1.82 (m, 1H) 1.83-1.96 (m, 1H) 2.10-2.23 (m, 1 H) 2.28-2.43 (m, 1H) 3.53-3.63 (m, 1H) 3.66-3.79 (m, 1H) 3.84 (s, 9H) 4.14-4.24 (m, 1H) 5.48 (s, 1H) 5.60 (dd, J=8.35, 3.95 Hz, 1H) 6.77 (dd, J=8.35, 2.20 Hz, 1H) 7.02 (d, J=3.52 Hz, 2H) 7.06-7.11 (m, 1H) 7.13 (d, J=2.20 Hz, 1H) 7.37 (dd, J=8.79, 2.20 Hz, 1H) 7.42 (d, J=8.35 Hz, 1H) 7.75 (d, J=8.79 Hz, 1H) 7.89 (d, J=1.76 Hz, 1H), LCMS: 665 (M+1).

Example 19

Methyl 3-((R)-1-((R)-2-(5-carbamoyl-2-fluorophenylamino)-2-(3,4-dimethoxyphenyl)acetyl)pyrrolidin-2-yl)-4-(isopropylsulfonyl)phenylcarbamate

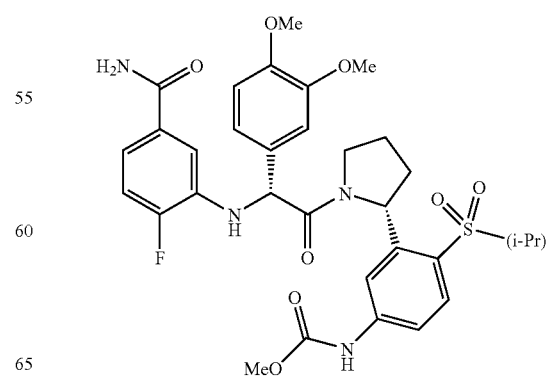

19A: 3-Amino-4-fluorobenzoic acid

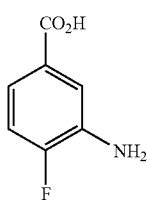

4-Fluoro-3-nitrobenzoic acid (270 mg, 2 mmol) and 10% Pd/C (80 mg) in MeOH (10 mL) was hydrogenated with a hydrogen balloon for 6.0 h. LC-MS indicated a completion of reaction. The mixture was filtered and the filtrate was concentrated to give 19A. $^1$H NMR (400 MHz, CDOD$_3$) δ ppm 7.00 (dd, J=10.99, 8.79 Hz, 1H) 7.27-7.36 (m, 1H) 7.49 (dd, J=8.79, 2.20 Hz, 1H).

19B: 3-Amino-4-fluorobenzamide

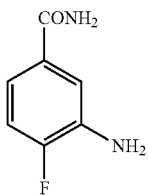

19A obtained above, ammonium carbonate (340 mg, 3.0 eq.), EDC (767 mg, 2.0 eq.), HOAt (15 mg) and DIEA (1.4 mL, 4.0 eq.) were combined in DMF (5.0 mL) and stirred at rt over night. LC-MS indicated a completion of reaction. It was diluted and extracted with EtOAc, washed with NaHCO$_3$ and brine. The organic layer was dried over Na$_2$SO$_4$ and concentrated to give 19B (400 mg with a small amount of DMF). $^1$H NMR (400 MHz, CDOD$_3$) δ ppm 6.99 (dd, J=10.99, 8.35 Hz, 1H) 7.09-7.16 (m, 1H) 7.32 (dd, J=8.79, 2.20 Hz, 1H).

19C: 2-(5-Carbamoyl-2-fluorophenylamino)-2-(3,4-dimethoxyphenyl)acetic acid

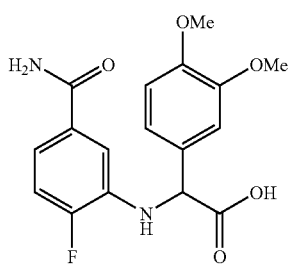

19C was prepared in a procedure similar to that of 1A using 19B, 3,4-dimethoxyphenylboronic acid and glyoxylic acid monohydrate. Yield: 55%. $^1$H NMR (400 MHz, Methanol-d$_4$) δ ppm 3.78 (s, 3H) 3.81 (s, 3H) 5.15 (s, 1H) 6.90 (d, J=7.91 Hz, 1H) 7.01-7.08 (m, 2H) 7.12 (d, J=1.76 Hz, 1H) 7.13-7.17 (m, 2H), LCMS: 349 (M+1).

19D: Example 19

Example 19 was prepared according to the general coupling condition using 19C and 1G. $^1$H NMR (400 MHz, Methanol-d$_4$) δ ppm 1.19 (d, J=6.59 Hz, 3 H) 1.44 (d, J=6.59 Hz, 3H) 1.64-1.77 (m, 1H) 1.99-2.16 (m, 2H) 2.43-2.55 (m, 1 H) 3.68 (s, 3H) 3.70 (s, 3H) 3.70-3.75 (m, 1H) 3.82 (s, 3H) 3.91-4.02 (m, 1H) 4.10-4.19 (m, 1H) 5.40 (s, 1H) 5.66 (dd, J=8.13, 5.05 Hz, 1H) 6.86-6.91 (m, 2H) 6.94-7.02 (m, 3H) 7.09-7.15 (m, 1H) 7.20 (dd, J=8.35, 2.20 Hz, 1H) 7.33 (dd, J=8.35, 2.20 Hz, 1H) 7.74 (d, J=8.79 Hz, 1H), LCMS: 657 (M+1).

Example 20

Diastereoisomer of Example 19

Methyl 3-((R)-1-((S)-2-(5-carbamoyl-2-fluorophenylamino)-2-(3,4-dimethoxyphenyl)acetyl)pyrrolidin-2-yl)-4-(isopropylsulfonyl)phenylcarbamate

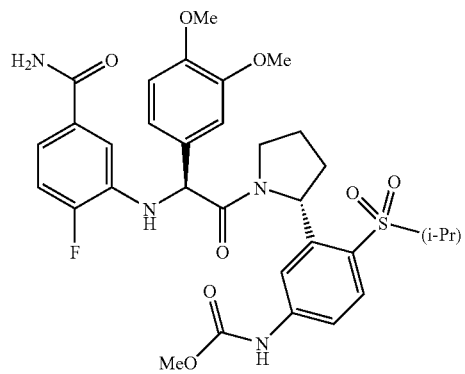

Example 20 was obtained as a diastereomer of Example 19 during its HPLC purification. $^1$H NMR (400 MHz, Methanol-d$_4$) δ ppm 1.16 (d, J=6.59 Hz, 3 H) 1.42 (d, J=7.03 Hz, 3H) 1.70-1.81 (m, 1H) 1.80-1.92 (m, 1H) 2.08-2.20 (m, 1H) 2.29-2.42 (m, 1H) 3.58-3.71 (m, 1H) 3.73-3.80 (m, 1H) 3.75 (s, 3H) 3.83 (s, 3H) 3.84 (s, 3H) 4.18-4.28 (m, 1H) 5.47 (s, 1H) 5.57 (dd, J=8.35, 3.95 Hz, 1H) 6.96-7.02 (m, 2H) 7.06-7.10 (m, 1H) 7.13 (d, J=1.76 Hz, 1H) 7.14-7.18 (m, 1H) 7.39 (dd, J=8.57, 1.98 Hz, 1H) 7.46 (d, J=2.20 Hz, 1H) 7.70-7.73 (m, 1H) 7.79 (d, 1H), LCMS: 657 (M+1).

Example 21

Methyl 3-((R)-1-((R)-2-(3-carbamoyl-4-fluorophenylamino)-2-(3-ethoxy-4-isopropoxyphenyl)acetyl)pyrrolidin-2-yl)-4-(isopropylsulfonyl)phenylcarbamate

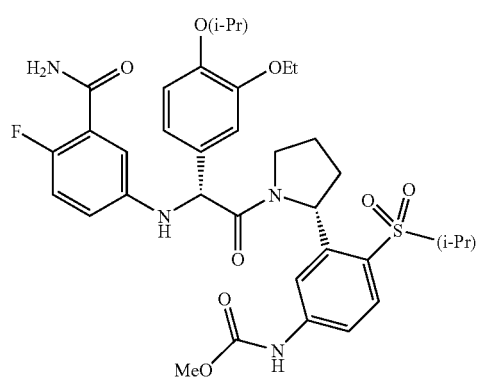

21A: 2-(3-Carbamoyl-4-fluorophenylamino)-2-(3-ethoxy-4-isopropoxyphenyl)acetic acid

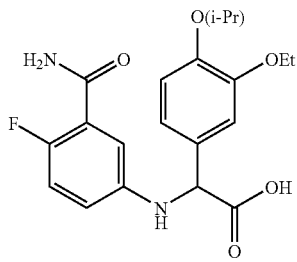

21A was prepared in a procedure similar to that of 13A using 3-amino-6-fluorobenzamide, 3-ethoxy-4-isopropoxyphenylboronic acid and glyoxylic acid monohydrate. Yield: 55%. $^1$H NMR (400 MHz, Methanol-$d_4$) δ ppm 1.28 (s, 3H) 1.29 (s, 3H) 1.37 (t, J=7.03 Hz, 3H) 4.05 (q, J=7.03 Hz, 2H) 4.46-4.55 (m, 1H) 5.00 (s, 1H) 6.78-6.84 (m, 1H) 6.90-6.99 (m, 2H) 7.02 (dd, J=8.35, 2.20 Hz, 1H) 7.07-7.12 (m, 2H), LCMS: 391 (M+1).

21B: Example 21

Example 21 was prepared according to the general coupling condition using 21A and 1G. $^1$H NMR (400 MHz, Methanol-$d_4$) δ ppm 1.16 (d, J=6.59 Hz, 3H) 1.26-1.35 (m, 9H) 1.42 (d, J=6.59 Hz, 3H) 1.65-1.76 (m, 1H) 1.97-2.15 (m, 2 H) 2.41-2.56 (m, 1H) 3.58-3.69 (m, 1H) 3.73 (s, 3H) 3.75-3.84 (m, 1H) 3.84-4.00 (m, 2H) 4.01-4.14 (m, 1H) 4.49-4.61 (m, 1H) 5.33 (s, 1H) 5.66 (dd, J=8.13, 5.05 Hz, 1H) 6.81 (s, 1H) 6.85-6.96 (m, 3H) 7.01-7.07 (m, 1H) 7.17-7.28 (m, 3 H) 7.75 (d, J=8.79 Hz, 1H), LCMS: 699 (M+1).

Example 22

Diastereoisomer of Example 21

Methyl 3-((R)-1-((S)-2-(3-carbamoyl-4-fluorophenylamino)-2-(3-ethoxy-4-isopropoxyphenyl)acetyl)pyrrolidin-2-yl)-4-(isopropylsulfonyl)phenylcarbamate

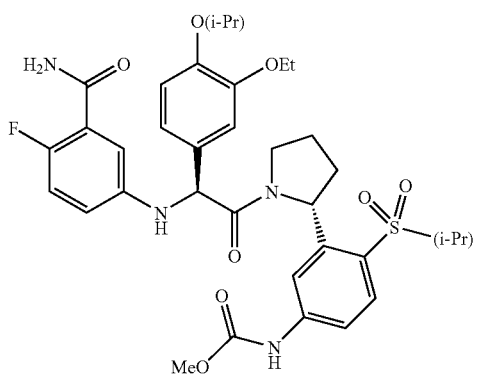

Example 22 was obtained as a diastereomer of Example 21 during its HPLC purification. $^1$H NMR (400 MHz, Methanol-$d_4$) δ ppm 1.12 (d, J=6.59 Hz, 3H) 1.31 (d, J=6.15 Hz, 6H) 1.39 (t, J=6.81 Hz, 6H) 1.69-1.80 (m, 1H) 1.81-1.95 (m, 1H) 2.07-2.19 (m, 1H) 2.29-2.45 (m, 1H) 3.57-3.65 (m, 1H) 3.74-3.80 (m, 1H) 3.80 (s, 3H) 4.01-4.11 (m, 2H) 4.13-4.24 (m, 1H) 4.51-4.60 (m, 1H) 5.33 (s, 1H) 5.57 (dd, J=8.13, 4.17 Hz, 1H) 6.76-6.82 (m, 1H) 6.86-6.92 (m, 1H) 6.97-7.04 (m, 2H) 7.11 (d, J=1.76 Hz, 1H) 7.18 (dd, J=5.93, 2.86 Hz, 1H) 7.55-7.60 (m, 1H) 7.61 (d, J=2.20 Hz, 1H) 7.77 (d, 1H), LCMS: 699 (M+1).

Example 23

Methyl 3-((R)-1-((R)-2-(5-carbamoyl-2,4-difluorophenylamino)-2-(3,4-dimethoxyphenyl)acetyl)pyrrolidin-2-yl)-4-(isopropylsulfonyl)phenylcarbamate

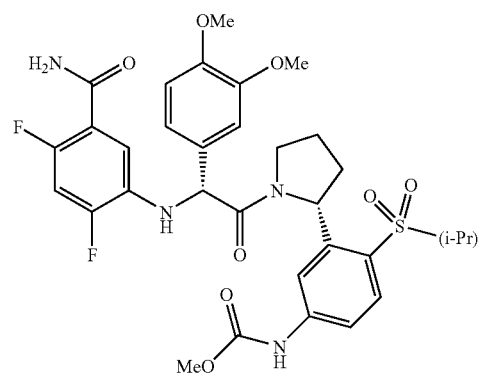

23A: 2-(5-Carbamoyl-2,4-difluorophenylamino)-2-(3,4-dimethoxyphenyl)acetic acid

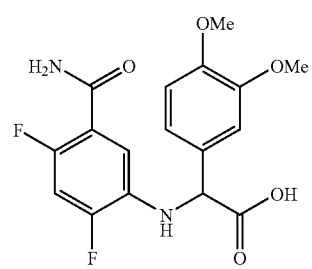

23A was prepared in a procedure similar to that of 13A using 3-amino-4,6-difluorobenzamide, 3,4-dimethoxyphenylboronic acid and glyoxylic acid monohydrate. Yield: 80%. $^1$H NMR (400 MHz, Methanol-$d_4$) δ ppm 3.73-3.87 (m, 6H) 5.07 (s, 1H) 6.92 (t, J=7.69 Hz, 1H) 6.96-7.13 (m, 4H), LCMS: 367 (M+1).

23B: Example 23

Example 23 was prepared according to the general coupling condition using 23A and 1G. $^1$H NMR (400 MHz, Methanol-$d_4$) δ ppm 1.19 (d, J=6.59 Hz, 3 H) 1.44 (d, J=6.59 Hz, 3H) 1.64-1.76 (m, 1H) 1.99-2.16 (m, 2H) 2.42-2.56 (m, 1H) 3.63-3.74 (m, 7H) 3.82 (s, 3H) 3.91-4.01 (m, 1H) 4.09-4.18 (m, 1H) 5.35 (s, 1H) 5.65 (dd, J=8.13, 5.05 Hz, 1H) 6.88

(d, J=8.35 Hz, 2H) 6.91-7.00 (m, 3H) 7.21 (dd, J=8.57, 1.98 Hz, 1H) 7.26 (dd, J=9.67, 7.47 Hz, 1H) 7.73 (d, J=8.79 Hz, 1H), LCMS: 675 (M+1).

Example 24

Diastereoisomer of Example 23

Methyl 3-((R)-1-((S)-2-(5-carbamoyl-2,4-difluorophenylamino)-2-(3,4-dimethoxyphenyl)acetyl)pyrrolidin-2-yl)-4-(isopropylsulfonyl)phenylcarbamate

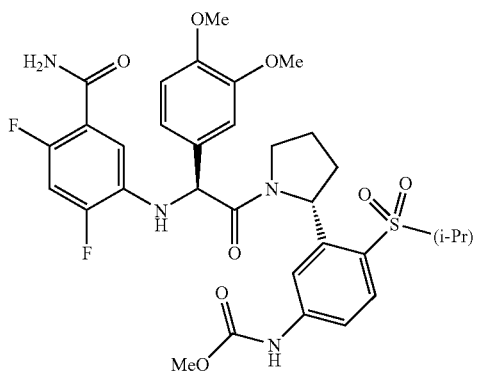

Example 24 was obtained as a diastereomer of Example 23 during its HPLC purification. $^1$H NMR (400 MHz, Methanol-d$_4$) δ ppm 1.16 (d, J=6.59 Hz, 3 H) 1.42 (d, J=7.03 Hz, 3H) 1.70-1.80 (m, 1H) 1.82-1.91 (m, 1H) 2.07-2.14 (m, 1H) 2.28-2.40 (m, 1H) 3.55-3.64 (m, 1H) 3.76 (s, 3H) 3.77-3.81 (m, 1H) 3.83 (s, 3H) 3.84 (s, 3H) 4.14-4.27 (m, 1H) 5.43 (s, 1H) 5.56 (dd, J=8.13, 4.17 Hz, 1H) 6.95-7.00 (m, 2H) 7.04-7.08 (m, 1H) 7.13 (d, J=1.76 Hz, 1H) 7.30 (dd, J=9.23, 7.03 Hz, 1H) 7.41 (d, J=1.76 Hz, 1H) 7.72-7.77 (m, 1H) 7.80 (d, 1H), LCMS: 675 (M+1).

Example 25

Methyl 3-((R)-1-((R)-2-(5-carbamoyl-2-fluorophenylamino)-2-(4-chloro-3-methoxyphenyl)acetyl)pyrrolidin-2-yl)-4-(isopropylsulfonyl)phenylcarbamate

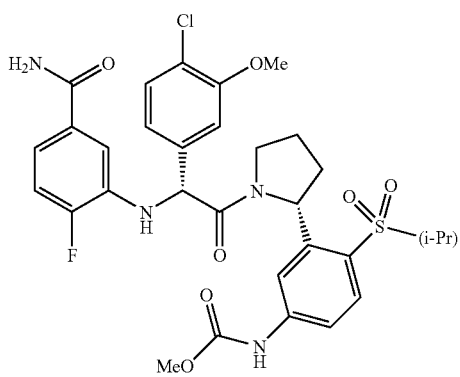

25A: 4-Chloro-3-methoxyphenylboronic acid

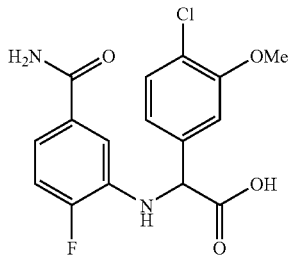

To 4-bromo-1-chloro-2-methoxybenzene (2.2 g, 9.9 mmol) in toluene/THF (16/6 mL) at −78° C. was added n-butyl lithium (8.7 mL, 1.6 M in hexane, 14 mmol) dropwise. The reaction was stirred at −78° C. for 30 min, then trimethylborate (2.2 mL, 19.8 mmol) was added. The reaction was allowed to warm to rt and stirred overnight and then quenched with 1 M HCl (15 mL). The organic layer was separated and dried over sodium sulfate. The solvent was removed and the crude product was purified by flash column chromatography to give 25A (1.2 g, 65% yield) as a white solid. $^1$H NMR (400 MHz, CDOD$_3$) δ ppm 3.87 (m, 3H) 7.11 (d, J=7.83 Hz, 1H) 7.20 (s, 1H) 7.29 (d, J=7.83 Hz, 1H).

25B: 2-(5-Carbamoyl-2-fluorophenylamino)-2-(4-chloro-3-methoxyphenyl)acetic acid 25B was prepared in a procedure similar to that of 1A using 25A, 19B and glyoxylic acid monohydrate. Yield: 37%. $^1$H NMR (400 MHz, Methanol-d$_4$) δ ppm 3.88 (s, 3H) 5.21 (s, 1H) 7.03-7.12 (m, 3H) 7.13-7.19 (m, 1H) 7.25 (d, J=1.76 Hz, 1H) 7.33 (d, J=7.91 Hz, 1H), LCMS: 353 (M+1).

25C: Example 25

Example 25 was prepared according to the general coupling condition using 25B and 1G. $^1$H NMR (400 MHz, Methanol-d$_4$) δ ppm 1.19 (d, J=6.59 Hz, 3 H) 1.45 (d, J=7.03 Hz, 3H) 1.65-1.79 (m, 1H) 2.00-2.18 (m, 2H) 2.44-2.57 (m, 1 H) 3.67-3.77 (m, 7H) 3.94-4.06 (m, 1H) 4.13-4.24 (m, 1H) 5.47 (s, 1H) 5.66 (dd, J=8.13, 5.49 Hz, 1H) 6.97-7.05 (m, 3H) 7.10-7.19 (m, 3H) 7.29-7.35 (m, 2 H) 7.74 (d, J=8.35 Hz, 1H), LCMS: 661 (M+1).

Example 26

Diastereoisomer of Example 25

Methyl 3-((R)-1-((S)-2-(5-carbamoyl-2-fluorophenylamino)-2-(4-chloro-3-methoxyphenyl)acetyl)pyrrolidin-2-yl)-4-(isopropylsulfonyl)phenylcarbamate

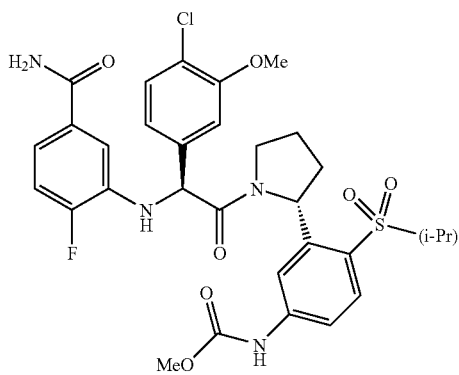

Example 26 was obtained as a diastereomer of Example 25 during its HPLC purification. $^1$H NMR (400 MHz, Methanol-$d_4$) δ ppm 1.15 (d, J=6.59 Hz, 3H) 1.42 (d, J=6.59 Hz, 3H) 1.71-1.83 (m, 1H) 1.85-1.96 (m, 1H) 2.10-2.22 (m, 1 H) 2.32-2.43 (m, 1H) 3.59-3.68 (m, 1H) 3.75 (s, 3H) 3.75-3.80 (m, 1H) 3.90 (s, 3H) 4.19-4.28 (m, 1H) 5.55 (s, 1H) 5.58 (dd, J=8.35, 3.95 Hz, 1H) 6.97-7.03 (m, 1H) 7.07 (dd, J=8.13, 1.98 Hz, 1H) 7.14-7.19 (m, 1H) 7.26 (d, J=1.76 Hz, 1H) 7.39 (d, J=7.91 Hz, 2H) 7.49 (d, J=2.20 Hz, 1H) 7.67 (dd, J=8.79, 2.20 Hz, 1H) 7.79 (d, 1H), LCMS: 661 (M+1).

Example 27

Methyl 3-((R)-1-((R)-2-(5-carbamoyl-2-fluorophenylamino)-2-(4-fluoro-3-methoxyphenyl)acetyl)pyrrolidin-2-yl)-4-(isopropylsulfonyl)phenylcarbamate

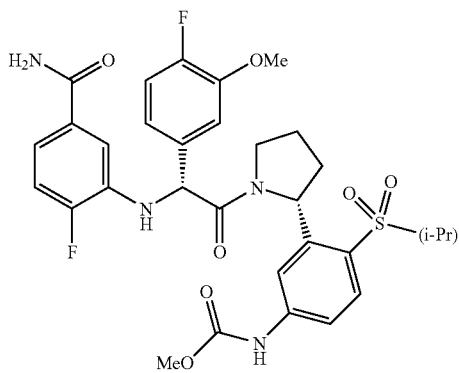

27A: 2-(5-Carbamoyl-2-fluorophenylamino)-2-(4-fluoro-3-methoxyphenyl)acetic acid

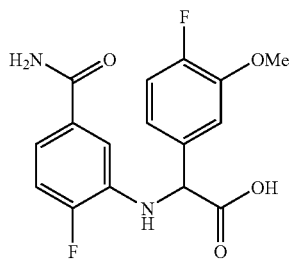

27A was prepared in a procedure similar to that of 1A using 19B, 7C and glyoxylic acid monohydrate. Yield: 72%. $^1$H NMR (400 MHz, Methanol-$d_4$) δ ppm 3.87 (s, 3H) 5.18 (s, 1H) 7.02-7.12 (m, 4H) 7.13-7.18 (m, 1H) 7.27 (d, J=8.79 Hz, 1H), LCMS: 337 (M+1).

27B: Example 27

Example 27 was prepared according to the general coupling condition using 27A and 1G. $^1$H NMR (400 MHz, Methanol-$d_4$) δ ppm 1.19 (d, J=6.59 Hz, 3 H) 1.45 (d, J=7.03 Hz, 3H) 1.64-1.77 (m, 1H) 2.00-2.17 (m, 2H) 2.44-2.58 (m, 1 H) 3.65-3.76 (m, 7H) 3.92-4.03 (m, 1H) 4.11-4.22 (m, 1H) 5.44 (s, 1H) 5.65 (dd, J=7.91, 5.27 Hz, 1H) 6.96-7.06 (m, 4H) 7.07-7.10 (m, 1H) 7.11-7.17 (m, 2 H) 7.32 (dd, J=8.35, 2.20 Hz, 1H) 7.73 (d, J=8.35 Hz, 1H), LCMS: 645 (M+1).

Example 28

Diastereoisomer of Example 27

Methyl 3-((R)-1-((S)-2-(5-carbamoyl-2-fluorophenylamino)-2-(4-fluoro-3-methoxyphenyl)acetyl)pyrrolidin-2-yl)-4-(isopropylsulfonyl)phenylcarbamate

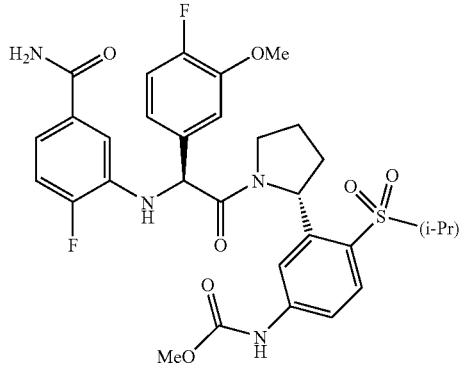

Example 28 was obtained as a diastereomer of Example 27 during its HPLC purification. $^1$H NMR (400 MHz, Methanol-$d_4$) δ ppm 1.15 (d, J=6.59 Hz, 3 H) 1.42 (d, J=7.03 Hz, 3H) 1.73-1.82 (m, 1H) 1.86-1.95 (m, 1H) 2.10-2.21 (m, 1 H) 2.31-2.43 (m, 1H) 3.59-3.67 (m, 1H) 3.74-3.79 (m, 4H) 3.88 (s, 3H) 4.20-4.28 (m, 1H) 5.52 (s, 1H) 5.58 (dd, J=8.35, 3.95 Hz, 1H) 6.99-7.10 (m, 2H) 7.11-7.15 (m, 1H) 7.15-7.19 (m, 1H) 7.27-7.31 (m, 1H) 7.38 (dd, J=8.35, 2.20 Hz, 1H) 7.47 (d, J=2.20 Hz, 1H) 7.66-7.71 (m, 1H) 7.79 (d, J=8.79 Hz, 1H), LCMS: 645 (M+1).

Example 29

Methyl 3-((R)-1-((R)-2-(5-carbamoyl-2-fluorophenylamino)-2-(3-ethoxy-4-fluorophenyl)acetyl)pyrrolidin-2-yl)-4-(isopropylsulfonyl)phenylcarbamate

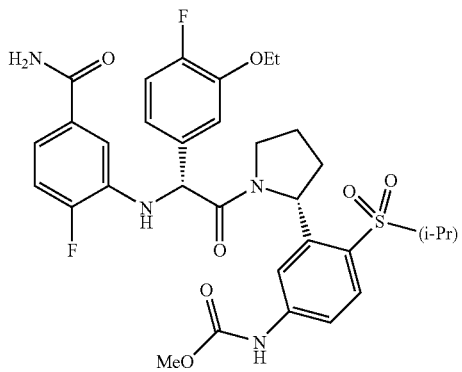

29A: 2-(5-Carbamoyl-2-fluorophenylamino)-2-(3-ethoxy-4-fluorophenyl)acetic acid

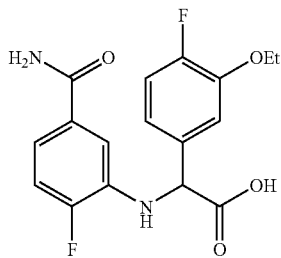

29A was prepared in a procedure similar to that of 1A using 19B, 9B and glyoxylic acid monohydrate. Yield: 50%. $^1$H NMR (400 MHz, Methanol-d$_4$) δ ppm 1.40 (t, J=7.03 Hz, 3H) 4.10 (q, J=7.03 Hz, 2H) 5.17 (s, 1H) 7.03-7.11 (m, 3 H) 7.13-7.17 (m, 1H) 7.24 (d, J=8.79 Hz, 1H) 7.28 (d, J=9.23 Hz, 1H), LCMS: 351 (M+1).

29B: Example 29

Example 29 was prepared according to the general coupling condition using 29A and 1G. $^1$H NMR (400 MHz, Methanol-d$_4$) δ ppm 1.19 (d, J=6.59 Hz, 3 H) 1.33 (t, J=7.03 Hz, 3H) 1.44 (d, J=7.03 Hz, 3H) 1.64-1.77 (m, 1H) 1.98-2.16 (m, 2H) 2.42-2.57 (m, 1H) 3.64-3.71 (m, 1H) 3.72 (s, 3H) 3.77-3.86 (m, 1H) 3.88-4.03 (m, 2H) 4.10-4.20 (m, 1H) 5.43 (s, 1H) 5.65 (dd, J=8.13, 5.49 Hz, 1H) 6.93 (d, J=8.79 Hz, 1H) 6.96-7.06 (m, 3H) 7.09-7.17 (m, 3H) 7.31 (dd, J=8.35, 2.20 Hz, 1H) 7.73 (d, J=8.79 Hz, 1H), LCMS: 659 (M+1).

Example 30

Diastereoisomer of Example 29

Methyl 3-((R)-1-((S)-2-(5-carbamoyl-2-fluorophenylamino)-2-(3-ethoxy-4-fluorophenyl)acetyl)pyrrolidin-2-yl)-4-(isopropylsulfonyl)phenylcarbamate

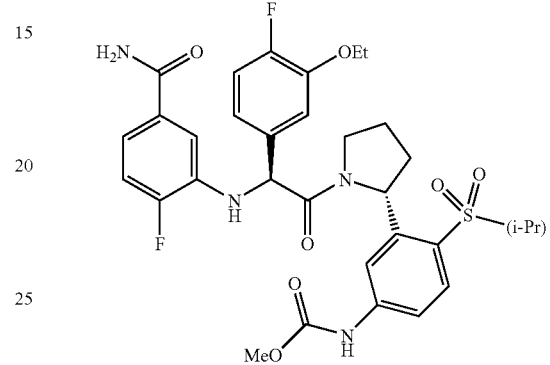

Example 30 was obtained as a diastereomer of Example 29 during its HPLC purification. $^1$H NMR (400 MHz, Methanol-d$_4$) δ ppm 1.15 (d, J=6.59 Hz, 3H) 1.38-1.43 (m, 6H) 1.71-1.82 (m, 1H) 1.85-1.95 (m, 1H) 2.09-2.22 (m, 1H) 2.30-2.43 (m, 1H) 3.59-3.67 (m, 1H) 3.75 (s, 3H) 3.82-3.90 (m, 1H) 4.12 (q, J=7.03 Hz, 2H) 4.18-4.28 (m, 1H) 5.51 (s, 1H) 5.57 (dd, J=8.35, 3.95 Hz, 1H) 7.00 (dd, J=11.43, 8.35 Hz, 1H) 7.08 (dd, J=4.61, 1.98 Hz, 1H) 7.11 (d, J=10.55 Hz, 1H) 7.14-7.17 (m, 1H) 7.26 (dd, J=7.91, 2.20 Hz, 1H) 7.37 (dd, J=8.35, 2.20 Hz, 1H) 7.47 (d, J=1.76 Hz, 1H) 7.66-7.71 (m, 1H) 7.79 (d, J=8.79 Hz, 1H), LCMS: 659 (M+1).

Example 31

3-((R)-2-((R)-2-(5-(3,3-Dimethylureido)-2-(isopropylsulfonyl)phenyl)pyrrolidin-1-yl)-1-(4-fluoro-3-methoxyphenyl)-2-oxoethylamino)-4-fluorobenzamide

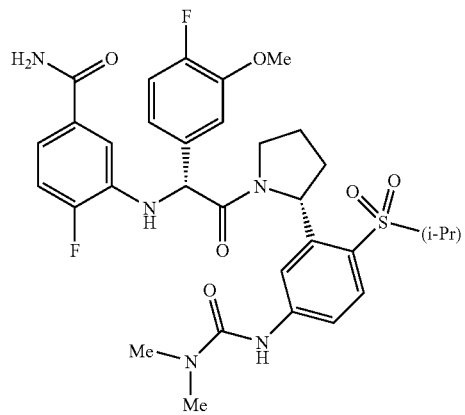

31A: (R)-3-(4-(Isopropylsulfonyl)-3-(pyrrolidin-2-yl)phenyl)-1,1-dimethylurea hydrochloride

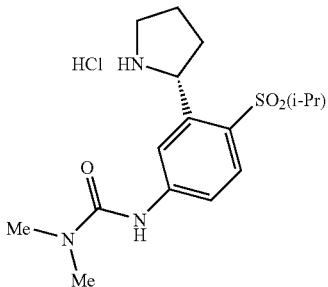

To 1F (0.25 g, 0.68 mmol) in dichloromethane (5 mL) at 0° C. was added sodium bicarbonate (0.57 g, 6.8 mmol), then phosgene (0.71 mL, 1.36 mmol, 20% in toluene). The reaction was stirred at 0° C. for 30 min. The crude mixture was filtered and washed with dichloromethane. To the filtrate was added triethylamine (0.27 mL, 2.04 mmol), then dimethylamine hydrochloride (0.083 g, 1.02 mmol) and the reaction was stirred for 2 h at rt. The solution was washed with water and brine and dried over sodium sulfate. The solvent was removed and the residue was redissolved in ethyl acetate (2 mL). HCl (4 mL, 4M in dioxane) was added and the reaction was stirred at rt for 4 h. The solvent was removed and dried under high vacuo to give 31A. $^1$H NMR (400 MHz, Methanol-$d_4$) δ ppm 1.23 (d, J=6.59 Hz, 3H) 1.31-1.40 (m, 3H) 2.14-2.27 (m, 1H) 2.29-2.43 (m, 2H) 2.44-2.60 (m, 1H) 3.02-3.11 (m, 6H) 3.37-3.53 (m, 3H) 5.42 (t, J=7.69 Hz, 1H) 7.64 (dd, J=8.79, 1.76 Hz, 1H) 7.91 (d, J=8.79 Hz, 1H) 8.08 (d, J=2.20 Hz, 1H).

31B: Example 31

Example 31 was prepared according to the general coupling condition using 27A and 31A. $^1$H NMR (400 MHz, Methanol-$d_4$) δ ppm 1.07 (d, J=6.59 Hz, 3 H) 1.32 (d, J=6.59 Hz, 3H) 1.56-1.66 (m, 1H) 1.86-1.95 (m, 1H) 1.95-2.07 (m, 1 H) 2.31-2.43 (m, 1H) 2.87 (s, 6H) 3.53-3.64 (m, 4H) 3.75-3.87 (m, 1H) 3.97-4.08 (m, 1H) 5.33 (s, 1H) 5.52 (dd, J=7.91, 5.27 Hz, 1H) 6.69 (d, J=2.20 Hz, 1H) 6.84-6.91 (m, 2H) 6.91 (s, 1H) 6.93 (s, 1H) 6.98-7.04 (m, 1H) 7.14 (dd, J=8.79, 2.20 Hz, 1H) 7.19 (dd, J=8.35, 2.20 Hz, 1H) 7.59 (d, J=8.35 Hz, 1H), LCMS: 658 (M+1).

Example 32

Diastereoisomer of Example 31

3-((S)-2-((R)-2-(5-(3,3-Dimethylureido)-2-(isopropylsulfonyl)phenyl)pyrrolidin-1-yl)-1-(4-fluoro-3-methoxyphenyl)-2-oxoethylamino)-4-fluorobenzamide

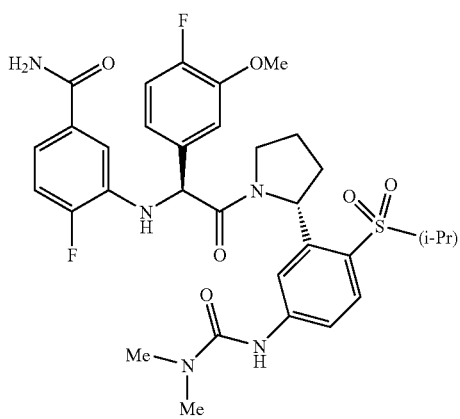

Example 32 was obtained as a diastereomer of Example 31 during its HPLC purification. $^1$H NMR (400 MHz, Methanol-$d_4$) δ ppm 1.17 (d, J=6.59 Hz, 3H) 1.43 (d, J=7.03 Hz, 3H) 1.72-1.82 (m, 1H) 1.83-1.95 (m, 1H) 2.11-2.23 (m, 1 H) 2.28-2.40 (m, 1H) 3.02 (s, 6H) 3.56-3.66 (m, 1H) 3.76-3.85 (m, 1H) 3.88 (s, 3H) 4.15-4.25 (m, 1H) 5.51 (s, 1H) 5.59 (dd, J=8.35, 3.52 Hz, 1H) 6.99 (dd, J=11.42, 8.35 Hz, 1H) 7.06-7.15 (m, 3H) 7.26-7.30 (m, 1H) 7.35 (dd, J=8.79, 2.20 Hz, 1H) 7.52 (dd, J=8.79, 2.20 Hz, 1H) 7.57 (d, J=2.20 Hz, 1H) 7.76 (d, J=8.79 Hz, 1H), LCMS: 658 (M+1).

Example 33

3-((R)-2-((R)-2-(5-(3,3-Dimethylureido)-2-(isopropylsulfonyl)phenyl)pyrrolidin-1-yl)-1-(3-ethoxy-4-fluorophenyl)-2-oxoethylamino)-4-fluorobenzamide

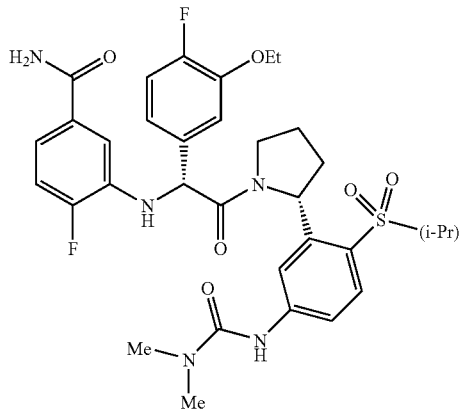

Example 33 was prepared according to the general coupling condition using 29A and 31A. $^1$H NMR (400 MHz, Methanol-$d_4$) δ ppm 1.19 (d, J=6.59 Hz, 3 H) 1.31 (t, J=7.03 Hz, 3H) 1.44 (d, J=6.59 Hz, 3H) 1.68-1.81 (m, 1H) 1.99-2.09 (m, 1H) 2.08-2.19 (m, 1H) 2.40-2.57 (m, 1H) 3.00 (s, 6H) 3.69-3.78 (m, 1H) 3.79-3.89 (m, 1H) 3.90-4.02 (m, 2H) 4.11-4.20 (m, 1H) 5.44 (s, 1H) 5.65 (dd, J=8.35, 5.27 Hz, 1H) 6.80 (d, J=2.20 Hz, 1H) 6.96-7.05 (m, 4H) 7.10-7.19 (m, 1 H) 7.30 (d, J=8.79 Hz, 2H) 7.71 (d, J=8.35 Hz, 1H), LCMS: 672 (M+1).

Example 34

Diastereoisomer of Example 33

3-((S)-2-((R)-2-(5-(3,3-Dimethylureido)-2-(isopropylsulfonyl)phenyl)pyrrolidin-1-yl)-1-(3-ethoxy-4-fluorophenyl)-2-oxoethylamino)-4-fluorobenzamide

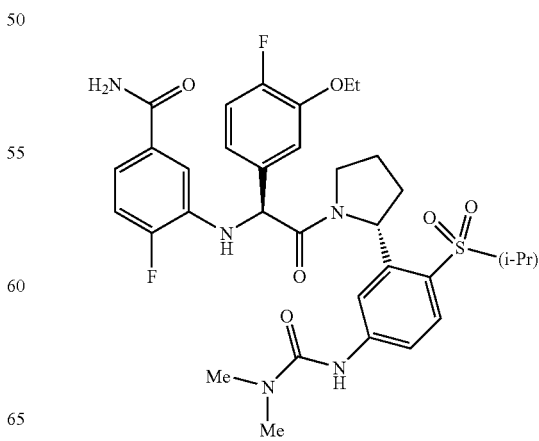

Example 34 was obtained as a diastereomer of Example 33 during its HPLC purification. $^1$H NMR (400 MHz, Methanol-$d_4$) δ ppm 1.17 (d, J=6.59 Hz, 3 H) 1.37-1.44 (m, 6H) 1.72-1.82 (m, 1H) 1.83-1.94 (m, 1H) 2.10-2.25 (m, 1H) 2.26-2.40 (m, 1H) 3.03 (s, 6H) 3.56-3.65 (m, 1H) 3.76-3.85 (m, 1H) 4.08-4.15 (m, 2H) 4.16-4.25 (m, 1H) 5.50 (s, 1H) 5.58 (dd, J=8.13, 3.74 Hz, 1H) 6.98 (dd, J=11.42, 8.35 Hz, 1H) 7.06-7.16 (m, 3H) 7.24-7.28 (m, 1H) 7.34 (dd, J=8.57, 1.98 Hz, 1H) 7.52 (dd, J=8.79, 2.20 Hz, 1H) 7.56 (d, J=2.20 Hz, 1H) 7.76 (d, J=8.79 Hz, 1H), LCMS: 672 (M+1).

Example 35

(2R,3S)-Ethyl 1-((R)-2-(5-carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylate

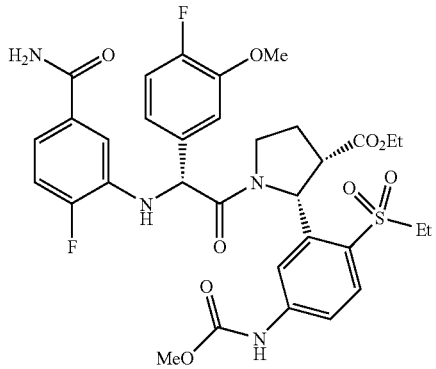

35A: 2-(Ethylthio)-5-nitrobenzaldehyde

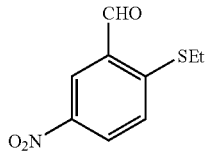

To 2-fluoro-5-nitrobenzaldehyde (25 g, 148 mmol) and ethylthiol (15.1 mL, 203 mmol) in DMF (100 mL) was added potassium carbonate (35.8 g, 260 mmol). The reaction mixture was stirred at 60° C. for 8.0 h. After it cooled to rt, cold water (200 mL) was added and stirred at rt for 15 min. The precipitate was collected by filtration and washed with water. After drying, 35A (25 g) was obtained as a yellow solid. The filtrate was extracted with EtOAc, washed with brine and dried over $Na_2SO_4$. After evaporation of solvent, the crude was triturated with EtOAc/hexane (1:3) to give a second crop of 35A (3 g, total 90% yield). $^1$H NMR (400 MHz, CDCl$_3$) δ ppm 1.44 (t, J=7.47 Hz, 3H) 3.08 (q, J=7.47 Hz, 2H) 7.46 (d, J=8.79 Hz, 1H) 8.30 (dd, J=8.79, 2.64 Hz, 1H) 8.62 (d, J=2.20 Hz, 1H) 10.25 (s, 1 H).

35B: (E)-Ethyl 4-(2-(ethylthio)-5-nitrobenzylideneamino)butanoate

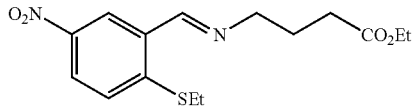

To ethyl aminobutyric ester (3.92 g, 23.4 mmol) in dichloromethane (100 mL) was added triethylamine (4.5 mL, 32.2 mmol) and then 35A (4.94 g, 23.4 mmol) and 4 Å molecular sieves (3.0 g). The reaction was stirred overnight at rt and filtered to remove the molecular sieves. The solvent was evaporated to give a solid 35B together with triethylamine HCl salt. $^1$H NMR (400 MHz, CDCl$_3$) δ ppm 1.10 (t, J=7.03 Hz, 3H) 1.86-1.95 (m, 2H) 2.29 (t, J=7.47 Hz, 2H) 2.92 (q, J=7.47 Hz, 2 H) 3.56 (t, J=6.15 Hz, 2H) 3.98 (q, J=7.32 Hz, 2H) 7.99 (dd, J=8.79, 2.64 Hz, 1H) 8.47 (d, J=2.64 Hz, 1H) 8.51 (s, 1H).

35C: trans-1-tert-Butyl 3-ethyl 2-(2-(ethylthio)-5-nitrophenyl)pyrrolidine-1,3-dicarboxylate and 35D: cis-1-tert-Butyl 3-ethyl 2-(2-(ethylthio)-5-nitrophenyl)pyrrolidine-1,3-dicarboxylate

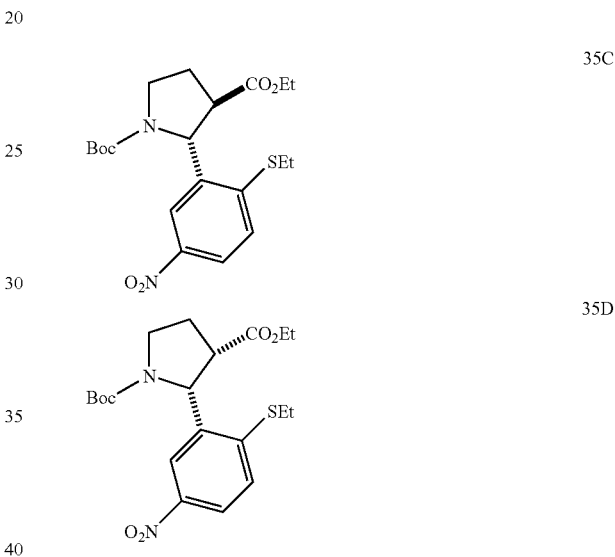

To 35B (23.4 mmol) in CH$_2$Cl$_2$ (200 mL) at −15° C. was added Et$_3$N (5.7 mL, 41 mmol) followed by TiCl$_4$ (1.0 M in CH$_2$Cl$_2$, 41 mL, 41 mmol). The mixture was stirred from −15° C. to rt over 3.0 h before it was quenched with sat. K$_2$CO$_3$ (200 mL) at 0° C. and stirred at rt for 1.0 h. The mixture was filtered through a pad of wet Celite®, extracted with CH$_2$Cl$_2$ (3×60 mL). The organic layer was washed with water, dried over Na$_2$SO$_4$. A small portion of the dried organic layer was concentrated to give crude ethyl 2-(2-(ethylthio)-5-nitrophenyl)pyrrolidine-3-carboxylate: $^1$H NMR indicated a mixture of cis and trans isomer in ca. 1:1 ratio, LC-MS 325 (M+H). To the above ethyl 2-(2-(ethylthio)-5-nitrophenyl)pyrrolidine-3-carboxylate in THF (100 mL) was added Et$_3$N (3.3 mL) and di-tert-butyl dicarbonate (1.0 M in THF, 24 mL, 24 mmol). The mixture was stirred at rt for 3.0 h before it was quenched with 0.5 N HCl (50 mL). The organic layer was washed with brine, dried (Na$_2$SO$_4$), filtered and concentrated. The crude product was first triturated with EtOAc, the precipitate was collected by filtration and washed with EtOAc to give the trans 35C (1.7 g). The filtrate was concentrated and further purified by flash silica gel column chromatography using gradient EtOAc in hexane to give predominantly cis isomer 35D ($^1$H NMR indicated presence of 30% trans isomer). To this cis isomer was added mixture of EtOAc/hexane (1:3), the precipitate was collected and washed with the same mixture of EtOAc/hexanes (1:3) to give a second crop of the trans 35C (0.8 g, total 2.5 g, 25% yield). The filtrate was concentrated to give enriched cis isomer 35D (3.0 g, >92% purity, 30% yield). 35C: $^1$H NMR (500 MHz, DMSO-d$_6$, 90° C.) δ ppm 1.20 and 1.23 (m, 12H) 1.33 (t, J=7.42 Hz, 3H) 2.08-2.19 (m, 2H) 2.90 (br s, 1H) 3.15 (q, J=7.15 Hz, 2H) 3.48-3.58 (m, 1H) 3.70 (m, 1H) 4.10-4.19 (m, 2H) 5.31 (br s, 1H) 7.58 (d, J=8.79 Hz, 1H) 7.84 (s, 1H) 8.02-8.09 (m, 1H). LC-MS 425 (M+H). 35D: $^1$H NMR (500 MHz, DMSO-d$_6$, 90° C.) δ ppm 0.86 (t, J=6.87 Hz, 3H) 1.18 (s, 9H) 1.34 (t, J=7.15 Hz, 3H) 2.12-2.22 (m, 2H) 3.09-3.17 (m, 2H) 3.56-3.67 (m, 3H) 3.69-3.83 (m, 2H) 5.43 (d, J=8.79 Hz, 1H) 7.50-7.58 (m, 1H) 7.81 (s, 1H) 8.03 (d, J=8.79 Hz, 1H); LC-MS 425 (M+H).

35E: trans-1-tert-Butyl 3-ethyl 2-(2-(ethylsulfonyl)-5-nitrophenyl)pyrrolidine-1,3-dicarboxylate

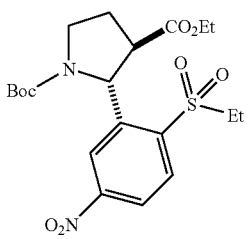

To 35C (2.15 g, 5.06 mmol) in CH$_2$Cl$_2$ (100 mL) was added NaHCO$_3$ (1.28 g, 15.2 mmol) and MCPBA (75% purity, 2.9 g, 12.6 mmol). The mixture was stirred at rt overnight. It was quenched with sat. NaHCO$_3$ and extracted with CH$_2$Cl$_2$. The organic layer was dried over Na$_2$SO$_4$. After removal of solvent, the crude was purified with flash silica gel column chromatography eluting with gradient EtOAc in CH$_2$Cl$_2$ to give 35E (2.1 g, 95% yield). $^1$H NMR (500 MHz, DMSO-d$_6$, 100° C.) δ ppm 1.16-1.25 (m, 6H) 1.30 (s, 9H) 2.07 (m, 1H) 2.27 (m, 1H) 2.97 (br s, 2H) 3.45 (m, 3H) 3.74-3.82 (m, 1H) 4.14 (q, J=7.15 Hz, 2H) 5.80 (s, 1H) 8.09 (s, 1H) 8.19 (d, J=8.79 Hz, 1H) 8.32 (d, J=8.80 Hz, 1H); LC-MS 401 (M-tert-Bu).

35F: cis-1-tert-Butyl 3-ethyl 2-(2-(ethylsulfonyl)-5-nitrophenyl)pyrrolidine-1,3-dicarboxylate

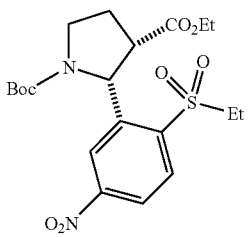

To 35D (2.74 g, 6.45 mmol) in CH$_2$Cl$_2$ (100 mL) was added NaHCO$_3$ (1.63 g, 19.2 mmol) and MCPBA (75% purity, 3.7 g, 16.1 mmol). The mixture was stirred at rt overnight. It was quenched with sat. NaHCO$_3$ and extracted with CH$_2$Cl$_2$. The organic layer was dried over Na$_2$SO$_4$. After removal of solvent, the crude was purified with silica gel column chromatography eluting with gradient EtOAc in CH$_2$Cl$_2$ to give 35F (2.1 g, 95% yield): $^1$H NMR (500 MHz, DMSO-d$_6$, 100° C.) δ ppm 0.82 (t, J=7.15 Hz, 3H) 1.19-1.27 (m, 12H) 2.13-2.23 (m, 2H) 3.39-3.49 (m, 2H) 3.62-3.73 (m, 4H) 3.79-3.87 (m, 1H) 5.86 (d, J=9.34 Hz, 1H) 8.07 (s, 1H) 8.15 (d, J=8.79 Hz, 1H) 8.29 (d, J=8.79 Hz, 1H); LC-MS 401 (M-tert-Bu).

35G: trans-1-tert-Butyl 3-ethyl 2-(5-amino-2-(ethylsulfonyl)phenyl)pyrrolidine-1,3-dicarboxylate

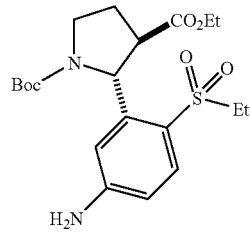

To 35E (2.2 g) in methanol (50 mL) and THF (30 mL) was added 10% Pd/C (700 mg). The mixture was hydrogenated with a hydrogen balloon for 6.0 h. The Pd/C was removed by filtration and the filtrate was concentrated to afford 35G (2.1 g, 95% yield). $^1$H NMR (500 MHz, DMSO-d$_6$, 100° C.) δ ppm 1.13 (t, J=7.42 Hz, 3H) 1.16-1.23 (t, J=7.42 Hz, 3H) 1.31 (s, 9H) 1.93-2.01 (m, 1H) 2.17 (m, 1H) 2.78 (br s, 1H) 3.14 (br s, 2H) 3.38-3.47 (m, 1H) 3.66 (t, J=8.52 Hz, 1H) 4.10 (q, J=7.42 Hz, 2H) 5.60 (s, 1H) 5.83 (br s, 1H) 6.51-6.58 (m, 2H) 7.49 (d, J=9.34 Hz, 1H); LC-MS 427 (M+H).

35H: cis-1-tert-Butyl 3-ethyl 2-(5-amino-2-(ethylsulfonyl)phenyl)pyrrolidine-1,3-dicarboxylate

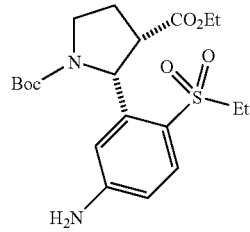

To 35F (2.2 g) in methanol (50 mL) and THF (30 mL) was added 10% Pd/C (580 mg). The mixture was hydrogenated with a hydrogen balloon for 6.0 h. The Pd/C was removed by filtration and the filtrate was concentrated to afford 35H (2.1 g, 95% yield). $^1$H NMR (500 MHz, DMSO-d$_6$, 100° C.) δ ppm 0.88 (t, J=6.87 Hz, 3H) 1.16 (t, J=7.42 Hz, 3H) 1.26 (s, 9H) 2.07-2.13 (m, 2H) 3.13-3.21 (m, 2H) 3.49 (br s, 1H) 3.63-3.75 (m, 4H) 5.69 (d, J=8.25 Hz, 1H) 6.50-6.55 (m, 2H) 7.44 (d, J=8.79 Hz, 1H); LC-MS 427 (M+H).

35I: (2R,3R)-1-tert-Butyl 3-ethyl 2-(5-amino-2-(ethylsulfonyl)phenyl)pyrrolidine-1,3-dicarboxylate and 35J: (2S,3S)-1-tert-Butyl 3-ethyl 2-(5-amino-2-(ethylsulfonyl)phenyl)pyrrolidine-1,3-dicarboxylate

35I

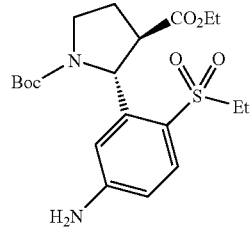

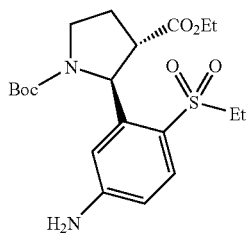
35J 35I and 35J were separated from 35G using a preparative HPLC equipped with a Chiralpak® AD column (5 cm×50 cm, 20μ). The separations were performed using an isocratic method of 5% MeOH-EtOH/heptane with 0.1% diethylamine with a flow rate of 50 mL/min. Alternatively, the isomers were separated by Berger SFC equipped with Chiralpak® AD column (25 cm×3 cm, 10μ). The separations were performed using an isocratic method of $CO_2$/MeOH/DEA: 90/10/0.1 with a flow rate of 65 mL/min at 35° C. The first peak is 35I: $^1$H NMR (400 MHz, Methanol-$d_4$) δ ppm 1.15-1.34 (m, 12H) 1.46 (s, 3H) 1.96-2.11 (m, 1 H) 2.18-2.43 (m, 1H) 2.80-3.00 (m, 1H) 3.07-3.23 (m, 1H) 3.24-3.34 (m, 1H) 3.40-3.59 (m, 1H) 3.77 (t, J=9.73 Hz, 1H) 4.06-4.26 (m, 2H) 5.61 (d, J=20.97 Hz, 1H) 6.52-6.69 (m, 2H) 7.53-7.66 (m, 1H). LC-MS 327 (M-Boc). The second peak is 35J: $^1$H NMR (400 MHz, Methanol-$d_4$) δ ppm 1.14-1.33 (m, 12H) 1.45 (s, 3 H) 1.97-2.08 (m, 1H) 2.15-2.41 (m, 1H) 2.78-3.00 (m, 1H) 3.08-3.22 (m, 1H) 3.22-3.29 (m, 1H) 3.38-3.58 (m, 1H) 3.70-3.83 (m, 1H) 4.18 (q, J=6.74 Hz, 2H) 5.60 (d, J=21.22 Hz, 1H) 6.51-6.68 (m, 2H) 7.58 (dd, J=8.46, 5.43 Hz, 1H). LC-MS 327 (M-Boc).

35K: (2R,3S)-1-tert-Butyl 3-ethyl 2-(5-amino-2-(ethylsulfonyl)phenyl)pyrrolidine-1,3-dicarboxylate and

35L: (2S,3R)-1-tert-Butyl 3-ethyl 2-(5-amino-2-(ethylsulfonyl)phenyl)pyrrolidine-1,3-dicarboxylate

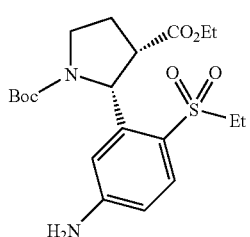
35K

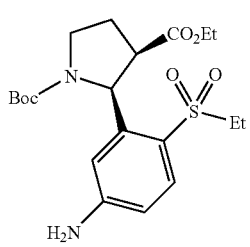
35L 35K and 35L were separated from 35H using a preparative HPLC equipped with a Chiralpak® AD column (5 cm×50 cm, 20 μl). The separations were performed using an isocratic method of 10% MeOH-EtOH/heptane with 0.1% diethylamine with a flow rate of 50 mL/min. The first peak is 35K: $^1$H NMR (400 MHz, Methanol-$d_4$) δ ppm 0.89 (t, J=7.07 Hz, 3H) 1.04-1.58 (m, 12H) 2.04-2.13 (m, 1H) 2.15-2.31 (m, 1H) 3.13-3.29 (m, 2H) 3.57-3.69 (m, 2H) 3.69-3.80 (m, 2H) 3.82-3.98 (m, 1H) 5.70 (d, J=8.08 Hz, 1H) 6.48-6.70 (m, 2H) 7.55 (d, J=8.59 Hz, 1H). LC-MS 327 (M-Boc). The second peak is 35L: $^1$H NMR (400 MHz, Methanol-$d_4$) δ ppm 0.89 (t, J=7.20 Hz, 3H) 1.07-1.56 (m, 12H) 1.96-2.14 (m, 1H) 2.22 (d, J=11.12 Hz, 1H) 3.17-3.28 (m, 2H) 3.58-3.70 (m, 2H) 3.69-3.81 (m, 2H) 3.81-3.94 (m, 1H) 5.70 (d, J=8.34 Hz, 1H) 6.48-6.68 (m, 2H) 7.55 (d, J=8.59 Hz, 1H). LC-MS 327 (M-Boc).

35M: (2R,3R)-Ethyl 2-(2-(ethylsulfonyl)-5-(methoxycarbonylamino)phenyl)pyrrolidine-3-carboxylate hydrochloride

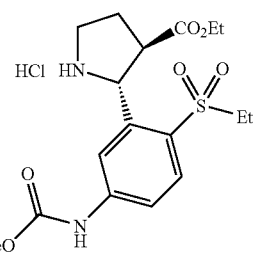

35M was prepared in a procedure similar to that of 1G using 35I and methyl chloroformate. $^1$H NMR (400 MHz, Methanol-$d_4$) δ ppm 1.17-1.33 (m, 6H) 2.33-2.50 (m, 1H) 2.63-2.79 (m, 1H) 3.35-3.45 (m, 2H) 3.46-3.61 (m, 2H) 3.75-3.89 (m, 4H) 4.10-4.27 (m, 2H) 5.74 (dd, J=8.84, 1.52 Hz, 1H) 7.64-7.74 (m, 1H) 7.95-8.04 (m, 1H) 8.09 (d, J=1.77 Hz, 1H), LC-MS 385 (M+H).

35N: (2S,3S)-Ethyl 2-(2-(ethylsulfonyl)-5-(methoxycarbonylamino)phenyl)pyrrolidine-3-carboxylate hydrochloride

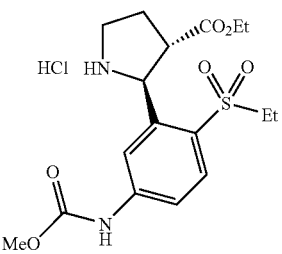

35N was prepared in a procedure similar to that of 1G using 35J and methyl chloroformate. $^1$H NMR (400 MHz, Methanol-$d_4$) δ ppm 1.18-1.38 (m, 6H) 2.35-2.50 (m, 1H) 2.65-2.80 (m, 1H) 3.37-3.46 (m, 2H) 3.46-3.60 (m, 2H) 3.62-3.91 (m, 4H) 4.08-4.28 (m, 2H) 5.68-5.83 (m, 1H) 7.63-7.76 (m, 1H) 7.97-8.05 (m, 1H) 8.10 (d, J=2.02 Hz, 1H), LC-MS 385 (M+H).

35O: (2R,3S)-Ethyl 2-(2-(ethylsulfonyl)-5-(methoxycarbonylamino)phenyl)pyrrolidine-3-carboxylate hydrochloride

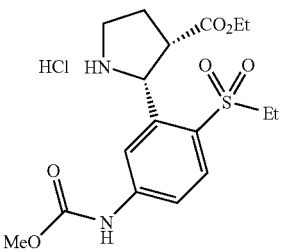

35O was prepared in a procedure similar to that of 1G using 35K and methyl chloroformate. $^1$H NMR (400 MHz, Methanol-d$_4$) δ ppm 0.89 (t, J=7.20 Hz, 3H) 1.25-1.33 (m, 3H) 2.45-2.60 (m, 1H) 2.63-2.79 (m, 1H) 3.31-3.41 (m, 2 H) 3.50-3.62 (m, 1H) 3.67-3.75 (m, 1H) 3.79 (s, 3H) 3.83-3.96 (m, 3H) 5.89 (d, J=8.59 Hz, 1H) 7.57 (dd, J=8.84, 2.02 Hz, 1H) 7.89 (d, J=2.02 Hz, 1H) 7.96-8.02 (m, 1H), LC-MS 385 (M+H).

35P: (2S,3R)-Ethyl 2-(2-(ethylsulfonyl)-5-(methoxycarbonylamino)phenyl)pyrrolidine-3-carboxylate hydrochloride

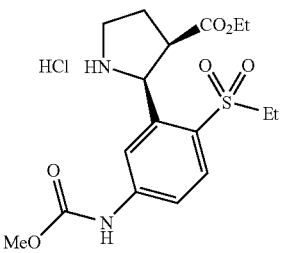

35P was prepared in a procedure similar to that of 1G using 35L and methyl chloroformate. $^1$H NMR (400 MHz, Methanol-d$_4$) δ ppm 0.89 (t, J=7.07 Hz, 3H) 1.29 (t, J=7.33 Hz, 3H) 2.45-2.61 (m, 1H) 2.64-2.79 (m, 1H) 3.32-3.40 (m, 2H) 3.51-3.62 (m, 1H) 3.66-3.76 (m, 1H) 3.79 (s, 3H) 3.83-3.97 (m, 3H) 5.90 (d, J=8.59 Hz, 1H) 7.56 (dd, J=8.72, 2.15 Hz, 1H) 7.90 (d, J=2.02 Hz, 1H) 7.99 (d, J=8.59 Hz, 1H), LC-MS 385 (M+H).

35Q: Example 35

Example 35 was prepared according to the general coupling condition using 35O and 27A. $^1$H NMR (400 MHz, Methanol-d$_4$) δ ppm 0.83 (t, J=7.03 Hz, 3H) 1.28 (t, J=7.25 Hz, 3H) 2.21-2.33 (m, 1H) 2.34-2.46 (m, 1H) 3.40-3.51 (m, 1 H) 3.53-3.62 (m, 3H) 3.65-3.70 (m, 4H) 3.71 (s, 3H) 3.84-3.97 (m, 1H) 4.16-4.29 (m, 1H) 5.46 (s, 1H) 6.08 (d, J=8.79 Hz, 1H) 6.92-6.98 (m, 1H) 6.96-7.08 (m, 4H) 7.11-7.17 (m, 1H) 7.21 (dd, J=8.79, 2.20 Hz, 1H) 7.31 (dd, J=8.35, 2.20 Hz, 1H) 7.76 (d, J=8.35 Hz, 1H), LCMS: 703 (M+1).

Example 36

Diastereoisomer of Example 35

(2R,3S)-Ethyl 1-((S)-2-(5-carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylate

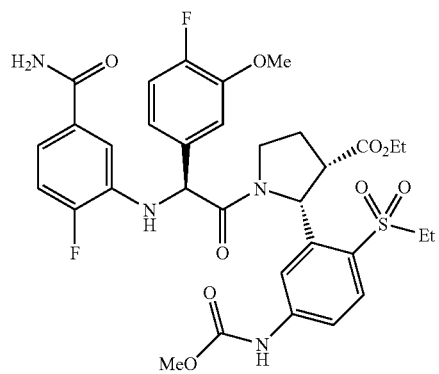

Example 36 was obtained as a diastereomer of Example 35 during its HPLC purification. $^1$H NMR (400 MHz, Methanol-d$_4$) δ ppm 0.88 (t, J=7.25 Hz, 3 H) 1.25 (t, J=7.25 Hz, 3H) 1.99-2.13 (m, 1H) 2.35-2.50 (m, 1H) 3.34-3.44 (m, 1 H) 3.44-3.53 (m, 2H) 3.57-3.65 (m, 1H) 3.70-3.75 (m, 2H) 3.75 (s, 3H) 3.88 (s, 3H) 4.34-4.48 (m, 1H) 5.53 (s, 1H) 5.99 (d, J=8.79 Hz, 1H) 6.99 (dd, J=11.42, 8.35 Hz, 1H) 7.07 (dd, J=4.39, 2.20 Hz, 1H) 7.11-7.19 (m, 2H) 7.29 (dd, J=8.13, 1.98 Hz, 1H) 7.37 (dd, J=8.35, 2.20 Hz, 1H) 7.44 (d, J=2.20 Hz, 1H) 7.70 (dd, J=8.79, 1.76 Hz, 1H) 7.78-7.82 (m, 1H), LCMS: 703 (M+1).

Example 37

(2R)-1-((S)-2-(5-Carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylic acid

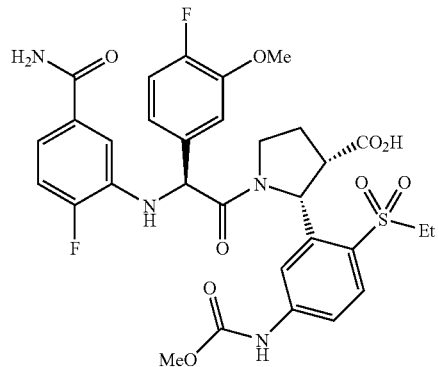

Example 37 was prepared by hydrolysis of the ethyl ester in Example 36 with NaOH in MeOH/H₂O at rt and purified by prep HPLC. ¹H NMR (400 MHz, Methanol-d₄) δ ppm 1.25 and 1.34 (t, J=7.25 Hz, 3H) 2.13-2.61 (m, 2H) 2.82-2.91 (m, 1H) 3.36-3.51 (m, 3H) 3.78 and 3.73 (s, 3H) 3.91 and 3.75 (s, 3H) 4.36 (t, J=9.01 Hz, 1H) 5.58 and 5.50 (s, 1H) 5.99 and 6.03 (s, 1H) 6.97-7.26 (m, 5H) 7.38-7.49 (m, 2H) 7.73-7.91 (m, 2H), LCMS: 675 (M+1).

Example 38

(2R,3S)-1-((R)-2-(5-Carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylic acid

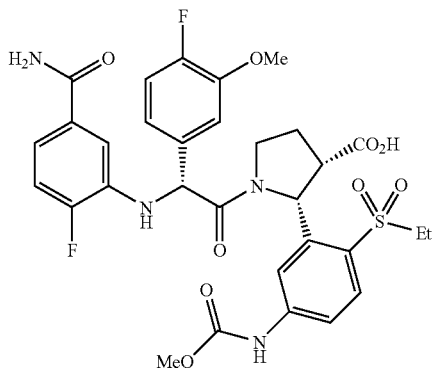

Example 38 was prepared by hydrolysis of the ethyl ester in Example 35 with NaOH in MeOH/H₂O at rt and purified by prep HPLC. ¹H NMR (400 MHz, Methanol-d₄) δ ppm 1.29 (t, J=7.25 Hz, 3H) 2.28 (dd, J=13.84, 7.25 Hz, 1H) 2.37-2.54 (m, 1H) 2.86 (d, J=7.91 Hz, 1H) 3.40-3.51 (m, 1H) 3.51-3.63 (m, 1H) 3.71 (s, 6H) 3.86-3.96 (m, 1H) 4.00-4.12 (m, 1H) 5.42 (s, 1H) 6.03 (s, 1H) 6.97-7.07 (m, 4H) 7.13-7.20 (m, 3H) 7.29 (dd, J=8.13, 1.98 Hz, 1H) 7.80 (d, J=8.79 Hz, 1H), LCMS: 675 (M+1).

Example 39

(2R,3S)-Ethyl 1-((R)-2-(3-carbamoyl-4-fluorophenylamino)-2-(4-fluoro-3-methoxyphenyl)acetyl)-2-(2-(ethylsulfonyl)-5-(methoxycarbonylamino)phenyl)pyrrolidine-3-carboxylate

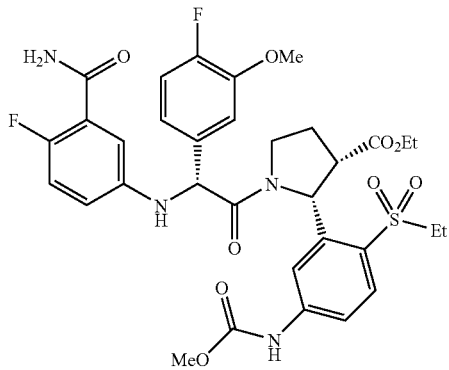

39A: 2-(3-Carbamoyl-4-fluorophenylamino)-2-(4-fluoro-3-methoxyphenyl)acetic acid

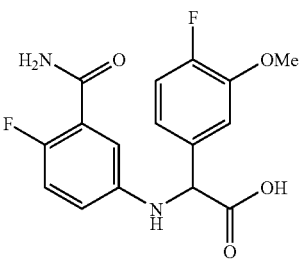

39A was prepared in a procedure similar to that of 1A using 3-amino-6-fluorobenzamide, 7C and glyoxylic acid monohydrate. Yield: 43%. ¹H NMR (400 MHz, Methanol-d₄) δ ppm 3.85 (s, 3H) 5.05 (s, 1H) 6.75-6.82 (m, 1H) 6.92-6.97 (m, 1H) 7.03-7.08 (m, 3H) 7.24-7.29 (m, 1H), LCMS: 337 (M+1).

39B: Example 39

Example 39 was prepared according to the general coupling condition using 39A and 350. ¹H NMR (400 MHz, Methanol-d₄) δ ppm 0.84 (t, J=7.03 Hz, 3 H) 1.23 (t, J=7.25 Hz, 3H) 2.22-2.33 (m, 1H) 2.34-2.47 (m, 1H) 3.36-3.48 (m, 1 H) 3.49-3.64 (m, 3H) 3.66 (s, 3H) 3.68-3.73 (m, 4H) 3.84-3.95 (m, 1H) 4.14-4.26 (m, 1H) 5.36 (s, 1H) 6.07 (d, J=8.79 Hz, 1H) 6.82-6.90 (m, 1H) 6.91-7.01 (m, 3H) 7.01-7.09 (m, 2H) 7.13 (dd, J=6.15, 3.08 Hz, 1H) 7.22 (dd, J=8.57, 1.98 Hz, 1H) 7.75 (d, J=8.79 Hz, 1H), LCMS: 703 (M+1).

Example 40

Diastereoisomer of Example 39

(2R,3S)-Ethyl 1-((S)-2-(3-carbamoyl-4-fluorophenylamino)-2-(4-fluoro-3-methoxyphenyl)acetyl)-2-(2-(ethylsulfonyl)-5-(methoxycarbonylamino)phenyl)pyrrolidine-3-carboxylate

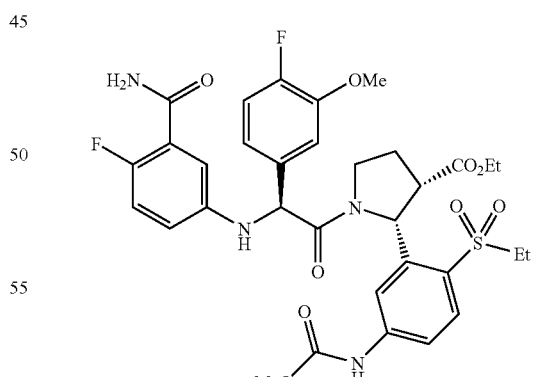

Example 40 was obtained as a diastereomer of Example 39 during its HPLC purification. ¹H NMR (400 MHz, Methanol-d₄) δ ppm 0.88 (t, J=7.25 Hz, 3 H) 1.23 (t, J=7.25 Hz, 3H) 2.06 (dd, J=12.74, 7.47 Hz, 1H) 2.34-2.51 (m, 1H) 3.36-3.53 (m, 3H) 3.57-3.65 (m, 1H) 3.71-3.76 (m, 2H) 3.81 (s, 3H) 3.87 (s, 3H) 4.31-4.42 (m, 1H) 5.40 (s, 1H) 5.98 (d, J=8.35 Hz, 1H) 6.77-6.86 (m, 1H) 6.87-6.96 (m, 1H) 7.00-7.06 (m, 1H) 7.08-

7.15 (m, 1H) 7.17 (dd, J=6.15, 3.08 Hz, 1H) 7.25 (dd, J=8.13, 1.98 Hz, 1H) 7.55-7.60 (m, 2H) 7.78 (d, J=8.35 Hz, 1H), LCMS: 703 (M+1).

Example 41

(2R,3S)-Ethyl 1-((R)-2-(5-carbamoyl-2,4-difluorophenylamino)-2-(4-fluoro-3-methoxyphenyl)acetyl)-2-(2-(ethylsulfonyl)-5-(methoxycarbonylamino)phenyl)pyrrolidine-3-carboxylate

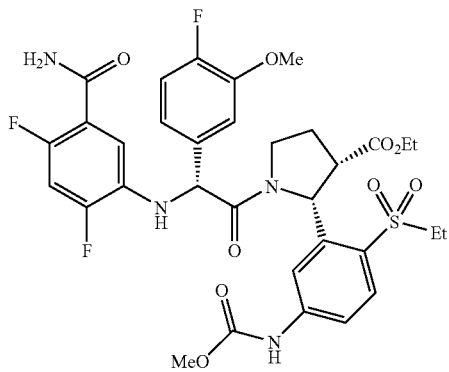

41A: 2-(5-Carbamoyl-2,4-difluorophenylamino)-2-(4-fluoro-3-methoxyphenyl)acetic acid

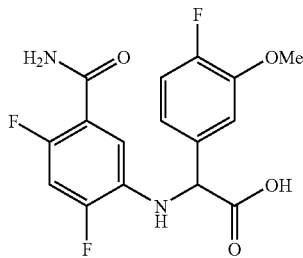

41A was prepared in a procedure similar to that of 1A using 3-amino-4,6-difluorobenzamide, 7C, and glyoxylic acid monohydrate. Yield: 87%. $^1$H NMR (400 MHz, Methanol-$d_4$) δ ppm 3.87 (s, 3H) 5.11 (s, 1H) 6.97-7.11 (m, 4H) 7.26 (d, J=8.79 Hz, 1H), LCMS: 355 (M+1).

41B: Example 41

Example 41 was prepared according to the general coupling condition using 41A and 35O. $^1$H NMR (400 MHz, Methanol-$d_4$) δ ppm 0.83 (t, J=7.25 Hz, 3 H) 1.27 (t, J=7.25 Hz, 3H) 2.21-2.33 (m, 1H) 2.33-2.47 (m, 1H) 3.39-3.51 (m, 1 H) 3.52-3.64 (m, 3H) 3.67-3.69 (m, 4H) 3.71 (s, 3H) 3.83-3.94 (m, 1H) 4.15-4.29 (m, 1H) 5.41 (s, 1H) 6.07 (d, J=8.79 Hz, 1H) 6.91-7.08 (m, 5H) 7.19-7.27 (m, 2H) 7.76 (d, J=8.35 Hz, 1H), LCMS: 721 (M+1).

Example 42

Diastereoisomer of Example 41

(2R,3S)-Ethyl 1-((S)-2-(5-carbamoyl-2,4-difluorophenylamino)-2-(4-fluoro-3-methoxyphenyl)acetyl)-2-(2-(ethylsulfonyl)-5-(methoxycarbonylamino)phenyl)pyrrolidine-3-carboxylate

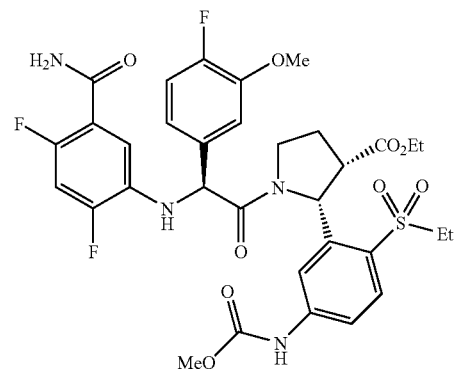

Example 42 was obtained as a diastereomer of Example 41 during its HPLC purification. $^1$H NMR (400 MHz, Methanol-$d_4$) δ ppm 0.89 (t, J=7.25 Hz, 3 H) 1.25 (t, J=7.47 Hz, 3H) 2.04 (dd, J=12.74, 7.03 Hz, 1H) 2.34-2.46 (m, 1H) 3.35-3.53 (m, 3H) 3.55-3.65 (m, 1H) 3.69-3.80 (m, 5H) 3.88 (s, 3H) 4.33-4.44 (m, 1H) 5.48 (s, 1H) 5.98 (d, J=8.35 Hz, 1H) 6.95 (t, J=10.77 Hz, 1H) 7.02-7.08 (m, 1H) 7.09-7.15 (m, 1H) 7.26-7.33 (m, 2H) 7.39 (d, J=2.20 Hz, 1H) 7.71-7.75 (m, 1 H) 7.78-7.82 (m, 1H), LCMS: 721 (M+1).

Example 43

(2R,3S)-Ethyl 1-((R)-2-(1,3-dioxoisoindolin-5-ylamino)-2-(4-fluoro-3-methoxyphenyl)acetyl)-2-(2-(ethylsulfonyl)-5-(methoxycarbonylamino)phenyl)pyrrolidine-3-carboxylate

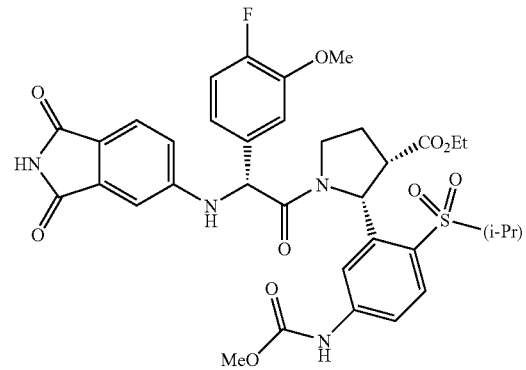

43A: 2-(1,3-Dioxoisoindolin-5-ylamino)-2-(4-fluoro-3-methoxyphenyl)acetic acid

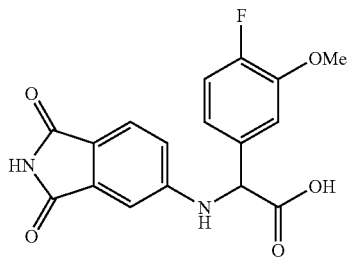

43A was prepared in a procedure similar to that of 1A using 5-iminoisoindoline-1,3-dione, 7C and glyoxylic acid monohydrate. Yield: 17%. $^1$H NMR (400 MHz, Methanol-$d_4$) δ ppm 3.87 (s, 3H) 5.21 (s, 1H) 6.90 (dd, J=8.35, 2.20 Hz, 1H) 6.99 (d, J=1.76 Hz, 1H) 7.06-7.12 (m, 2H) 7.28 (d, J=8.79 Hz, 1H) 7.51 (d, J=8.35 Hz, 1H), LCMS: 345 (M+1).

43B: Example 43

Example 43 was prepared according to the general coupling condition using 43A and 350. $^1$H NMR (400 MHz, Methanol-$d_4$) δ ppm 0.84 (t, J=7.25 Hz, 3 H) 1.22 (t, J=7.47 Hz, 3H) 2.22-2.35 (m, 1H) 2.35-2.47 (m, 1H) 3.38-3.54 (m, 2 H) 3.54-3.64 (m, 2H) 3.67 (s, 3H) 3.68-3.71 (m, 1H) 3.72 (s, 3H) 3.86-3.96 (m, 1H) 4.19-4.28 (m, 1H) 5.49 (s, 1H) 6.09 (d, J=8.35 Hz, 1H) 6.90 (dd, J=8.35, 2.20 Hz, 1H) 6.95 (d, J=8.35 Hz, 1H) 6.98 (d, J=1.76 Hz, 1H) 7.02-7.10 (m, 3H) 7.22 (dd, J=8.79, 2.20 Hz, 1H) 7.49 (d, J=8.35 Hz, 1H) 7.75 (d, J=8.79 Hz, 1H), LCMS: 711 (M+1).

Example 44

Diastereoisomer of Example 43

(2R,3S)-Ethyl 1-((S)-2-(1,3-dioxoisoindolin-5-ylamino)-2-(4-fluoro-3-methoxyphenyl)acetyl)-2-(2-(ethylsulfonyl)-5-(methoxycarbonylamino)phenyl)pyrrolidine-3-carboxylate

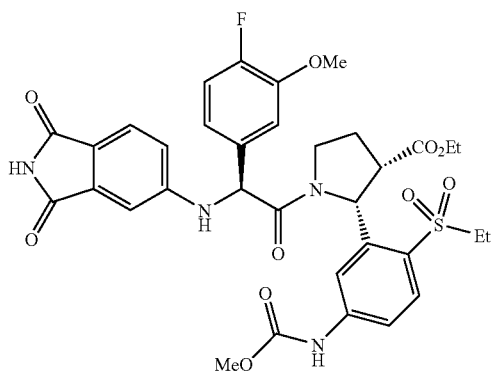

Example 44 was obtained as a diastereomer of Example 43 during its HPLC purification. $^1$H NMR (400 MHz, Methanol-$d_4$) δ ppm 0.89 (t, J=7.03 Hz, 3 H) 1.22 (t, J=7.25 Hz, 3H) 2.05-2.15 (m, 1H) 2.38-2.51 (m, 1H) 3.35-3.52 (m, 3 H) 3.58-3.67 (m, 1H) 3.71-3.77 (m, 2H) 3.84 (s, 3H) 3.88 (s, 3H) 4.30-4.42 (m, 1H) 5.55 (s, 1H) 6.02 (d, J=8.79 Hz, 1H) 6.81 (dd, J=8.35, 2.20 Hz, 1H) 7.04-7.10 (m, 2H) 7.11-7.19 (m, 1H) 7.26 (dd, J=8.13, 1.98 Hz, 1H) 7.39 (dd, J=8.79, 2.20 Hz, 1H) 7.45 (d, J=8.35 Hz, 1H) 7.77 (d, J=8.35 Hz, 1H) 7.83 (d, J=2.20 Hz, 1H), LCMS: 711 (M+1).

Example 45

(2R,3S)-1-((R)-2-(3-Carbamoyl-4-fluorophenylamino)-2-(4-fluoro-3-methoxyphenyl)acetyl)-2-(2-(ethylsulfonyl)-5-(methoxycarbonylamino)phenyl)pyrrolidine-3-carboxylic acid

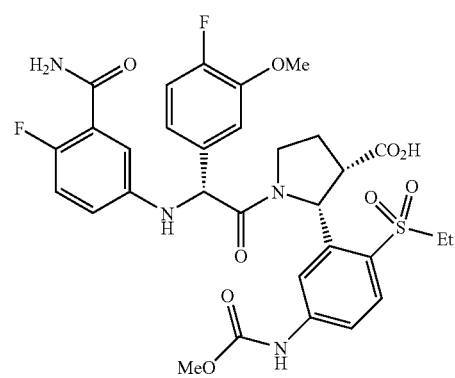

Example 45 was prepared by hydrolysis of the ethyl ester in Example 39 with NaOH in MeOH/$H_2O$ at rt and purified by prep HPLC. $^1$H NMR (400 MHz, Methanol-$d_4$) δ ppm 1.25 (t, J=7.25 Hz, 3H) 2.22-2.33 (m, 1H) 2.36-2.50 (m, 1H) 2.85 (d, J=7.91 Hz, 1H) 3.36-3.48 (m, J=14.61, 14.61, 7.69 Hz, 1H) 3.47-3.58 (m, 1H) 3.69 (s, 3H) 3.70 (s, 3H) 3.85-3.94 (m, 1H) 4.00-4.10 (m, 1H) 5.31 (s, 1H) 6.02 (s, 1H) 6.78-6.85 (m, 1H) 6.95-7.09 (m, 4H) 7.13 (dd, J=6.15, 3.08 Hz, 1H) 7.15-7.22 (m, 2H) 7.80 (d, J=8.79 Hz, 1H), LCMS: 675 (M+1).

Example 46

(2R,3S)-1-((R)-2-(5-Carbamoyl-2,4-difluorophenylamino)-2-(4-fluoro-3-methoxyphenyl)acetyl)-2-(2-(ethylsulfonyl)-5-(methoxycarbonylamino)phenyl)pyrrolidine-3-carboxylic acid

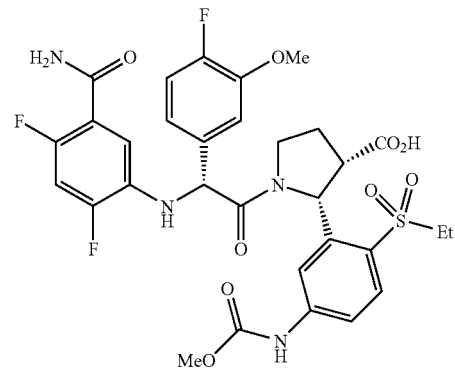

Example 46 was prepared by hydrolysis of the ethyl ester in Example 41 with NaOH in MeOH/$H_2O$ at rt and purified by prep HPLC. $^1$H NMR (400 MHz, Methanol-$d_4$) δ ppm 1.29 (t, J=7.47 Hz, 3H) 2.20-2.34 (m, 1H) 2.36-2.50 (m, 1H) 2.84 (d, J=7.91 Hz, 1H) 3.41-3.52 (m, 1H) 3.52-3.63 (m, 1H) 3.71 (s, 6H) 3.84-3.95 (m, 1H) 3.97-4.12 (m, 1H) 5.38 (s, 1H) 6.02 (s, 1H) 6.96 (t, J=10.99 Hz, 1H) 6.99-7.08 (m, 3H) 7.12-7.18 (m, 2H) 7.27 (dd, J=9.67, 7.47 Hz, 1H) 7.80 (d, J=8.79 Hz, 1H), LCMS: 693 (M+1).

Example 47

(2R,3S)-1-((R)-2-(1,3-Dioxoisoindolin-5-ylamino)-2-(4-fluoro-3-methoxyphenyl)acetyl)-2-(2-(ethylsulfonyl)-5-(methoxycarbonylamino)phenyl)pyrrolidine-3-carboxylic acid

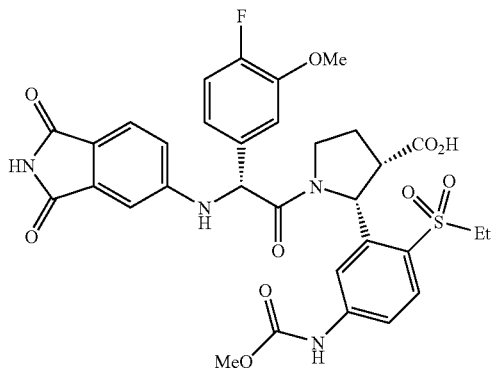

Example 47 was prepared by hydrolysis of the ethyl ester in Example 43 with NaOH in MeOH/H$_2$O at rt and purified by prep HPLC. $^1$H NMR (400 MHz, Methanol-$d_4$) δ ppm 1.25 (t, J=7.25 Hz, 3H) 2.24-2.37 (m, J=6.59 Hz, 1H) 2.36-2.54 (m, 1H) 3.10-3.22 (m, 1H) 3.42 (dd, J=14.28, 7.25 Hz, 1H) 3.46-3.59 (m, 1 H) 3.71 (s, 6H) 3.80-3.91 (m, 1H) 4.02-4.16 (m, 1H) 5.45 (s, 1H) 6.04 (s, 1H) 6.87 (dd, J=8.35, 2.20 Hz, 1H) 7.02-7.12 (m, 4H) 7.17 (dd, J=8.79, 2.20 Hz, 1H) 7.22 (s, 1H) 7.54 (d, J=8.35 Hz, 1H) 7.80 (d, J=8.79 Hz, 1H), LCMS: 683 (M+1).

Example 48

(2R,3S)-Ethyl 1-((R)-2-(3-carbamoylphenylamino)-2-(3,4-dimethoxyphenyl)acetyl)-2-(2-(isopropylsulfonyl)phenyl)pyrrolidine-3-carboxylate

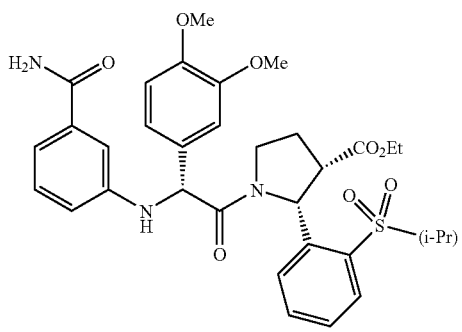

48A: (cis)-Ethyl 2-(2-(isopropylsulfonyl)phenyl)pyrrolidine-3-carboxylate hydrochloride

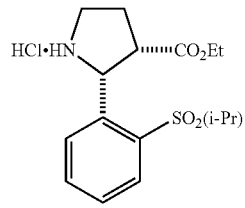

48A was prepared according to the procedure of 35A-35F starting with 2-fluorobenzaldehyde and isopropyl thiol.

48B: (2R,3S)-Ethyl 2-(2-(isopropylsulfonyl)phenyl)pyrrolidine-3-carboxylate and

48C: (2S,3R)-Ethyl 2-(2-(isopropylsulfonyl)phenyl)pyrrolidine-3-carboxylate

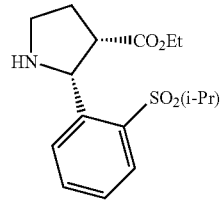

48B

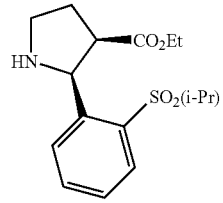

48C

The enantiomers of 48A were separated using a preparative HPLC equipped with a Chiralpak® AS column (5 cm×50 cm, 20μ). The separation was performed using an isocratic method of 10% isopropanol/heptane with 0.1% diethylamine with a flow rate of 50 mL/min. The first peak is 48B: $^1$H NMR (400 MHz, Methanol-$d_4$) δ ppm 1.13 (t, J=7.07 Hz, 3H) 1.25 (dd, J=6.82, 4.04 Hz, 6H) 2.11-2.39 (m, 2H) 3.05-3.28 (m, 3H) 3.48-3.63 (m, 1H) 3.98-4.15 (m, 2H) 5.12 (d, J=7.83 Hz, 1H) 7.47-7.58 (m, 1H) 7.71-7.77 (m, 1H) 7.77-7.84 (m, 1H) 7.95 (dd, J=8.08, 1.26 Hz, 1H). The second peak corresponds to 48C: $^1$H NMR (400 MHz, Methanol-$d_4$) δ ppm 1.08-1.17 (m, 3H) 1.20-1.30 (m, 6H) 2.10-2.39 (m, 2H) 3.01-3.27 (m, 3H) 3.46-3.66 (m, 1H) 3.97-4.14 (m, 2H) 5.13 (d, J=7.83 Hz, 1H) 7.45-7.61 (m, 1H) 7.69-7.79 (m, 1H) 7.76-7.83 (m, 1H) 7.95 (dd, J=8.08, 1.26 Hz, 1H).

48D: Example 48

Example 48 was prepared according to the general coupling condition using 48B and 1A. $^1$H NMR (400 MHz, Methanol-$d_4$) δ ppm 1.09 (t, J=7.20 Hz, 6H) 1.38 (d, J=7.07 Hz, 3H) 2.09 (dd, J=13.39, 6.82 Hz, 1H) 2.37-2.55 (m, 1H) 2.85 (d, J=7.83 Hz, 1H) 3.31-3.43 (m, 1H) 3.67-3.80 (m, 1H) 3.82 (s, 3H) 3.85 (s, 3 H) 4.03 (q, J=7.07 Hz, 2H) 4.34 (t, J=9.22 Hz, 1H) 5.46 (s, 1H) 5.98 (s, 1H) 6.81-6.91 (m, 1H) 6.93-7.01 (m, 1H) 7.03-7.10 (m, 2H) 7.10-7.21 (m, 3H) 7.41-7.49 (m, 1H) 7.52-7.57 (m, 1H) 7.59-7.70 (m, 1H) 7.87 (dd, J=7.96, 1.14 Hz, 1H), LC-MS 638 (M+H).

Example 49

Diastereoisomer of Example 48

(2R,3S)-Ethyl 1-((S)-2-(3-carbamoylphenylamino)-2-(3,4-dimethoxyphenyl)acetyl)-2-(2-(isopropylsulfonyl)phenyl)pyrrolidine-3-carboxylate

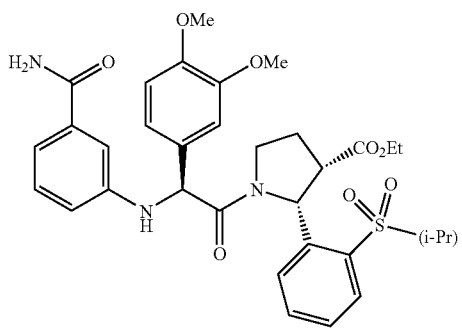

Example 49 was obtained as a diastereomer of Example 48 during its HPLC purification. $^1$H NMR (400 MHz, Methanol-$d_4$) δ ppm 1.07-1.17 (m, 3H) 1.17-1.28 (m, 3H) 1.39 (d, J=6.82 Hz, 3H) 2.09-2.36 (m, 2H) 2.78-2.90 (m, 1H) 3.68 (s, 3H) 3.75-3.91 (m, 6H) 3.95-4.09 (m, 1H) 4.19 (q, J=7.07 Hz, 2H) 5.34 (s, 1H) 6.00 (d, J=1.77 Hz, 1H) 6.66 (d, J=7.07 Hz, 1H) 6.83-6.93 (m, 2H) 6.95-7.06 (m, 2H) 7.16-7.26 (m, 3H) 7.36-7.43 (m, 1H) 7.44-7.52 (m, 1H) 7.90 (dd, J=7.83, 1.26 Hz, 1H), LC-MS 638 (M+H).

Example 50

(2R,3S)-Methyl 1-((R)-2-(3-carbamoylphenylamino)-2-(3,4-dimethoxyphenyl)acetyl)-2-(2-(isopropylsulfonyl)-5-(methoxycarbonylamino)phenyl)pyrrolidine-3-carboxylate

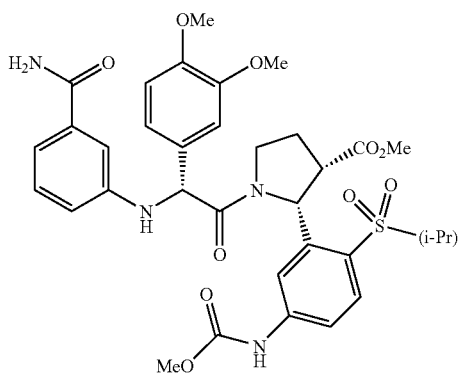

50A: 2-(Isopropylthio)-5-nitrobenzaldehyde

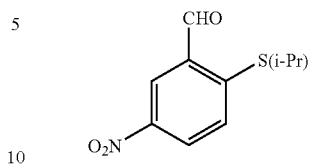

To 2-fluoro-5-nitrobenzaldehyde (5.8 g, 34.2 mmol) and 2-thiopropane (3.5 mL, 37.7 mmol) in DMF (20 mL) was added potassium carbonate (5.2 g, 37.7 mmol). The reaction mixture was stirred at 70° C. overnight. The crude reaction mixture was filtered and washed with ethyl acetate. The combined filtrate and washings were concentrated. The residue was redissolved in ethyl acetate and washed with water (3×) and then dried over sodium sulfate. Purification was performed by flash column chromatography to give 6.7 g of yellow oil 50A. $^1$H NMR (400 MHz, DMSO-$d_6$) δ ppm 1.36 (d, J=6.60 Hz, 6H) 3.73-3.93 (m, 1H) 7.77 (d, J=9.05 Hz, 1H) 8.36 (dd, J=9.05, 2.69 Hz, 1H) 8.71 (d, J=2.69 Hz, 1H) 10.20 (s, 1H).

50B: (E)-Methyl 4-(2-(isopropylthio)-5-nitrobenzylideneamino)butanoate

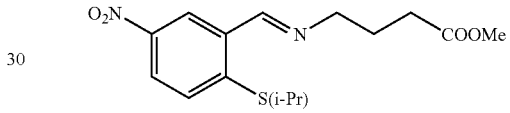

To the methyl aminobutyric ester (3.95 g, 25.7 mmol) in dichloromethane (200 mL) was added triethylamine (5.4 mL, 38.5 mmol) and then 50A (5.8 g, 25.7 mmol) and 4 Å molecular sieves (5.0 g). The reaction was stirred overnight at rt. The reaction mixture was filtered to remove the molecular sieves and the solvent was evaporated to give 12.0 g of a solid 50B together with triethylamine HCl salt. $^1$H NMR (400 MHz, Methanol-$d_4$) δ ppm 1.37 (t, J=6.24 Hz, 6H) 1.93-2.11 (m, 2H) 2.45 (t, J=7.21 Hz, 2H) 7.68 (d, J=8.80 Hz, 1H) 8.21 (dd, J=8.80, 2.69 Hz, 1H) 8.61 (d, J=2.69 Hz, 1H) 8.79 (d, J=1.47 Hz, 1H).

50C: Methyl 2-(2-(isopropylthio)-5-nitrophenyl)pyrrolidine-3-carboxylate

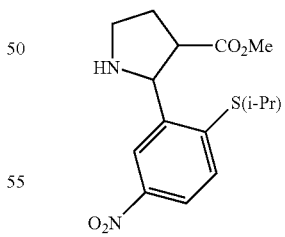

To 50B (12.0 g, 28.2 mmol) and triethylamine (7.86 mL, 56.4 mmol) in dichloromethane at −10° C. was added titanium chloride (113 mL, 1M in dichloromethane) dropwise under argon. The reaction was stirred at rt for 4 h and then quenched with saturated potassium carbonate. The mixture was filtered through Celite® and the aqueous layer was extracted with dichloromethane (2×). The organic extracts were combined, washed with brine and dried over sodium sulfate. The solvent was evaporated to give 7.3 g of crude pyrrolidine 50C.

50D: trans-1-tert-Butyl-3-methyl 2-(2-(isopropylthio)-5-nitrophenyl)pyrrolidine-1,3-dicarboxylate and

50E: cis-1-tert-Butyl-3-methyl 2-(2-(isopropylthio)-5-nitrophenyl)pyrrolidine-1,3-dicarboxylate

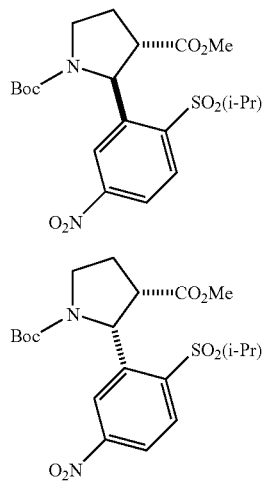

To the crude 50C (7.3 g, 22.5 mmol) in methanol (100 mL) was added triethylamine (6.3 mL, 45 mmol) and then di-tert-butyl dicarbonate (5.9 g, 27 mmol). The reaction was stirred at rt for 2 h. The solvent was removed and crude residue was redissolved in ethyl acetate. The solution was washed with water and brine and dried over sodium sulfate. The solvent was evaporated and the crude residue was purified by flash column chromatography to give 4.3 g of yellow semi-solid 50D and 50E. $^1$H NMR analysis reveals approximately a 2:1 cis:trans ratio. 50D and 50E were separated in 95% purity by repeated (3×) trituration with EtOAc/hexanes (1:3). The solid collected was identified to be 50D, the filtrate was 50E. 50D: $^1$H NMR (400 MHz, DMSO-d$_6$, 100° C.) δ ppm 1.24 (s, 9H) 1.33 (d, J=6.60 Hz, 3H) 1.36 (d, J=6.60 Hz, 3H) 2.08-2.19 (m, 2H) 2.92 (ddd, J=7.28, 3.85, 3.71 Hz, 1H) 3.50-3.61 (m, 1H) 3.67-3.73 (m, 4H) 3.73-3.82 (m, 1H) 5.35 (d, J=3.30 Hz, 1H) 7.65 (d, J=8.79 Hz, 1H) 7.85 (d, J=2.20 Hz, 1H) 8.07 (dd, J=8.52, 2.47 Hz, 1H). 50E: $^1$H NMR (400 MHz, DMSO-d$_6$, 100° C.) δ ppm 1.19 (s, 9H) 1.34 (d, J=6.60 Hz, 3H) 1.39 (d, J=6.60 Hz, 3H) 2.17 (q, J=6.96 Hz, 2H) 3.17-3.24 (s, 3H) 3.56-3.67 (m, 2H) 3.69-3.77 (m, 1H) 3.77-3.83 (m, 1H) 5.45 (d, J=8.25 Hz, 1H) 7.60 (d, J=8.79 Hz, 1H) 7.81 (d, J=2.20 Hz, 1H) 7.98-8.05 (m, 1H).

50F: cis-1-tert-Butyl 3-methyl 2-(2-(isopropylsulfonyl)-5-nitrophenyl)pyrrolidine-1,3-dicarboxylate

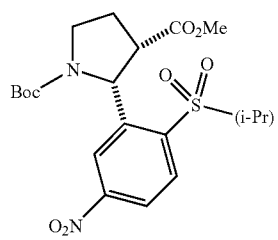

To 50E (5.5 g, 13 mmol) in CH$_2$Cl$_2$ (100 mL) was added NaHCO$_3$ (3.28 g, 39 mmol) and MCPBA (75% purity, 7.4 g, 32 mmol). The mixture was stirred at rt for 4.0 h. It was quenched with sat. NaHCO$_3$ and extracted with CH$_2$Cl$_2$. The organic layer was dried over Na$_2$SO$_4$. After removal of solvent, the crude was purified with silica gel column chromatography eluting with gradient CH$_2$Cl$_2$ in hexanes to give 50F (5.7 g, 95% yield). $^1$H NMR (500 MHz, DMSO-d$_6$, 100° C.) δ ppm 1.18 (d, J=6.60 Hz, 3H) 1.27 (s, 9H) 1.35 (d, J=6.60 Hz, 3H) 2.18 (dd, J=17.86, 6.87 Hz, 2H) 3.17 (s, 3H) 3.61-3.72 (m, 3H) 3.83 (m, 1H) 5.82 (d, J=8.25 Hz, 1H) 8.06 (s, 1H) 8.13 (d, J=8.79 Hz, 1H) 8.23-8.31 (m, 1H).

50G: cis-1-tert-Butyl 3-methyl 2-(5-amino-2-(isopropylsulfonyl)phenyl)pyrrolidine-1,3-dicarboxylate

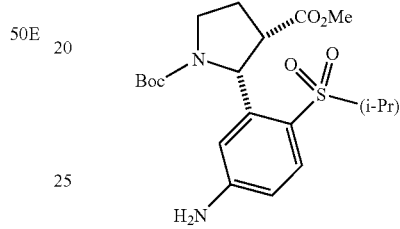

To 10% palladium on carbon (1.3 g) was added 50F (5.7 g) in methanol (150 mL) and THF (50 mL) under a stream of nitrogen. The vessel was flushed and degassed with nitrogen gas (3×) and a balloon containing hydrogen gas was introduced. The reaction was stirred at rt for 4.0 h. The catalyst was filtered through Celite® and washed with methanol several times. The filtrate and the combined washings were evaporated and dried to give 5.5 g of 50G. $^1$H NMR (400 MHz, DMSO-d$_6$, 100° C.) δ ppm 1.10 (d, J=6.60 Hz, 3H) 1.21-1.30 (m, 12H) 2.01-2.13 (m, 2H) 3.20 (s, 3H) 3.29-3.40 (m, 1H) 3.44-3.53 (m, 1H) 3.65 (ddd, J=10.17, 7.97, 5.50 Hz, 1H) 3.70-3.78 (m, 1H) 5.64 (d, J=8.25 Hz, 1H) 6.46-6.55 (m, 2H) 7.41 (d, J=7.70 Hz, 1H).

50H: (2R,3S)-1-tert-Butyl 3-methyl 2-(5-amino-2-(isopropylsulfonyl)phenyl)pyrrolidine-1,3-dicarboxylate

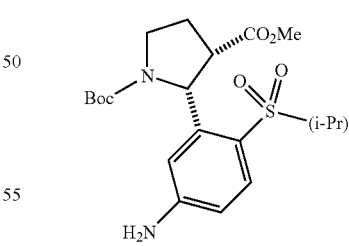

The enantiomers of the cis isomer 50G were separated using a semi-preparative HPLC equipped with a Chiralpak® AD column. The separation was performed using an isocratic method of 15% isopropanol/heptane with 0.1% diethylamine for 30 min with a flow rate of 15 mL/min. The first peak corresponds to 50H: $^1$H NMR (400 MHz, CDCl$_3$) δ ppm 1.06-1.53 (m, 15H) 1.96-2.26 (m, 3H) 3.19-3.31 (m, 3H) 3.52-4.01 (m, 3H) 5.69 (d, J=8.07 Hz, 1H) 6.41-6.67 (m, 2H) 7.66 (d, J=8.31 Hz, 1H).

50I: (2R,3S)-Methyl 2-(2-(isopropylsulfonyl)-5-(methoxycarbonyl)phenyl)pyrrolidine-3-carboxylate HCl salt

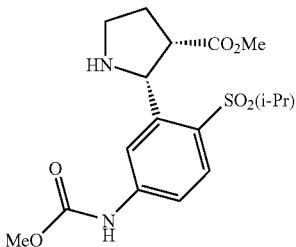

To 50H (0.09 g, 0.21 mmol) in pyridine (1 mL) at 0° C. was added methyl chloroformate (32 μL, 0.42 mmol). After 2.0 h stirring at rt the reaction was acidified with 1M HCl to pH 3-4. The product was extracted with ethyl acetate and was washed with brine and dried over sodium sulfate. After evaporation of the solvent, the crude product was redissolved in ethyl acetate (1.5 mL) and hydrogen chloride (2 mL, 4M in dioxane) was added. The reaction was stirred for 3 h at rt. The solvent was removed and placed on the lyophilizer to give 0.11 g solid 50I. $^1$H NMR (400 MHz, Methanol-$d_4$) δ ppm 1.22-1.40 (m, 6H) 2.43-2.60 (m, 1H) 2.62-2.80 (m, 1H) 3.42 (s, 3H) 3.45-3.65 (m, 2H) 3.67-3.77 (m, 1H) 3.78 (s, 3H) 3.83-3.96 (m, 1H) 5.84 (d, J=8.56 Hz, 1H) 7.55-7.67 (m, 1H) 7.81-7.90 (m, 1H) 7.94 (d, J=8.80 Hz, 1H).

50J: Example 50

Example 50 was prepared according to the general coupling condition using 1A and 50I. $^1$H NMR (400 MHz, Methanol-$d_4$) δ ppm 1.13 (d, J=6.57 Hz, 3H) 1.39 (d, J=7.07 Hz, 3H) 2.17-2.43 (m, 2H) 3.21 (s, 3H) 3.54 (q, J=7.41 Hz, 1H) 3.62 (s, 3H) 3.67 (s, 3H) 3.79-3.83 (m, 3H) 3.84-3.96 (m, 2H) 4.05-4.19 (m, 1 H) 5.36 (s, 1H) 6.02 (d, J=8.34 Hz, 1H) 6.81 (s, 1H) 6.85-6.92 (m, 3H) 6.95 (d, J=1.77 Hz, 1H) 7.09-7.41 (m, 4H) 7.71 (d, J=8.59 Hz, 1H) 9.23 (s, 1H), LC-MS 697 (M+H).

Example 51

Diastereoisomer of Example 50

(2R,3S)-Methyl 1-((S)-2-(3-carbamoylphenylamino)-2-(3,4-dimethoxyphenyl)acetyl)-2-(2-(isopropylsulfonyl)-5-(methoxycarbonylamino)phenyl)pyrrolidine-3-carboxylate

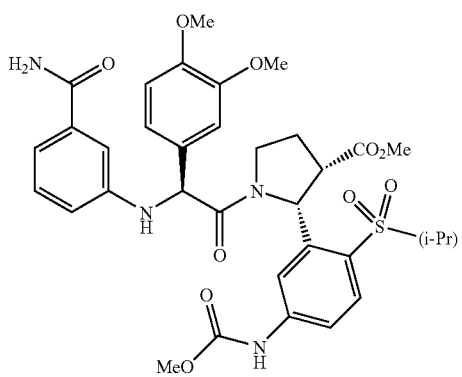

Example 51 was obtained as a diastereomer of Example 50 during its HPLC purification. $^1$H NMR (400 MHz, Methanol-$d_4$) δ ppm 1.10 (d, J=6.82 Hz, 3 H) 1.38 (d, J=6.82 Hz, 3H) 2.03 (dd, J=12.51, 7.20 Hz, 1H) 2.31-2.41 (m, 1H) 3.23 (s, 3H) 3.40-3.51 (m, 1H) 3.68-3.76 (m, 2H) 3.77-3.82 (m, 9H) 4.29-4.37 (m, 1H) 5.93 (d, J=8.59 Hz, 1H) 6.80-6.85 (m, 1H) 6.93-6.99 (m, 1H) 7.00-7.05 (m, 1H) 7.07-7.17 (m, 3H) 7.23 (d, J=1.77 Hz, 1H) 7.55 (td, J=9.22, 2.02 Hz, 2H) 7.73 (d, J=8.59 Hz, 1H) 9.54 (s, 1H), LC-MS 697 (M+H).

Example 52

(2R,3S)-1-((R)-2-(3-Carbamoylphenylamino)-2-(3,4-dimethoxyphenyl)acetyl)-2-(2-(isopropylsulfonyl)phenyl)pyrrolidine-3-carboxylic acid

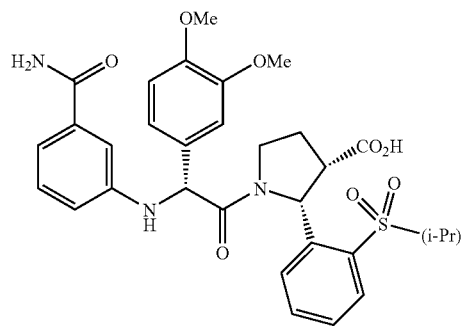

Example 52 was prepared by hydrolysis of the ethyl ester in Example 48 with NaOH in MeOH/$H_2$O at rt and purified by prep HPLC. $^1$H NMR (400 MHz, Methanol-$d_4$) δ ppm 1.16 (d, J=6.82 Hz, 3H) 1.42 (d, J=6.82 Hz, 3H) 2.16-2.38 (m, 2H) 2.87 (d, J=7.33 Hz, 1H) 3.70 (s, 3H) 3.81-3.92 (m, 5H) 3.95-4.07 (m, 1H) 5.35 (s, 1H) 6.08 (s, 1H) 6.65-6.72 (m, 1H) 6.86-6.93 (m, 1H) 6.95 (d, J=1.77 Hz, 1H) 6.98-7.09 (m, 2H) 7.17-7.27 (m, 3H) 7.38-7.46 (m, 1H) 7.46-7.54 (m, 1H) 7.93 (dd, J=7.83, 1.52 Hz, 1H), LC-MS 610 (M+H).

Example 53

(2R)-1-((R)-2-(3-Carbamoylphenylamino)-2-(3,4-dimethoxyphenyl)acetyl)-2-(2-(isopropylsulfonyl)-5-(methoxycarbonylamino)phenyl)pyrrolidine-3-carboxylic acid

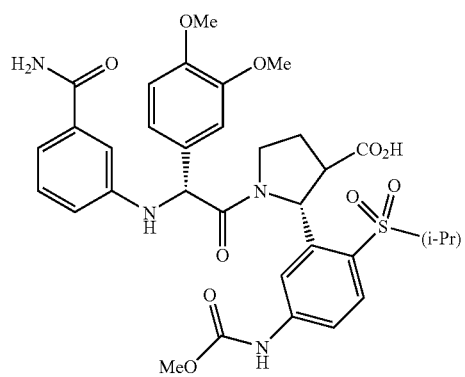

Example 53 was prepared by hydrolysis of the methyl ester in Example 50 with NaOH in MeOH/H$_2$O at rt and purified by prep HPLC. $^1$H NMR (400 MHz, Methanol-d$_4$) δ ppm 1.06-1.19 (m, 3H) 1.39 (d, J=6.82 Hz, 3H) 2.13-2.48 (m, 2H) 2.75-2.90 (m, 1H) 3.59-3.69 (m, 6H) 3.81 (s, 3H) 3.83-4.19 (m, 3 H) 5.24-5.41 (m, 1H) 5.97-6.13 (m, 1H) 6.77-7.02 (m, 5H) 7.09-7.30 (m, 4H) 7.60-7.81 (m, 1H) 9.26 (d, 1H), LC-MS 683 (M+H).

Example 54

(2R,3S)-1-((R)-2-(3-Carbamoylphenylamino)-2-(3,4-dimethoxyphenyl)acetyl)-2-(2-(isopropylsulfonyl)-5-(methoxycarbonylamino)phenyl)pyrrolidine-3-carboxylic acid

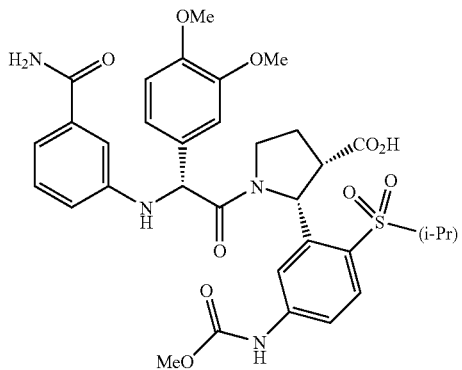

Example 54 was isolated as a single isomer during HPLC purification of Example 53. $^1$H NMR (400 MHz, Methanol-d$_4$) δ ppm 1.14 (d, J=6.57 Hz, 3H) 1.39 (d, J=7.07 Hz, 3H) 2.12-2.53 (m, 2H) 2.77-2.90 (m, 1H) 3.66 (d, J=2.53 Hz, 6H) 3.76-3.94 (m, 5H) 3.95-4.18 (m, 1H) 5.28 (s, 1H) 6.01 (s, 1H) 6.73-7.01 (m, 4H) 7.02-7.30 (m, 5H) 7.75 (d, J=8.59 Hz, 1H) 9.37 (s, 1H), LC-MS 683 (M+H).

Example 55

(2R,3S)-1-((S)-2-(3-Carbamoylphenylamino)-2-(3,4-dimethoxyphenyl)acetyl)-2-(2-(isopropylsulfonyl)-5-(methoxycarbonylamino)phenyl)pyrrolidine-3-carboxylic acid

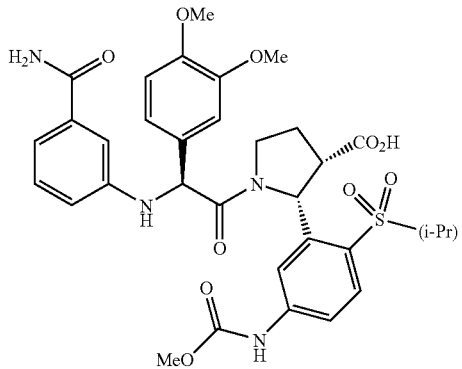

Example 55 was prepared by hydrolysis of the methyl ester in Example 51 with NaOH in MeOH/H$_2$O at rt and purified by prep HPLC. $^1$H NMR (400 MHz, Methanol-d$_4$) δ ppm 1.06-1.24 (m, 3H) 1.40 (t, J=7.58 Hz, 3H) 2.06-2.59 (m, 2H) 2.79-2.91 (m, 1H) 3.31-3.52 (m, 2H) 3.62-3.89 (m, 9H) 4.28 (t, J=9.35 Hz, 1H) 5.26-5.49 (m, 1H) 5.98 (s, 1H) 6.78-7.16 (m, 5H) 7.17-7.37 (m, 2H) 7.52-7.67 (m, 2H) 7.68-7.85 (m, 1H) 9.30-9.72 (m, 1H), LC-MS 683 (M+H).

Example 56

3-((R)-1-(3,4-Dimethoxyphenyl)-2-((R)-2-(5-(3,3-dimethylureido)-2-(isopropylsulfonyl)phenyl)pyrrolidin-1-yl)-2-oxoethylamino)benzamide

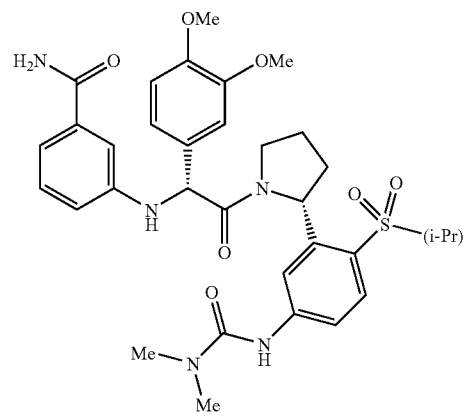

Example 56 was prepared according to the general coupling condition using 1A and 31A. $^1$H NMR (400 MHz, Methanol-d$_4$) δ ppm 1.17 (d, J=6.60 Hz, 3 H) 1.42 (d, J=7.15 Hz, 3H) 1.73 (dd, J=12.64, 5.50 Hz, 1H) 1.91-2.21 (m, 2H) 2.47 (dd, J=13.19, 7.70 Hz, 1H) 2.97 (s, 6H) 3.61 (s, 3H) 3.63-3.74 (m, 1H) 3.80-3.85 (m, 3H) 3.87-3.99 (m, 1H) 4.03-4.16 (m, 1H) 5.37 (s, 1H) 5.66 (dd, J=8.25, 4.95 Hz, 1H) 6.79 (s, 1H) 6.83-6.96 (m, 3H) 7.02 (d, J=8.25 Hz, 1H) 7.17-7.28 (m, 3H) 7.39 (dd, J=8.79, 2.20 Hz, 1H) 7.72 (d, J=8.79 Hz, 1H), LC-MS 652 (M+H).

Example 57

Diastereoisomer of Example 56

3-((S)-1-(3,4-Dimethoxyphenyl)-2-OR)-2-(5-(3,3-dimethylureido)-2-(isopropylsulfonyl)phenyl)pyrrolidin-1-yl)-2-oxoethylamino)benzamide

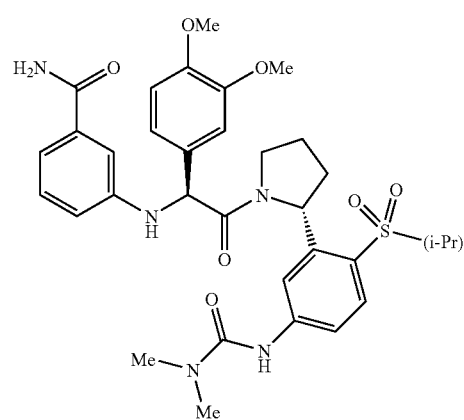

Example 57 was obtained as a diastereomer of Example 56 during its HPLC purification. ¹H NMR (400 MHz, Methanol-d₄) δ ppm 1.15 (d, J=6.60 Hz, 3 H) 1.36-1.53 (m, 3H) 1.67-2.43 (m, 4H) 2.93-3.11 (m, 6H) 3.52 (d, J=9.89 Hz, 1H) 3.64-3.93 (m, 7H) 4.05-4.19 (m, 1H) 5.38-5.47 (m, 1H) 5.60 (dd, J=8.24, 4.40 Hz, 1H) 6.90-7.09 (m, 4H) 7.09-7.21 (m, 1H) 7.21-7.47 (m, 3H) 7.65-7.79 (m, 2H), LC-MS 652 (M+H).

Example 58

(2R,3S)-Ethyl 1-(2-(3-carbamoylphenylamino)-2-(3,4-dimethoxyphenyl)acetyl)-2-(2-(cyclopropylsulfonyl)phenyl)pyrrolidine-3-carboxylate

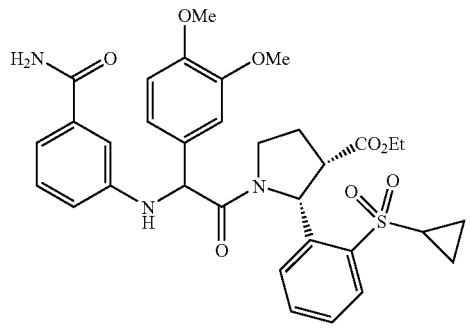

58A: 2-(Cyclopropylthio)benzonitrile

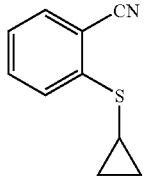

To a solution of 0.5 M cyclopropyl magnesium bromide in THF (150 mL, 75 mmol) at −78° C. was added 2,2'-dithio-bis(benzonitrile) (Sumitomo Seika Chemical Co., 6.4 g, 23.4 mmol). The mixture was stirred between −70 to −65° C. for 15 min before it was quenched with sat. NH₄Cl (200 mL) and extracted with ethyl acetate. The organic layer was washed with brine, dried (Na₂SO₄), filtered and concentrated. The resulting residue was purified via silica gel chromatography (0-30% ethyl acetate in hexanes) to provide 58A (4.0 g, 100%) as an oil. ¹H NMR (400 MHz, CDCl₃) δ ppm 0.74 (ddd, J=6.70, 4.83, 4.72 Hz, 2H) 1.10-1.16 (m, 2H) 2.20-2.26 (m, 1H) 7.16-7.21 (m, 1H) 7.48-7.52 (m, 1H) 7.55 (d, J=7.91 Hz, 1H) 7.62 (d, J=7.91 Hz, 1H).

58B: 2-(Cyclopropylthio)benzaldehyde

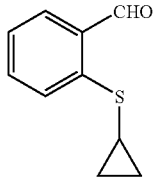

To 58A (3.4 g, 19.4 mmol) in toluene (30 mL) at −78° C. was added 1.5 M DIBAL in toluene (18.1 mL, 27.2 mmol) slowly. After stirring for 1.5 h, another portion of DIBAL (3.8 mL, 5.7 mmol) was added and stirred for additional 50 min. TLC indicated a clean conversion of 58A. The reaction was quenched at −78° C. with acetic acid (28 mL) and water (15 mL). After stirring at rt for 1.0 h, it was extracted with diethyl ether. The organic layer was washed with sat. NaHCO₃, brine, dried (Na₂SO₄), filtered and concentrated. The resulting residue was purified via silica gel chromatography (0-30% ethyl acetate/hexanes) to provide 58B (3.4 g, 95%) as an oil. ¹H NMR (400 MHz, CDCl₃) δ ppm 0.69-0.76 (m, 2H) 1.10-1.17 (m, 2H) 2.07-2.15 (m, 1H) 7.27 (t, J=7.47 Hz, 1H) 7.49-7.56 (m, 1H) 7.77 (d, J=7.47 Hz, 2H) 10.14 (s, 1H).

58C: (E)-Ethyl 4-(2-(cyclopropylthio)benzylideneamino)butanoate

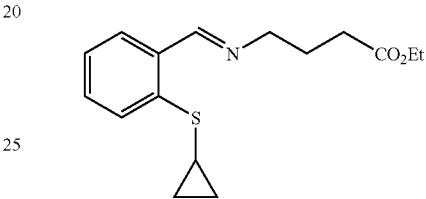

To ethyl aminobutyric ester HCl salt (2.56 g, 15.3 mmol) in CH₂Cl₂ (50 mL) was added 4 Å molecular sieve (1.3 g), Et₃N (3.2 mL, 23 mmol) and 58B (2.72 g, 15.3 mmol). The mixture was stirred at rt over night. After removal of the solid by filtration, the filtrate was concentrated to give a white solid containing imine 58C and triethylamine HCl salt. The triethylamine HCl salt could be completely removed by trituration with dry diethyl ether and filtration. However, presence of the salt did not affect the next step conversion. ¹H NMR (400 MHz, CDCl₃) δ ppm 0.65 (ddd, J=6.37, 4.83, 4.61 Hz, 2H) 0.99-1.06 (m, 2H) 1.18 (t, J=7.25 Hz, 3H) 1.94-2.02 (m, J=7.14, 7.14, 7.03, 6.81 Hz, 2H) 2.02-2.10 (m, 1H) 2.36 (t, J=7.47 Hz, 2 H) 3.60 (t, J=6.15 Hz, 2H) 4.06 (q, J=7.18 Hz, 2H) 7.13 (t, J=7.47 Hz, 1H) 7.27-7.34 (m, 1H) 7.59 (d, J=8.35 Hz, 1H) 7.73 (d, J=7.47 Hz, 1H) 8.53 (s, 1H).

58D: 1-tert-Butyl 3-ethyl 2-(2-(cyclopropylthio)phenyl)pyrrolidine-1,3-dicarboxylate

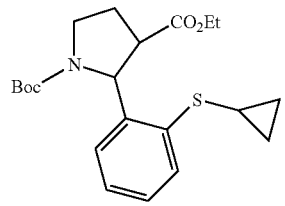

To 58C (15 mmol) in CH₂Cl₂ (100 mL) at −15° C. was added Et₃N (2.1 mL, 15 mmol) followed by TiCl₄ (1.0 M in CH₂Cl₂, 30 mL, 30 mmol). The mixture was stirred from −15° C. to rt over 3.0 h before it was quenched with sat. K₂CO₃ (100 mL) at 0° C. and stirred at rt for 1.0 h. The mixture was filtered through a pad of wet Celite®, extracted with CH₂Cl₂ (3×40 mL). The organic layer was washed with water, dried over Na₂SO₄. A small portion of the dried organic layer was concentrated to give crude ethyl 2-(2-(cyclopropylthio)phenyl)pyrrolidine-3-carboxylate: $^1$H NMR indicated a mixture of cis and trans isomer in ca. 1:1 ratio. LC-MS 292 (M+H). To the above ethyl 2-(2-(cyclopropylthio)phenyl) pyrrolidine-3-carboxylate in CH$_2$Cl$_2$ was added Et$_3$N (2.1 mL, 15 mmol) and di-tert-butyl dicarbonate (1.0 M in THF, 15 mL, 15 mmol). The mixture was stirred at rt over night before it was quenched with 0.5 N HCl (50 mL). The organic layer was washed with brine, dried (Na$_2$SO$_4$), filtered and concentrated. The resulting residue was purified via silica gel chromatography (0-30% ethyl acetate/hexanes) to provide 58D (3.3 g, 56%) as an oil. $^1$H NMR indicated a mixture of cis and trans isomer in 1:1 ratio. $^1$H NMR (400 MHz, CDCl$_3$) δ ppm 0.66-0.75 (m, 2H) 0.87 (t, J=7.03 Hz, 3 H) 1.05-1.08 (m, 2H) 1.14-1.16 (s, 9H) 2.02-2.18 (m, 3H) 3.43-4.19 (m, 5H) 7.06-7.13 (m, 2H) 7.16-7.25 (m, 1H) 7.51-7.60 (m, 1H); LC-MS 292 (M+H).

58E: 1-tert-Butyl 3-ethyl 2-(2-(cyclopropylsulfonyl) phenyl)pyrrolidine-1,3-dicarboxylate

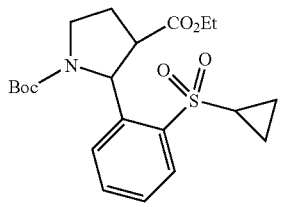

To 58D (3.3 g, 8.43 mmol) in EtOH (25 mL) at 0° C. was added a solution of Oxone® (11.4 g, 18.6 mmol) in water (60 mL). The mixture was stirred at rt over night. The precipitate was filtered. The filtrate was neutralized with sat. NaHCO$_3$ and EtOH was removed under reduced pressure. The residue was extracted with EtOAc. The organic layer was washed with brine, dried (Na$_2$SO$_4$), filtered and concentrated to give crude 58E with >90% purity. $^1$H NMR of the crude 58E indicated a mixture of cis and trans isomer in ca 1:1 ratio and complicated by the presence of rotomers. LC-MS 424 (M+H).

58F: cis-Ethyl 2-(2-(cyclopropylsulfonyl)phenyl) pyrrolidine-3-carboxylate and

58G: trans-Ethyl 2-(2-(cyclopropylsulfonyl)phenyl) pyrrolidine-1,3-dicarboxylate

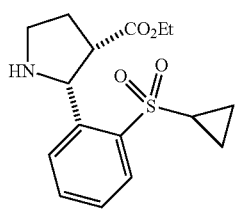

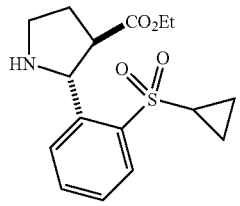

The cis and trans diastereomers of 58E were separated by the preparative HPLC equipped with a C18 Luna column (30×100 mm, 5μ). The separations were performed using a linear gradient (mobile phase A:10% Acetonitrile—90% water—0.1% TFA; mobile phase B: 90% Acetonitrile—10% water—0.1% TFA; 40 to 65% B in 10 min, then 65% B for 2 min) with a flow rate of 40 mL/min. 58F was obtained as HCl salt after treatment of the cis isomer with 4.0 N HCl in dioxane (50 eq.), LC-MS 324 (M+H); 58G was obtained as HCl salt after treatment of the trans isomer with 4.0N HCl in dioxane (50 eq.), LC-MS 324 (M+H).

58H: (2R,3S)-Ethyl 2-(2-(cyclopropylsulfonyl)phenyl)pyrrolidine-3-carboxylate and 58I: (2S,3R)-Ethyl 2-(2-(cyclopropylsulfonyl)phenyl)pyrrolidine-3-carboxylate

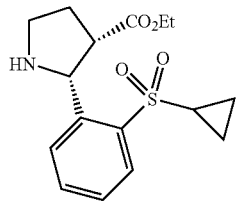

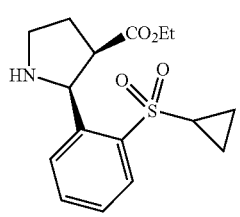

The enantiomers of racemic cis 58F were separated using a semi-preparative HPLC equipped with a Chiralpak® AS-H column (250 mm×20 mm, 5μ). The separation was performed using an isocratic method of 10% isopropanol/heptane with 0.1% diethylamine with a flow rate of 15 mL/min. The first peak is 58H: $^1$H NMR (400 MHz, Methanol-d$_4$) δ ppm 0.73 (t, J=7.20 Hz, 3H) 0.99-1.37 (m, 4H) 2.09-2.23 (m, 1H) 2.28-2.44 (m, 1H) 2.80-2.94 (m, 1H) 2.95-3.09 (m, 1H) 3.37-3.75 (m, 4H) 5.32 (d, J=8.34 Hz, 1H) 7.46-7.56 (m, 1H) 7.59-7.72 (m, 2H) 7.90-7.98 (m, 1H). The second peak is 58I: $^1$H NMR (400 MHz, Methanol-d$_4$) δ ppm 0.73 (t, J=7.07 Hz, 3H) 0.99-1.37 (m, 4H) 2.11-2.25 (m, 1H) 2.30-2.45 (m, 1H) 2.81-2.93 (m, 1H) 2.97-3.15 (m, 1H) 3.39-3.75 (m, 4H) 5.38 (d, J=8.34 Hz, 1H) 7.44-7.58 (m, 1H) 7.64 (d, J=3.79 Hz, 2H) 7.96 (t, 1H).

58J: (2R,3R)-Ethyl 2-(2-(cyclopropylsulfonyl)phenyl)pyrrolidine-3-carboxylate and 58K: (2S,3S)-Ethyl 2-(2-(cyclopropylsulfonyl)phenyl)pyrrolidine-3-carboxylate

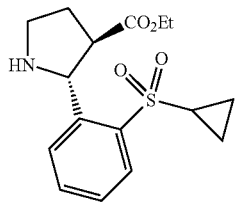
58J

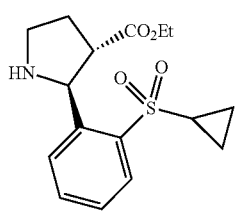
58K

The enantiomers of racemic trans 58G were separated using a preparative HPLC equipped with a Chiralpak® AS column (5 cm×50 cm, 20μ). The separation was performed using an isocratic method of 10% isopropanol/heptane with 0.1% diethylamine with a flow rate of 50 mL/min. The first peak is 58J: $^1$H NMR (400 MHz, Methanol-$d_4$) δ ppm 1.02-1.37 (m, 7H) 2.18-2.31 (m, 1H) 2.31-2.50 (m, 1H) 2.89-3.09 (m, 2H) 3.15-3.29 (m, 2H) 3.98-4.16 (m, 2H) 5.38 (d, J=7.83 Hz, 1H) 7.48-7.60 (m, 1H) 7.68-7.78 (m, 1H) 7.78-7.86 (m, 1H) 7.93 (dd, J=7.83, 1.26 Hz, 1H). The second peak is 58K: $^1$H NMR (400 MHz, Methanol-$d_4$) δ ppm 1.01-1.33 (m, 7H) 2.15-2.29 (m, 1H) 2.30-2.43 (m, 1H) 2.88-3.27 (m, 4H) 4.00-4.14 (m, 2H) 5.35 (d, J=7.83 Hz, 1H) 7.50-7.58 (m, 1H) 7.70-7.78 (m, 1H) 7.79-7.85 (m, 1H) 7.92 (dd, J=7.96, 1.39 Hz, 1H).

58L: Example 58

Example 58 was prepared according to the general coupling condition using 1A and 58H. $^1$H NMR (400 MHz, Methanol-$d_4$) δ ppm 0.55-0.87 (m, 3H) 0.85-1.16 (m, 3H) 1.27-1.48 (m, 1H) 2.12-2.39 (m, 2H) 3.04-3.21 (m, 1H) 3.40-3.72 (m, 5H) 3.74-3.91 (m, 5H) 4.17-4.44 (m, 1H) 5.32-5.47 (m, 1H) 6.11-6.27 (m, 1H) 6.42 (d, J=7.83 Hz, 1H) 6.75-7.06 (m, 3H) 7.06-7.30 (m, 4H) 7.31-7.55 (m, 2H) 7.70-7.91 (m, 1H), LC-MS 636 (M+H).

Example 59

3-((R)-2-((R)-2-(5-(3,3-Dimethylureido)-2-(isopropylsulfonyl)phenyl)pyrrolidin-1-yl)-1-(4-fluoro-3-methoxyphenyl)-2-oxoethylamino)benzamide

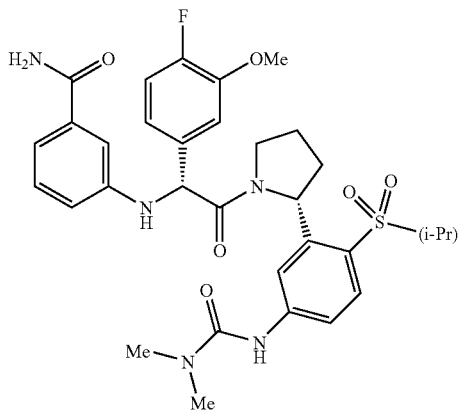

Example 59 was prepared according to the general coupling condition using 7D and 31A. $^1$H NMR (400 MHz, Methanol-$d_4$) δ ppm 1.15 (d, J=6.57 Hz, 3 H) 1.40 (d, J=6.82 Hz, 3H) 1.64-1.80 (m, 1H) 1.92-2.20 (m, 2H) 2.39-2.57 (m, 1H) 2.97 (s, 6H) 3.62-3.76 (m, 4H) 3.81-3.95 (m, 1H) 4.06-4.18 (m, 1H) 5.38 (s, 1H) 5.63 (dd, J=8.08, 5.05 Hz, 1H) 6.78-6.89 (m, 2H) 6.93-7.08 (m, 3H) 7.09-7.22 (m, 3H) 7.25 (dd, J=8.72, 2.15 Hz, 1H) 7.69 (d, J=8.84 Hz, 1H), LC-MS 640 (M+H).

Example 60

Diastereoisomer of Example 59

3-((S)-2-((R)-2-(5-(3,3-Dimethylureido)-2-(isopropylsulfonyl)phenyl)pyrrolidin-1-yl)-1-(4-fluoro-3-methoxyphenyl)-2-oxoethylamino)benzamide

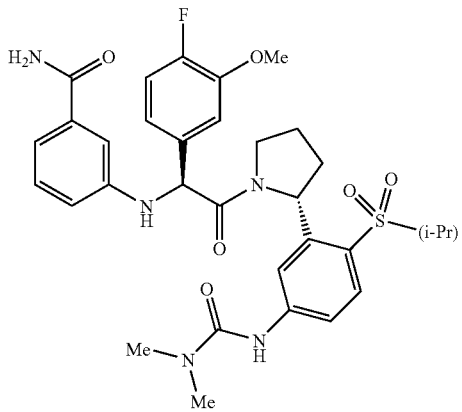

Example 60 was obtained as a diastereomer of Example 59 during its HPLC purification. $^1$H NMR (400 MHz, Methanol-$d_4$) δ ppm 1.08-1.19 (m, 3H) 1.32-1.51 (m, 3H) 1.66-1.96 (m, 2H) 2.08-2.23 (m, 1H) 2.26-2.43 (m, 1H) 2.93-3.10 (m, 6H) 3.60-3.72 (m, 1H) 3.70-3.81 (m, J=6.82, 6.82 Hz, 1H) 3.81-3.89 (m, 3H) 4.08-4.24 (m, 1H) 5.42 (s, 1H) 5.50-5.62 (m, 1H) 6.78-6.92 (m, 1 H) 6.98-7.14 (m, 3H) 7.15-7.26 (m, 3H) 7.38 (dd, J=8.72, 2.15 Hz, 1H) 7.64-7.77 (m, 2H), LC-MS 640 (M+H).

Example 61

(2R,3S)-1-((R)-2-(3-Carbamoylphenylamino)-2-(3,4-dimethoxyphenyl)acetyl)-2-(2-(cyclopropylsulfonyl)phenyl)pyrrolidine-3-carboxylic acid

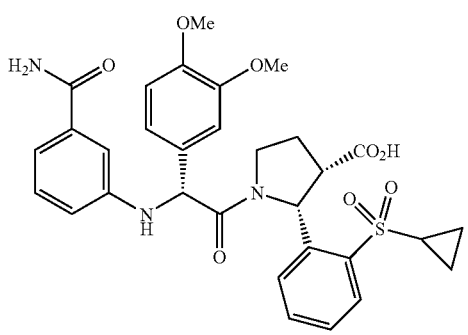

Example 61 was prepared by hydrolysis of the ethyl ester in Example 58 with NaOH in MeOH/H$_2$O at rt and purified by prep HPLC. $^1$H NMR (400 MHz, Methanol-d$_4$) δ ppm 0.89-1.57 (m, 4H) 2.07-2.59 (m, 2H) 2.85 (d, J=2.53 Hz, 1H) 2.96-3.13 (m, 1H) 3.62-3.75 (m, 1H) 3.78-3.92 (m, 6H) 4.33-4.46 (m, 1H) 5.48 (s, 1H) 6.23 (s, 1H) 6.78-6.88 (m, J=7.83 Hz, 1H) 6.92-7.01 (m, 1H) 7.02-7.20 (m, 5H) 7.39-7.48 (m, 1H) 7.53-7.67 (m, 2H) 7.81-7.87 (m, 1H), LC-MS 608 (M+H).

Example 62

Diastereoisomer of Example 61

(2R,3S)-1-((S)-2-(3-Carbamoylphenylamino)-2-(3,4-dimethoxyphenyl)acetyl)-2-(2-(cyclopropylsulfonyl)phenyl)pyrrolidine-3-carboxylic acid

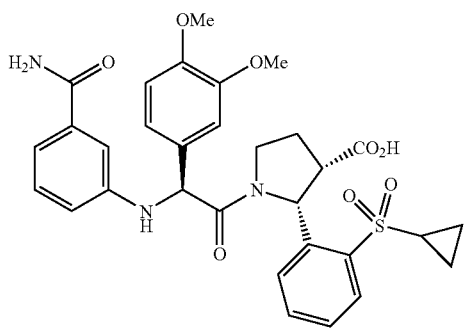

Example 62 was obtained as a diastereomer of Example 61 during its HPLC purification. $^1$H NMR (400 MHz, Methanol-d$_4$) δ ppm 0.92-1.19 (m, 2H) 1.24-1.36 (m, 1H) 1.37-1.52 (m, 1H) 2.17-2.38 (m, 2H) 2.87 (d, J=10.36 Hz, 1H) 3.03-3.18 (m, 1H) 3.68-3.82 (m, 3H) 3.82-3.94 (m, 4H) 3.96-4.14 (m, J=7.07 Hz, 1H) 5.32 (s, 1H) 6.25 (s, 1H) 6.67 (d, J=7.83 Hz, 1H) 6.79-6.87 (m, 1H) 6.94-7.03 (m, 2H) 7.04-7.26 (m, 4H) 7.31-7.44 (m, 1H) 7.43-7.55 (m, 1H) 7.88 (dd, J=7.83, 1.26 Hz, 1H), LC-MS 608 (M+H).

Example 63

(2R,3S)-Ethyl 1-((R)-2-(3-carbamoylphenylamino)-2-(4-fluoro-3-methoxyphenyl)acetyl)-2-(2-(cyclopropylsulfonyl)phenyl)pyrrolidine-3-carboxylate

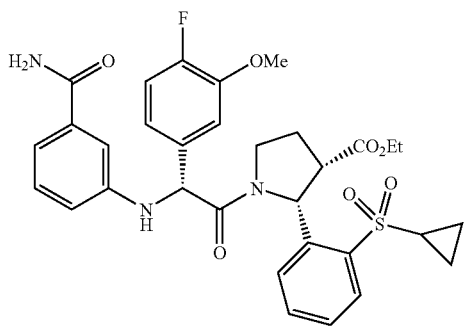

Example 63 was prepared according to the general coupling condition using 7D and 58H. $^1$H NMR (400 MHz, Methanol-d$_4$) δ ppm 0.70-0.87 (m, 3H) 0.90-1.18 (m, 3H) 1.35-1.48 (m, 1H) 2.06 (dd, J=12.76, 7.20 Hz, 1H) 2.34-2.48 (m, 1H) 3.04-3.19 (m, 1H) 3.44-3.59 (m, 2H) 3.62-3.82 (m, 3H) 3.88 (s, 3H) 4.37-4.50 (m, 1H) 5.44-5.52 (m, 1H) 6.22 (d, J=8.59 Hz, 1H) 6.78-6.90 (m, 1H) 7.01-7.11 (m, 1H) 7.08-7.21 (m, 4H) 7.27 (dd, J=8.08, 2.02 Hz, 1H) 7.33-7.42 (m, 1H) 7.41-7.47 (m, 1H) 7.47-7.56 (m, 1H), LC-MS 624 (M+H).

Example 64

Diastereoisomer of Example 63

(2R,3S)-Ethyl 1-((S)-2-(3-carbamoylphenylamino)-2-(4-fluoro-3-methoxyphenyl)acetyl)-2-(2-(cyclopropylsulfonyl)phenyl)pyrrolidine-3-carboxylate

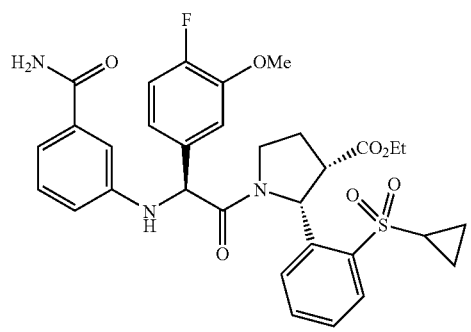

Example 64 was obtained as a diastereomer of Example 63 during its HPLC purification. $^1$H NMR (400 MHz, Methanol-d$_4$) δ ppm 0.71 (t, J=7.20 Hz, 3H) 0.89-1.17 (m, 3H) 1.34-1.46 (m, 1H) 2.19-2.36 (m, 2H) 3.10-3.23 (m, 1H) 3.30-3.40 (m, 1H) 3.50-3.69 (m, 2H) 3.75 (s, 3H) 3.86 (dd, J=10.23, 7.20 Hz, 1H) 4.20-4.36 (m, 1H) 5.45 (s, 1H) 6.22 (d, J=8.59 Hz, 1H) 6.43 (d, J=7.07 Hz, 1H) 6.79-6.87 (m, 1H) 6.98-7.19 (m, 6H) 7.20-7.27 (m, 1H) 7.33-7.44 (m, 1H) 7.80 (dd, J=7.83, 1.26 Hz, 1H), LC-MS 624 (M+H).

Example 64

Diastereoisomer of Example 63

(2R,3S)-Ethyl 1-((S)-2-(3-carbamoylphenylamino)-2-(4-fluoro-3-methoxyphenyl)acetyl)-2-(2-(cyclopropylsulfonyl)phenyl)pyrrolidine-3-carboxylate

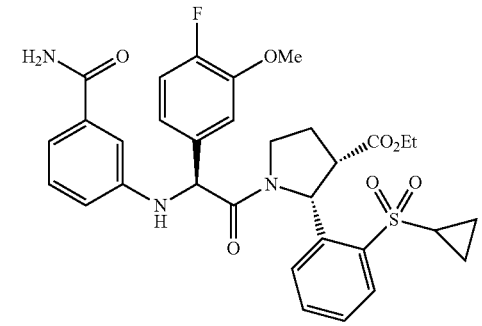

Example 64 was obtained as a diastereomer of Example 63 during its HPLC purification. $^1$H NMR (400 MHz, Methanol-d$_4$) δ ppm 0.71 (t, J=7.20 Hz, 3H) 0.89-1.17 (m, 3H) 1.34-1.46 (m, 1H) 2.19-2.36 (m, 2H) 3.10-3.23 (m, 1H) 3.30-3.40

(m, 1H) 3.50-3.69 (m, 2H) 3.75 (s, 3H) 3.86 (dd, J=10.23, 7.20 Hz, 1H) 4.20-4.36 (m, 1H) 5.45 (s, 1H) 6.22 (d, J=8.59 Hz, 1H) 6.43 (d, J=7.07 Hz, 1H) 6.79-6.87 (m, 1H) 6.98-7.19 (m, 6H) 7.20-7.27 (m, 1H) 7.33-7.44 (m, 1H) 7.80 (dd, J=7.83, 1.26 Hz, 1H), LC-MS 624 (M+H).

Example 65

(2R,3R)-1-((R)-2-(3-Carbamoylphenylamino)-2-(4-fluoro-3-methoxyphenyl)acetyl)-2-(3-(isopropylsulfonyl)pyridin-2-yl)pyrrolidine-3-carboxylic acid

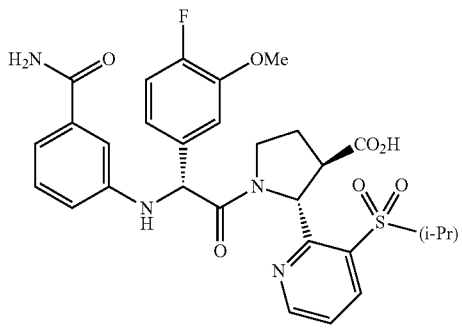

65A: 3-Fluoropicolinaldehyde

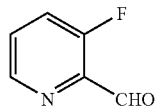

To a solution of DABCO (8.8 g, 78.2 mmol) in anhydrous diethyl ether (250 mL) at −25° C. was added n-BuLi (1.6 M in hexanes, 49 mL, 78.2 mmol). The mixture was stirred between −25 to −10° C. for 45 min and then cooled to −70° C. To the above solution was added 3-fluoropyridine (5.9 mL, 71 mmol) dropwise. The reaction was stirred between −70 to −60° C. for 1.5 h before DMF (11.0 mL, 2.0 eq.) was added. After 1.0 h stirring at −70° C., water (150 mL) was added and warmed up to rt. The layers were separated and the aqueous layer was extracted with methylene chloride (5×100 mL). The combined organic layer was washed with brine and dried over $Na_2SO_4$. After removal of solvent, the crude was purified by silica gel column chromatography using gradient EtOAc in hexanes to give 5.4 g (55-60% yield) of 65A. $^1$H NMR (400 MHz, $CDCl_3$) δ ppm 7.54-7.57 (m, 2H) 8.61 (d, J=2.20 Hz, 1H) 10.20 (s, 1H).

65B: 3-(Isopropylthio)picolinaldehyde

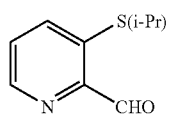

To 65A (5.4 g, 43 mmol) and 2-thiopropane (6.0 mL, 65 mmol) in DMF (50 mL) was added potassium carbonate (10.4 g, 75 mmol). The reaction mixture was stirred at 60° C. for 4.0 h. The crude reaction mixture was diluted and extracted with ethyl acetate, washed with water (3×) and then dried over sodium sulfate. Purification was performed by flash column chromatography using gradient EtOAc in hexanes to give 5.7 g (73% yield) of yellow solid 65B. $^1$H NMR (400 MHz, $CDCl_3$) δ ppm 1.42 (d, J=6.59 Hz, 6H) 3.49-3.59 (m, 1H) 7.41 (dd, J=8.35, 4.39 Hz, 1H) 7.76 (d, J=8.35 Hz, 1H) 8.54 (d, J=3.08 Hz, 1H) 10.21 (s, 1H).

65C: (E)-Ethyl 4-((3-(isopropylthio)pyridin-2-yl)methyleneamino)butanoate

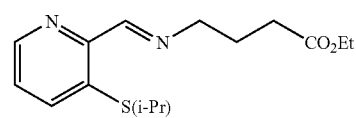

To ethyl aminobutyric ester (1.68 g, 10 mmol) in dichloromethane (30 mL) was added triethylamine (2.1 mL, 15 mmol) and then 65B (1.82 g, 10 mmol) and 4 Å molecular sieves (0.8 g). The reaction was stirred overnight at rt. The reaction mixture was filtered to remove the molecular sieves and the solvent was evaporated to give a solid 65C together with triethylamine HCl salt. $^1$H NMR (400 MHz, $CDCl_3$) δ ppm 1.18-1.24 (t, J=7.32 Hz, 3H) 1.28 (d, J=6.59 Hz, 6H) 2.04-2.13 (m, 2H) 2.41 (t, J=7.47 Hz, 2H) 3.27-3.37 (m, 1H) 3.73 (t, J=5.93 Hz, 2H) 4.09 (q, J=7.32 Hz, 2H) 7.21-7.27 (m, 1H) 7.71-7.76 (m, 1H) 8.53 (d, J=3.08 Hz, 1H) 8.83 (s, 1H).

65D: trans-1-tert-Butyl 3-ethyl 2-(3-(isopropylthio)pyridin-2-yl)pyrrolidine-1,3-dicarboxylate and 65E: cis-1-tert-Butyl 3-ethyl 2-(3-(isopropylthio)pyridin-2-yl)pyrrolidine-1,3-dicarboxylate

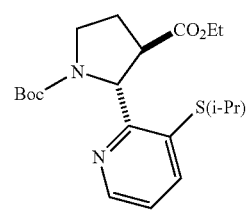

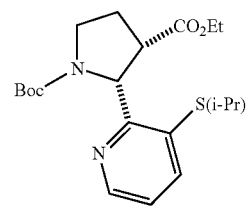

To 65C (10 mmol) in $CH_2Cl_2$ (100 mL) at −15° C. was added $Et_3N$ (1.4 mL, 10 mmol) followed by $TiCl_4$ (1.0 M in $CH_2Cl_2$, 20 mL, 20 mmol). The mixture was stirred from −15° C. to rt over 3.0 h before it was quenched with sat. $K_2CO_3$ (100 mL) at 0° C. and stirred at rt for 1.0 h. Methylene chloride was removed under vacuum and the crude was diluted with EtOAc. The mixture was filtered through a pad of wet Celite®, extracted with EtOAc (3×40 mL). The organic layer was washed with water, dried over $Na_2SO_4$. A small portion of the dried organic layer was concentrated to give crude ethyl 2-(3-(isopropylthio)pyridin-2-yl)pyrrolidine-3-carboxylate: ¹H NMR indicated a mixture of cis and trans isomer in ca. 1:3 ratio. LC-MS 295 (M+H). To the above ethyl 2-(3-(isopropylthio)pyridin-2-yl)pyrrolidine-3-carboxylate in THF (10 mL) was added Et₃N (1.4 mL) and di-tert-butyl dicarbonate (1.0 M in THF, 10 mL, 10 mmol). The mixture was stirred at rt over night before it was quenched with 0.5 N HCl (50 mL). The organic layer was washed with brine, dried (Na₂SO₄), filtered and concentrated. The resulting residue was purified via silica gel chromatography (gradient ethyl acetate in hexanes) to provide a major product trans 65D (1.8 g, 45% yield) and a minor product cis 65E (900 mg still contaminated with 65D, 20% yield). 65D: ¹H NMR (400 MHz, CDCl₃) δ ppm two rotomers: 1.07-1.16 (m, 6H) 1.25 (t, J=6.81 Hz, 3H) 1.30 and 1.39 (s, 9 H) 2.12-2.20 (m, 1H) 2.22-2.32 (m, 1H) 2.93-3.04 (m, 1H) 3.32-3.44 (m, 1H) 3.60-3.70 (m, 1H) 3.73-3.83 (m, 1H) 4.17 (q, J=7.18 Hz, 2H) 5.61 and 5.75 (d, J=3.95 Hz, 1H) 7.11 (dd, J=7.47, 4.83 Hz, 1H) 7.62 (d, J=7.91 Hz, 1H) 8.38 (d, J=3.52 Hz, 1H); LC-MS 395 (M+H). 65E: ¹H NMR (400 MHz, CDCl₃) δ ppm two rotomers: 0.93 (t, J=6.81 Hz, 3H) 1.12-1.33 (m, 15H) 2.48-2.58 (m, 1H) 3.35-4.12 (m, 6H) 5.67 and 5.88 (d, J=7.91 Hz, 1H) 7.08 (dd, J=7.47, 4.39 Hz, 1H) 7.53-7.65 (m, 1H) 8.36 (d, J=3.08 Hz, 1H). LC-MS 395 (M+H).

65F: trans-1-tert-Butyl 3-ethyl 2-(3-(isopropylsulfonyl)pyridin-2-yl)pyrrolidine-1,3-dicarboxylate

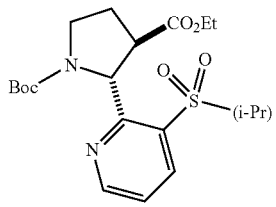

To 65D (1.51 g, 3.83 mmol) in EtOH (25 mL) at 0° C. was added Oxone® (3.53 g, 1.5 eq.) in water (25 mL). The mixture was stirred from 0° C. to rt over 18 h. It was quenched with sat. NaHCO₃ and Na₂S₂O₃. The precipitate was removed by filtration and the filtrate was condensed, diluted with EtOAc and washed with brine. The organic layer was dried over Na₂SO₄. After removal of solvent, the crude was purified by silica column chromatography using gradient EtOAc in hexanes to give 65F (1.51 g, 90% yield). ¹H NMR (400 MHz, 90° C., DMSO-d₆) δ ppm 1.19 and 1.32 (br s, 18H) 2.10 (br s 1H) 2.34 (br s, 1H) 2.95 (br s, 1H) 3.49 and 3.70 (br 3H), 4.12 (br s, 2H), 5.79 (br s, 1H), 7.57 (br s, 1H), 8.20 (br s, 1H), 8.81 (br s, 1 H). LS-MS 427 (M+H).

65G: trans-Ethyl 2-(3-(isopropylsulfonyl)pyridin-2-yl)pyrrolidine-3-carboxylate

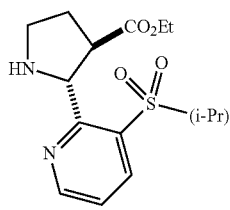

To 65F (1.51 g, 3.53 mmol) in EtOAc (15 mL) at rt was added 4.0 N HCl in dioxane (15 mL, 60 mmol). The mixture was stirred at rt for 8.0 h. After removal of the solvent, the crude was diluted in methylene chloride and washed with sat. NaHCO₃. The aqueous was extracted with methylene chloride (3×80 mL). The combined organic layer was dried over Na₂SO₄. After removal of solvent 65G (1.1 g, 95% yield) was obtained as viscous oil. ¹H NMR (400 MHz, Methanol-d₄) δ ppm 1.15 (t, J=7.03 Hz, 3H) 1.25 (d, J=7.03 Hz, 3H) 1.30 (d, J=7.03 Hz, 3H) 2.11-2.38 (m, 2H) 3.00-3.12 (m, 1H) 3.24-3.29 (m, 1H) 3.36-3.47 (m, 1H) 3.53-3.64 (m, 1H) 4.02-4.14 (m, 2H) 7.58 (dd, J=7.91, 4.83 Hz, 1H) 8.32 (dd, J=8.35, 1.76 Hz, 1H) 8.83-8.93 (m, 1H); LC-MS 327 (M+H).

65H: (2R,3R)-Ethyl 2-(3-(isopropylsulfonyl)pyridin-2-yl)pyrrolidine-3-carboxylate and 65I: (2S,3S)-Ethyl 2-(3-(isopropylsulfonyl)pyridin-2-yl)pyrrolidine-3-carboxylate

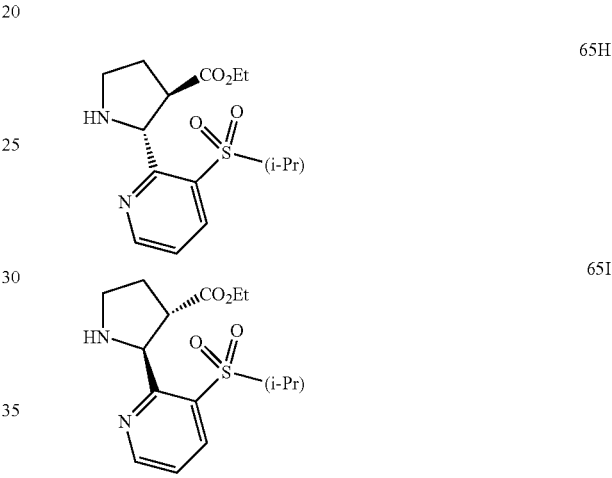

65G were separated using a preparative HPLC equipped with a Chiralpak® AD column (5 cm×50 cm, 20µ). The separations were performed using an isocratic method of 15% isopropanol/heptane with 0.1% diethylamine with a flow rate of 50 mL/min. 65H: ¹H NMR (400 MHz, CDCl₃) δ ppm 0.80 (t, J=7.20 Hz, 3H) 1.24 (d, J=6.82 Hz, 3H) 1.32 (d, J=6.82 Hz, 3H) 2.04-2.19 (m, 1H) 2.32-2.48 (m, 1H) 2.91-3.06 (m, 1H) 3.36-3.58 (m, 4H) 3.66-3.80 (m, 1H) 5.12 (d, J=7.58 Hz, 1H) 7.56 (dd, J=7.96, 4.67 Hz, 1H) 8.31 (dd, J=7.96, 1.64 Hz, 1H) 8.76 (dd, J=4.67, 1.64 Hz, 1H); 65I: ¹H NMR (400 MHz, CDCl₃) δ ppm 0.81 (t, J=7.07 Hz, 3H) 1.18-1.30 (m, 3H) 1.29-1.41 (m, 3H) 2.05-2.20 (m, 1H) 2.29-2.49 (m, 1H) 2.90-3.07 (m, 1H) 3.38-3.61 (m, 4H) 3.65-3.86 (m, 1H) 5.13 (d, J=7.58 Hz, 1H) 7.57 (dd, J=8.08, 4.80 Hz, 1H) 8.32 (dd, J=8.08, 1.77 Hz, 1H) 8.77 (dd, J=4.80, 1.77 Hz, 1H).

65J: cis-1-tert-Butyl 3-ethyl 2-(3-(isopropylsulfonyl)pyridin-2-yl)pyrrolidine-1,3-dicarboxylate

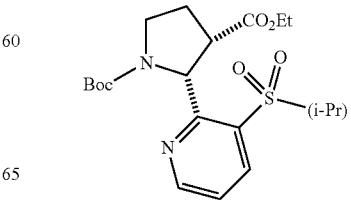

To 65E (0.45 g, 1.15 mmol) in EtOH (8 mL) at 0° C. was added Oxone® (0.99 g, 1.6 mmol, 1.4 eq.) in water (8 mL). The mixture was stirred from 0° C. to rt over 18 h. It was quenched with sat. NaHCO₃ and Na₂S₂O₃. The precipitate was removed by filtration and the filtrate was condensed, diluted with EtOAc and washed with brine. The organic layer was dried over Na₂SO₄. After removal of solvent, the crude was purified by silica column chromatography using gradient EtOAc in hexanes to give 65J (0.44 g, 81% yield). $^1$H NMR (400 MHz, 90° C., DMSO-$d_6$) δ ppm 0.88 (t, J=7.15 Hz, 3H) 1.13-1.17 (m, 3H) 1.19-1.27 (m, 9H) 1.34 (d, J=7.15 Hz, 3H) 2.10 (dd, J=7.42, 4.67 Hz, 1H) 2.39 (br s, 1H) 3.45-3.56 (m, 2H) 3.59-3.69 (m, 1H) 3.70-3.80 (m, 3H) 5.86 (d, J=8.25 Hz, 1H) 7.50 (dd, J=7.97, 4.67 Hz, 1H) 8.15 (d, J=7.70 Hz, 1H) 8.76 (d, J=4.40 Hz, 1H), LC-MS 427 (M+H).

65K: cis-Ethyl 2-(3-(isopropylsulfonyl)pyridin-2-yl)pyrrolidine-3-carboxylate hydrochloride

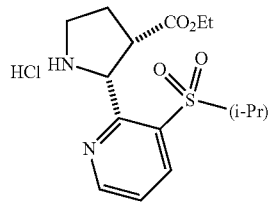

To 65J (0.38 g, 0.89 mmol) in EtOAc (5 mL) at rt was added 4.0 N HCl in dioxane (5 mL, 20 mmol). The mixture was stirred at rt for 8.0 h. After removal of the solvent, the crude was diluted in methylene chloride and washed with sat. NaHCO₃. The aqueous was extracted with methylene chloride (3×80 mL). The combined organic layer was dried over Na₂SO₄. After removal of solvent 65K (0.28 g, 95% yield) was obtained as viscous oil. $^1$H NMR (400 MHz, Methanol-$d_4$) δ ppm 1.15 (t, J=7.03 Hz, 3H) 1.23-1.27 (d, J=7.03 Hz, 3H) 1.30 (d, J=7.03 Hz, 3H) 2.21-2.27 (m, 2H) 3.07 (ddd, J=11.10, 7.47, 7.36 Hz, 1H) 3.41 (ddd, J=9.34, 7.25, 7.14 Hz, 1H) 3.54-3.63 (m, 1H) 4.03-4.12 (m, 2H) 5.14 (d, J=7.03 Hz, 1H) 7.58 (dd, J=7.91, 4.83 Hz, 1H) 8.32 (dd, J=8.35, 1.76 Hz, 1H) 8.86-8.91 (m, 1H), LC-MS 327 (M+H).

65L: (2R,3S)-Ethyl 2-(3-(isopropylsulfonyl)pyridin-2-yl)pyrrolidine-3-carboxylate and 65M: (2S,3R)-Ethyl 2-(3-(isopropylsulfonyl)pyridin-2-yl)pyrrolidine-3-carboxylate

65L

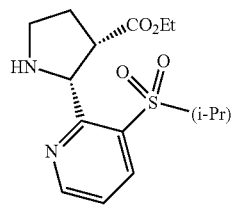

65M

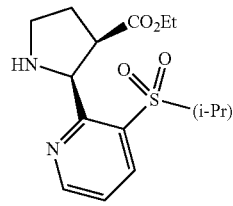

65K was separated using a preparative HPLC equipped with a Chiralpak® AS column (5 cm×50 cm, 20μ). The separations were performed using an isocratic method of 10% isopropanol/heptane with 0.1% diethylamine with a flow rate of 50 mL/min. 65L: $^1$H NMR (400 MHz, Methanol-$d_4$) δ ppm 1.15 (t, J=7.20 Hz, 3H) 1.27 (dd, J=15.66, 6.82 Hz, 6H) 2.10-2.36 (m, 2H) 3.02-3.13 (m, 1H) 3.25-3.35 (m, 1H) 3.37-3.47 (m, 1H) 3.53-3.64 (m, 1H) 4.01-4.13 (m, 2 H) 5.16 (d, J=7.07 Hz, 1H) 7.57 (dd, J=8.08, 4.55 Hz, 1H) 8.27-8.36 (m, 1H) 8.87 (dd, J=4.80, 1.77 Hz, 1H); 65M: $^1$H NMR (400 MHz, Methanol-$d_4$) δ ppm 1.15 (t, J=7.07 Hz, 3H) 1.27 (dd, J=15.66, 6.82 Hz, 6H) 2.11-2.41 (m, 2H) 2.98-3.13 (m, 1H) 3.24-3.35 (m, 1H) 3.35-3.48 (m, 1H) 3.52-3.66 (m, 1H) 3.97-4.17 (m, 2 H) 5.16 (d, J=7.07 Hz, 1H) 7.57 (dd, J=7.96, 4.67 Hz, 1H) 8.31 (dd, J=7.96, 1.64 Hz, 1H) 8.87 (dd, J=4.80, 1.52 Hz, 1H).

65N: (2R,3R)-Ethyl 1-((R)-2-(3-carbamoylphenylamino)-2-(4-fluoro-3-methoxyphenyl)acetyl)-2-(3-(isopropylsulfonyl)pyridin-2-yl)pyrrolidine-3-carboxylate

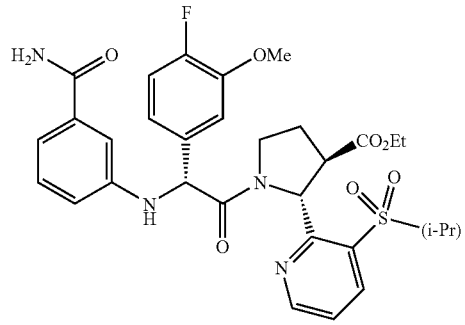

65N was prepared according to the general coupling condition using 7D and 65H. $^1$H NMR (400 MHz, Methanol-$d_4$) δ ppm 0.89 (t, J=7.20 Hz, 3H) 1.12 (d, J=6.57 Hz, 3H) 1.41 (d, J=7.07 Hz, 3H) 2.12-2.33 (m, 1H) 2.37-2.62 (m, J=8.59 Hz, 1H) 3.43-3.67 (m, 2H) 3.70 (s, 3H) 3.72-3.88 (m, 2H) 3.91-4.11 (m, 2H) 5.37 (s, 1H) 6.03-6.14 (m, 1H) 6.80-6.94 (m, 2H) 6.94-7.08 (m, 2H) 7.11-7.23 (m, 3H) 7.42 (dd, J=7.96, 4.67 Hz, 1H) 8.15 (dd, J=7.96, 1.64 Hz, 1H) 8.43 (dd, J=4.80, 1.52 Hz, 1H), LC-MS 627 (M+H).

65O: Example 65

Example 65 was prepared by hydrolysis of the ethyl ester in 65N with NaOH in MeOH/H₂O at rt and purified by prep HPLC. $^1$H NMR (400 MHz, Methanol-$d_4$) δ ppm 1.16 (d, J=6.57 Hz, 3H) 1.42 (d, J=6.82 Hz, 3H) 2.19-2.34 (m, J=7.58 Hz, 1H) 2.52 (dd, J=13.14, 8.34 Hz, 1H) 2.90-3.00 (m, 1H) 3.73 (s, 3H) 3.75-3.84 (m, 1H) 3.94-4.12 (m, 2H) 5.35 (s, 1H)

6.06 (d, J=2.02 Hz, 1H) 6.79-6.87 (m, 1H) 6.89-6.99 (m, 1H) 6.99-7.25 (m, 5H) 7.47 (dd, J=8.08, 4.80 Hz, 1H) 8.21 (dd, J=7.96, 1.64 Hz, 1H) 8.50 (dd, J=4.80, 1.52 Hz, 1H), LC-MS 599 (M+H).

Example 66

(2R,3S)-1-((R)-2-(3-Carbamoylphenylamino)-2-(4-fluoro-3-methoxyphenyl)acetyl)-2-(2-(cyclopropyl-sulfonyl)phenyl)pyrrolidine-3-carboxylic acid

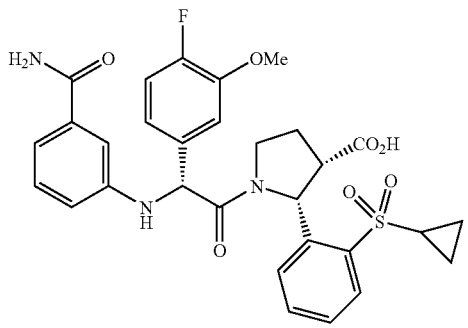

Example 66 was prepared by hydrolysis of the ethyl ester in Example 63 with NaOH in MeOH/H$_2$O at rt and purified by prep HPLC. $^1$H NMR (400 MHz, Methanol-d$_4$) δ ppm 0.97-1.07 (m, 1H) 1.08-1.20 (m, 1H) 1.24-1.36 (m, 1H) 1.38-1.52 (m, 1H) 2.19-2.38 (m, 2H) 2.85-2.93 (m, 1H) 3.06-3.16 (m, 1H) 3.34-3.38 (m, 1H) 3.78 (s, 3H) 4.00-4.14 (m, 1H) 5.38 (s, 1H) 6.26 (s, 1H) 6.70 (d, J=7.07 Hz, 1H) 6.79-6.87 (m, 1H) 7.02-7.26 (m, 6H) 7.31-7.55 (m, 2H) 7.88 (dd, J=7.83, 1.26 Hz, 1H), LC-MS 596 (M+H).

Example 67

(2R,3S)-Ethyl 1-((R)-2-(5-carbamoyl-2-fluorophenylamino)-2-(4-fluoro-3-methoxyphenyl)acetyl)-2-(5-(3,3-dimethylureido)-2-(ethylsulfonyl)phenyl)pyrrolidine-3-carboxylate

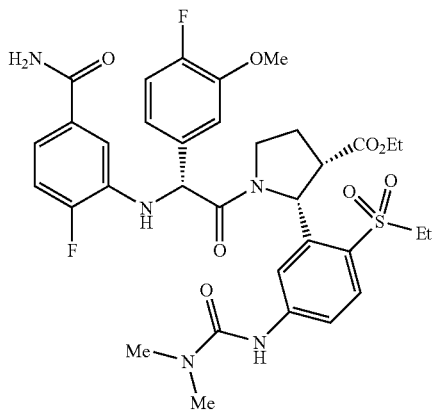

67A: (2R,3S)-Ethyl 2-(5-(3,3-dimethylureido)-2-(ethylsulfonyl)phenyl)pyrrolidine-3-carboxylate hydrochloride

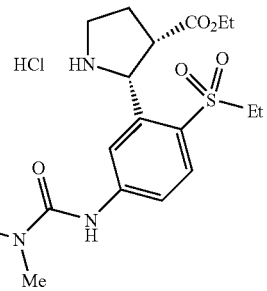

67A was prepared in a procedure similar to that of 31A using 35K, phosgene and dimethylamine $^1$H NMR (400 MHz, Methanol-d$_4$) δ ppm 0.84-0.93 (m, 3H) 1.24-1.39 (m, 3H) 2.45-2.59 (m, 1H) 2.64-2.78 (m, 1H) 3.01-3.11 (m, 6H) 3.32-3.41 (m, 2H) 3.47-3.61 (m, 1H) 3.67-3.81 (m, 1H) 3.81-3.96 (m, 3H) 5.89 (dd, J=8.59, 2.53 Hz, 1H) 7.46-7.57 (m, 1H) 7.89 (t, J=2.27 Hz, 1H) 7.92-8.01 (m, 1H), LC-MS 398 (M+H).

67B: Example 67

Example 67 was prepared according to the general coupling condition using 27A and 67A. $^1$H NMR (400 MHz, Methanol-d$_4$) δ ppm 0.84 (t, J=7.07 Hz, 3 H) 1.20-1.36 (m, 6H) 2.19-2.34 (m, 1H) 2.35-2.51 (m, 1H) 2.93-3.03 (m, 6H) 3.15-3.26 (m, 1H) 3.38-3.49 (m, 1H) 3.49-3.63 (m, 2H) 3.64-3.79 (m, 4H) 3.81-3.97 (m, 1H) 4.11-4.27 (m, 1H) 5.40-5.49 (m, 1H) 6.04-6.12 (m, 1H) 6.68 (d, J=2.02 Hz, 1H) 6.91-7.09 (m, 4H) 7.08-7.20 (m, 1H) 7.23-7.36 (m, 1H) 7.44 (dd, J=8.72, 2.15 Hz, 1H) 7.75 (d, 1H). LC-MS 716 (M+H).

Example 68

Diastereoisomer of Example 67

(2R,3S)-Ethyl 1-((S)-2-(5-carbamoyl-2-fluorophenylamino)-2-(4-fluoro-3-methoxyphenyl)acetyl)-2-(5-(3,3-dimethylureido)-2-(ethylsulfonyl)phenyl)pyrrolidine-3-carboxylate

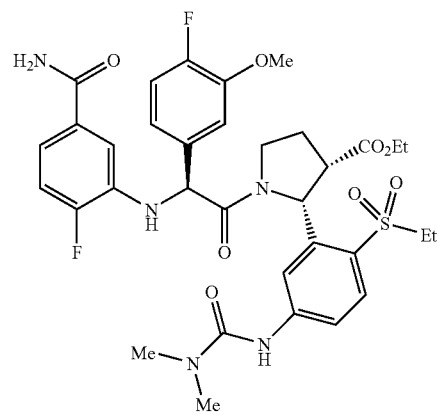

Example 68 was obtained as a diastereomer of Example 67 during its HPLC purification. ¹H NMR (400 MHz, Methanol-d₄) δ ppm 0.88 (t, J=7.07 Hz, 3H) 1.24 (t, J=7.45 Hz, 3H) 1.98-2.11 (m, 1H) 2.33-2.51 (m, 1H) 2.99-3.03 (m, 6 H) 3.36-3.51 (m, 3H) 3.60 (dd, J=10.74, 7.20 Hz, 1H) 3.65-3.79 (m, 2H) 3.85 (s, 3H) 4.27-4.39 (m, 1H) 5.49 (s, 1H) 5.99 (d, J=8.59 Hz, 1H) 6.96 (dd, J=11.24, 8.46 Hz, 1H) 7.02-7.15 (m, 3H) 7.22-7.29 (m, 1H) 7.32 (dd, J=8.46, 1.89 Hz, 1H) 7.48-7.60 (m, 2H) 7.74 (d, J=8.84 Hz, 1H), LC-MS 716 (M+H).

Example 69

(2R,3R)-Ethyl 1-((R)-2-(5-carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylate

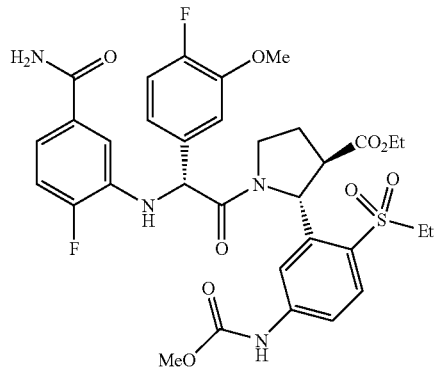

Example 69 was prepared according to the general coupling condition using 35M and 27A. ¹H NMR (400 MHz, Methanol-d₄) δ ppm 1.17-1.31 (m, 6H) 2.17-2.32 (m, 1H) 2.31-2.48 (m, 1H) 2.79-2.93 (m, 1H) 3.36-3.62 (m, 2H) 3.69 (d, J=3.03 Hz, 6H) 3.84 (t, J=9.09 Hz, 1H) 4.02-4.14 (m, 1H) 4.17 (q, J=7.07 Hz, 2H) 5.42 (s, 1H) 5.97 (d, J=2.02 Hz, 1H) 6.93-7.07 (m, 4H) 7.10-7.20 (m, 3 H) 7.27 (dd, J=8.21, 1.89 Hz, 1H) 7.72-7.83 (m, 1H) 9.48 (s, 1H), LC-MS 703 (M+H).

Example 70

Diastereoisomer of Example 69

(2R,3R)-Ethyl 1-((S)-2-(5-carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylate

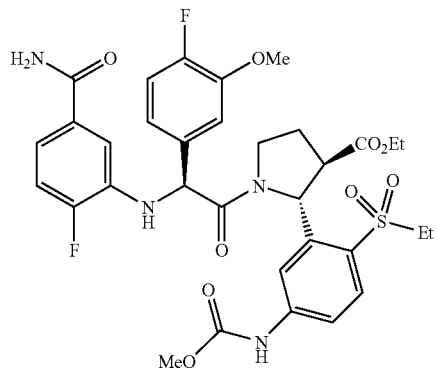

Example 70 was obtained as a diastereomer of Example 69 during its HPLC purification. ¹H NMR (400 MHz, Methanol-d₄) δ ppm 1.05-1.14 (m, 3H) 1.19-1.28 (m, 3H) 2.04-2.18 (m, 1H) 2.45-2.58 (m, 1H) 2.84 (d, J=7.83 Hz, 1H) 3.33-3.50 (m, 2H) 3.70-3.79 (m, 4H) 3.88-3.93 (m, 3H) 3.97-4.08 (m, 2H) 4.33 (t, J=9.73 Hz, 1H) 5.54 (d, J=2.02 Hz, 1H) 5.94 (s, 1H) 6.93-7.03 (m, 1H) 7.07-7.12 (m, 2H) 7.13-7.19 (m, 1H) 7.25 (d, J=1.77 Hz, 1H) 7.38 (dd, J=8.34, 2.27 Hz, 1H) 7.43 (d, J=2.27 Hz, 1H) 7.69-7.77 (m, 1H) 7.80-7.86 (m, 1H) 9.46 (s, 1H), LC-MS 703 (M+H).

Example 71

(2R,3S)-1-((R)-2-(5-Carbamoyl-2-fluorophenylamino)-2-(4-fluoro-3-methoxyphenyl)acetyl)-2-(5-(3,3-dimethylureido)-2-(ethylsulfonyl)phenyl)pyrrolidine-3-carboxylic acid

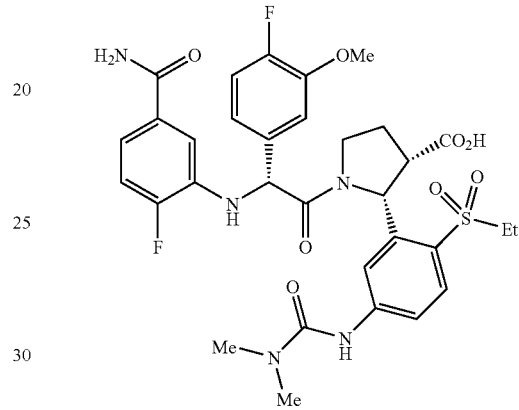

Example 71 was prepared by hydrolysis of the ethyl ester in Example 67 with NaOH in MeOH/H₂O at rt and purified by prep HPLC. ¹H NMR (400 MHz, Methanol-d₄) δ ppm 1.28 (t, J=7.33 Hz, 3H) 2.19-2.32 (m, 1H) 2.38-2.56 (m, 1H) 2.82-2.93 (m, 1H) 2.93-3.04 (m, 6H) 3.38-3.59 (m, 2H) 3.67-3.74 (m, 3H) 3.91 (d, J=6.06 Hz, 1H) 3.96-4.10 (m, 1H) 5.41 (s, 1H) 6.02 (s, 1H) 6.88 (d, J=2.02 Hz, 1H) 6.93-7.10 (m, 4H) 7.11-7.21 (m, 1H) 7.28 (d, J=8.84 Hz, 2H) 7.78 (d, J=8.84 Hz, 1H), LC-MS 688 (M+).

Example 72

(2R,3S)-1-((S)-2-(5-Carbamoyl-2-fluorophenylamino)-2-(4-fluoro-3-methoxyphenyl)acetyl)-2-(5-(3,3-dimethylureido)-2-(ethylsulfonyl)phenyl)pyrrolidine-3-carboxylic acid

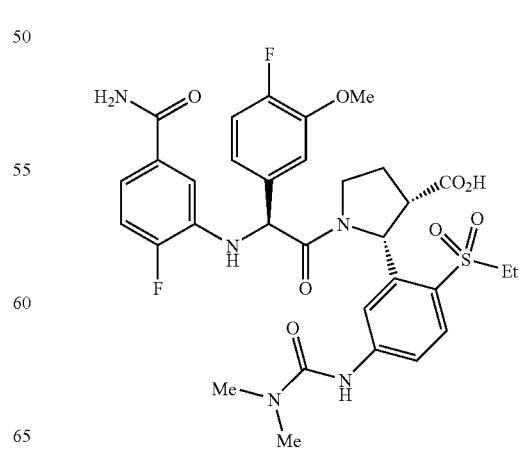

Example 72 was prepared by hydrolysis of the ethyl ester in Example 68 with NaOH in MeOH/H$_2$O at rt and purified by prep HPLC. $^1$H NMR (400 MHz, Methanol-d$_4$) δ ppm 1.18-1.38 (m, 3H) 2.15 (dd, J=13.52, 6.69 Hz, 1H) 2.48-2.65 (m, 1H) 2.77-2.90 (m, 1H) 2.96-3.09 (m, 6H) 3.35-3.54 (m, 2H) 3.72 (s, 1H) 3.89 (s, 3H) 4.28 (t, J=9.47 Hz, 1H) 5.53 (s, 1H) 5.98 (s, 1H) 6.91-7.19 (m, 4H) 7.18-7.27 (m, 1H) 7.29-7.43 (m, 1H) 7.48-7.62 (m, 2H) 7.80 (d, J=8.59 Hz, 1H), LC-MS 688 (M+).

Example 73

(2R,3R)-1-((R)-2-(5-Carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylic acid

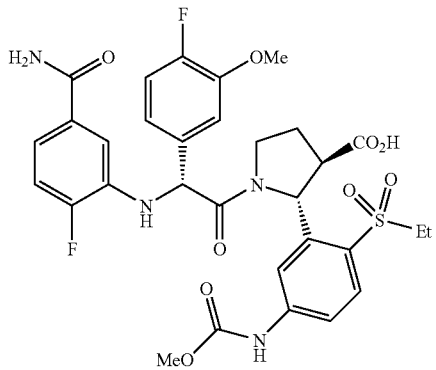

Example 73 was prepared by hydrolysis of the ethyl ester in Example 69 with NaOH in MeOH/H$_2$O at rt and purified by prep HPLC. $^1$H NMR (400 MHz, Methanol-d$_4$) δ ppm 1.19-1.37 (m, 3H) 2.19-2.51 (m, 2H) 2.85 (s, 1H) 3.37-3.63 (m, 3H) 3.66-3.74 (m, 6H) 3.82-3.95 (m, 1H) 3.97-4.14 (m, 1H) 5.41 (s, 1H) 6.03 (s, 1H) 6.94-7.09 (m, 4H) 7.10-7.21 (m, 3H) 7.27 (dd, J=8.21, 2.15 Hz, 1H) 7.79 (d, J=9.09 Hz, 1H) 9.47 (s, 1H), LC-MS 675 (M+H).

Example 74

(2R,3R)-1-((S)-2-(5-Carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylic acid

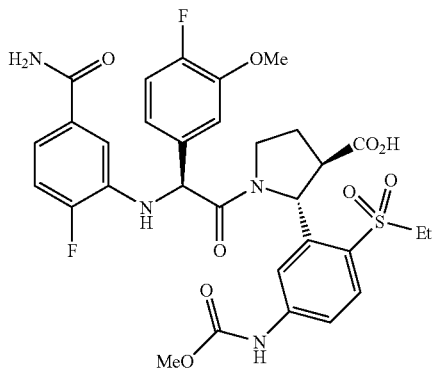

Example 74 was prepared by hydrolysis of the ethyl ester in Example 70 with NaOH in MeOH/H$_2$O at rt and purified by prep HPLC. $^1$H NMR (400 MHz, Methanol-d$_4$) δ ppm 1.16-1.37 (m, 3H) 2.05-2.60 (m, 2H) 2.84 (s, 1H) 3.34-3.50 (m, 2H) 3.65-3.79 (m, 5H) 3.89 (s, 3H) 4.33 (t, J=8.97 Hz, 1H) 5.55 (s, 1H) 5.97 (s, 1H) 6.93-7.17 (m, 4H) 7.19-7.28 (m, 1H) 7.34-7.48 (m, 2H) 7.66-7.90 (m, 2H) 9.46 (s, 1H), LC-MS 675 (M+H).

Example 75

(2S,3S)-1-((R)-2-(5-Carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylic acid

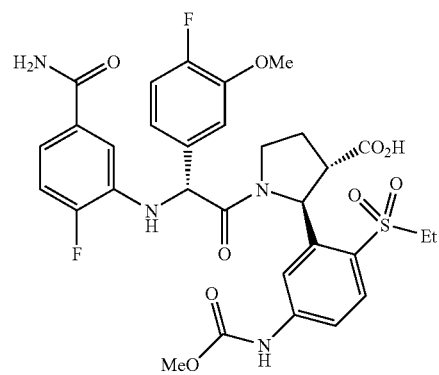

75A: (2S,3S)-Ethyl 1-((R)-2-(5-carbamoyl-2-fluorophenylamino)-2-(4-fluoro-3-methoxyphenyl)acetyl)-2-(2-(ethylsulfonyl)-5-(methoxycarbonylamino)phenyl)pyrrolidine-3-carboxylate

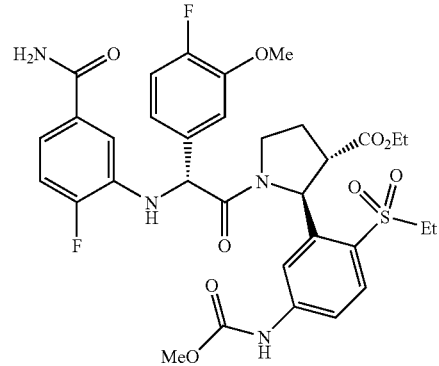

75A was prepared according to the general coupling condition using 27A and 35N. $^1$H NMR (400 MHz, Methanol-d$_4$) δ ppm 1.16-1.33 (m, 6H) 2.19-2.34 (m, 1H) 2.33-2.50 (m, 1H) 2.87 (dd, J=4.80, 2.78 Hz, 1H) 3.38-3.62 (m, 2 H) 3.65-3.77 (m, 6H) 3.78-3.92 (m, 1H) 4.10 (d, J=8.34 Hz, 1H) 4.19 (q, J=7.07 Hz, 2H) 5.44 (s, 1H) 5.99 (d, J=2.02 Hz, 1H) 6.92-7.10 (m, 4H) 7.11-7.22 (m, 3H) 7.28 (dd, J=8.21, 1.89 Hz, 1H) 7.69-7.91 (m, 1H) 9.49 (s, 1H), LC-MS 703 (M+H).

75B: Example 75

Example 75 was prepared by hydrolysis of the ethyl ester 75A with NaOH in MeOH/H$_2$O at rt and purified by prep HPLC. $^1$H NMR (400 MHz, Methanol-d$_4$) δ ppm 1.17-1.34 (m, 3H) 2.16-2.32 (m, 1H) 2.32-2.53 (m, 1H) 2.78-2.92 (m, 1H) 3.35-3.58 (m, 2H) 3.68 (s, 6H) 3.80-3.97 (m, 1H) 3.95-4.11 (m, 1H) 5.39 (s, 1H) 6.01 (s, 1H) 6.92-7.07 (m, 4H) 7.09-7.18 (m, 3H) 7.26 (dd, J=8.34, 2.02 Hz, 1H) 7.77 (d, J=9.09 Hz, 1H) 9.46 (s, 1H), LC-MS 675 (M+H).

Example 76

(2R,3S)-Ethyl 1-((R)-2-(5-carbamoyl-2-fluorophenylamino)-2-(4-fluoro-3-methoxyphenyl)acetyl)-2-(2-(cyclopropylsulfonyl)-5-(methoxycarbonylamino)phenyl)pyrrolidine-3-carboxylate

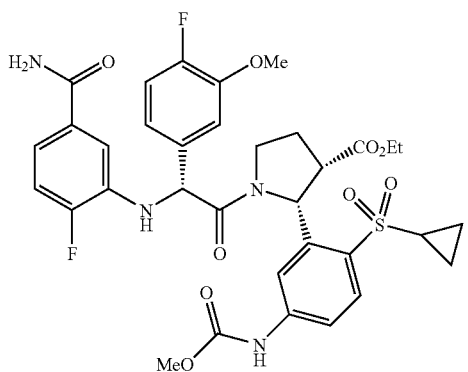

76A: 2-(Cyclopropylthio)-5-nitrobenzaldehyde

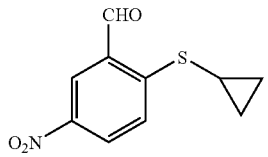

Freshly prepared cyclopropyl thiol in THF/diethyl ether (*J. Am. Chem. Soc.* 1992, 114(9), 3497) was added to 2-fluoro-5-nitrobenzaldehyde (3.4 g, 20 mmol, 1.0 eq.) and K$_2$CO$_3$ (4.83 g, 35 mmol) in DMF (20 mL). The mixture was stirred at 45° C. for 1.0 h and at rt over night. It was diluted with EtOAc and washed with water. The aqueous was extracted with EtOAc and the combined organic layers were washed with brine and dried over Na$_2$SO$_4$. After evaporation of solvent, the crude was tritutated with EtOAc/hexanes (70/120). The solid was collected to give 76A (3.2 g). The filtrate was condensed and triturated again to give a second crop of 76A (0.5 g, total yield 85%). $^1$H NMR (400 MHz, CDCl$_3$) δ ppm 0.74-0.83 (m, 2H) 1.20-1.28 (m, 2H) 2.13-2.19 (m, 1H) 7.95 (d, J=9.23 Hz, 1H) 8.33 (dd, J=8.79, 2.64 Hz, 1H) 8.62 (d, J=2.64 Hz, 1H) 10.15 (s, 1H).

76B: (E)-Ethyl 4-(2-(cyclopropylthio)-5-nitrobenzylideneamino)butanoate

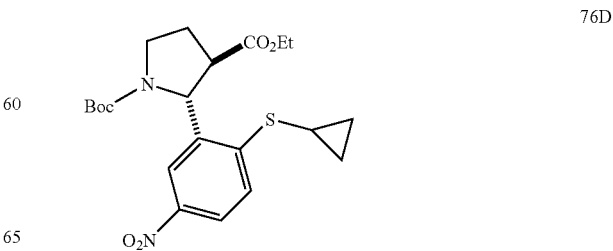

To the ethyl aminobutyric ester (5.26 g, 31.3 mmol) in dichloromethane (120 mL) was added triethylamine (6.0 mL, 43 mmol) and then 76A (7.0 g, 23.4 mmol) and 4 Å molecular sieves (5.0 g). The reaction was stirred over night at rt. The reaction mixture was filtered to remove the molecular sieves and the solvent was evaporated to give a solid 76B together with triethylamine HCl salt. $^1$H NMR (400 MHz, CDCl$_3$) δ ppm 1.18 (m, 5H) 1.94-2.04 (m, 2H) 2.07-2.16 (m, 1 H) 2.38 (t, J=7.25 Hz, 2H) 3.64 (t, J=6.59 Hz, 2H) 4.07 (q, J=7.32 Hz, 2H) 7.76 (d, J=8.79 Hz, 1H) 8.11 (dd, J=9.01, 2.42 Hz, 1H) 8.45 (s, 1H) 8.49 (d, J=2.64 Hz, 1H).

76C: Ethyl 2-(2-(cyclopropylthio)-5-nitrophenyl)pyrrolidine-3-carboxylate

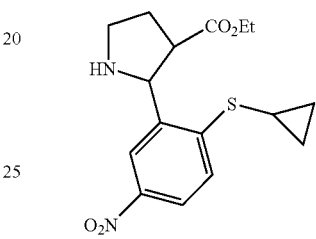

To 76B (ca 31 mmol) in CH$_2$Cl$_2$ (150 mL) at −15° C. was added Et$_3$N (5.94 mL, 43 mmol) followed by TiCl$_4$ (1.0 M in CH$_2$Cl$_2$, 37.2 mL, 37.2 mmol). The mixture was stirred from −15° C. to rt over 3.0 h before it was quenched with sat. K$_2$CO$_3$ (200 mL) at 0° C. and stirred at rt for 1.0 h. CH$_2$Cl$_2$ was removed under vacuo and EtOAc was added to the crude (for better filtration). The mixture was filtered through a pad of wet Celite®, extracted with EtOAc (3×100 mL). The organic layer was washed with water, dried over Na$_2$SO$_4$. The cude was purified by silica gel flash column chromatography using gradient CH$_2$Cl$_2$ in hexanes to give 76C (3.77 g, 56% yield) and retrieved 76A (2.8 g). LC-MS indicated a mixture of cis and trans isomer in ca. 1:1 ratio. LC-MS 337 (M+H).

76D: trans-1-tert-Butyl 3-ethyl 2-(2-(cyclopropylthio)-5-nitrophenyl)pyrrolidine-1,3-dicarboxylate
and 76E: cis-1-tert-Butyl 3-ethyl 2-(2-(cyclopropylthio)-5-nitrophenyl)pyrrolidine-1,3-dicarboxylate

76E

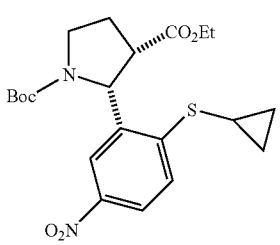

To 76C (3.77 g, 11.2 mmol) in THF (10 mL) was added Et₃N (1.95 mL, 14 mmol) and di-tert-butyl dicarbonate (1.0 M in THF, 14 mL, 14 mmol). The mixture was stirred at rt for 3.0 h before it was quenched with 0.5 N HCl (50 mL). The organic layer was washed with brine, dried (Na₂SO₄), filtered and concentrated. The crude product was first triturated with EtOAc/hexanes (50/125), the precipitate was collected by filtration and washed with EtOAc/hexanes (50/125) to give trans 76D (1.35 g). The filtrate was concentrated and further purified by flash silica gel column chromatography using gradient EtOAc in hexane to give predominantly cis isomer 76E. To this cis isomer was added mixture of EtOAc/hexane (1:3), the precipitate was collected and washed with the same mixture of EtOAc/hexanes (1:3) to give a second crop of the trans 76D (0.4 g). The filtrate was concentrated to give enriched cis isomer 76E (2.95 g, >92% purity). 76D: ¹H NMR (500 MHz, DMSO-d₆, 25° C.) δ ppm 0.55-0.68 (br, m, 2H) 1.06 (s, 5H) 1.14-1.25 (m, 6H) 1.38 (s, 4 H) 2.05-2.17 (m, 2H) 2.38 (br,s, 1H) 3.45 (br,s, 1H) 3.67 (br, s, 1H) 4.11 (d, J=6.05 Hz, 2H) 5.10 (d, J=13.19 Hz, 1H) 7.76-7.88 (m, 2H) 8.16 (d, J=8.79 Hz, 1H), ¹H NMR (400 MHz, DMSO-d₆, 100° C.) δ ppm 0.62-0.69 (m, 2H) 1.17-1.28 (m, 13H) 2.08-2.19 (m, 2H) 2.38 (d, J=4.40 Hz, 1H) 2.91 (s, 1H) 3.49-3.58 (m, 1 H) 3.63-3.72 (m, 1H) 4.15 (q, J=6.78 Hz, 2H) 5.17 (d, J=2.75 Hz, 1H) 7.84 (s, 1 H) 7.87 (d, J=8.79 Hz, 1H) 8.06-8.14 (m, 1H), LC-MS 337 (M-Boc); 7.6E: ¹H NMR (400 MHz, DMSO-d₆, 100° C.) δ ppm 0.64 (s, 1H) 0.67 (d, J=2.75 Hz, 1H) 0.86 (t, J=6.87 Hz, 3H) 1.14-1.24 (m, 11H) 2.18 (td, J=13.33, 6.87 Hz, 2H) 2.37 (d, J=3.30 Hz, 1H) 3.53-3.64 (m, 3H) 3.67-3.73 (m, 1H) 3.75-3.79 (m, 1H) 5.26 (d, J=8.79 Hz, 1H) 7.76-7.85 (m, 2H) 8.08 (d, J=8.79 Hz, 1H)), LC-MS 337 (M-Boc).

76F: trans-1-tert-Butyl 3-ethyl 2-(2-(cyclopropylsulfonyl)-5-nitrophenyl)pyrrolidine-1,3-dicarboxylate

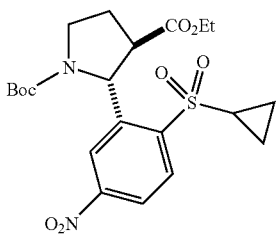

To 76D (1.64 g, 3.76 mmol) in CH₂Cl₂ (60 mL) was added NaHCO₃ (0.95 g, 11.3 mmol) and MCPBA (75% purity, 2.14 g, 9.28 mmol). The mixture was stirred at rt for 5.0 h. It was quenched with sat. NaHCO₃ and extracted with CH₂Cl₂. The organic layer was dried over Na₂SO₄. After removal of solvent, the crude was purified with silica gel column chromatography eluting with gradient CH₂Cl₂ in hexanes to give 76F (1.65 g, 95% yield). ¹H NMR (400 MHz, DMSO-d₆, 100° C.) δ ppm 1.09-1.13 (m, 1H) 1.16-1.24 (m, 5H) 1.25-1.35 (m, 8H) 2.06 (d, J=7.15 Hz, 1H) 2.20-2.31 (m, 1H) 3.42-3.51 (m, 1H) 3.74-3.81 (m, 1H) 4.14 (q, J=6.96 Hz, 2H) 5.92 (s, 1H) 8.08 (d, J=2.20 Hz, 1H) 8.19 (d, J=8.79 Hz, 1H) 8.24-8.31 (m, 1H), LC-MS 413 (M-tert-butyl).

76G: cis-1-tert-Butyl 3-ethyl 2-(2-(cyclopropylsulfonyl)-5-nitrophenyl)pyrrolidine-1,3-dicarboxylate

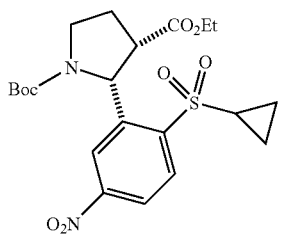

To 76E (2.9 g, 6.65 mmol) in CH₂Cl₂ (40 mL) was added NaHCO₃ (1.68 g, 20 mmol) and MCPBA (75% purity, 3.83 g, 16.6 mmol). The mixture was stirred at rt for overnight. It was quenched with sat. NaHCO₃ and extracted with CH₂Cl₂. The organic layer was dried over Na₂SO₄. After removal of solvent, the crude was purified with silica gel column chromatography eluting with gradient CH₂Cl₂ in hexanes to give 76G (2.87 g, 95% yield). ¹H NMR (400 MHz, DMSO-d₆, 100° C.) δ ppm 0.83 (t, J=6.87 Hz, 3H) 1.14-1.22 (m, 11H) 1.28-1.37 (m, 2H) 2.13-2.24 (m, 2H) 2.99-3.06 (m, 1H) 3.60-3.69 (m, 3H) 3.71-3.74 (m, 1H) 3.79-3.87 (m, 1H) 5.95 (d, J=8.25 Hz, 1H) 8.07 (d, J=2.20 Hz, 1H) 8.15 (d, J=8.79 Hz, 1H) 8.27 (dd, J=8.79, 2.20 Hz, 1H). LC-MS 413 (M-tert-butyl).

76H: trans-1-tert-Butyl 3-ethyl 2-(5-amino-2-(cyclopropylsulfonyl)phenyl)pyrrolidine-1,3-dicarboxylate

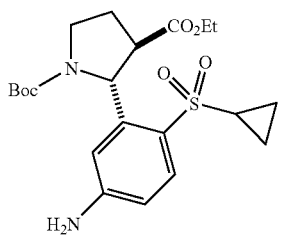

To 76F (1.6 g) in methanol (40 mL) and THF (20 mL) was added 10% Pd/C (500 mg). The mixture was hydrogenated with a hydrogen balloon for 2.0 h. The Pd/C was removed by filtration and the filtrate was concentrated to afford 76H (1.54 g, 95% yield). ¹H NMR (400 MHz, DMSO-d₆, 100° C.) δ ppm 0.86-0.97 (m, 2H) 0.98-1.06 (m, 3H) 1.13-1.24 (m, 4H) 1.30 (s, 9H) 1.98 (dd, J=12.09, 8.24 Hz, 1H) 2.16 (d, J=11.54 Hz, 1H) 2.68 (s, 1H) 2.83 (d, J=7.15 Hz, 1H) 3.42 (d, J=7.15

Hz, 1H) 3.61-3.71 (m, 1H) 4.11 (q, J=7.15 Hz, 2H) 5.74 (s, 1H) 6.50-6.57 (m, 2H) 7.47 (d, J=9.34 Hz, 1H), LC-MS 439 (M+H).

76I: cis-1-tert-Butyl 3-ethyl 2-(5-amino-2-(cyclopropylsulfonyl)phenyl)pyrrolidine-1,3-dicarboxylate

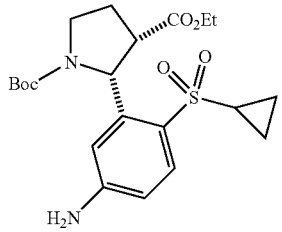

To 76G (2.9 g) in methanol (60 mL) was added 10% Pd/C (990 mg). The mixture was hydrogenated with a hydrogen balloon for 2.0 h. The Pd/C was removed by filtration and the filtrate was concentrated to afford 76I (2.54 g, 95% yield). $^1$H NMR (400 MHz, DMSO-$d_6$, 100° C.) δ ppm 0.83-0.93 (m, 5H) 0.95-1.04 (m, 2H) 1.13-1.24 (m, 11H) 2.02-2.07 (m, 1H) 2.09-2.16 (m, 1H) 2.73-2.79 (m, 1H) 3.48-3.56 (m, 1H) 3.63-3.74 (m, 4H) 5.79 (d, J=7.70 Hz, 1H) 6.48-6.54 (m, 2H) 7.40 (d, J=8.79 Hz, 1H), LC-MS 439 (M+H).

76J: (2R,3R)-1-tert-Butyl 3-ethyl 2-(5-amino-2-(cyclopropylsulfonyl)phenyl)pyrrolidine-1,3-dicarboxylate and

76K: (2S,3S)-1-tert-Butyl 3-ethyl 2-(5-amino-2-(cyclopropylsulfonyl)phenyl)pyrrolidine-1,3-dicarboxylate

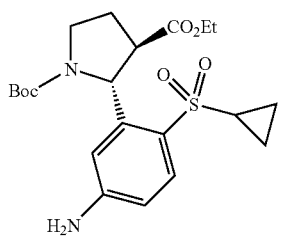

76J

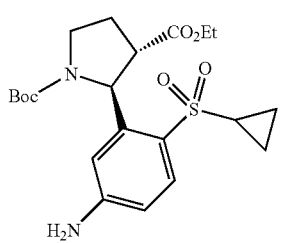

76K

Enantiomers of 76H were separated by Berger SFC equipped with Chiralpak® AD column (25 cm×3 cm, 10µ). The separations were performed using an isocratic method of $CO_2$/MeOH/DEA:90/10/0.1 with a flow rate of 65 mL/min at 35° C. 76J: $^1$H NMR (400 MHz, Methanol-$d_4$) δ ppm 0.77-1.13 (m, 4H) 1.17-1.34 (m, 9H) 1.42 (s, 3H) 1.90-2.10 (m, 1H) 2.09-2.38 (m, 1H) 2.47-2.73 (m, 1 H) 2.74-3.07 (m, 1H) 3.35-3.58 (m, 1H) 3.73 (d, J=8.08 Hz, 1H) 4.02-4.26 (m, 2 H) 5.73 (d, J=35.87 Hz, 1H) 6.39-6.70 (m, 2H) 7.36-7.65 (m, 1H); 76K: $^1$H NMR (400 MHz, Methanol-$d_4$) δ ppm 0.72-1.11 (m, 3H) 1.11-1.36 (m, 10H) 1.41 (d, J=3.28 Hz, 3H) 1.86-2.09 (m, 1H) 2.22 (d, J=11.62 Hz, 1H) 2.50-3.02 (m, 2H) 3.34-3.53 (m, 1H) 3.73 (s, 1H) 4.13 (d, J=6.57 Hz, 2H) 5.72 (d, J=36.38 Hz, 1H) 6.43-6.71 (m, 2H) 7.41-7.58 (m, 1H).

76L: (2R,3S)-1-tert-Butyl 3-ethyl 2-(5-amino-2-(cyclopropylsulfonyl)phenyl)pyrrolidine-1,3-dicarboxylate and

76M: (2S,3R)-1-tert-Butyl 3-ethyl 2-(5-amino-2-(cyclopropylsulfonyl)phenyl)pyrrolidine-1,3-dicarboxylate

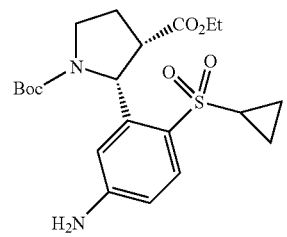

76L

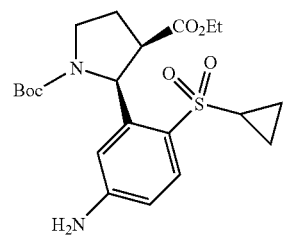

76M

Enantiomers of 76I were separated using a preparative HPLC equipped with a Chiralpak® AD column (5 cm×50 cm, 20µ). The separations were performed using an isocratic method of 10% MeOH-EtOH/heptane with 0.1% diethylamine with a flow rate of 50 mL/min. 76L: $^1$H NMR (400 MHz, Methanol-$d_4$) δ ppm 0.79-0.99 (m, 4H) 1.00-1.56 (m, 12H) 1.96-2.33 (m, 2H) 2.60-2.85 (m, 1H) 3.54-3.83 (m, 4H) 3.82-4.00 (m, 1H) 5.83 (s, 1H) 6.45-6.68 (m, 2H) 7.51 (d, J=8.59 Hz, 1H); 76M: $^1$H NMR (400 MHz, Methanol-$d_4$) δ ppm 0.79-1.01 (m, 4H) 1.00-1.57 (m, 12H) 2.03-2.36 (m, 2H) 2.61-2.88 (m, 1H) 3.50-3.82 (m, 4H) 3.82-3.96 (m, 1H) 5.83 (s, 1H) 6.45-6.67 (m, 2H) 7.50 (d, J=8.34 Hz, 1H).

76N: (2R,3S)-Ethyl 2-(2-(cyclopropylsulfonyl)-5-(methoxycarbonylamino)phenyl)pyrrolidine-3-carboxylate hydrochloride

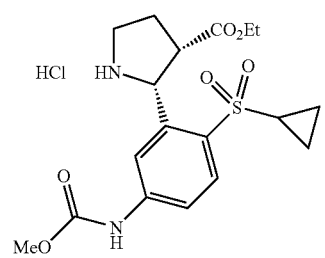

76N was prepared in a procedure similar to that of 1G using 76L and methyl chloroformate. $^1$H NMR (400 MHz, Methanol-$d_4$) δ ppm 0.84 (t, J=7.20 Hz, 3 H) 1.05-1.37 (m, 4H) 2.46-2.61 (m, 1H) 2.65-2.78 (m, 1H) 2.84-2.96 (m, 1H) 3.50-3.61 (m, 1H) 3.66-3.76 (m, 1H) 3.79 (s, 3H) 3.81-3.98 (m, 3H) 5.99 (d, J=8.59 Hz, 1H) 7.53 (dd, J=8.84, 2.02 Hz, 1H) 7.89 (d, J=2.27 Hz, 1H) 7.95 (d, J=8.59 Hz, 1H), LC-MS 397 (M+H).

76O: (2R,3S)-Ethyl 2-(2-(cyclopropylsulfonyl)-5-(3,3-dimethylureido)phenyl)pyrrolidine-3-carboxylate hydrochloride

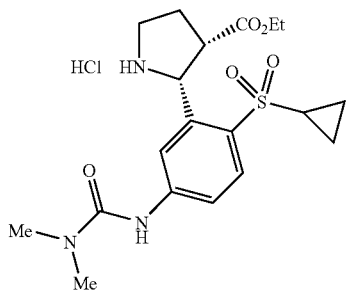

76O was prepared in a procedure similar to that of 31A starting with 76L, phosgene and dimethylamine $^1$H NMR (400 MHz, Methanol-$d_4$) δ ppm 0.84 (t, J=7.07 Hz, 3H) 1.07-1.17 (m, 2H) 1.21-1.28 (m, 2H) 2.43-2.56 (m, 1H) 2.63-2.75 (m, 1H) 2.91-3.02 (m, 1H) 3.02-3.08 (m, 6H) 3.50-3.63 (m, 1H) 3.68-3.81 (m, 1H) 3.80-3.94 (m, 3H) 5.96 (d, J=8.59 Hz, 1H) 7.55 (dd, J=8.72, 2.15 Hz, 1H) 7.83 (d, J=2.02 Hz, 1H) 7.89 (d, J=8.84 Hz, 1H), LC-MS 410 (M+H).

76P: (2R,3R)-Ethyl 2-(2-(cyclopropylsulfonyl)-5-(methoxycarbonylamino)phenyl)pyrrolidine-3-carboxylate hydrochloride

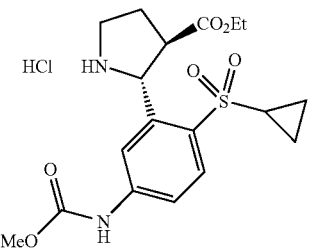

76P was prepared in a procedure similar to that of 1G using 76J and methyl chloroformate. $^1$H NMR (400 MHz, Methanol-$d_4$) δ ppm 0.96-1.19 (m, 3H) 1.17-1.28 (m, 3H) 1.36-1.53 (m, 1H) 2.34-2.55 (m, 1H) 2.64-2.83 (m, 1H) 2.87-3.06 (m, 1H) 3.40-3.64 (m, 3H) 3.74-3.90 (m, 3H) 4.08-4.30 (m, 2H) 5.86 (d, J=8.34 Hz, 1H) 7.62 (dd, J=8.84, 2.02 Hz, 1H) 7.95 (d, J=8.84 Hz, 1H) 8.09 (d, J=2.02 Hz, 1H)

76Q: Example 76

Example 76 was prepared according to the general coupling condition using 27A and 76N. $^1$H NMR (400 MHz, Methanol-$d_4$) δ ppm 0.84 (t, 3H) 0.98-1.09 (m, 2H) 1.07-1.18 (m, 1H) 1.35-1.47 (m, 1H) 2.20-2.48 (m, 2H) 3.18-3.27 (m, 1H) 3.51-3.64 (m, 2H) 3.64-3.79 (m, 7H) 3.81-3.99 (m, 1H) 4.15-4.31 (m, 1H) 5.46 (s, 1H) 6.27 (d, J=8.59 Hz, 1H) 6.93-7.08 (m, 5H) 7.08-7.16 (m, 1H) 7.19 (dd, J=8.72, 2.15 Hz, 1H) 7.30 (dd, J=8.34, 2.02 Hz, 1H) 7.67 (d, J=8.84 Hz, 1H) 9.29 (s, 1H); LC-MS 715 M+H).

Example 77

Diastereoisomer of Example 76

(2R,3S)-Ethyl 1-((S)-2-(5-carbamoyl-2-fluorophenylamino)-2-(4-fluoro-3-methoxyphenyl)acetyl)-2-(2-(cyclopropylsulfonyl)-5-(methoxycarbonylamino)phenyl)pyrrolidine-3-carboxylate

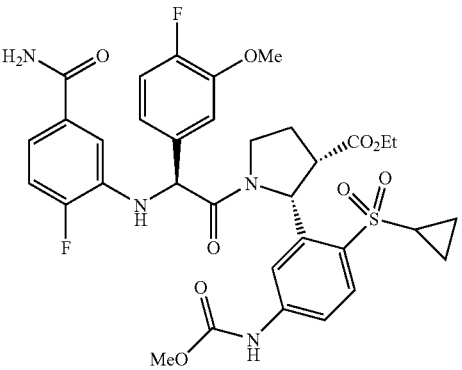

Example 77 was obtained as a diastereomer of Example 76 during its HPLC purification. $^1$H NMR (400 MHz, Methanol-$d_4$) δ ppm 0.81-0.95 (m, 3H) 0.94-1.16 (m, 2H) 1.18-1.52 (m, 2H) 1.98-2.14 (m, 1H) 2.36-2.49 (m, 1H) 3.05-3.19 (m, 1H) 3.43-3.66 (m, 2H) 3.66-3.84 (m, 5H) 3.87 (s, 3H) 4.30-4.49 (m, 1H) 5.38-5.60 (m, 1H) 6.18 (d, J=8.84 Hz, 1H) 6.91-7.21 (m, 4H) 7.27 (dd, J=8.34, 1.77 Hz, 1H) 7.32-7.48 (m, 2H) 7.59-7.82 (m, 2H) 9.29-9.47 (m, 1H), LC-MS 715 (M+H).

Example 78

(2R,3S)-1-((R)-2-(5-Carbamoyl-2-fluorophenylamino)-2-(4-fluoro-3-methoxyphenyl)acetyl)-2-(2-(cyclopropylsulfonyl)-5-(methoxycarbonylamino)phenyl)pyrrolidine-3-carboxylic acid

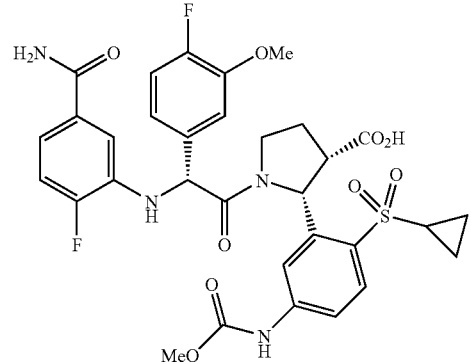

Example 78 was prepared by hydrolysis of the ethyl ester in Example 76 with NaOH in MeOH/H$_2$O at rt and purified by prep HPLC. $^1$H NMR (400 MHz, Methanol-d$_4$) δ ppm 0.99-1.09 (m, 1H) 1.10-1.22 (m, 1H) 1.21-1.32 (m, 1H) 1.36-1.48 (m, 1H) 2.19-2.35 (m, 1H) 2.36-2.55 (m, 1H) 2.82-2.98 (m, 1H) 3.01-3.21 (m, 1H) 3.66-3.77 (m, 6H) 3.83-3.98 (m, 1H) 4.06 (t, J=10.23 Hz, 1H) 5.43 (s, 1H) 6.22 (s, 1H) 6.97-7.10 (m, 4H) 7.09-7.21 (m, 3H) 7.28 (dd, J=8.21, 2.15 Hz, 1H) 7.67-7.80 (m, 1H) 9.46 (s, 1H), LC-MS 687 (M+H).

Example 79

(2R,3S)-1-((S)-2-(5-Carbamoyl-2-fluorophenylamino)-2-(4-fluoro-3-methoxyphenyl)acetyl)-2-(2-(cyclopropylsulfonyl)-5-(methoxycarbonylamino)phenyl)pyrrolidine-3-carboxylic acid

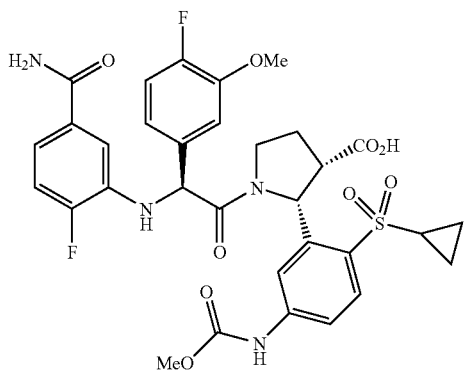

Example 79 was prepared by hydrolysis of the ethyl ester in Example 77 with NaOH in MeOH/H$_2$O at rt and purified by prep HPLC. $^1$H NMR (400 MHz, Methanol-d$_4$) δ ppm 0.98-1.10 (m, 1H) 1.11-1.22 (m, 1H) 1.23-1.39 (m, 1H) 1.36-1.51 (m, 1H) 2.20-2.38 (m, 1H) 2.36-2.50 (m, 1H) 2.82-2.96 (m, 1H) 3.07-3.23 (m, 1H) 3.67-3.79 (m, 6H) 3.85-3.99 (m, 1H) 4.00-4.17 (m, 1H) 5.37-5.50 (m, 1H) 6.23 (s, 1H) 6.94-7.10 (m, 4H) 7.09-7.22 (m, 3H) 7.24-7.38 (m, 1H) 7.62-7.83 (m, 1H) 9.47 (s, 1H), LC-MS 687 (M+H).

Example 80

(2R,3S)-Ethyl 1-((R)-2-(5-carbamoyl-2-fluorophenylamino)-2-(4-fluoro-3-methoxyphenyl)acetyl)-2-(2-(cyclopropylsulfonyl)-5-(3,3-dimethylureido)phenyl)pyrrolidine-3-carboxylate

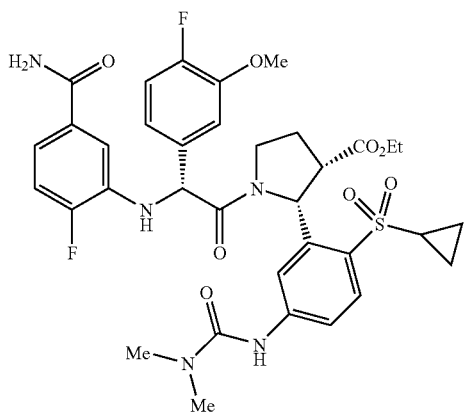

Example 80 was prepared according to the general coupling condition using 27A and 76O. $^1$H NMR (400 MHz, Methanol-d$_4$) δ ppm 0.84 (t, J=7.20 Hz, 3H) 0.95-1.17 (m, 3H) 1.33-1.47 (m, 1H) 2.20-2.35 (m, 1H) 2.41 (d, J=6.82 Hz, 1H) 2.91-3.06 (m, 6H) 3.16-3.27 (m, 1H) 3.50-3.64 (m, 2H) 3.69 (s, 3H) 3.71-3.79 (m, 1H) 3.81-3.97 (m, 1H) 4.13-4.28 (m, 1H) 5.46 (s, 1H) 6.26 (d, J=8.34 Hz, 1H) 6.66 (d, J=2.27 Hz, 1H) 6.90-7.09 (m, 4H) 7.10-7.17 (m, 1H) 7.30 (dd, J=8.34, 2.02 Hz, 1H) 7.38-7.45 (m, 1H) 7.66 (d, J=8.84 Hz, 1H), LC-MS 728 (M+H).

Example 81

(2R,3R)-Ethyl 1-((R)-2-(5-carbamoyl-2-fluorophenylamino)-2-(4-fluoro-3-methoxyphenyl)acetyl)-2-(2-(cyclopropylsulfonyl)-5-(methoxycarbonylamino)phenyl)pyrrolidine-3-carboxylate

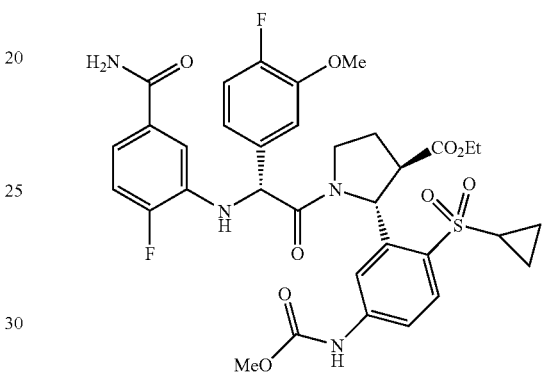

Example 81 was prepared according to the general coupling condition using 27A and 76P. $^1$H NMR (400 MHz, Methanol-d$_4$) δ ppm 0.92-1.09 (m, 2H) 1.08-1.19 (m, 1H) 1.19-1.28 (m, 3H) 1.33-1.48 (m, 1H) 2.18-2.51 (m, 2H) 2.89 (dd, J=5.31, 2.27 Hz, 1H) 3.03-3.19 (m, 1H) 3.64-3.76 (m, 6H) 3.79-3.96 (m, 1H) 4.00-4.27 (m, 3H) 5.44 (s, 1H) 6.18 (d, J=2.02 Hz, 1H) 6.93-7.22 (m, 7 H) 7.27 (dd, J=8.21, 2.15 Hz, 1H) 7.66-7.75 (m, 1H) 9.48 (s, 1H), LC-MS 715 (M+H).

Example 82

Diastereoisomer of Example 81

(2R,3R)-Ethyl 1-((S)-2-(5-carbamoyl-2-fluorophenylamino)-2-(4-fluoro-3-methoxyphenyl)acetyl)-2-(2-(cyclopropylsulfonyl)-5-(methoxycarbonylamino)phenyl)pyrrolidine-3-carboxylate

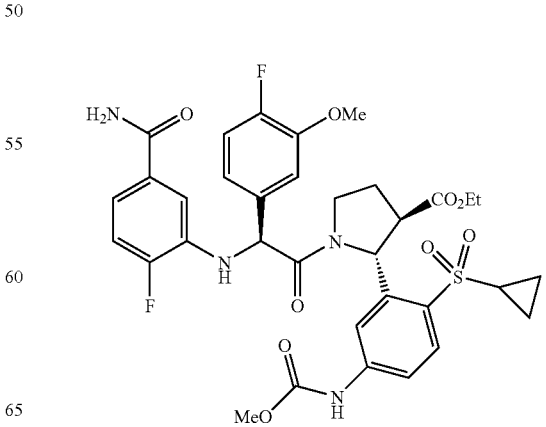

Example 82 was obtained as a diastereomer of Example 81 during its HPLC purification. $^1$H NMR (400 MHz, Methanol-$d_4$) δ ppm 0.93-1.06 (m, 2H) 1.07-1.28 (m, 3H) 1.31-1.50 (m, 2H) 2.19 (d, J=36.88 Hz, 1H) 2.39-2.57 (m, 1 H) 2.88 (d, J=6.82 Hz, 1H) 2.92-3.06 (m, 1H) 3.65-3.99 (m, 6H) 3.98-4.10 (m, 2 H) 4.12-4.29 (m, 1H) 4.27-4.41 (m, 1H) 5.34-5.63 (m, 1H) 6.15 (s, 1H) 6.47-6.82 (m, 1H) 6.93-7.20 (m, 4H) 7.22-7.36 (m, 1H) 7.35-7.47 (m, 1H) 7.63-7.92 (m, 2H) 9.47 (d, J=2.27 Hz, 1H), LC-MS 715 (M+H).

Example 83

(2R,3S)-1-((R)-2-(5-Carbamoyl-2-fluorophenylamino)-2-(4-fluoro-3-methoxyphenyl)acetyl)-2-(2-(cyclopropylsulfonyl)-5-(3,3-dimethylureido)phenyl)pyrrolidine-3-carboxylic acid

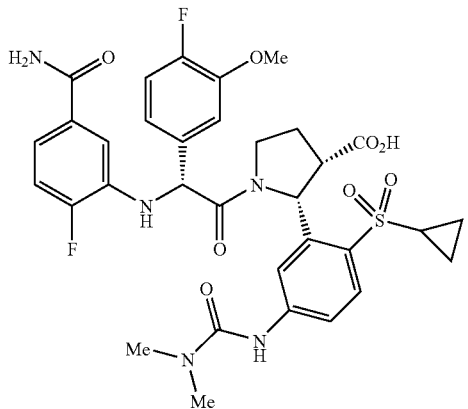

Example 83 was prepared by hydrolysis of the ethyl ester in Example 80 with NaOH in MeOH/H$_2$O at rt and purified by prep HPLC. $^1$H NMR (400 MHz, Methanol-$d_4$) δ ppm 0.95-1.10 (m, 2H) 1.10-1.21 (m, 1H) 1.36-1.51 (m, 1H) 2.16-2.32 (m, 1H) 2.36-2.54 (m, 1H) 2.91 (d, J=8.24 Hz, 1H) 2.96-3.02 (m, 6H) 3.05-3.18 (m, 1H) 3.67-3.76 (m, 3H) 3.84-3.97 (m, 1H) 3.97-4.11 (m, 1H) 5.42 (s, 1H) 6.20 (s, 1H) 6.86 (d, J=2.20 Hz, 1H) 6.94-7.11 (m, 4H) 7.16 (dd, J=5.50, 3.30 Hz, 1H) 7.22-7.32 (m, 2H) 7.72 (d, J=8.79 Hz, 1H), LC-MS 700 (M+H).

Example 84

(2R,3R)-1-((R)-2-(5-Carbamoyl-2-fluorophenylamino)-2-(4-fluoro-3-methoxyphenyl)acetyl)-2-(2-(cyclopropylsulfonyl)-5-(methoxycarbonylamino)phenyl)pyrrolidine-3-carboxylic acid

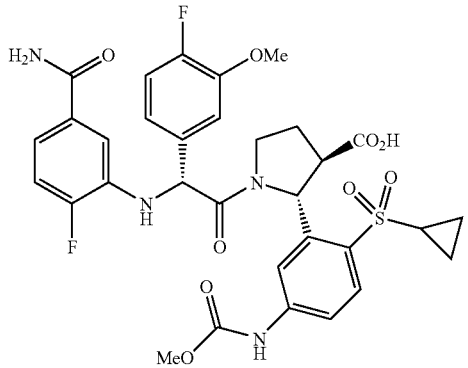

Example 84 was prepared by hydrolysis of the ethyl ester in Example 81 with NaOH in MeOH/H$_2$O at rt and purified by prep HPLC. $^1$H NMR (400 MHz, Methanol-$d_4$) δ ppm 0.96-1.09 (m, 2H) 1.09-1.21 (m, 1H) 1.35-1.49 (m, 1H) 2.28 (dd, J=13.74, 7.15 Hz, 1H) 2.34-2.51 (m, 1H) 2.89 (d, J=7.70 Hz, 1H) 3.06-3.20 (m, 1H) 3.72 (t, J=9.89 Hz, 6H) 3.83-3.95 (m, 1H) 3.98-4.13 (m, 1H) 5.43 (s, 1H) 6.22 (s, 1H) 6.94-7.21 (m, 7H) 7.23-7.44 (m, 1H) 7.68-7.79 (m, 1H) 9.50 (s, 1H), LC-MS 687 (M+H).

Example 85

Methyl 3-((R)-1-((R)-2-(5-Carbamoyl-2-fluorophenylamino)-2-(3-ethoxy-4-fluorophenyl)acetyl)pyrrolidin-2-yl)-4-(cyclopropylsulfonyl)phenylcarbamate

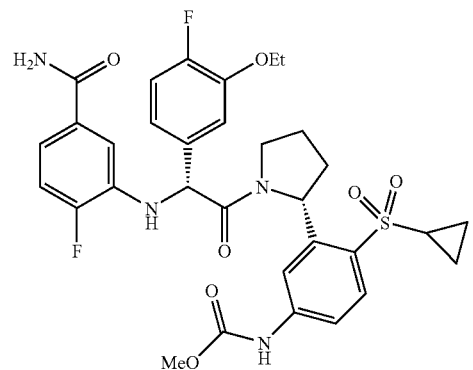

85A: (S,E)-N-(2-(Cyclopropylthio)-5-nitrobenzylidene)-2-methylpropane-2-sulfinamide

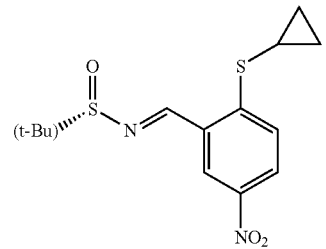

To 76A (2.02 g, 9.0 mmol), (S)-tert-butylsulfinamide (1.21 g, 10 mmol) in CH$_2$Cl$_2$ (40 mL) was added Ti(OEt)$_4$ (10 mL, 45 mmol). The mixture was heated at 73° C. for 6.0 h. CH$_2$Cl$_2$ was removed under vacuo and the residue was suspended in EtOAc. To this suspension was added brine. The mixture was stirred at rt for 15 min before it was filtered through a pad of wet Celite®. The filtrate was extracted with EtOAc (3×50 mL). The organic layer was washed with brine and dried over Na$_2$SO$_4$. After removal of solvent, 85A (3.0 g, 100% yield) was obtained as a solid. $^1$H NMR (400 MHz, CDCl$_3$) δ ppm 0.72-0.81 (m, 2H) 1.21 (m, 2H) 1.28 (s, 9H) 2.14-2.21 (m, 1H) 7.89 (d, J=8.79 Hz, 1H) 8.24 (dd, J=8.79, 2.64 Hz, 1H) 8.60 (d, J=2.64 Hz, 1H) 8.77 (s, 1H).

85B: (S)—N-(1-(2-(Cyclopropylthio)-5-nitrophenyl)allyl)-2-methylpropane-2-sulfinamide

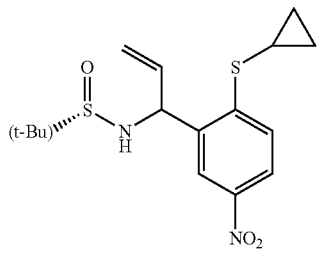

To 85A (3.0 g, 9.2 mmol) in THF (30 mL) and methyl tert-butylether (50 mL) at −78° C. was added vinylmagnesium bromide (1.0 M in THF, 20 mL, 20 mmol) dropwise. The mixture was stirred at −78° C. for 1.0 h before it was quenched with sat. $NH_4Cl$ (50 mL) at −78° C. The mixture was extracted with EtOAc (3×50 mL), the organic layer was washed with brine and dried over $Na_2SO_4$. After removal of solvent, the crude was purified by silica gel column chromatography using gradient EtOAc in hexanes to give 85B (2.45 g, 78% yield). HPLC and $^1$H NMR indicated 85B is a mixture of two diastereoisomers in a ratio of 5:1. Major isomer: $^1$H NMR (400 MHz, $CDCl_3$) δ ppm 0.70-0.81 (m, 2H) 1.17-1.24 (m, 2H) 1.26 (s, 9H) 2.17 (m, 1H) 3.53 (d, J=2.64 Hz, 1H) 5.21-5.32 (m, 3H) 5.91 (m, 1H) 7.72 (d, J=8.79 Hz, 1H) 8.09 (dd, J=8.79, 2.64 Hz, 1H) 8.26 (d, J=2.64 Hz, 1H), LC-MS 355 (M+H).

85C: (S)—N-Allyl-N-(1-(2-(cyclopropylthio)-5-nitrophenyl)allyl)-2-methylpropane-2-sulfinamide

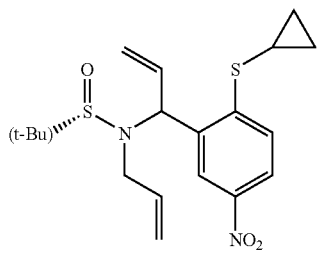

To 85B (2.46 g, 6.95 mmol) in DMF (20 mL) at −20° C. was added lithium bis(trimethylsilyl)amide (1.0 M in THF, 12.2 mL, 12.2 mmol) dropwise. The mixture was stirred at −20° C. for 20 min followed by addition of allyl bromide (3.0 mL, 34.8 mmol). After 1.0 h stirring at −20° C., the reaction was quenched with sat. $NH_4Cl$ and warmed to rt. It was extracted with EtOAc (3×50 mL), the organic layer was washed with brine and dried over $Na_2SO_4$. After removal of solvent, the crude was purified by silica gel column chromatography using gradient EtOAc in hexanes to give 85C (2.2 g, 80% yield). HPLC and $^1$H NMR indicated 85C is a mixture of two diastereoisomers in a ratio of 5:1. Major isomer: $^1$H NMR (400 MHz, $CDCl_3$) δ ppm 0.67-0.76 (m, 2H) 1.15-1.20 (m, 2H) 1.25 (s, 9H) 2.12-2.20 (m, 1H) 3.02 (dd, J=17.14, 6.59 Hz, 1H) 4.05 (dd, J=17.14, 4.83 Hz, 1H) 5.06-5.26 (m, 5H) 6.00 (ddd, J=17.03, 10.22, 7.03 Hz, 1H) 7.70 (t, J=8.13 Hz, 1H) 8.10 (dd, J=8.79, 2.64 Hz, 1H) 8.49 (d, J=2.64 Hz, 1H), LC-MS 395 (M+H).

85D: (R)-1-((S)-tert-Butylsulfinyl)-2-(2-(cyclopropylthio)-5-nitrophenyl)-2,5-dihydro-1H-pyrrole and

85E: (S)-1-((S)-tert-Butylsulfinyl)-2-(2-(cyclopropylthio)-5-nitrophenyl)-2,5-dihydro-1H-pyrrole

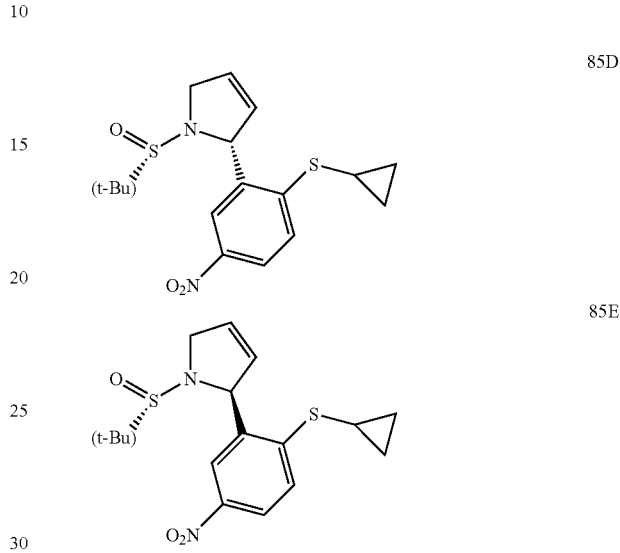

A solution of 85C (2.2 g, 5.5 mmol) in $CH_2Cl_2$ (200 mL) was degassed by bubbling argon for 8 min. To this solution was added Grubb's catalyst ($2^{nd}$ generation, 380 mg, 0.45 mmol). The mixture was heated at 72° C. for 5.0 h. After removal of solvent, the crude was purified by silica gel column chromatography using gradient EtOAc in hexanes to give 85D as a major product (1.66 g, 82% yield): $^1$H NMR (400 MHz, $CDCl_3$) δ ppm 0.71-0.80 (m, 2H) 1.15-1.19 (s, 9H) 1.19-1.25 (m, 2H) 2.14-2.22 (m, 1H) 3.78 (dt, J=14.50, 2.64 Hz, 1H) 4.69 (dd, J=14.50, 2.64 Hz, 1H) 5.73 (dd, J=6.15, 2.20 Hz, 1H) 5.85 (dd, J=5.05, 2.42 Hz, 1H) 5.88 (ddd, J=4.06, 2.20, 2.09 Hz, 1H) 7.69 (d, J=8.79 Hz, 1H) 8.06 (dd, J=8.57, 2.42 Hz, 1H) 8.19 (d, J=2.20 Hz, 1H), LC-MS 367 (M+H). 85E was obtained as a minor product (0.31 g, 14% yield): $^1$H NMR (400 MHz, $CDCl_3$) δ ppm 0.65-0.73 (m, 1H) 0.73-0.82 (m, 1H) 1.01 (s, 9H) 1.17-1.26 (m, 2H) 2.15-2.24 (m, J=7.96, 3.90, 3.74, 3.74 Hz, 1H) 4.36-4.43 (m, 1H) 4.51-4.58 (m, 1H) 5.82 (dd, J=6.15, 2.20 Hz, 1H) 5.87 (d, J=1.76 Hz, 1H) 5.90 (dd, J=5.05, 2.86 Hz, 2H) 7.66 (d, J=8.79 Hz, 1H) 8.06 (dd, J=8.57, 2.42 Hz, 1H) 8.13 (d, J=2.20 Hz, 1H), LC-MS 367 (M+H).

85F: (R)-tert-Butyl 2-(2-(cyclopropylthio)-5-nitrophenyl)-2,5-dihydro-1H-pyrrole-1-carboxylate

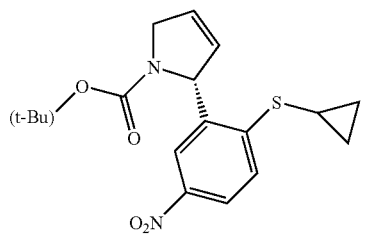

To 85D (1.6 g, 4.37 mmol) in MeOH (20 mL) at rt was added 4.0 N HCl in dioxane (4.37 mL, 17.5 mmol). The mixture was stirred at rt for 20 min. Solvent was evaporated and the crude (R)-2-(2-(cyclopropylthio)-5-nitrophenyl)-2,5-dihydro-1H-pyrrole HCl salt (LC-MS 263) was dried under high vacuum for 1.0 h. To the crude HCl salt in THF (20 mL) and MeOH (5.0 mL) was added di-tert-butyl dicarbonate (1.0 M in THF, 6.0 mL, 6.0 mmol) and triethylamine (1.28 mL, 9.18 mmol). The mixture was stirred at rt for 1.0 h. It was diluted and extracted with EtOAc. The organic layer was washed with 0.5 N HCl, sat. NaHCO$_3$, brine and dried over Na$_2$SO$_4$. After evaporation of solvent, the crude was purified by silica gel column chromatography eluting with gradient EtOAc in hexanes to give 85F (1.52 g, 95% yield) as a solid. $^1$H NMR (400 MHz, CDCl$_3$) δ ppm 0.73-0.80 (m, 2H) 1.15 (s, 9H) 1.18-1.27 (m, 2H) 2.13-2.20 (m, 1H) 4.33-4.42 (m, 2H) 5.68-5.90 (m, 3H) 7.68 (d, J=8.79 Hz, 1H) 7.93 (dd, J=8.13, 2.42 Hz, 1H) 8.05 (td, J=8.90, 2.42 Hz, 1H), LC-MS 307 (M-tert-Bu).

85G: (R)-tert-Butyl 2-(5-amino-2-(cyclopropylthio)phenyl)pyrrolidine-1-carboxylate

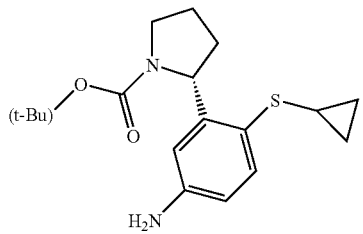

85F (1.52 g, 4.19 mmol) and 10% Pd/C (560 mg) in MeOH (100 mL) was hydrogenated under 45 psi for 3.5 h. TLC and LC-MS indicate a clean conversion to the product. Pd/C was removed by filtration through a pad of Celite®. The filtrate was concentrated to give 85G (1.37 g, 97% yield) as a solid. $^1$H NMR (400 MHz, Methanol-d$_4$) δ ppm 0.52-0.64 (m, 2H) 0.85-0.95 (m, 2H) 1.16-1.24 (s, 7H) 1.45 (s, 2H) 1.71 (m, 1H) 1.82-1.94 (m, 2H) 2.09-2.19 (m, 1H) 2.32 (m, 1H) 3.47-3.57 (m, 1H) 3.59-3.69 (m, 1H) 5.18-5.25 (m, 1H) 6.48 (d, J=2.20 Hz, 1H) 6.58 (dd, J=8.13, 2.42 Hz, 1H) 7.30 (t, J=8.35 Hz, 1H), LC-MS 235 (M-Boc).

85H: (R)-tert-Butyl 2-(2-(cyclopropylthio)-5-(methoxycarbonylamino)phenyl)pyrrolidine-1-carboxylate

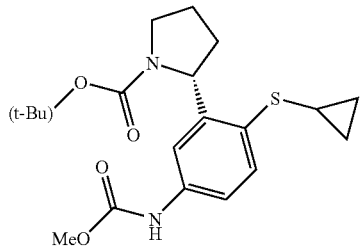

To 85G (1.25 g, 3.74 mmol) in pyridine (8.0 mL) at 0° C. was added methyl chloroformate (0.4 mL, 5.23 mmol). After 30 min, the reaction was quenched by MeOH (2.0 mL). Pyridine was removed under high vacuum. The crude was suspended in EtOAc and washed by 1.0 N HCl (2×20 mL), sat. NaHCO$_3$ and brine. The organic layer was dried over Na$_2$SO$_4$. After evaporation of solvent, 85H (1.6 g, 95% yield) was obtained as a solid used for next step without purification. $^1$H NMR (400 MHz, DMSO-d$_6$, 100° C.) δ ppm 0.52-0.64 (m, 2H) 0.94-1.05 (m, 2H) 1.17-1.28 (s, 9H) 1.54-1.63 (m, 1H) 1.77-1.86 (m, 2H) 2.18-2.29 (m, 2H) 3.46-3.57 (m, 2H) 3.62-3.68 (s, 3H) 5.05 (dd, J=7.70, 3.85 Hz, 1H) 7.23 (s, 1H) 7.32-7.40 (m, 1H) 7.40-7.47 (m, 1H) 9.26 (s, 1H), LC-MS 293 (M-Boc).

85I: (R)-tert-Butyl 2-(2-(cyclopropylsulfonyl)-5-(methoxycarbonylamino)phenyl)pyrrolidine-1-carboxylate

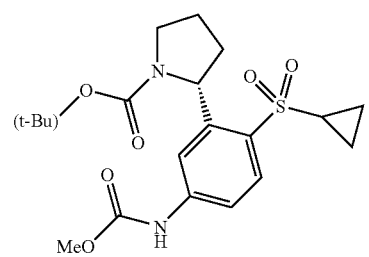

To 85H (1.60 g, 4.0 mmol) in CH$_2$Cl$_2$ (50 mL) was added NaHCO$_3$ (1.0 g, 11.9 mmol) and MCPBA (75% purity, 2.15 g, 9.4 mmol). The mixture was stirred at rt for 5.0 h. It was quenched with sat. NaHCO$_3$ and extracted with CH$_2$Cl$_2$. The organic layer was dried over Na$_2$SO$_4$. After removal of solvent, the crude was purified with silica gel column chromatography eluting with gradient EtOAc in hexanes to give 85I (1.64 g, 96%). $^1$H NMR (400 MHz, DMSO-d$_6$, 100° C.) δ ppm 0.95-1.00 (m, 1H) 1.03-1.11 (m, 2H) 1.20 (s, 9H) 1.17-1.28 (m, 1H) 1.72 (m, 1 H) 1.81-1.92 (m, 2H) 2.83 (m, 1H) 3.52-3.64 (m, 2H) 3.74 (s, 3H) 5.56 (dd, J=8.24, 4.40 Hz, 1H) 7.52 (d, J=2.20 Hz, 1H) 7.59 (dd, J=8.79, 2.20 Hz, 1H) 7.74 (d, J=8.79 Hz, 1H) 9.80 (s, 1H); LC-MS 425 (M+H).

85J: (R)-Methyl 4-(cyclopropylsulfonyl)-3-(pyrrolidin-2-yl)phenylcarbamate hydrochloride

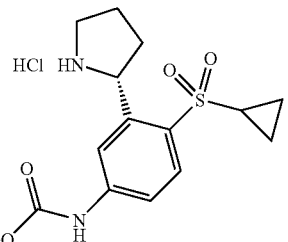

To 85I (1.63 g, 3.84 mmol) in EtOAc (15.0 mL) at rt was added 4.0 N HCl in dioxane (30 mL, 120 mmol). The mixture was stirred at rt for 4.0 h. TLC and LC-MS indicated a clean formation of the product. After evaporation of solvent, 85J (1.31 g, 95% yield) was obtained as a white solid. $^1$H NMR (400 MHz, Methanol-d$_4$) δ ppm 0.98-1.10 (m, 3H) 1.21-1.33 (m, 1H) 2.10-2.20 (m, 1H) 2.24-2.34 (m, 2 H) 2.41-2.50 (m, 1H) 2.80-2.89 (m, 1H) 3.31-3.41 (m, 2H) 3.70 (s, 3H) 5.45 (t, J=7.69 Hz, 1H) 7.54 (dd, J=8.79, 2.20 Hz, 1H) 7.85 (d, J=8.79 Hz, 1H) 7.99 (d, J=2.20 Hz, 1H), LC-MS 325 (M+H).

85K: Example 85

Example 85 was prepared according to the general coupling condition using 29A and 85J. ¹H NMR (400 MHz, Methanol-d₄) δ ppm ¹H NMR (400 MHz, Solvent) d ppm 0.99-1.08 (m, 2H) 1.09-1.18 (m, 1H) 1.30-1.36 (t, J=7.04 Hz, 3 H) 1.36-1.44 (m, 1H) 1.71 (m, 1H) 2.01-2.12 (m, 2H) 2.51 (m, 1H) 3.22-3.28 (m, 1H), 3.65-3.75 (m, 1H) 3.74 (s, 3H) 3.78-3.87 (m, 1H) 3.88-3.98 (m, 1H) 4.09-4.19 (m, 1H) 5.43 (s, 1H) 5.87 (dd, J=7.91, 5.27 Hz, 1H) 6.92-7.01 (m, 2H) 7.04 (d, J=7.91 Hz, 2H) 7.08-7.15 (m, 3H) 7.31 (dd, J=8.35, 2.20 Hz, 1H) 7.68 (d, J=8.79 Hz, 1H) 9.45 (s, 1H), LC-MS 657 (M+H).

Example 86

Diastereoisomer of Example 85

Methyl 3-((R)-1-((S)-2-(5-carbamoyl-2-fluorophenylamino)-2-(3-ethoxy-4-fluorophenyl)acetyl)pyrrolidin-2-yl)-4-(cyclopropylsulfonyl)phenylcarbamate

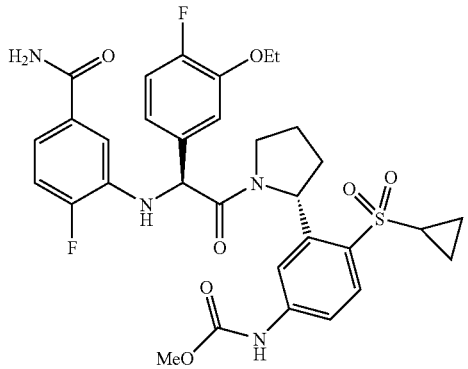

Example 86 was obtained as a diastereomer of Example 85 during its HPLC purification. ¹H NMR (400 MHz, Methanol-d₄) δ ppm 0.95-1.15 (m, 4H), 1.33 and 1.38 (t, J=6.95 Hz, 3H), 1.98-3.11 (m, 5H), 3.72 and 3.75 (s, 3H), 4.12 (q, J=6.95 Hz, 2H) 5.2 and 5.4 (s, 1H) 5.78-5.82 (m, 1H) 6.40-7.78 (m, 9H) 9.4 (s, 1H); LC-MS 657 (M+H).

Example 87

Methyl 3-((R)-1-((R)-2-(5-carbamoyl-2-fluorophenylamino)-2-(4-fluoro-3-methoxyphenyl)acetyl)pyrrolidin-2-yl)-4-(cyclopropylsulfonyl)phenylcarbamate

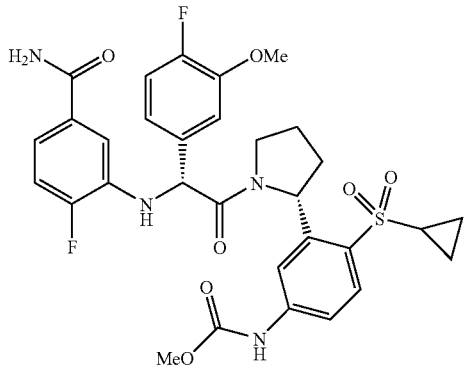

Example 87 was prepared according to the general coupling condition using 27A and 85J. ¹H NMR (400 MHz, Methanol-d₄) δ ppm 1.00-1.08 (m, 2H) 1.13 (m, 1H) 1.36-1.43 (m, 1H) 1.73 (m, 1H) 2.02-2.14 (m, 2H) 2.52 (m, 1H) 3.22-3.29 (m, 1H) 3.71 (s, 6H) 4.16 (ddd, J=10.22, 6.81, 6.70 Hz, 1H) 5.46 (s, 1H) 5.88 (dd, J=7.91, 5.27 Hz, 1H) 6.98-7.06 (m, 4H) 7.08-7.15 (m, 3H) 7.32 (dd, J=8.35, 1.76 Hz, 1H) 7.68 (d, J=9.23 Hz, 1H) 9.44 (s, 1H), LC-MS 643 (M+H).

Example 88

Diastereoisomer of Example 87

Methyl 3-((R)-1-((S)-2-(5-carbamoyl-2-fluorophenylamino)-2-(4-fluoro-3-methoxyphenyl)acetyl)pyrrolidin-2-yl)-4-(cyclopropylsulfonyl)phenylcarbamate

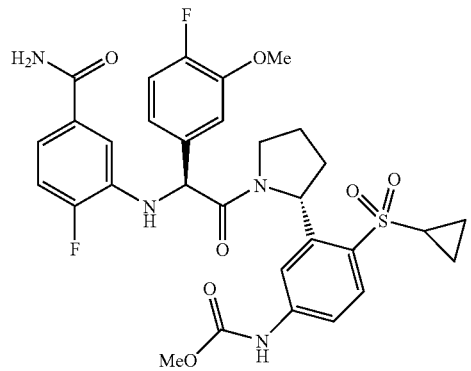

Example 88 was obtained as a diastereomer of Example 87 during its HPLC purification. ¹H NMR (400 MHz, Methanol-d₄) δ ppm 0.99-1.20 (m, 4H), 1.98-3.71 (m, 5H), 3.72 and 3.75 (s, 6H) 5.4 and 5.5 (s, 1H) 5.78-5.82 (m, 1H) 6.40-7.78 (m, 9H) 9.4 (s, 1H); LC-MS 643 (M+H).

Example 89

Methyl 3-((R)-1-((R)-2-(3-carbamoyl-5-methylphenylamino)-2-(3,4-dimethoxyphenyl)acetyl)pyrrolidin-2-yl)-4-(isopropylsulfonyl)phenylcarbamate

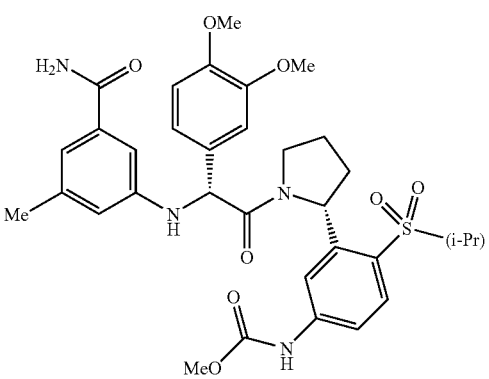

89A: Methyl 3-methyl-5-nitrobenzoate

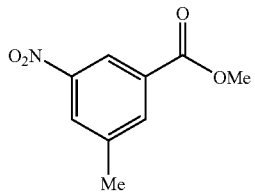

Following a general procedure from *Applied Organometallic Chemistry* 2004, 18, 602-604, a solution of 3-(methoxycarbonyl)-5-nitrophenylboronic acid (900 mg, 4.0 mmol) in tetrahydrofuran (16 mL) was added to a round bottom flask charged with palladium acetate (27 mg, 0.12 mmol), tri-1-napthylphosphine (112 mg, 0.27 mmol), potassium phosphate (1.70 g, 8.00 mmol), and methyl iodide (0.370 mL, 5.9 mmol) under nitrogen atmosphere. Water (0.14 mL, 7.8 mmol) was added and the mixture was stirred overnight at rt. The reaction mixture was diluted with water and extracted with ethyl acetate (3×). The combined organics were washed with water and brine, dried, and concentrated in vacuo. The residue was purified by silica gel chromatography (gradient from 0 to 40% ethyl acetate in hexanes) to give 89A (0.36 g, 46%) as a white solid. ¹H NMR (400 MHz, CDCl₃) δ ppm 2.54 (s, 3H) 3.98 (s, 3H) 8.19 (s, 1H) 8.23 (s, 1H) 8.67 (s, 1H).

89B: 3-Methyl-5-nitrobenzoic acid

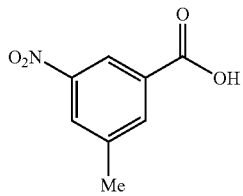

A solution of 89A (0.36 g, 1.8 mmol) and aqueous sodium hydroxide (1N, 3 mL, 3 mmol) in a mixture of methanol (1.5 mL) and tetrahydrofuran (3 mL) was heated at 80° C. for 1 h and at rt for 2 h. An additional portion of sodium hydroxide solution (1 mL) was added and the mixture was heated at 80° C. for 5 min. The reaction mixture was concentrated in vacuo, diluted with ethyl acetate and acidified with hydrochloric acid (1N). The aqueous layer was extracted with ethyl acetate (2×). The combined organic layers were washed with brine, dried (MgSO₄), and concentrated in vacuo to give 89B (0.314 g, 94%) as a white solid. LCMS: 182 (M+1)

89C: 3-Amino-5-methylbenzamide

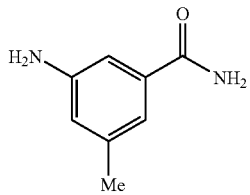

Oxalyl chloride (0.30 mL, 3.4 mmol) was added dropwise to a solution of 89B (0.300 g, 1.66 mmol) and DMF (1 drop) in dichloromethane (10 mL). The reaction mixture was stirred at rt for 3 h and then concentrated in vacuo. The residue was coevaporated with toluene (2×) and then suspended in THF (5 mL). Cold concentrated aqueous ammonia (2 mL) was added slowly dropwise. After 15 min, the reaction mixture was concentrated in vacuo to give the nitrobenzamide as a crude white solid (0.519 g). This material was suspended in methanol (20 mL) and hydrogenated (30 psi) over 10% Pd/C (56 mg) overnight. The reaction mixture was filtered and concentrated in vacuo to give 89C as a white solid (0.306 g, 100%). ¹H NMR (400 MHz, CD₃OD) δ ppm 2.26 (s, 3H) 6.71 (s, 1H) 6.98 (s, 2H).

89D: 2-(3-Carbamoyl-5-methylphenylamino)-2-(3,4-dimethoxyphenyl)acetic acid

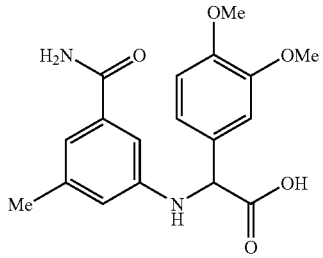

A mixture of 89C (75 mg, 0.5 mmol), 3,4-dimethoxyphenylboronic acid (91 mg, 0.5 mmol) and glyoxylic acid monohydrate (46 mg, 0.5 mmol) in acetonitrile (1.0 mL) and DMF (0.1 mL) was heated at in a microwave reactor at 100° C. for 10 min. The precipitate formed was collected by filtration. The filtrate was concentrated and the residue was triturated with ethyl acetate and ether. This solid was combined with the original precipitate to give 89D (76 mg, 44%) as an orange solid. ¹H NMR (400 MHz, CD₃OD) δ ppm 2.26 (s, 3H) 3.81 (s, 3H) 3.82 (s, 3H) 5.09 (s, 1H) 6.70 (s, 1H) 6.92 (d, J=8.4 Hz, 1H) 7.00 (s, 1H) 7.02 (s, 1H) 7.07 (dd, J=8.4, 2.2 Hz, 1H) 7.11 (d, J=1.8 Hz, 1H).

89E: Example 89

Example 89 was prepared according to the general coupling condition using 89D and 1G. ¹H NMR (400 MHz, CD₃OD) δ ppm 1.18 (d, J=6.59 Hz, 3H) 1.43 (d, J=6.59 Hz, 3H) 1.70 (td, J=12.41, 6.81 Hz, 1H) 1.99-2.14 (m, 2H) 2.29 (s, 3H) 2.43-2.54 (m, 1H) 3.59-3.64 (m, 1H) 3.66 (s, 3H) 3.70 (s, 3H) 3.84 (s, 3H) 3.97 (ddd, J=13.51, 6.70, 6.59 Hz, 1H) 4.03-4.12 (m, 1H) 5.39 (s, 1H) 5.67 (dd, J=8.13, 5.05 Hz, 1H) 6.81 (s, 1H) 6.83 (s, 1H) 6.90 (s, 2H) 7.09 (s, 1H) 7.12 (s, 1H) 7.19 (s, 1H) 7.23 (dd, J=8.57, 1.98 Hz, 1H) 7.75 (d, J=8.79 Hz, 1H) 9.43 (s, 1 H); LC/MS 654 (M+H).

Example 90

Diastereoisomer of Example 89

Methyl 3-((R)-1-((S)-2-(3-carbamoyl-5-methylphenylamino)-2-(3,4-dimethoxyphenyl)acetyl)pyrrolidin-2-yl)-4-(isopropylsulfonyl)phenylcarbamate

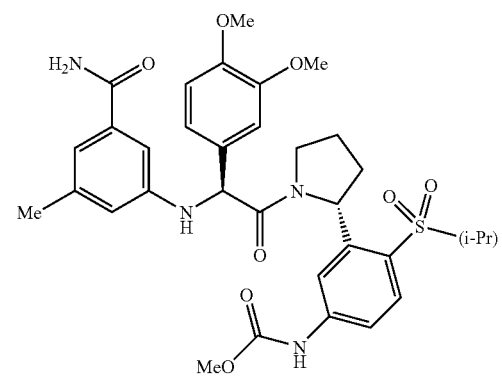

Example 90 was obtained as a diastereomer of Example 89 during its HPLC purification. ¹H NMR (400 MHz, Methanol-d₄) δ ppm ¹H NMR (400 MHz, CD₃OD) δ ppm 1.15 (d, J=6.59 Hz, 3H) 1.42 (d, J=7.03 Hz, 2H) 1.50 (d, J=6.59 Hz, 1H) 1.69-1.79 (m, 1H) 1.80-1.91 (m, 1H) 2.07-2.18 (m, 1H) 2.23 (s, 3H) 2.26-2.38 (m, 3H) 3.51-3.59 (m, 1H) 3.65 (s, 1H) 3.71 (s, 1H) 3.73 (s, 1H) 3.78 (s, 2H) 3.83 (s, 3H) 3.84 (s, 3H) 4.09-4.17 (m, 1H) 5.41 (s, 1H) 5.61 (dd, J=8.35, 3.95 Hz, 1H) 6.44-6.55 (m, 1H) 6.76 (s, 1H) 6.94-7.03 (m, 1H) 7.03-7.33 (m, 5H) 7.55 (s, 1H) 7.71-7.81 (m, 1H) 9.44-9.58 (m, 1H); LC-MS 654 (M+H).

Example 91

Methyl 3-((R)-1-((R)-2-(3-carbamoyl-5-fluorophenylamino)-2-(3,4-dimethoxyphenyl)acetyl)pyrrolidin-2-yl)-4-(isopropylsulfonyl)phenylcarbamate

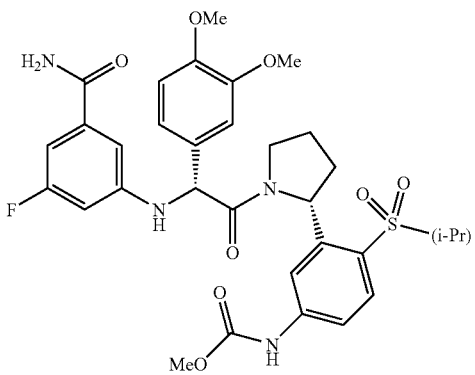

91A: 3-Amino-5-fluorobenzamide

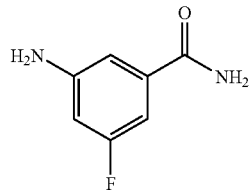

Using a procedure analogous to that described for preparation of 89C, 3-fluoro-5-nitrobenzoic acid was converted to an acid chloride, reacted with aqueous ammonia, and hydrogenated to give 91A. ¹H NMR (400 MHz, CD₃OD) δ ppm 6.55 (dt, J=10.99, 2.20 Hz, 1H) 6.79 (m, 1H) 6.95 (t, J=1.54 Hz, 1H); LC/MS 155 (M+H).

91B: 2-(3-Carbamoyl-5-fluorophenylamino)-2-(3,4-dimethoxyphenyl)acetic acid

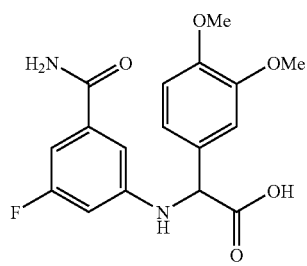

Using a procedure analogous to that described for the preparation of 89D, 91A was reacted with 3,4-dimethoxyphenylboronic acid and glyoxylic acid monohydrate to give 91B. ¹H NMR (400 MHz, CD₃OD) δ ppm 3.81 (s, 3H) 3.82 (s, 3H) 5.06 (s, 1H) 6.49 (d, J=11.43 Hz, 1H) 6.79 (d, J=9.23 Hz, 1H) 6.93 (d, J=8.35 Hz, 1H) 6.97 (s, 1H) 7.04-7.10 (m, 1H) 7.12 (s, 1H); LC/MS 349 (M+H).

91C: Example 91

Example 91 was prepared according to the general coupling condition using 91B and 1G. ¹H NMR (400 MHz, CD₃OD) δ ppm 1.16 (d, J=6.59 Hz, 3H) 1.42 (d, J=7.03 Hz, 3H) 1.64-1.76 (m, 1H) 2.00-2.15 (m, 2H) 2.43-2.55 (m, 1H) 3.67 (s, 3H) 3.70 (s, 3H) 3.71-3.77 (m, 1H) 3.84 (s, 3H) 3.90-4.00 (m, 1H) 4.08-4.19 (m, 1H) 5.32 (s, 1H) 5.66 (dd, J=8.35, 4.83 Hz, 2H) 6.56 (dt, J=11.42, 2.20 Hz, 1H) 6.80 (d, J=8.79 Hz, 1H) 6.84-6.99 (m, 4H) 7.01 (s, 1H) 7.07-7.19 (m, 1H) 7.21 (dd, J=8.35, 2.20 Hz, 1H) 7.73 (d, J=8.79 Hz, 1H) 9.35 (s, 1H); LC/MS 658 (M+H).

Example 92

Diastereoisomer of Example 91

Methyl 3-((R)-1-((S)-2-(3-carbamoyl-5-fluorophenylamino)-2-(3,4-dimethoxyphenyl)acetyl)pyrrolidin-2-yl)-4-(isopropylsulfonyl)phenylcarbamate

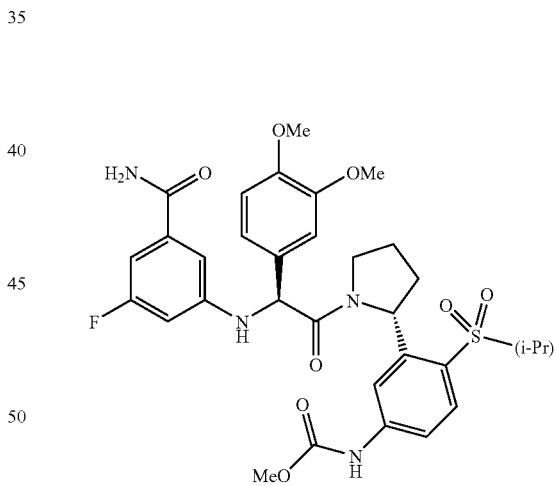

Example 92 was obtained as a diastereomer of Example 91 during its HPLC purification. ¹H NMR (400 MHz, CD₃OD) δ ppm 1.09-1.19 (m, 3H) 1.38-1.52 (m, 3H) 1.71-1.80 (m, 1H) 1.82-1.92 (m, 1H) 2.08-2.20 (m, 1H) 2.29-2.40 (m, 1H) 3.56-3.66 (m, 1H) 3.66-3.74 (m, 3H) 3.78 (s, 3H) 3.83 (s, 3H) 3.84 (s, 3H) 4.15-4.24 (m, 1H) 5.36 (s, 1H) 5.59 (dd, J=8.13, 3.73 Hz, 1H) 6.39-6.60 (m, 2H) 6.75-7.24 (m, 7H) 7.53 (dd, J=8.79, 2.20 Hz, 1H) 7.70-7.73 (m, 1H) 7.77 (d, J=8.79 Hz, 1H) 9.44 (s, 1H) 9.58 (s, 1H); LC-MS 658 (M+H).

Example 93

Methyl 3-((R)-1-((R)-2-(3-carbamoyl-5-methoxyphenylamino)-2-(3,4-dimethoxyphenyl)acetyl)pyrrolidin-2-yl)-4-(isopropylsulfonyl)phenylcarbamate

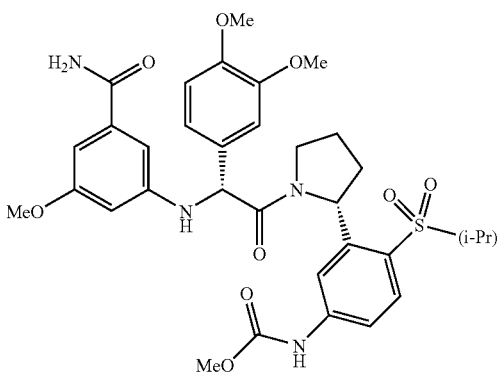

93A: Methyl 3-hydroxy-5-nitrobenzoate

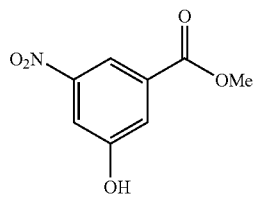

3-Nitro-5-methoxycarbonylphenylboronic acid (225 mg, 1.0 mmol) was added to a vigorously stirred solution of sodium hydroxide (59 mg, 1.5 mmol) in water (15 mL), followed by sodium bicarbonate (681 mg, 8.1 mmol) and acetone (1 mL). Oxone® (543 mg, 0.88 mmol) was added slowly, keeping the temperature below 8° C. The reaction mixture was stirred 5 min and quenched with sodium bisulfite (600 mg). The reaction mixture was diluted with ethyl acetate and carefully acidified with concentrated hydrochloric acid. The reaction mixture was extracted with ethyl acetate (3×) and the combined organic layers were washed with water and brine and concentrated in vacuo to give 93A (258 mg, 100%) as a yellow solid. $^1$H NMR (400 MHz, CD$_3$OD) δ ppm 3.95 (s, 3H) 7.74-7.78 (m, 1H) 7.78-7.83 (m, 1 H) 8.23-8.28 (m, 1H); LC/MS 198 (M+H).

93B: Methyl 3-methoxy-5-nitrobenzoate

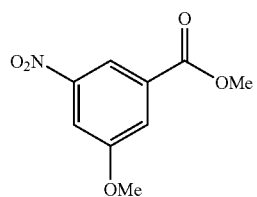

A mixture of methyl iodide (0.200 mL, 3.2 mmol), 93A (328 mg, 1.66 mmol), and potassium carbonate (250 mg, 1.80 mmol) in DMF (2 mL) was stirred overnight at rt. The reaction mixture was diluted with water and extracted with ethyl acetate (3×). The combined organic layers were washed with water and concentrated in vacuo. The residue was purified by silica gel chromatography (gradient of 0 to 50% ethyl acetate in hexanes) to give 93B (0.22 g, 63%) as a white solid. $^1$H NMR (400 MHz, CDCl$_3$) δ ppm 3.95 (s, 3H) 3.98 (s, 3H) 7.87-7.90 (m, 1H) 7.90-7.93 (m, 1H) 8.44-8.48 (m, 1H); LC/MS 212 (M+H).

93C: 3-Methoxy-5-nitrobenzoic acid

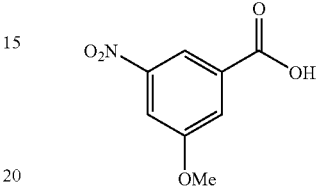

Using a procedure analogous to that described for the preparation of 89B, 93B was reacted with sodium hydroxide to give 93C. LC/MS 198 (M+H).

93D: 3-Amino-5-methoxybenzamide

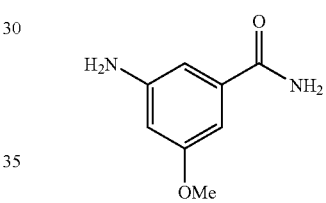

Using a procedure analogous to that described for preparation of 89C, 93C was converted to an acid chloride, reacted with aqueous ammonia, and hydrogenated to give 93D. $^1$H NMR (400 MHz, CD$_3$OD) δ ppm 3.76 (s, 3H) 6.45 (t, J=2.20 Hz, 1H) 6.71-6.74 (m, 1H) 6.77 (t, J=1.54 Hz, 1H); LC/MS 167 (M+H).

93E: 2-(3-Carbamoyl-5-methoxyphenylamino)-2-(3,4-dimethoxyphenyl)acetic acid

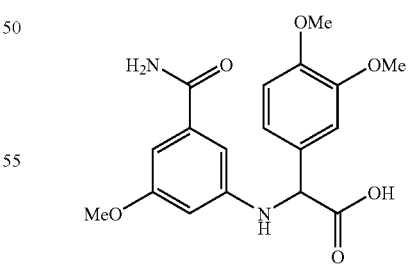

Using a procedure analogous to that described for the preparation of 89D, 93D was reacted with 3,4-dimethoxyphenylboronic acid and glyoxylic acid monohydrate to give 93E. $^1$H NMR (400 MHz, CD$_3$OD) δ ppm 3.73 (s, 3H) 3.80 (s, 3H) 3.81 (s, 3H) 5.07 (s, 1H) 6.39 (t, J=1.98 Hz, 1H) 6.75 (s, 1H) 6.81 (s, 1H) 6.92 (d, J=8.35 Hz, 1H) 7.07 (dd, J=8.35, 1.76 Hz, 1H) 7.11 (d, J=1.76 Hz, 1H).

93F: Example 93

Example 93 was prepared according to the general coupling condition using 93E and 1G. $^1$H NMR (400 MHz, CD$_3$OD) δ ppm 1.17 (d, J=6.59 Hz, 3H) 1.42 (d, J=6.96 Hz, 3H) 1.70 (td, J=12.36, 6.41 Hz, 1H) 1.99-2.14 (m, 2H) 2.48 (dt, J=20.78, 7.55 Hz, 1H) 3.66 (s, 3H) 3.70 (s, 3H) 3.75 (s, 3H) 3.84 (s, 3H) 3.92-4.01 (m, 1H) 4.04-4.13 (m, 1H) 5.37 (s, 1H) 5.67 (dd, J=8.24, 4.94 Hz, 1H) 6.48 (t, J=2.01 Hz, 1H) 6.81-6.93 (m, 5H) 7.07 (s, 1H) 7.23 (dd, J=8.60, 2.01 Hz, 1H) 7.74 (d, J=8.79 Hz, 1H) 9.38 (s, 1H); LC/MS 669 (M+H).

Example 94

Diastereoisomer of Example 93

Methyl 3-((R)-1-((S)-2-(3-carbamoyl-5-methoxyphenylamino)-2-(3,4-dimethoxyphenyl)acetyl)pyrrolidin-2-yl)-4-(isopropylsulfonyl)phenylcarbamate

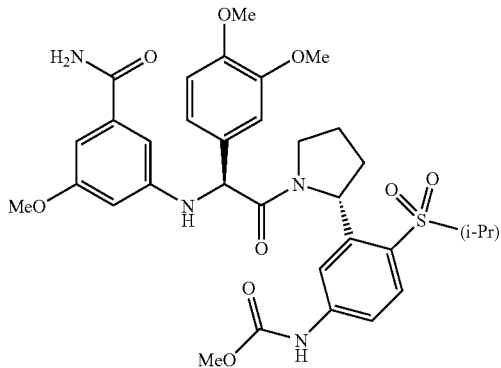

Example 94 was obtained as a diastereomer of Example 93 during its HPLC purification. $^1$H NMR (400 MHz, CD$_3$OD) δ ppm 1.15 (d, J=6.59 Hz, 3H) 1.39-1.52 (m, 3H) 1.68-1.80 (m, 1H) 1.80-1.92 (m, 1H) 1.96-2.21 (m, 1H) 2.27-2.42 (m, 1H) 3.48-3.61 (m, 1H) 3.62-3.90 (m, 12H) 3.84-3.86 (m, 3H) 4.07-4.24 (m, 1H) 5.36-5.45 (m, 1H) 5.61 (dd, J=8.42, 4.03 Hz, 1H) 6.42-6.56 (m, 2H) 6.81-7.14 (m, 4H) 7.48-7.63 (m, 2H) 7.71-7.80 (m, 1H) 9.42-9.58 (m, 1H); LC-MS 669 (M+H).

Example 95

Methyl 3-((R)-1-((R)-2-(5-carbamoyl-2-fluorophenylamino)-2-(3-ethyl-4-fluorophenyl)acetyl)pyrrolidin-2-yl)-4-(isopropylsulfonyl)phenylcarbamate

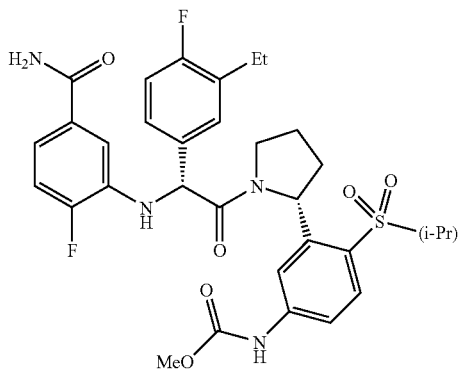

95A: 4-Bromo-2-ethyl-1-fluorobenzene

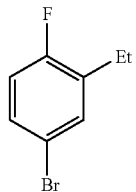

4-Bromo-1-fluoro-2-vinylbenzene (470 mg) was hydrogenated in EtOAc with 10% Pd/C (100 mg) with a hydrogen balloon for 2.0 h. The Pd/C was removed by filtration. The filtrate was condensed to give 95A (290 mg, 62% yield) as an orange oil. $^1$H NMR (400 MHz, CDCl$_3$) δ ppm 1.22 (t, J=6.81 Hz, 3H) 2.63 (d, J=7.03 Hz, 2H) 6.88 (t, J=8.57 Hz, 1H) 7.25 (s, 1H) 7.32 (d, J=4.39 Hz, 1H).

95B: 3-Ethyl-4-fluorophenylboronic acid

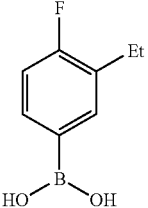

To a solution of 95A (290 mg, 1.43 mmol) in THF (5 mL) at −78° C. was added n-BuLi (2.5 M in hexanes, 0.86 mL, 2.15 mmol). The mixture was stirred at −78° C. for 30 min before trimethyl borate (0.32 mL, 2.86 mmol) was added. The reaction was left stirring from −78° C. to rt over 3 h. It was quenched with 1.0 N HCl (2 mL), extracted with EtOAc, washed with Na$_2$S$_2$O$_3$, brine and dried over Na$_2$SO$_4$. After evaporation of the solvent, the crude solid product was purified by silica gel column chromatography eluting with gradient CH$_2$Cl$_2$ in hexanes (0-15%) to give 95B (170 mg, 71% yield). $^1$H NMR (400 MHz, Methanol-d$_4$) δ ppm 1.09 (t, J=7.47 Hz, 3H) 2.54 (q, J=7.47 Hz, 2H) 6.81-6.88 (m, 1H) 7.42-7.47 (m, 1H) 7.51 (d, J=9.23 Hz, 1H).

95C: 2-(5-Carbamoyl-2-fluorophenylamino)-2-(3-ethyl-4-fluorophenyl)acetic acid

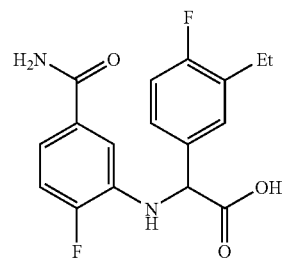

95C was prepared in a procedure similar to that of 1A using 19B, 95B and glyoxylic acid monohydrate. Yield: 48%. $^1$H NMR (400 MHz, Methanol-d$_4$) δ ppm 1.19 (t, J=7.69 Hz, 3H) 2.65 (q, J=7.47 Hz, 2H) 5.18 (s, 1H) 6.98-7.11 (m, 3 H) 7.12-7.18 (m, 1H) 7.31-7.38 (m, 1H) 7.40-7.45 (m, 1H); LCMS: 335 (M+1).

95D: Example 95

Example 95 was prepared according to the general coupling condition using 95C and 1G. $^1$H NMR (400 MHz, Methanol-d$_4$) δ ppm 1.11 (t, J=7.69 Hz, 3 H) 1.19 (d, J=6.59 Hz, 3H) 1.44 (d, J=7.03 Hz, 3H) 1.65-1.76 (m, 1H) 2.00-2.16 (m, 2H) 2.44-2.55 (m, 1H) 2.55-2.68 (m, 2H) 3.65-3.76 (m, 1H) 3.70 (s, 3H) 3.92-4.04 (m, 1H) 4.12-4.21 (m, 1H) 5.45 (s, 1H) 5.66 (dd, J=8.13, 5.05 Hz, 1H) 6.95-7.04 (m, 3H) 7.10-7.17 (m, 2H) 7.21-7.26 (m, 2H) 7.29 (dd, J=8.35, 1.76 Hz, 1H) 7.73 (d, J=8.79 Hz, 1H); LCMS: 643 (M+1).

Example 96

Diastereoisomer of Example 95

Methyl 3-((R)-1-((S)-2-(5-carbamoyl-2-fluorophenylamino)-2-(3-ethyl-4-fluorophenyl)acetyl)pyrrolidin-2-yl)-4-(isopropylsulfonyl)phenylcarbamate

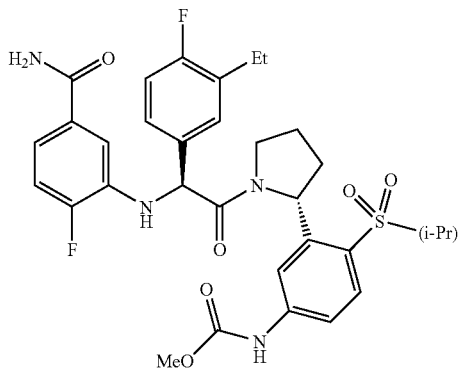

Example 96 was obtained as a diastereomer of Example 95 during its HPLC purification. $^1$H NMR (400 MHz, Methanol-d$_4$) δ ppm 1.15 (d, J=6.59 Hz, 3 H) 1.22 (t, J=7.47 Hz, 3H) 1.42 (d, J=7.03 Hz, 3H) 1.69-1.81 (m, 1H) 1.82-1.97 (m, 1H) 2.09-2.23 (m, 1H) 2.29-2.44 (m, 1H) 2.69 (q, J=7.47 Hz, 2H) 3.53-3.65 (m, 1H) 3.75 (s, 3H) 3.76-3.87 (m, 1H) 4.18-4.29 (m, 1H) 5.52 (s, 1H) 5.57 (dd, J=8.35, 3.95 Hz, 1H) 6.96-7.11 (m, 2H) 7.13-7.18 (m, 1H) 7.36 (d, J=7.47 Hz, 2 H) 7.44-7.48 (m, 2H) 7.67-7.71 (m, 1H) 7.79 (d, J=8.79 Hz, 1H); LCMS: 643 (M+1).

Example 97

Methyl 3-((R)-1-((R)-2-(5-carbamoylpyridin-3-ylamino)-2-(3,4-dimethoxyphenyl)acetyl)pyrrolidin-2-yl)-4-(isopropylsulfonyl)phenylcarbamate

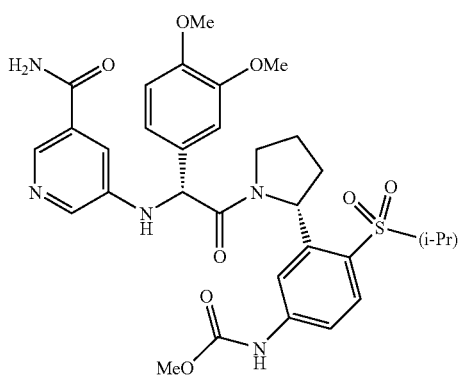

97A: 5-Azidonicotinamide

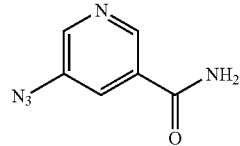

A solution of 5-bromonicotinamide (100 mg, 0.5 mmol), sodium azide (65 mg, 1.0 mmol), CuI (19.5 mg, 0.05 mmol), (1S,2S)—N1,N2-dimethylcyclohexane-1,2-diamine (11 mg, 0.08 mmol) and sodium ascorbate (5.0 mg, 0.03 mmol) in EtOH (0.7 mL) and H$_2$O (0.3 mL) was degassed for 5 min before heated at reflux for 1.0 h. After cooled to rt, the mixture was extracted with EtOAc. The organic layer was washed with brine and dried over Na$_2$SO$_4$. After removal of the solvent, the crude was purified by silica gel column chromatography eluting with gradient EtOAc in hexanes (0-100%) to give 97A. $^1$H NMR (400 MHz, Methanol-d$_4$) δ ppm 7.96-8.05 (m, 1H) 8.44 (d, J=2.64 Hz, 1H) 8.79 (d, J=1.76 Hz, 1H).

97B: 5-Aminonicotinamide

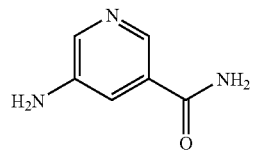

97A was hydrogenated in MeOH with 10% Pd/C (20 mg) with a hydrogen balloon for 0.5 h. The Pd/C was removed by filtration. The filtrate was concentrated to give 97B (25 mg, 36% yield for two steps). $^1$H NMR (400 MHz, Methanol-d$_4$) δ ppm 7.43-7.49 (m, 1H) 8.07 (d, J=2.64 Hz, 1H) 8.22 (d, J=1.76 Hz, 1H).

97C: 2-(5-Carbamoylpyridin-3-ylamino)-2-(3,4-dimethoxyphenyl)acetic acid

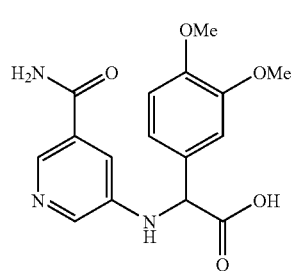

97C was prepared in a procedure similar to that of 13A using 97B, 3,4-dimethoxyphenylboronic acid and glyoxylic acid monohydrate. Yield: 63%. $^1$H NMR (400 MHz, Methanol-d$_4$) δ ppm 3.82 (s, 3H) 3.84 (s, 3H) 5.28 (s, 1H) 6.97 (d, J=8.35 Hz, 1H) 7.08 (s, 1H) 7.13 (d, J=2.20 Hz, 1H) 8.14 (s, 2H) 8.38 (s, 1H); LCMS: 331 (M+1).

97D: Example 97

Example 97 was prepared according to the general coupling condition using 97C and 1G. $^1$H NMR (400 MHz, Methanol-$d_4$) δ ppm 1.16 (d, J=6.59 Hz, 3 H) 1.41 (d, J=7.03 Hz, 3H) 1.66-1.76 (m, 1H) 2.00-2.18 (m, 2H) 2.45-2.56 (m, 1 H) 3.68 (s, 3H) 3.71 (s, 3H) 3.81-3.84 (m, 1H) 3.84 (s, 3H) 3.90-3.99 (m, 1H) 4.10-4.18 (m, 1H) 5.47 (s, 1H) 5.68 (dd, J=7.91, 5.27 Hz, 1H) 6.87 (d, J=1.76 Hz, 1H) 6.91-6.97 (m, 1H) 7.00-7.07 (m, 2H) 7.20 (dd, J=8.57, 1.98 Hz, 1H) 7.74 (d, J=8.79 Hz, 1H) 8.01 (s, 1H) 8.17 (d, J=2.64 Hz, 1H) 8.32 (s, 1H); LCMS: 639 (M+1).

Example 98

Diastereoisomer of Example 97

Methyl 3-((R)-1-((S)-2-(5-carbamoylpyridin-3-ylamino)-2-(3,4-dimethoxyphenyl)acetyl)pyrrolidin-2-yl)-4-(isopropylsulfonyl)phenylcarbamate

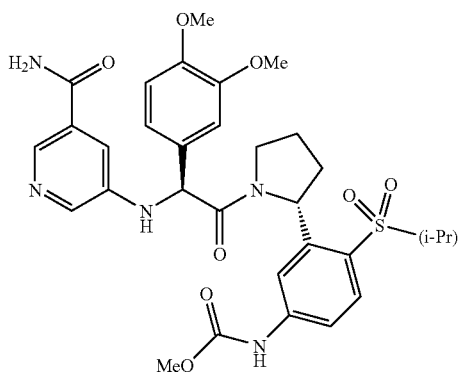

Example 98 was obtained as a diastereomer of Example 97 during its HPLC purification. $^1$H NMR (400 MHz, Methanol-$d_4$) δ ppm 1.14 and 1.17 (d, J=6.59 Hz, 3H) 1.42 and 1.53 (d, J=6.59 Hz, 3H) 1.68-2.57 (m, 4H) 3.53-3.62 (m, 1H) 3.74 and 3.78 (s, 3H) 3.84 and 3.69 (d, 6H) 3.88 (m, 1H) 4.17 (m, 1H) 5.56 and 5.52 (s, 1H) 5.62 (dd, J=8.13, 3.30 Hz, 1H) 6.49 and 6.58 (s, 1H) 6.99-7.14 (m, 2H) 7.43 and 7.30 (dd, J=8.79, 2.20 Hz, 1H) 7.70-7.82 (m, 2H) 8.00 and 8.07 (s, 1 H) 8.13-8.20 (m, 1H) 8.31 and 8.31 (s, 1H); LCMS: 639 (M+1).

Example 99

Methyl 3-((R)-1-((R)-2-(2-carbamoylpyridin-4-ylamino)-2-(3,4-dimethoxyphenyl)acetyl)pyrrolidin-2-yl)-4-(isopropylsulfonyl)phenylcarbamate

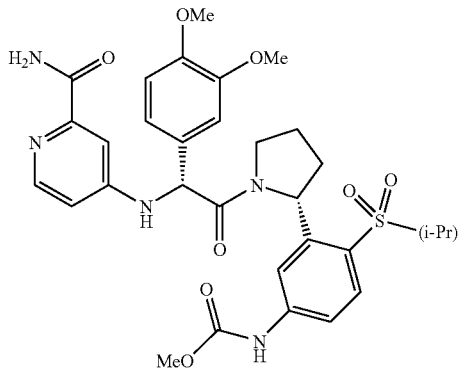

99A: 4-Nitropicolinamide

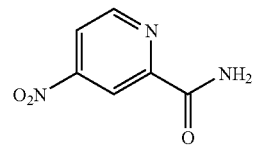

4-Nitropicolinonitrile (100 mg, 0.67 mmol), chlorotrimethylsilane (0.17 mL, 1.4 mmol) and H$_2$O (0.024 mL, 1.4 mmol) was sonicated in a sonicator at rt for 1.0 h. It was diluted with EtOAc, washed with NaHCO$_3$, brine and dried over Na$_2$SO$_4$. After removal of solvent, 99A (134 mg, 100% yield) was obtained as a solid. $^1$H NMR (400 MHz, Methanol-$d_4$) δ ppm 8.29 (dd, J=5.27, 2.20 Hz, 1H) 8.74 (d, J=2.20 Hz, 1H) 8.98 (d, J=5.27 Hz, 1H).

99B: 4-Aminopicolinamide

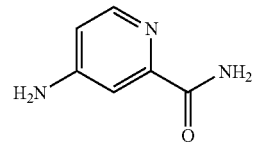

99A was hydrogenated in MeOH with 10% Pd/C (40 mg) with a hydrogen balloon for 8 h. The Pd/C was removed by filtration. The filtrate was condensed to give 99B (80 mg, 87% yield). $^1$H NMR (400 MHz, Methanol-$d_4$) δ ppm 6.65 (dd, J=5.71, 2.64 Hz, 1H) 7.27 (d, J=2.20 Hz, 1H) 8.03 (d, J=5.71 Hz, 1H).

99C: 2-(2-Carbamoylpyridin-4-ylamino)-2-(3,4-dimethoxyphenyl)acetic acid

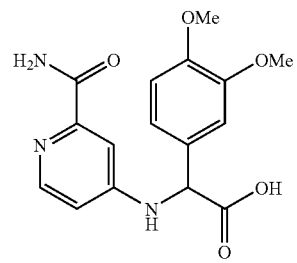

99C was prepared in a procedure similar to that of 13A using 99B, 3,4-dimethoxyphenylboronic acid and glyoxylic acid monohydrate. Yield: 63%. $^1$H NMR (400 MHz, Methanol-$d_4$) δ ppm 3.83 (s, 3H) 3.84 (s, 3H) 5.45 (s, 1H) 6.95-7.01 (m, 2H) 7.05-7.11 (m, 3H) 8.11 (d, J=6.59 Hz, 1H); LCMS: 331 (M+1).

99D: Example 99

Example 99 was prepared according to the general coupling condition using 99C and 1G. $^1$H NMR (400 MHz, Methanol-$d_4$) δ ppm 1.17 (d, J=6.59 Hz, 3H) 1.42 (d, J=7.03 Hz, 3H) 1.65-1.79 (m, 1H) 2.00-2.21 (m, 2H) 2.42-2.60 (m, 1 H) 3.59-3.66 (m, 1H) 3.67 (s, 3H) 3.71 (s, 3H) 3.86 (s, 3H) 3.89-4.02 (m, 1H) 4.08-4.16 (m, 1H) 5.65 (s, 1H) 5.70 (dd, J=8.13, 5.05 Hz, 1H) 6.85 (s, 1H) 6.95-6.99 (m, 2H) 7.04-7.14 (m, 3H) 7.20 (dd, J=8.79, 2.20 Hz, 1H) 7.45 (s, 1H) 7.75 (d, J=8.35 Hz, 1H); LCMS: 639 (M+1).

Example 100 Diastereoisomer of Example 99

Methyl 3-((R)-1-((S)-2-(2-carbamoylpyridin-4-ylamino)-2-(3,4-dimethoxyphenyl)acetyl)pyrrolidin-2-yl)-4-(isopropylsulfonyl)phenylcarbamate

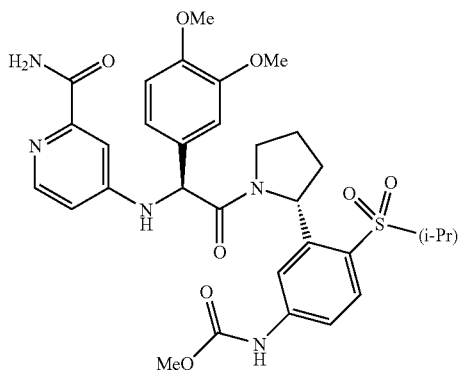

Example 100 was obtained as a diastereomer of Example 99 during its HPLC purification. $^1$H NMR (400 MHz, Methanol-$d_4$) δ ppm 1.15 (d, J=6.59 Hz, 3H) 1.42 (d, J=7.03 Hz, 3H) 1.69-1.95 (m, 2H) 1.98-2.21 (m, 1H) 2.29-2.44 (m, 1H) 3.43-3.58 (m, 1H) 3.67-3.77 (m, 3H) 3.78-3.84 (m, 1H) 3.83-3.89 (m, 6 H) 4.11-4.22 (m, 1H) 5.64 (dd, J=8.35, 3.52 Hz, 1H) 5.77 (s, 1H) 6.39-6.55 (m, 1 H) 6.56 (s, 1H) 7.02-7.18 (m, 3H) 7.27 (s, 2H) 7.79 (d, J=8.35 Hz, 1H) 8.00 (d, J=7.03 Hz, 1H); LCMS: 639 (M+1).

UTILITY

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders (or conditions)" as used herein includes arterial or venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, ischemic stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis.

It is noted that thrombosis includes vessel occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, atrial fibrillation, congenital thrombophilia, cancer, diabetes, effects of medications or hormones, and complications of pregnancy. The anticoagulant or antithrombotic effect of compounds of the present invention is believed to be due to inhibition of coagulation factor VIIa.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel. The term "stroke", as used herein, refers to embolic stroke or atherothrombotic stroke arising from occlusive thrombosis in the carotid communis, carotid interna, or intracerebral arteries.

The effectiveness of compounds of the present invention as inhibitors of the coagulation factors VIIa, IXa, Xa, XIa, or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of para-nitroaniline (pNA), which was monitored spectrophotometrically by measuring the increase in absorbance at 405 nM, or the release of aminomethylcoumarin (AMC), which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (S-2288; Chromogenix or BMPM-2; AnaSpec) at a concentration of 0.001-0.0075 M.

In general, preferred compounds of the present invention have been identified to be active and exhibit $K_i$'s of equal to or less than 15 μM in the Factor VIIa assay, thereby demonstrating the utility of the compounds of the present invention as especially effective inhibitors of coagulation Factor VIIa. More preferred compounds have $K_i$'s of equal to or less than 5 µM, preferably equal to or less than 1 µM, more preferably equal to or less than 0.5 µM, even more preferably equal to or less than 0.1 µM.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M. In general, compounds tested in the Factor IXa assay are considered to be active if they exhibit a $K_i$ of equal to or less than 15 µM.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.00035 M. In general, compounds tested in the Factor Xa assay are considered to be active if they exhibit a $K_i$ of equal to or less than 15 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix or AnaSpec) at a concentration of 0.0002-0.001 M. In general, compounds tested in the Factor XIa assay are considered to be active if they exhibit a $K_i$ of equal to or less than 15 µM.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002-0.00026 M. In general, compounds tested in the thrombin assay are considered to be active if they exhibit a $K_i$ of equal to or less than 15 µM.

The selectivity of a compound may be evaluated by taking the ratio of the $K_i$ value for a given protease with the $K_i$ value for the protease of interest (i.e., selectivity for FVIIa versus protease P=$K_i$ for protease P/$K_i$ for FVIIa). Compounds with selectivity ratios >20 are considered selective. Compounds with selectivity ratios >100 are preferred, and compounds with selectivity ratios >500 are more preferred.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_i$ values:

$(v_o-v_s)/v_s = I/(K_i(1+S/K_m))$ for a competitive inhibitor with one binding site; or $v_s/v_o = A+((B-A)/1+((IC_{50}/(I)^n)))$ and
$K_i = IC_{50}/(1+S/K_m)$ for a competitive inhibitor where:
$v_o$, is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis (ECAT) Model:

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

In Vivo Rabbit Arterio-Venous (AV) Shunt Thrombosis Model

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

The compounds of the present invention can be administered alone or in combination with one or more additional therapeutic agents. These other agents include, but are not limited to, other anti-coagulant or coagulation inhibitory agents, anti-platelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin, heparin (either unfractionated heparin or any commercially available low molecular weight heparin, for example LOVENOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA), and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR1) antagonists (e.g., SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include clopidogrel, ticlopidine, prasugrel, and AZD-6140, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril), angiotensin AT-1 receptor antagonists (e.g., irbesartan, losartan, valsartan); ET-A receptor antagonists (e.g., sitaxsentan, atrsentan and compounds disclosed in U.S. Pat. Nos. 5,612, 359 and 6,043,265); Dual ET-A/AT-1 antagonist (e.g., compounds disclosed in WO 00/01389); neutral endopeptidase (NEP) inhibitors; vasopepsidase inhibitors (dual ACE/NEP inhibitors, e.g., omapatrilat gemopatrilat, nitrates) and β-blockers (for example propranolol, nadolo, or carvedilol).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include spironolactone and eplirinone.

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DPP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat, aP2 inhibitors (such as those disclosed in WO00/59506), and cannabinoid receptor CB1 antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epothilones, cisplatin, and carboplatin.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), sequestrants (e.g., cholestyramine and colestipol), nicotonic acid, fenofibric acid derivatives (e.g., gemfibrozil, clofibrat, fenofibrate and benzafibrate), probucol, cholesterol absorption inhibitors, and cholesterol ester transfer protein inhibitors (e.g., CP-529414).

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor VIIa. Such compounds may be provided in a commercial kit, for example, for use in pharmaceutical research involving factor VIIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving plasma factor VIIa. For example, the presence of factor VIIa in an unknown sample could be determined by addition of the relevant chromogenic substrate, for example, S2288, to a series of solutions containing test sample and optionally one of the compounds of the present invention. If production of pNA is observed in the solutions containing test sample, but not in the presence of a compound of the present invention, then one would conclude factor VIIa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.1 to 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 0.1 to 7.5 milligrams of the second anticoagulant, per kilogram of patient body weight. For a tablet dosage form, the compounds of this invention generally may be present in an amount of about 5 to 100 milligrams per dosage unit, and the second anti-coagulant in an amount of about 1 to 50 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The invention claimed is:

1. A compound of Formula (I):

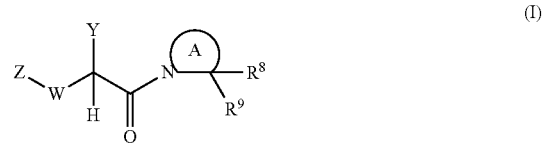

or a stereoisomer, tautomer, or pharmaceutically acceptable salt, thereof, wherein:

ring A is a 5-membered heterocycle comprising: the nitrogen atom shown in the ring, carbon atoms and 0-1 additional heteroatom selected from N, $NR^c$, O, and $S(O)_p$, 0-1 carbonyl, and 0-2 double bonds, wherein said heterocycle is substituted with 0-2 $R^7$;

Z is

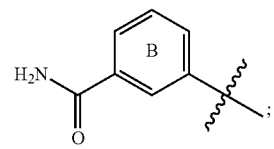

ring B is phenyl substituted with 0-3 $R^6$ or pyridyl substituted with 0-3 $R^6$;

W is NH or O;

Y is:

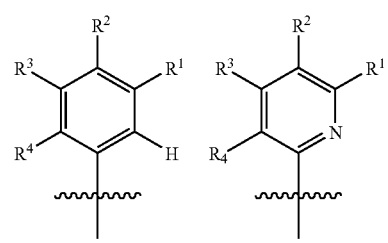

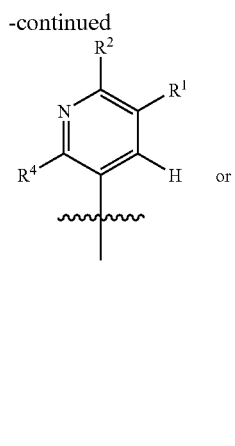

R¹ is, independently at each occurrence, H, F, Cl, Br, I, $C_{1-5}$ alkyl substituted with 0-1 OH, $C_{1-5}$ haloalkyl, $C_{2-5}$ alkenyl, $C_{2-5}$ alkynyl, —O—$C_{1-5}$ alkyl, —O—$C_{1-5}$ haloalkyl, —S—$C_{1-5}$ alkyl, or $C_{3-6}$ cycloalkyl;

R² and R³ are, independently at each occurrence, H, F, Cl, Br, I, $OR^a$, $SR^a$, $OCF_3$, $OCHF_2$, $OCH_2F$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle is substituted with 0-3 $R^f$;

R⁴ is, independently at each occurrence, H, F, Cl, Br, I, $OR^a$, $SR^a$, $OCF_3$, CN, $NO_2$, —$NR^bR^c$, —$C(O)R^a$, —$CO_2R^a$, —$NR^dC(O)R^a$, —$C(O)NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $C_{3-10}$ carbocycle substituted with 0-3 $R^f$, or a 5- to 10-membered heterocycle comprising: carbon atoms and 1-4 heteroatoms selected from N, $NR^c$, O, and $S(O)_p$, wherein said heterocycle are substituted with 0-3 $R^f$;

alternatively, R² and R³ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, R³ and R⁴ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

R⁶ is, independently at each occurrence, F, Cl, Br, I, CN, OH, $CF_3$, $C_{1-4}$ alkyl, $C_{1-4}$ haloalkyl, or $C_{1-4}$ alkoxy;

R⁷ is, independently at each occurrence, $OR^a$, F, Cl, Br, I, CN, $NO_2$, —$OCF_3$, —$NR^bR^c$, —$C(O)R^a$, —$CO_2R^a$, —$NR^dC(O)R^a$, —$C(O)NR^cR^d$, —$SO_2NR^cR^d$, —$NR^cSO_2R^i$, —$SO_2NHC(O)R^a$, —$C(O)NHSO_2R^a$, —$NR^cSO_2CF_3$, —$SO_2CF_3$, —$S(O)_pR^i$, —$(CF_2)_rCF_3$, tetrazole, —$(CH_2)_r$-phenyl substituted with 0-3 $R^f$, or a —$(CH_2)_r$-5- to 6-membered heterocycle comprising: carbon atoms and 1-4 heteroatoms selected from N, $NR^c$, O, and $S(O)_p$, wherein said heterocycle is substituted with 0-3 $R^f$;

R⁸ is H, CN, —$CO_2R^a$, —$C(O)NR^cR^d$, tetrazolyl, or $C_{1-4}$ alkyl substituted with 0-2 $R^{8a}$;

$R^{8a}$ is, independently at each occurrence, =O, $OR^a$, F, Cl, Br, I, CN, $NO_2$, —$OCF_3$, —$NR^bR^c$, —$C(O)R^a$, —$CO_2R^a$, —$OC(O)R^a$, —$OC(O)NR^cR^d$, —$NR^dC(O)R^a$, —$C(O)NR^cR^d$, —$NR^cC(O)NR^cR^d$, $NR^cC(O)OR^a$, —$SO_2NR^cR^d$, —$NR^cSO_2R^i$, —$NR^cSO_2NR^cR^d$, —$SO_2NHC(O)R^a$, —$C(O)NHSO_2R^a$, —$NR^cSO_2CF_3$, —$SO_2CF_3$, —$S(O)_pR^i$, —$(CF_2)_rCF_3$, tetrazole, $C_{3-6}$ cycloalkyl substituted with 0-3 $R^f$, phenyl substituted with 0-3 $R^f$, or 5- to 6-membered heterocycle comprising: carbon atoms and 1-4 heteroatoms selected from N, $NR^c$, O, and $S(O)_p$, wherein said heterocycle is substituted with 0-3 $R^f$;

R⁹ is phenyl or pyridyl substituted with 1-3 $R^{10}$;

$R^{10}$ is, independently at each occurrence, F, Cl, Br, I, —$(CH_2)_r$—$OR^a$, —$(CH_2)_r$—$SR^a$, $OCF_3$, $SCF_3$, CN, $NO_2$, —$(CH_2)_r$—$NR^bR^c$, —$C(O)R^a$, —$(CH_2)_r$—$CO_2R^a$, —$(CH_2)_r$—$NR^cCO_2R^a$, —$NR^dC(O)R^a$, —$(CH_2)_r$—$C(O)NR^cR^d$, —$NR^cC(O)NR^cR^d$, —$SO_2NR^cR^d$, —$OSO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^f$, or —$(CH_2)_r$-5- to 10-membered heterocycle comprising: carbon atoms and 1-4 heteroatoms selected from N, $NR^c$, O, and $S(O)_p$, wherein said heterocycle are substituted with 0-3 $R^f$;

$R^a$ is, independently at each occurrence, H, $C_{1-6}$ alkyl substituted with 0-4 $R^h$, —$(CH_2)_r$—$C_{3-7}$ carbocycle substituted with 0-4 $R^f$, or —$(CH_2)_r$-5- to 10-membered heterocycle comprising: carbon atoms and 1-4 heteroatoms selected from N, $NR^g$, O, and $S(O)_p$, wherein said heterocycle is substituted with 0-4 $R^f$;

$R^b$ is, independently at each occurrence, H, $C_{1-6}$ alkyl, —$(CH_2)_n$-phenyl, ($C_{1-6}$ alkyl)C(O)—, ($C_{3-6}$ cycloalkyl)-$C_{0-4}$ alkyl-C(O)—, ($C_{6-10}$ aryl)-($C_{0-4}$ alkyl)-C(O)—, (5- to 10-membered heteroaryl)-$C_{0-4}$ alkyl-C(O)—, ($C_{1-6}$ alkyl)-NHC(O)—, ($C_{1-6}$ alkyl)$_2$-NHC(O)—, ($C_{6-10}$ aryl)-$C_{0-4}$ alkyl-NHC(O)—, (5- to 10-membered heteroaryl)-$C_{0-4}$ alkyl-NHC(O)—, ($C_{1-6}$ alkyl)-$SO_2$—, ($C_{6-10}$ aryl)-$C_{0-4}$ alkyl-$SO_2$—, or (5- to 10-membered heteroaryl)-$C_{0-4}$ alkyl-$SO_2$—, wherein said phenyl, aryl and heteroaryl are substituted with 0-2 $R^f$;

$R^c$ is, independently at each occurrence, H, $C_{1-6}$ alkyl substituted with 0-3 $R^h$, —$(CH_2)_n$—$C_{3-7}$ cycloalkyl substituted with 0-3 $R^h$, or —$(CH_2)_n$-phenyl substituted with 0-3 $R^h$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, $NR^g$, O, and $S(O)_p$, wherein heterocycle are substituted with 0-3 $R^f$;

$R^d$ is, independently at each occurrence, H, $C_{1-6}$ alkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, $NR^g$, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, NR$^g$, O, and S(O)$_p$, wherein heterocycle are substituted with 0-3 R$^f$;

R$^e$ is, independently at each occurrence, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, —NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{3-10}$ carbocycle substituted with 0-3 R$^f$, or a 5- to 12-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-10}$ carbocycle substituted with 0-3 R$^h$, or a 5- to 12-membered heterocycle comprising: carbon atoms and 1-4 heteroatoms selected from N, NR$^g$, O, and S(O)$_p$, and substituted with 0-3 R$^h$;

R$^g$ is, independently at each occurrence, H, C$_{1-6}$ alkyl, or —(CH$_2$)$_n$-phenyl;

R$^h$ is, independently at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, —(CH$_2$)$_r$—C$_{3-10}$ carbocycle, or a —(CH$_2$)$_r$-5- to 12-membered heterocycle comprising: carbon atoms and 1-4 heteroatoms selected from N, NR$^g$, O, and S(O)$_p$;

R$^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^h$;

n, at each occurrence, is selected from 0, 1, 2, 3, and 4;

p, at each occurrence, is selected from 0, 1, and 2; and r, at each occurrence, is selected from 0, 1, 2, 3, and 4.

2. A compound according to claim 1, wherein the compound is of Formula (I), or stereoisomers, tautomers, or pharmaceutically acceptable salt, thereof, wherein:

ring A is a 5-membered heterocycle comprising: the nitrogen atom shown in the ring, carbon atoms and 0-1 additional heteroatom selected from N, NR$^c$, O, and S(O)$_p$, wherein said heterocycle is substituted with 0-2 R$^7$;

Z is:

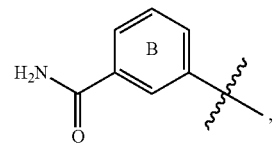

,

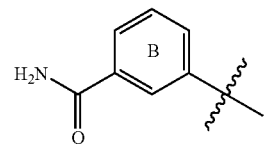

is:

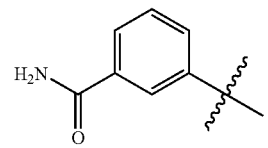

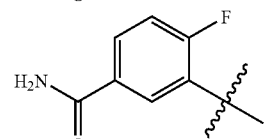

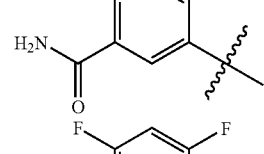

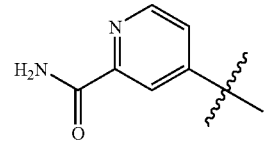

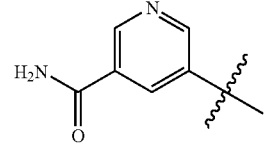

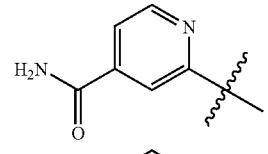

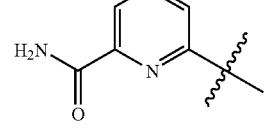

-continued

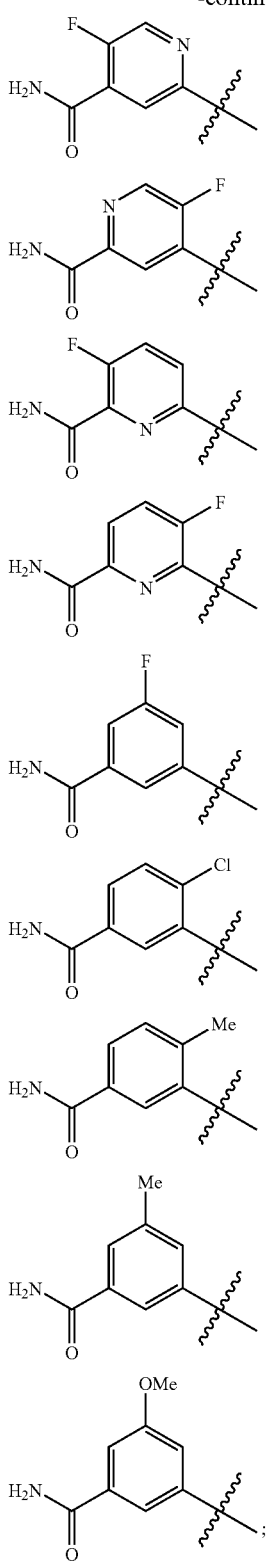

wherein each phenyl and pyridyl is substituted with 0-1 $R^6$; and $R^1$ is, independently at each occurrence, H, F, Cl, Br, $C_{1-3}$ alkyl substituted with 0-1 OH, $C_{1-3}$ haloalkyl, $C_{2-3}$ alkenyl, $C_{2-3}$ alkynyl, —O—$C_{1-3}$ alkyl, or $C_{3-5}$ cycloalkyl.

3. A compound according to claim 1, wherein the compound is of Formula (II):

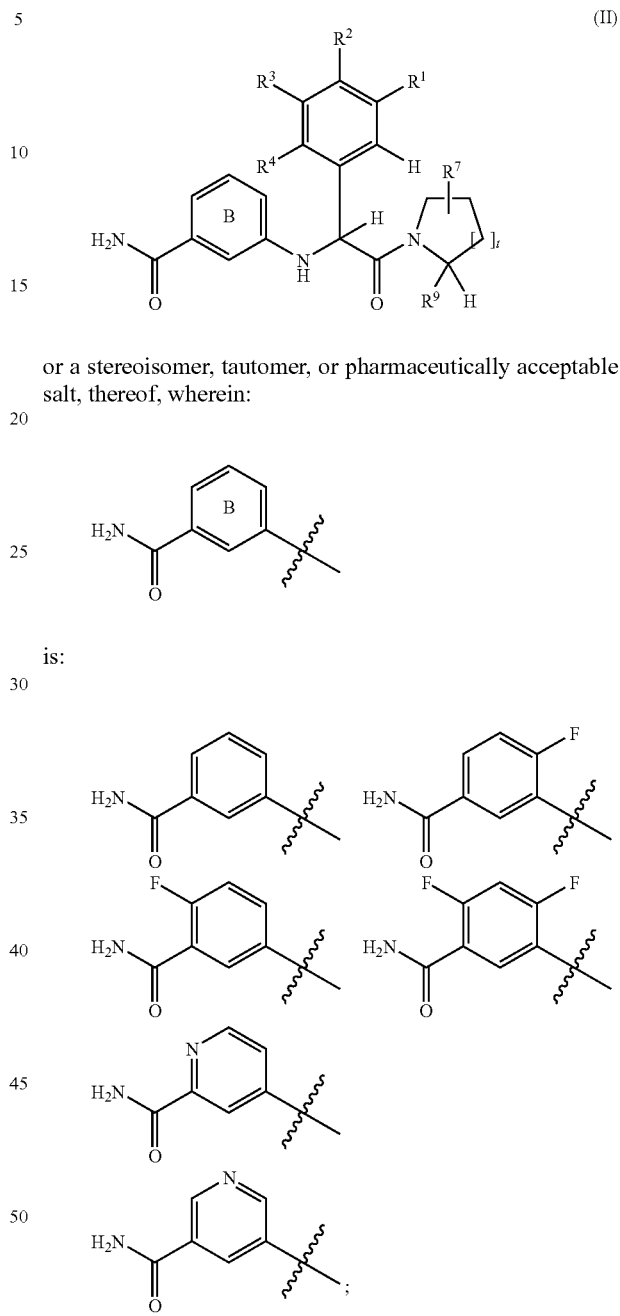

(II)

or a stereoisomer, tautomer, or pharmaceutically acceptable salt, thereof, wherein:

is:

wherein each phenyl and pyridyl is substituted with 0-1 $R^6$;

$R^1$ is H, F, Cl, Br, $C_{1-2}$ alkyl substituted with 0-1 OH, $C_{1-2}$ haloalkyl, $C_{2-3}$ alkenyl, $C_{2-3}$ alkynyl, —O—$C_{1-2}$ alkyl, or $C_{3-5}$ cycloalkyl;

$R^2$ and $R^3$ are, independently at each occurrence, H, F, Cl, Br, I, $OR^a$, $SR^a$, $OCF_3$, $OCHF_2$, $OCH_2F$, CN, $NO_2$, —$NR^bR^c$, —C(O)$R^a$, —$CO_2R^a$, —$NR^dC(O)R^a$, —C(O)$NR^cR^d$, —$NR^cC(O)OR^a$, —$NR^cC(O)NR^cR^d$, —$SO_2NR^cR^d$, —$NR^cSO_2NR^cR^d$, —$NR^cSO_2R^i$, —$NR^cSO_2CF_3$, —$SO_2CF_3$, —$S(O)_pR^i$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, C$_{3-10}$ carbocycle substituted with 0-3 R$^f$, or a 5- to 10-membered heterocycle comprising: carbon atoms and 1-4 heteroatoms selected from N, NR$^c$, O, and S(O)$_p$, wherein said heterocycle are substituted with 0-3 R$^f$;

R$^4$ is, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —NR$^c$C(O)OR$^a$, —NR$^c$C(O)NR$^c$R$^d$, —SO$_2$NR$^c$R$^d$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, C$_{3-10}$ carbocycle substituted with 0-3 R$^f$, or a 5- to 10-membered heterocycle comprising: carbon atoms and 1-4 heteroatoms selected from N, NR$^c$, O, and S(O)$_p$, wherein said heterocycle are substituted with 0-3 R$^f$;

alternatively, R$^2$ and R$^3$ may combine to form a 5- to 7-membered carbocycle or heterocycle comprising: carbon atoms and 0-4 heteroatoms selected from N, NR$^c$, O, and S(O)$_p$, wherein said carbocycle and heterocycle are substituted with 0-3 R$^f$;

alternatively, R$^3$ and R$^4$ may combine to form a 5- to 7-membered carbocycle or heterocycle comprising: carbon atoms and 0-4 heteroatoms selected from N, NR$^c$, O, and S(O)$_p$, wherein said carbocycle and heterocycle are substituted with 0-3 R$^f$;

R$^6$ is, independently at each occurrence, F, Cl, OH, CF$_3$, C$_{1-2}$ alkyl, or C$_{1-2}$ alkoxy;

R$^7$ is, independently at each occurrence, OR$^g$, F, Cl, Br, I, CN, NO$_2$, —OCF$_3$, —NR$^b$R$^c$, —C(O)R$^g$, —CO$_2$R$^a$, —NR$^d$C(O)R$^a$, —C(O)NR$^c$R$^d$, —SO$_2$NR$^c$R$^d$, —NR$^c$SO$_2$R$^i$, —SO$_2$NHC(O)R$^a$, —C(O)NHSO$_2$R$^a$, —NR$^c$SO$_2$CF$_3$, —SO$_2$CF$_3$, —S(O)$_p$R$^i$, —(CF$_2$)$_r$CF$_3$, tetrazole, —(CH$_2$)$_r$-phenyl substituted with 0-3 R$^f$, or a —(CH$_2$)$_r$-5- to 6-membered heterocycle comprising: carbon atoms and 1-4 heteroatoms selected from N, NR$^c$, O, and S(O)$_p$, wherein said heterocycle is substituted with 0-3 R$^f$;

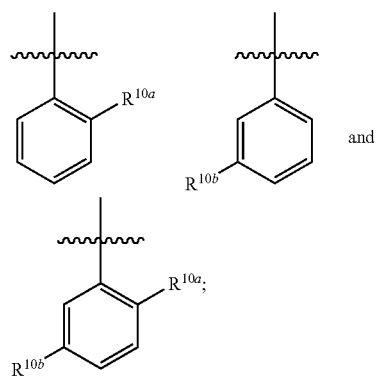

R$^9$ is selected from:

R$^{10a}$ and R$^{10b}$ are, independently at each occurrence, H, F, Cl, Br, I, —(CH$_2$)$_r$—OR$^a$, —(CH$_2$)$_r$—SR$^a$, OCF$_3$, SCF$_3$, CN, NO$_2$, —(CH$_2$)$_r$—NR$^b$R$^c$, —C(O)R$^a$, —(CH$_2$)$_r$—CO$_2$R$^a$, —(CH$_2$)$_r$—NR$^c$CO$_2$R$^a$, —NR$^d$C(O)R$^a$, —(CH$_2$)$_r$—C(O)NR$^c$R$^d$, —NR$^c$C(O)NR$^c$R$^d$, —SO$_2$NR$^c$R$^d$, —OSO$_2$NR$^c$R$^d$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-10}$ carbocycle substituted with 0-3 R$^f$, or —(CH$_2$)$_r$-5- to 10-membered heterocycle comprising: carbon atoms and 1-4 heteroatoms selected from N, NR$^c$, O, and S(O)$_p$, wherein said heterocycle are substituted with 0-3 R$^f$;

R$^a$ is, independently at each occurrence, H, C$_{1-6}$ alkyl substituted with 0-4 R$^h$, —(CH$_2$)$_r$—C$_{3-7}$ carbocycle substituted with 0-4 R$^f$, or —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-4 R$^f$;

R$^b$ is, independently at each occurrence, H, C$_{1-6}$ alkyl, —(CH$_2$)$_n$-phenyl, (C$_{1-6}$ alkyl)C(O)—, (C$_{3-6}$ cycloalkyl)-C$_{0-4}$alkyl-C(O)—, (C$_{6-10}$ aryl)-(C$_{0-4}$alkyl)-C(O)—, (5- to 10-membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5- to 10-membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, or (5- to 10-membered heteroaryl)-C$_{0-4}$ alkyl-SO$_2$—, wherein said phenyl, aryl and heteroaryl are substituted with 0-2 R$^f$;

R$^c$ is, independently at each occurrence, H, C$_{1-6}$ alkyl substituted with 0-3 R$^h$, —(CH$_2$)$_n$—C$_{3-7}$ cycloalkyl substituted with 0-3 R$^h$, or —(CH$_2$)$_n$-phenyl substituted with 0-3 R$^h$;

alternatively, R$^b$ and R$^c$, when attached to the same nitrogen atom, may be taken together with the nitrogen atom to form a 4- to 10-membered heterocycle comprising: carbon atoms and 1-4 heteroatoms selected from N, NR$^g$, O, and S(O)$_p$, wherein heterocycle are substituted with 0-3 R$^f$;

R$^d$ is, independently at each occurrence, H, C$_{1-6}$ alkyl, —(CH$_2$)$_r$—C$_{3-10}$ carbocycle substituted with 0-3 R$^f$, or a —(CH$_2$)$_r$-5- to 12-membered heterocycle comprising: carbon atoms and 1-4 heteroatoms selected from N, NR$^g$, O, and S(O)$_p$, wherein said heterocycle is substituted with 0-3 R$^f$;

alternatively, R$^c$ and R$^d$, when attached to the same nitrogen atom, may be taken together with the nitrogen atom to form a 4- to 10-membered heterocycle comprising: carbon atoms and 1-4 heteroatoms selected from N, NR$^g$, O, and S(O)$_p$, wherein heterocycle are substituted with 0-3 R$^f$;

R$^e$ is, independently at each occurrence, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, —NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{3-10}$ carbocycle substituted with 0-3 R$^f$, or a 5- to 12-membered heterocycle comprising: carbon atoms and 1-4 heteroatoms selected from N, NR$^g$, O, and S(O)$_p$, wherein said heterocycle is substituted with 0-3 R$^f$;

R$^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl, C$_{2-6}$ alkenyl, C$_{2-6}$ alkynyl, C$_{3-10}$ carbocycle substituted with 0-3 R$^h$, or a 5- to 12-membered heterocycle comprising: carbon atoms and 1-4 heteroatoms selected from N, NR$^g$, O, and S(O)$_p$, and substituted with 0-3 R$^h$;

R$^g$ is, independently at each occurrence, H, C$_{1-6}$ alkyl, or —(CH$_2$)$_n$-phenyl;

$R^h$ is, independently at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, —(CH$_2$)$_r$—C$_{3-10}$ carbocycle, or a —(CH$_2$)$_r$-5- to 12-membered heterocycle comprising: carbon atoms and 1-4 heteroatoms selected from N, NR$^g$, O, and S(O)$_p$;

$R^i$ is, independently at each occurrence, H, C$_{1-6}$ alkyl substituted with 0-3 R$^h$, C$_{3-6}$ cycloalkyl substituted with 0-3 R$^h$, —(CH$_2$)$_n$-phenyl substituted with 0-3 R$^h$, —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^h$;

n, at each occurrence, is selected from 0, 1, 2, 3, and 4;
p, at each occurrence, is selected from 0, 1, and 2;
r, at each occurrence, is selected from 0, 1, 2, 3, and 4; and
t is selected from 1 and 2.

4. A compound according to claim 3, wherein the compound is of Formula (II), or stereoisomers, tautomers, or pharmaceutically acceptable salt, thereof, wherein:

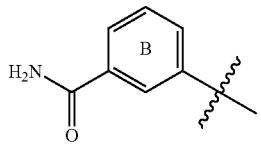

is:

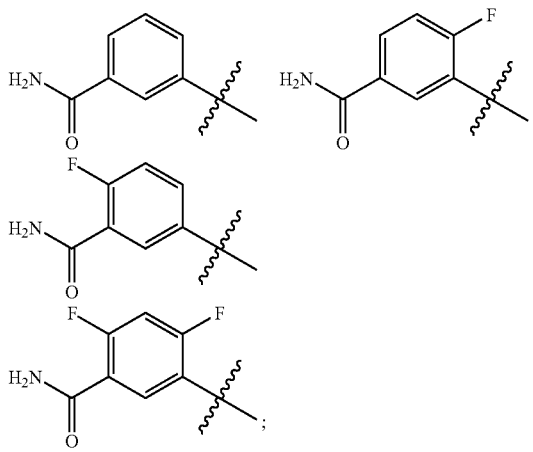

$R^1$ is, Cl, Br, Me, Et, vinyl, 2-propenyl, ethynyl, —CH(OH)Me, OMe, OEt, cyclopropyl, —OCHF$_2$, or —OCF$_2$CHF$_2$;

$R^2$ and $R^3$ are, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$, C$_{3-6}$ cycloalkyl substituted with 0-3 R$^f$, phenyl substituted with 0-3 R$^f$, or a 5- to 6-membered heterocycle comprising: carbon atoms and 1-4 heteroatoms selected from N, NR$^c$, O, and S(O)$_p$, wherein said heterocycle are substituted with 0-3 R$^f$;

$R^4$ is, independently at each occurrence, H, F, Cl, Br, I, OR$^a$, SR$^a$, OCF$_3$, CN, NO$_2$, —NR$^b$R$^c$, —C(O)R$^a$, —CO$_2$R$^a$, —NR$^d$C(O)R$^a$, —C(O)NR$^c$R$^d$, —SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, C$_{3-6}$ cycloalkyl substituted with 0-3 R$^f$, phenyl substituted with 0-3 R$^f$, or a 5- to 6-membered heterocycle comprising: carbon atoms and 1-4 heteroatoms selected from N, NR$^c$, O, and S(O)$_p$, wherein said heterocycle are substituted with 0-3 R$^f$;

$R^a$ is, independently at each occurrence, H, C$_{1-6}$ alkyl substituted with 0-2 R$^h$, —(CH$_2$)$_r$—C$_{3-6}$ cycloalkyl substituted with 0-2 R$^f$, —(CH$_2$)$_r$-phenyl substituted with 0-3 R$^f$, or —(CH$_2$)$_r$-5- to 6-membered heterocycle comprising: carbon atoms and 1-4 heteroatoms selected from N, NR$^g$, O, and S(O)$_p$, wherein said heterocycle is substituted with 0-3 R$^f$;

$R^b$ is, independently at each occurrence, H, C$_{1-6}$ alkyl, —(CH$_2$)$_n$-phenyl, (C$_{1-6}$ alkyl)C(O)—, (C$_{3-6}$ cycloalkyl)-C$_{0-4}$ alkyl-C(O)—, phenyl-(C$_{0-4}$ alkyl)-C(O)—, (5- to 6-membered heteroaryl)-C$_{0-4}$ alkyl-C(O)—, (C$_{1-6}$ alkyl)-NHC(O)—, (C$_{1-6}$ alkyl)$_2$-NHC(O)—, phenyl-C$_{0-4}$ alkyl-NHC(O)—, (5- to 6-membered heteroaryl)-C$_{0-4}$ alkyl-NHC(O)—, (C$_{1-6}$ alkyl)-SO$_{2-5}$ phenyl-C$_{0-4}$ alkyl-SO$_2$—, or (5- to 6-membered heteroaryl)-C$_{0-4}$ alkyl-SO$_2$—, wherein said phenyl and heteroaryl are substituted with 0-2 R$^f$;

$R^c$ is, independently at each occurrence, H, C$_{1-6}$ alkyl substituted with 0-3 R$^h$, —(CH$_2$)$_r$—, —C$_{3-6}$ cycloalkyl substituted with 0-2 R$^h$, or —(CH$_2$)$_r$-phenyl substituted with 0-3 R$^h$;

$R^d$ is, independently at each occurrence, H, C$_{1-6}$ alkyl, —(CH$_2$)$_n$—C$_{3-6}$ cycloalkyl substituted with 0-2 R$^f$, —(CH$_2$)$_r$-phenyl substituted with 0-3 R$^f$, or a —(CH$_2$)$_r$-5- to 10-membered heterocycle comprising: carbon atoms and 1-4 heteroatoms selected from N, NR$^g$, O, and S(O)$_p$, wherein said heterocycle is substituted with 0-3 R$^f$;

$R^e$ is, independently at each occurrence, =O, OR$^a$, F, Cl, Br, I, CN, NO$_2$, —SR$^a$, —OCF$_3$, —NR$^b$R$^c$, —C(O)R$^a$, —CO$_2$R$^a$, —NR$^d$C(O)R$^a$, —C(O)NR$^c$R$^d$, —OC(O)R$^a$, —NR$^d$C(O)OR$^a$, —NR$^d$C(O)NR$^c$R$^d$, —OC(O)NR$^c$R$^d$, —SO$_2$NR$^c$R$^d$, —NC(O)OR$^a$, —NR$^c$SO$_2$NR$^c$R$^d$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, C$_{3-6}$ cycloalkyl substituted with 0-2 R$^f$, phenyl substituted with 0-3 R$^f$, or a 5- to 10-membered heterocycle comprising: carbon atoms and 1-4 heteroatoms selected from N, NR$^g$, O, and S(O)$_p$, wherein said heterocycle is substituted with 0-3 R$^f$;

$R^f$ is, independently at each occurrence, =O, OR$^g$, F, Cl, Br, I, CN, NO$_2$, —SR$^g$, —OCF$_3$, —NR$^c$R$^c$, —C(O)R$^g$, —CO$_2$R$^g$, —NR$^c$C(O)R$^g$, —C(O)NR$^c$R$^c$, —OC(O)R$^g$, —NR$^c$C(O)OR$^g$, —NR$^c$C(O)NR$^c$R$^c$, —OC(O)NR$^c$R$^c$, —SO$_2$NR$^c$R$^c$, —NR$^c$SO$_2$NR$^c$R$^c$, —NR$^c$SO$_2$R$^i$, —NR$^c$SO$_2$CF$_3$, —SO$_2$CF$_3$, —S(O)$_p$R$^i$, —(CF$_2$)$_r$CF$_3$, $C_{1-6}$ alkyl, $C_{2-6}$ alkenyl, $C_{2-6}$ alkynyl, $C_{3-6}$ cycloalkyl substituted with 0-2 $R^f$, phenyl substituted with 0-3 $R^f$, or a 5- to 10-membered heterocycle comprising: carbon atoms and 1-4 heteroatoms selected from N, $NR^g$, O, and $S(O)_p$, and substituted with 0-3 $R^h$;

$R^h$ is, independently at each occurrence, =O, —(CH$_2$)$_r$OR$^g$, F, Cl, Br, I, CN, NO$_2$, —OCF$_3$, —NR$^g$R$^g$, —C(O)R$^g$, —CO$_2$R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —SO$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-SO$_2$—, (C$_{6-10}$ aryl)-C$_{0-4}$ alkyl-SO$_2$—, (5-10 membered heteroaryl)-C$_{0-4}$ alkyl-SO$_2$—, C$_{3-6}$ cycloalkyl, phenyl, or a —(CH$_2$)$_r$-5- to 10-membered heterocycle comprising: carbon atoms and 1-4 heteroatoms selected from N, NR$^g$, O, and S(O)$_p$; and $R^i$ is, independently at each occurrence, H, C$_{1-6}$ alkyl substituted with 0-3 $R^h$, C$_{3-6}$ cycloalkyl substituted with 0-3 $R^h$, —(CH$_2$)$_n$-phenyl substituted with 0-3 $R^h$, —(CH$_2$)$_r$-5- to 6-membered heterocycle comprising: carbon atoms and 1-4 heteroatoms selected from N, NR$^g$, O, and S(O)$_p$, wherein said heterocycle is substituted with 0-3 $R^h$.

5. A compound according to claim 1, wherein the compound is of Formula (III):

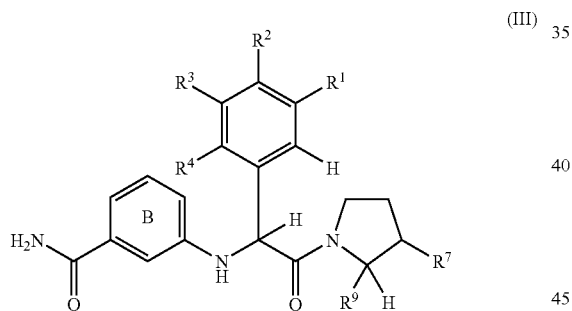

(III)

or a stereoisomer, tautomer, or pharmaceutically acceptable salt, thereof, wherein:

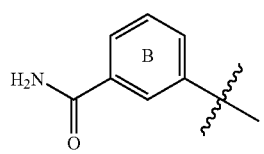

is:

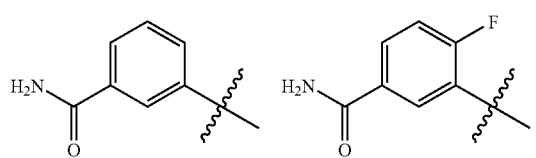

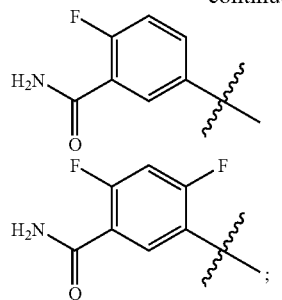

$R^1$ is Cl, Br, Me, Et, vinyl, 2-propenyl, ethynyl, —CH(OH)Me, OMe, OEt, cyclopropyl, —OCHF$_2$, or —OCF$_2$CHF$_2$;

$R^2$ is H, F, Cl, C$_{1-4}$ alkyl, C$_{1-4}$ alkoxy, or —OCHF$_2$;

$R^3$ is H, C$_{1-4}$ alkyl, or C$_{1-4}$ alkoxy;

$R^4$ is H or F;

$R^7$ is H, CO$_2$H, CO$_2$Me, CO$_2$Et, or CONMe$_2$;

$R^9$ is:

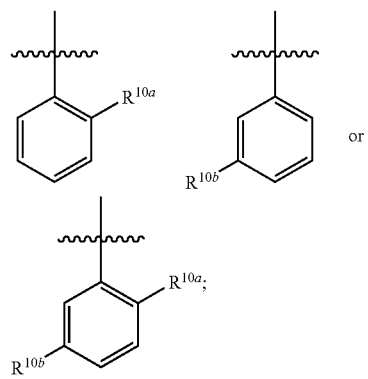

$R^{10a}$ is, independently at each occurrence, H, —SO$_2$Me, —SO$_2$Et, —SO$_2$Pr, —SO$_2$(i-Pr), —SO$_2$(i-Bu), —SO$_2$-cyclopropyl, —SO$_2$-cyclobutyl, —SO$_2$-cyclopentyl, —SO$_2$Ph, —SO$_2$-(1-pyrrolidinyl), —SO$_2$-(1-piperidyl), —SO$_2$-(1-azepanyl), —SO$_2$-(4-morpholinyl), —SO$_2$-(4-thiamorpholinyl), —SO$_2$-(4-Me-1-piperazinyl), —SO$_2$NH$_2$, —SO$_2$NHMe, —SO$_2$NHEt, —SO$_2$NH(i-Pr), —SO$_2$NH-cyclopropyl, —SO$_2$NH-cyclohexyl, —SO$_2$NH(t-Bu), —SO$_2$N(Me)Bn, —SO$_2$NMe$_2$, —OSO$_2$NH$_2$, —NHSO$_2$NH$_2$, —NHSO$_2$Me, Ph, 4-F-Ph, 1-piperidyl, 4-morpholinyl, 3,5-diethyl-1H-pyrazol-1-yl, NO$_2$, or —B(OH)$_2$; and $R^{10b}$ is, independently at each occurrence, H, CONH$_2$, NH$_2$, NHMe, NHEt, NMe$_2$, —NHCOH, —NHCOMe, —NHCOEt, —NHCOPr, —NHCO(i-Pr), —NHCO(i-Bu), —NHCO-cyclopropyl, —N(Me)COMe, —NHCO$_2$Me, —NHCO$_2$Et, —NHCONH$_2$, —NHCONHMe, —NHCONMe$_2$, —NHCON(Me)Et, —NHCON(Me)(i-Pr), —NHCO-(1-azetidinyl), —NHCO-(1-pyrrolidinyl), or —NHCO-(3-thiazolidinyl).

6. A compound according to claim 5, wherein the compound is of Formula (III), or stereoisomers, tautomers, or pharmaceutically acceptable salt, thereof, wherein:

$R^1$ is Cl, Me, Et, OMe, or OEt;

$R^2$ is F, Cl, OMe or O(i-Pr);

$R^3$ is H;

$R^4$ is H or F;

R⁷ is H, CO₂H, CO₂Me, or CO₂Et;
R⁹ is:

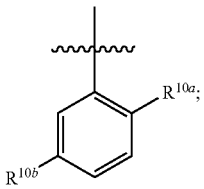

R¹⁰ᵃ is, independently at each occurrence, H, —SO₂—C₁₋₄ alkyl, —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂NH—C₁₋₄ alkyl, —SO₂NH-cyclopropyl, —SO₂NMe₂, CONMe₂, CO(1-pyrrolidinyl), CO(1-piperidinyl), 1-piperidyl, 4-morpholinyl, or 3,5-diethyl-1H-pyrazol-1-yl; and R¹⁰ᵇ is, independently at each occurrence, H, OH, NH₂, —NHCOH, —NHCOMe, —NHCOEt, —NHCO₂Me, —NHCO₂Et, —NHCONHMe, —NHCONH₂, —NHCONMe₂, —NHCON(Me)Et, —NHCON(Me)(i-Pr), —NHCO-(1-azetidinyl), —NHCO-(1-pyrrolidinyl), —NHCO-(3-thiazolidinyl), —OSO₂NH₂, —NHSO₂NH₂, —NHSO₂Me, —SO₂NH₂, or NO₂.

7. A compound according to claim 5, wherein the compound is of Formula (III), or stereoisomers, tautomers, or pharmaceutically acceptable salts thereof, wherein:
R⁷ is H;
R¹⁰ᵃ is, independently at each occurrence, —SO₂—C₁₋₄ alkyl, —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂NH—C₁₋₄ alkyl, —SO₂NH-cyclopropyl, —SO₂NMe₂, CONMe₂, CO(1-pyrrolidinyl), CO(1-piperidinyl), 1-piperidyl, 4-morpholinyl, or 3,5-diethyl-1H-pyrazol-1-yl; and
R¹⁰ᵇ is, independently at each occurrence, OH, NH₂, —NHCOH, —NHCOMe, —NHCOEt, —NHCO₂Me, —NHCO₂Et, —NHCONHMe, —NHCONMe₂, —NHCON(Me)Et, —NHCON(Me)(i-Pr), —NHCO-(1-azetidinyl), —NHCO-(1-pyrrolidinyl), —NHCO-(3-thiazolidinyl), —NHCONH₂, —OSO₂NH₂, —NHSO₂NH₂, —NHSO₂Me, or —SO₂NH₂.

8. A compound according to claim 5, wherein the compound is of Formula (III), or stereoisomers, tautomers, or pharmaceutically acceptable salt, thereof, wherein:
R⁷ is CO₂H, CO₂Me, or CO₂Et;
R¹⁰ᵃ is, independently at each occurrence, —SO₂—C₁₋₄ alkyl, —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂NH—C₁₋₄ alkyl, —SO₂NH-cyclopropyl, —SO₂NMe₂, CONMe₂, CO(1-pyrrolidinyl), CO(1-piperidinyl), 1-piperidyl, or 4-morpholinyl, or 3,5-diethyl-1H-pyrazol-1-yl; and
R¹⁰ᵇ is H.

9. A compound according to claim 5, wherein the compound is of Formula (III), or stereoisomers, tautomers, or pharmaceutically acceptable salt, thereof, wherein:
R⁷ is CO₂H, CO₂Me, or CO₂Et;
R¹⁰ᵃ is, independently at each occurrence, —SO₂—C₁₋₄ alkyl, —SO₂-cyclopropyl, —SO₂-cyclobutyl, —SO₂-cyclopentyl, —SO₂Ph, —SO₂-(1-pyrrolidinyl), —SO₂-(1-piperidyl), —SO₂-(1-azepanyl), —SO₂NH—C₁₋₄ alkyl, —SO₂NH-cyclopropyl, —SO₂NMe₂, CONMe₂, CO(1-pyrrolidinyl), CO(1-piperidinyl), 1-piperidyl, 4-morpholinyl, or 3,5-diethyl-1H-pyrazol-1-yl; and R¹⁰ᵇ is, independently at each occurrence, OH, NH₂, —NHCOH, —NHCOMe, —NHCOEt, —NHCO₂Me, —NHCO₂Et, —NHCONHMe, —NHCONMe₂, —NHCON(Me)Et, —NHCON(Me)(i-Pr), —NHCO-(1-azetidinyl), —NHCO-(1-pyrrolidinyl), —NHCO-(3-thiazolidinyl), —NHCONH₂, —OSO₂NH₂, —NHSO₂NH₂, —NHSO₂Me, or —SO₂NH₂.

10. A compound according to claim 5, wherein the compound is of Formula (III), or stereoisomers, tautomers, or pharmaceutically acceptable salt, thereof, wherein:
R⁷ is CO₂H, CO₂Me, or CO₂Et;
R¹⁰ᵃ is H;
R¹⁰ᵇ is, independently at each occurrence, OH, NH₂, —NHCOH, —NHCOMe, —NHCOEt, —NHCO₂Me, —NHCO₂Et, —NHCONHMe, —NHCONMe₂, —NHCON(Me)Et, —NHCON(Me)(i-Pr), —NHCO-(1-azetidinyl), —NHCO-(1-pyrrolidinyl), —NHCO-(3-thiazolidinyl), —NHCONH₂, —OSO₂NH₂, —NHSO₂NH₂, —NHSO₂Me, or —SO₂NH₂.

11. A compound according to claim 5, wherein the compound is of Formula (IIIa):

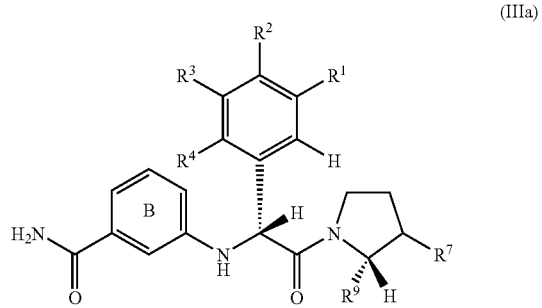

(IIIa)

or stereoisomers, tautomers, or pharmaceutically acceptable salt, thereof.

12. A compound according to claim 1, wherein the compound is selected from the group consisting of:

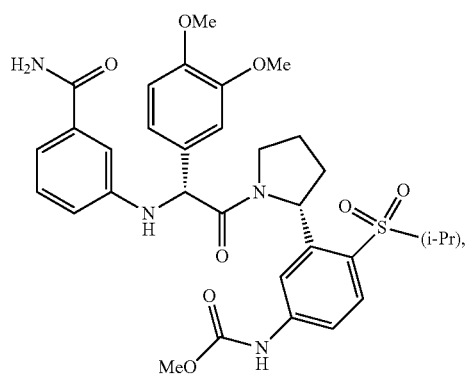

-continued
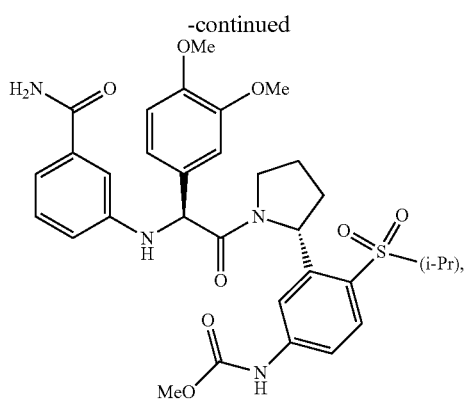
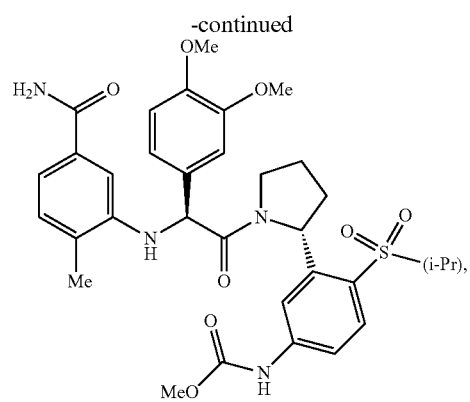
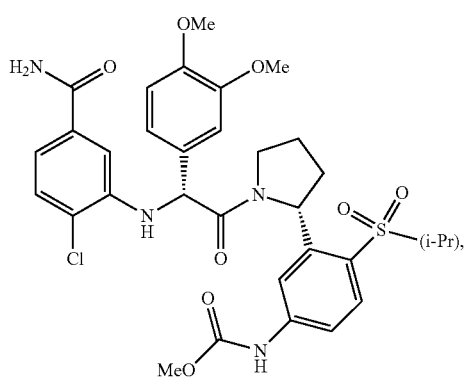
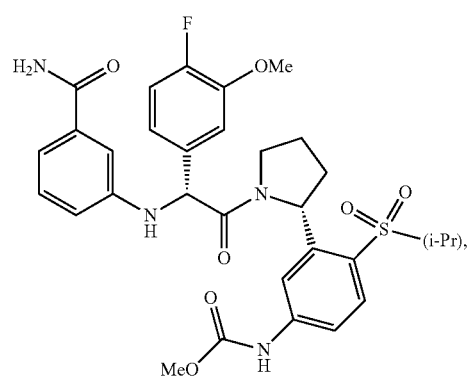
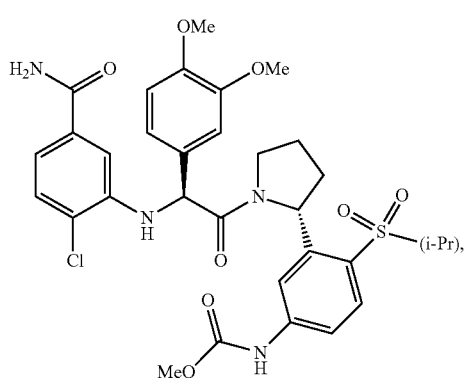
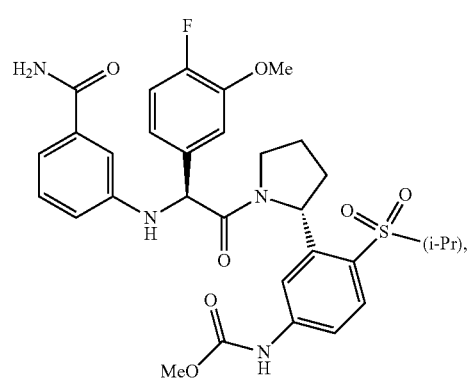
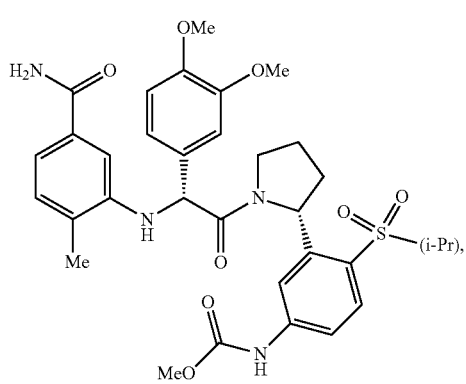
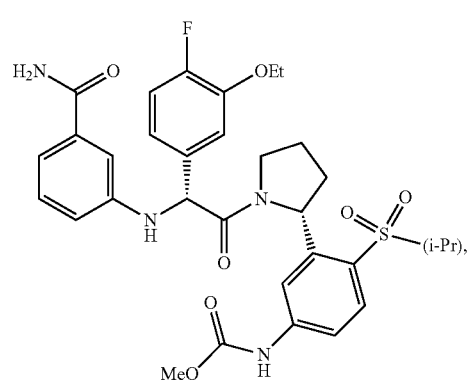

177
-continued
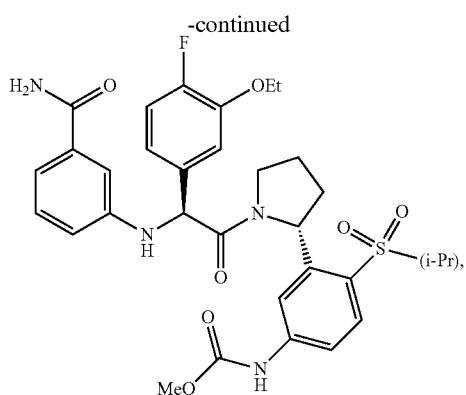
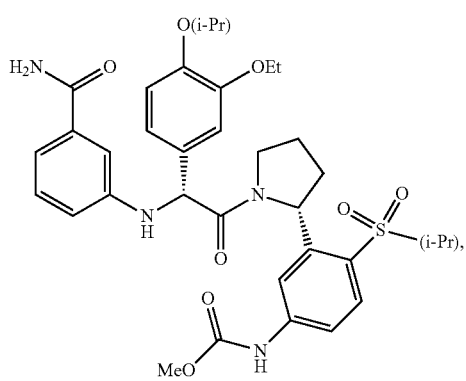
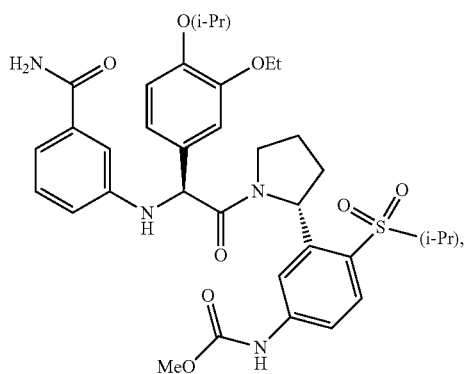
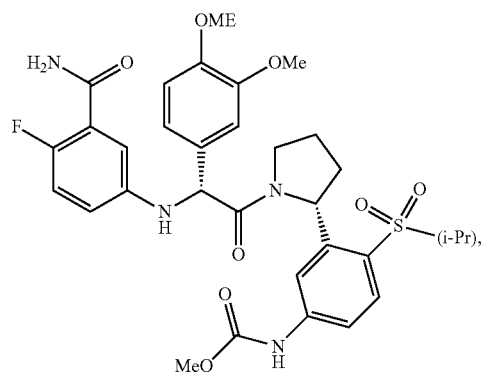
178
-continued
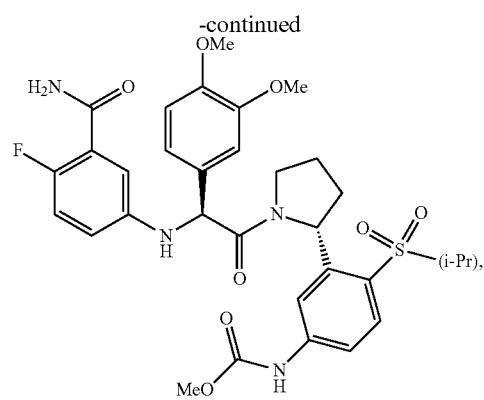
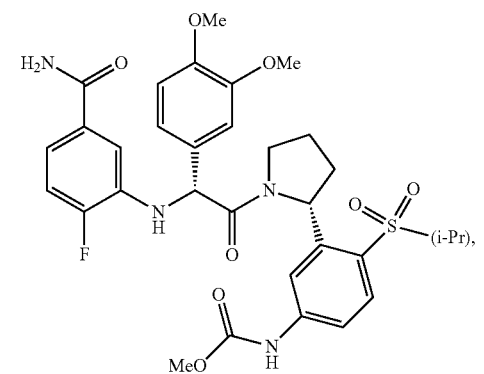
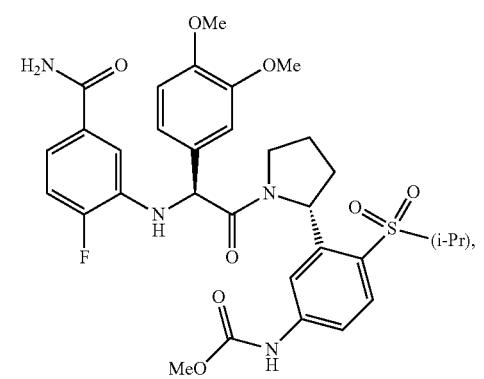
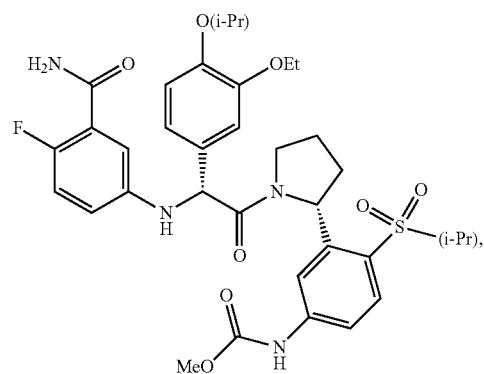

179
-continued
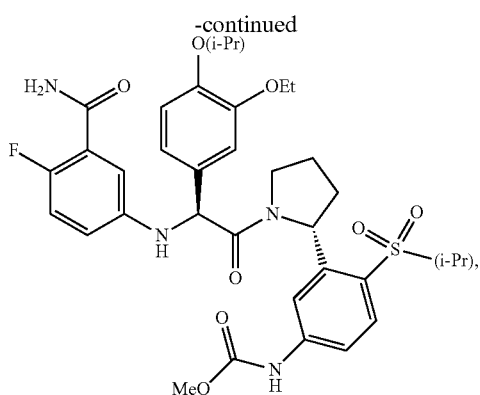
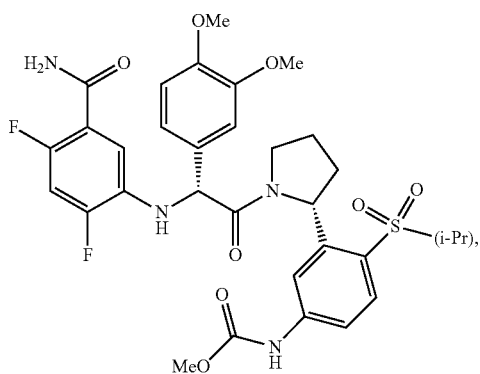
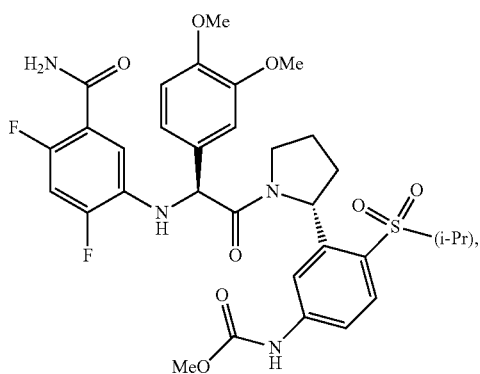
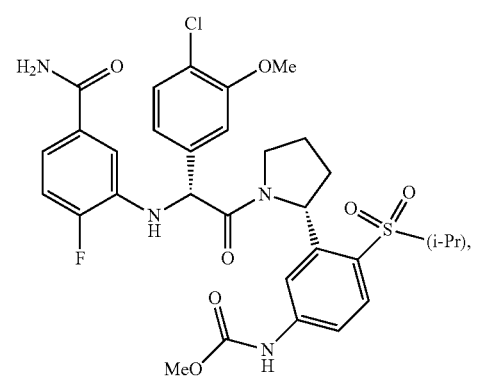
180
-continued
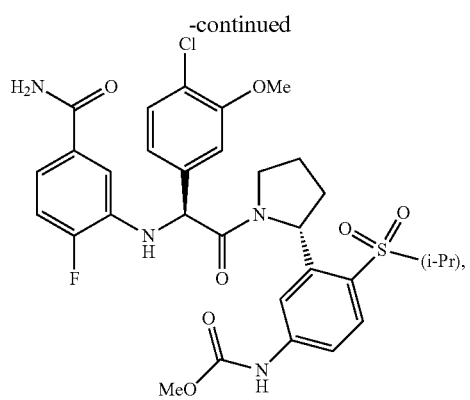
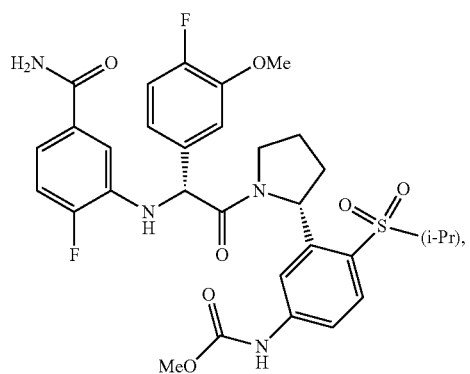
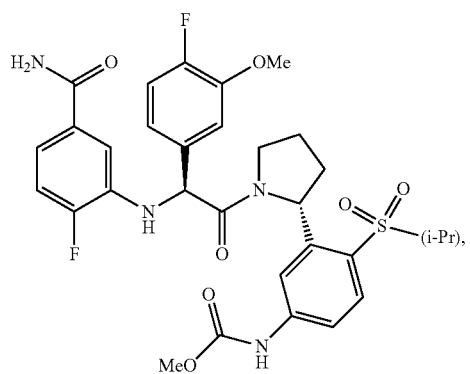
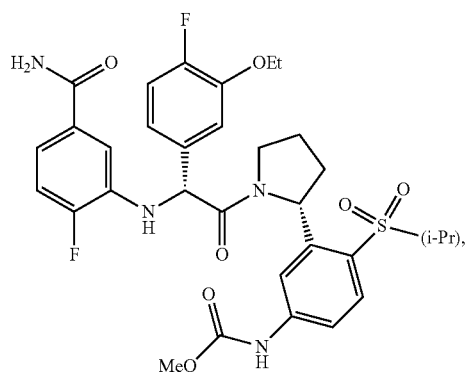

-continued
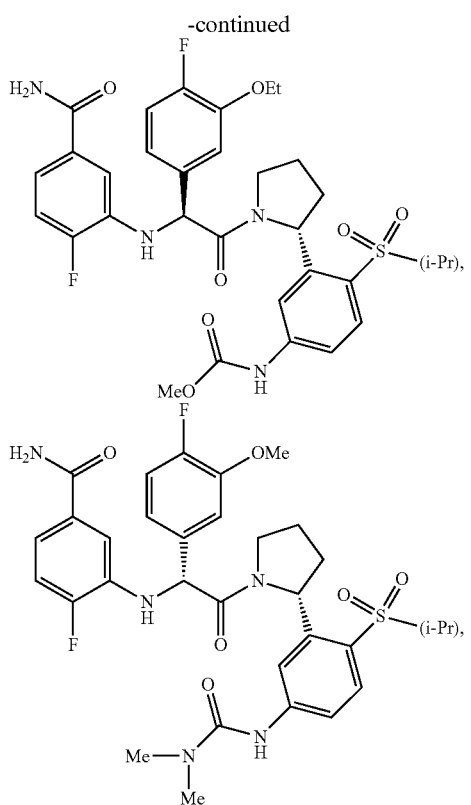
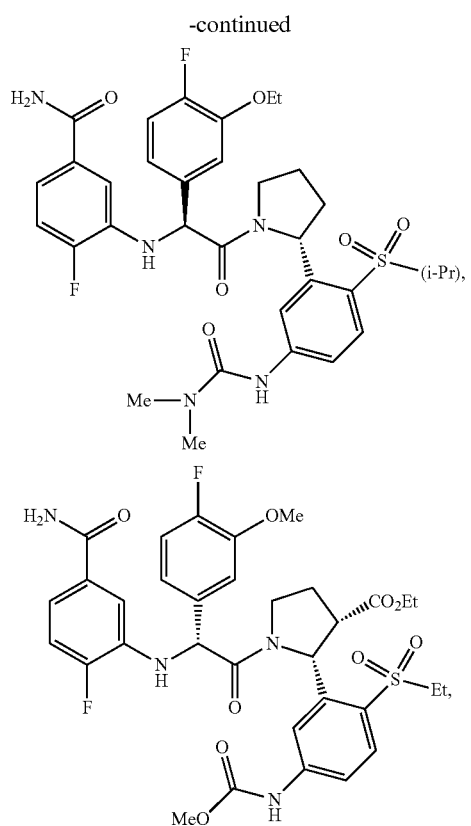
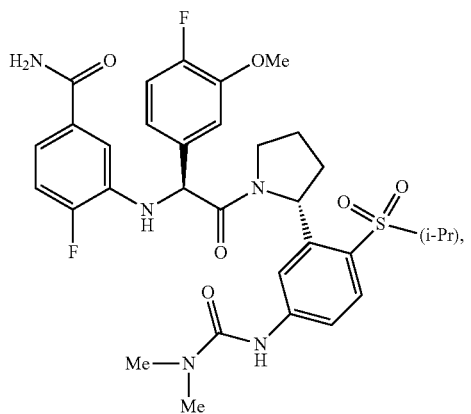
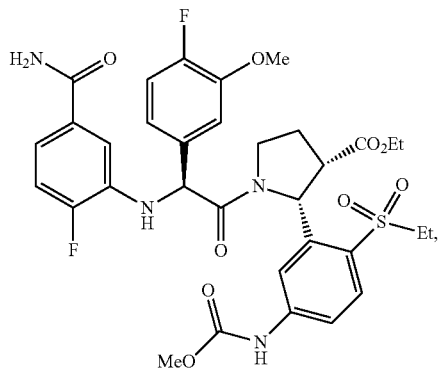
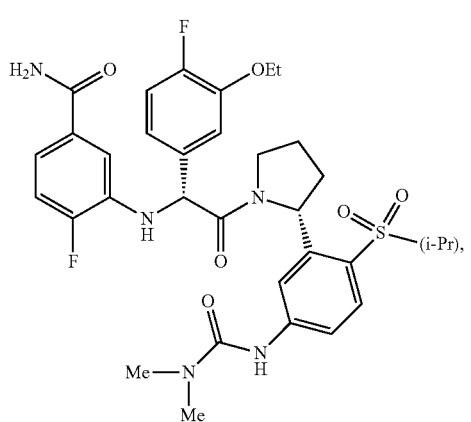
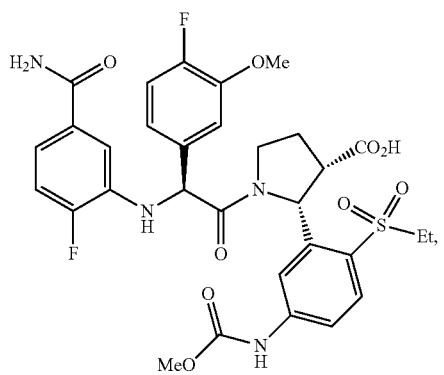

-continued
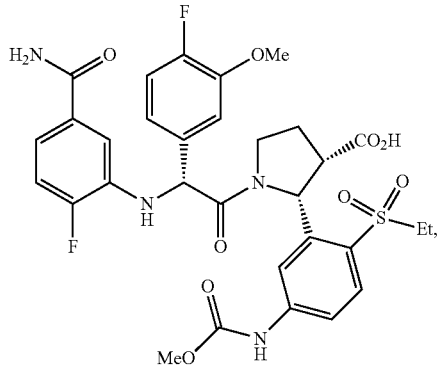
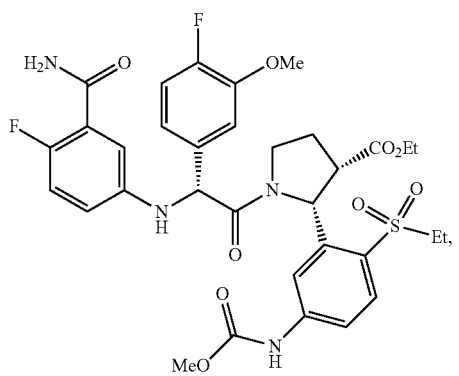
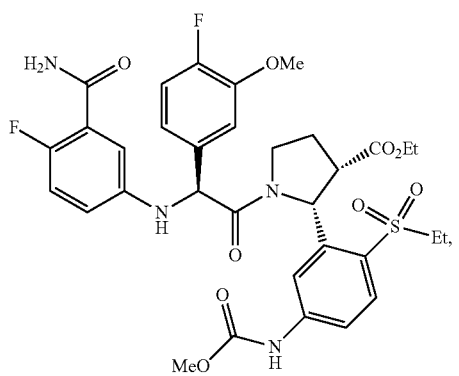
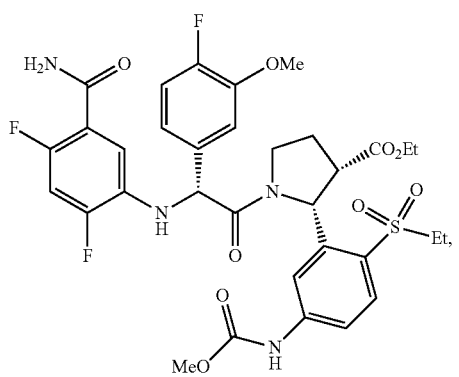
-continued
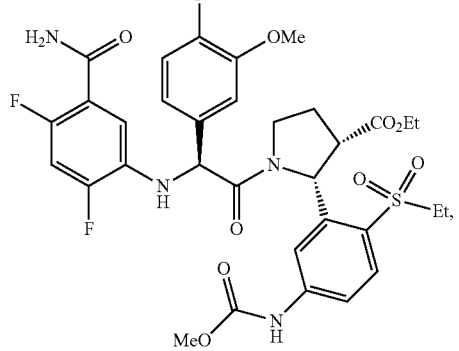
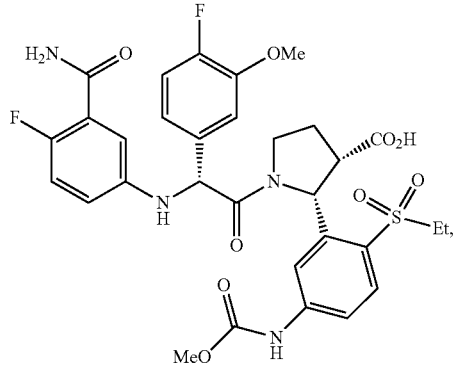
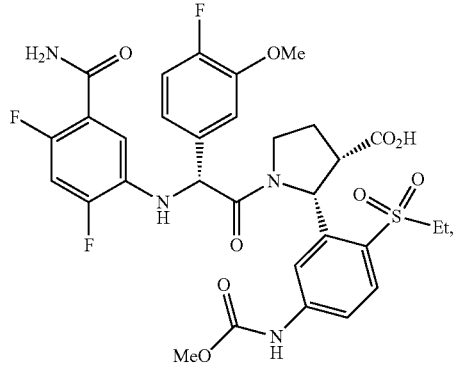
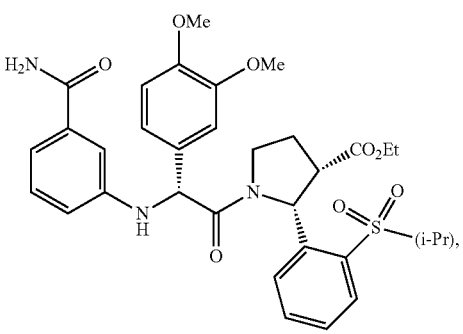

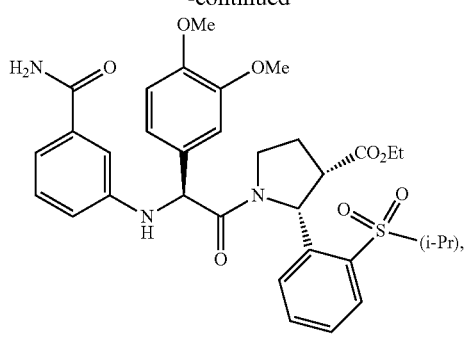
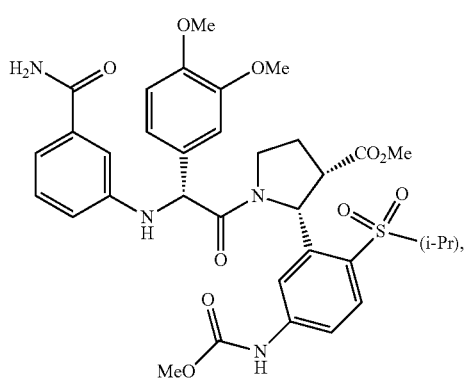
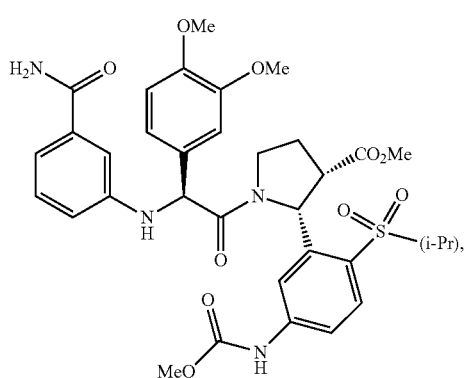
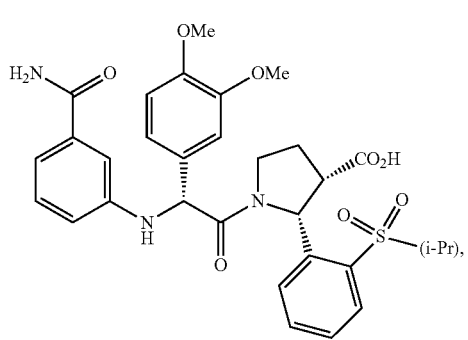
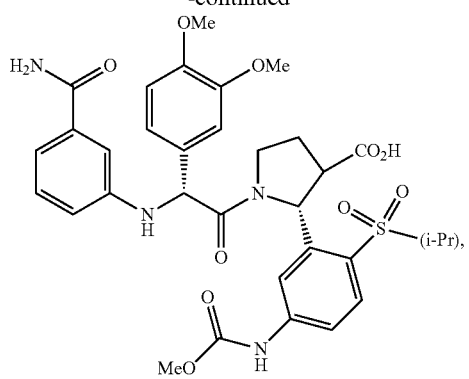
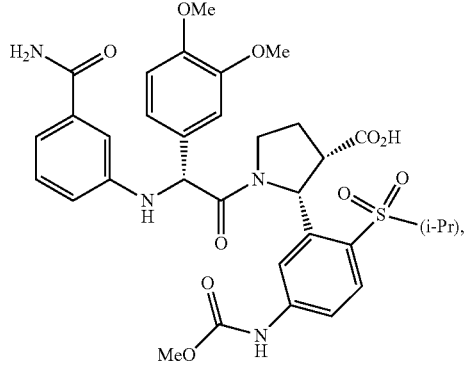
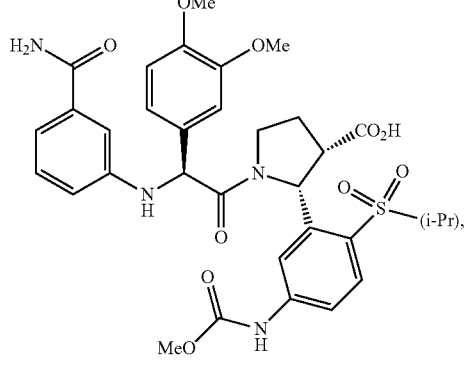
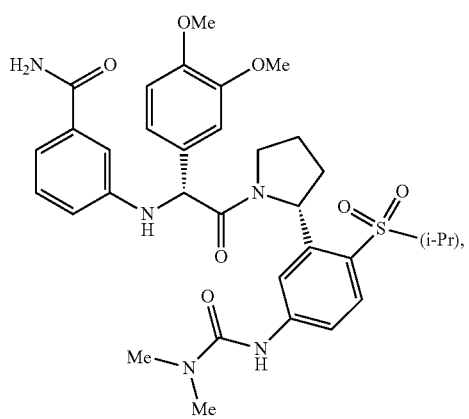

187
-continued
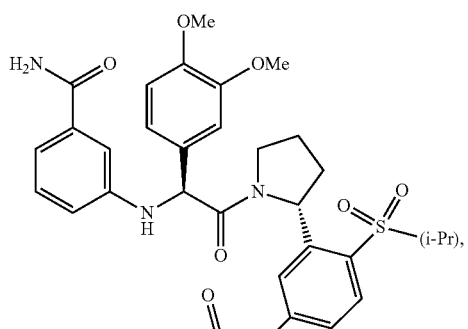
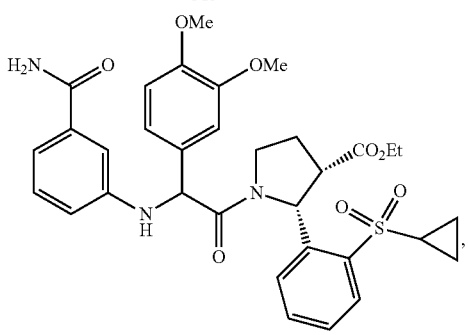
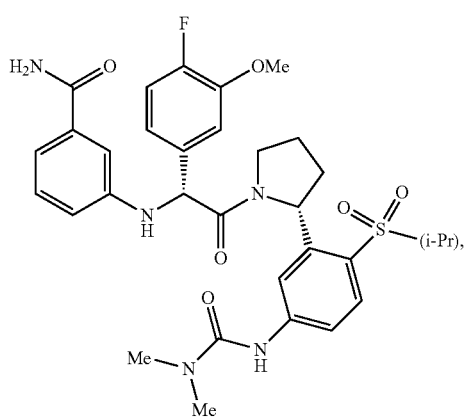
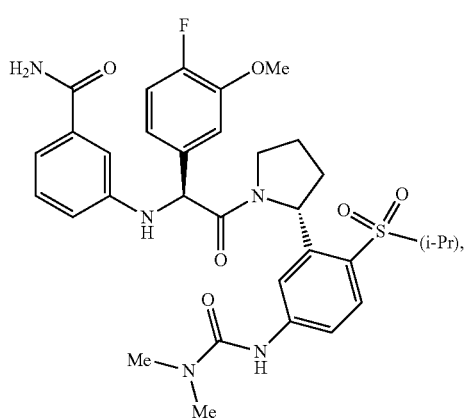
188
-continued
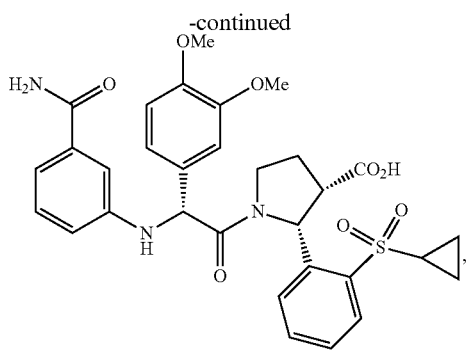
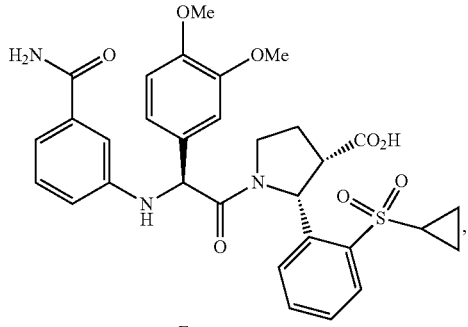
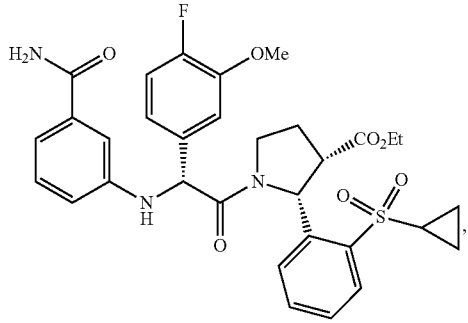
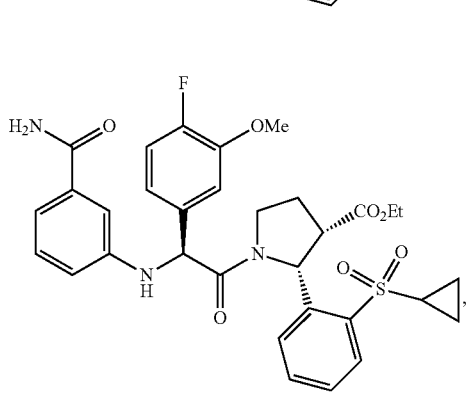
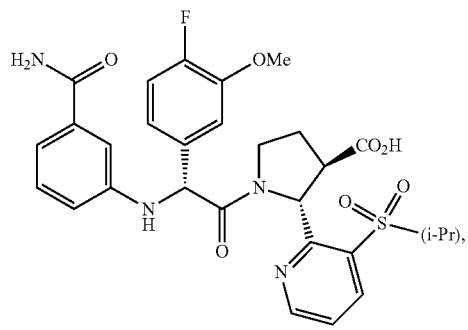

189
-continued
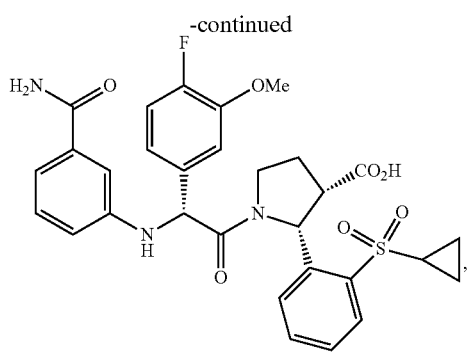
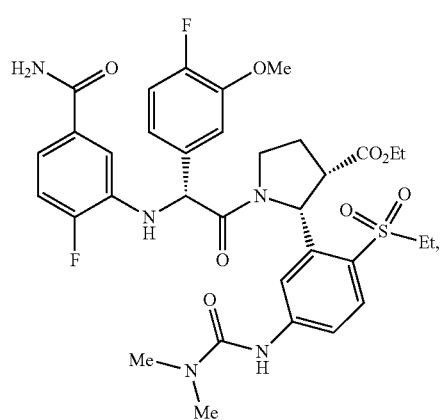
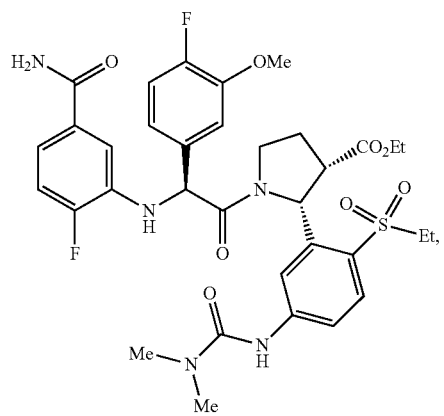
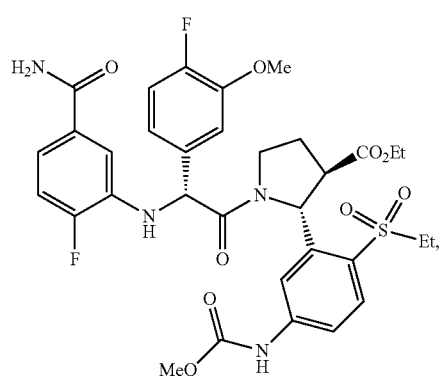
190
-continued
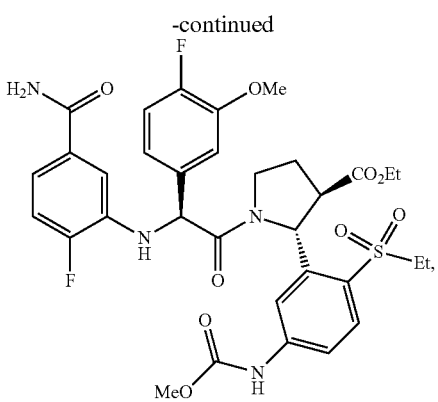
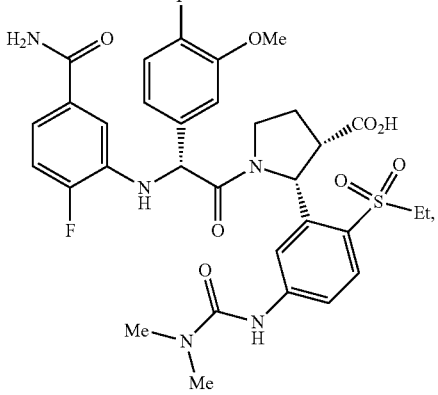
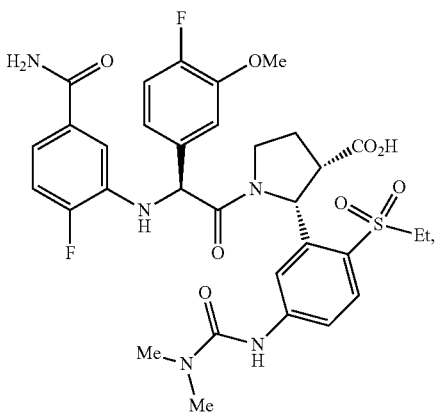
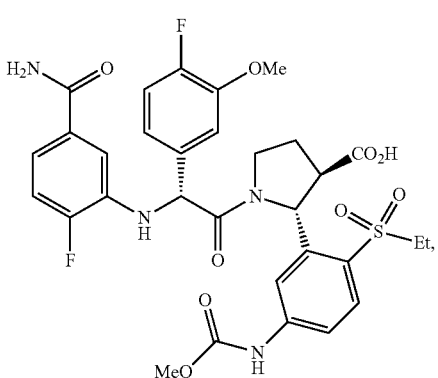

191
-continued
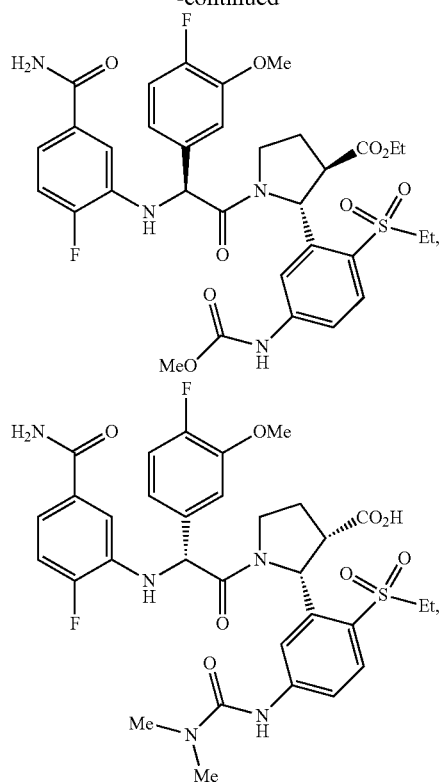
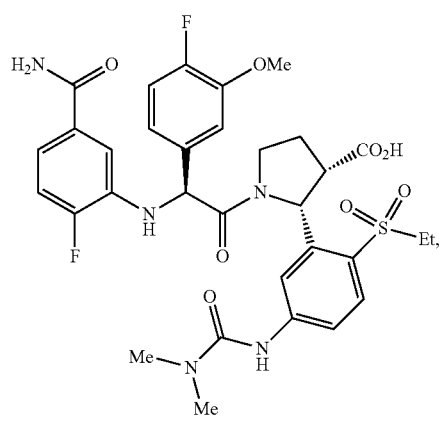
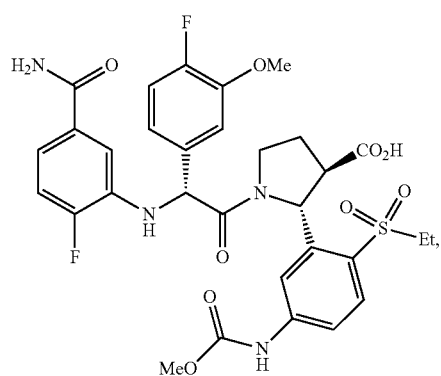
192
-continued
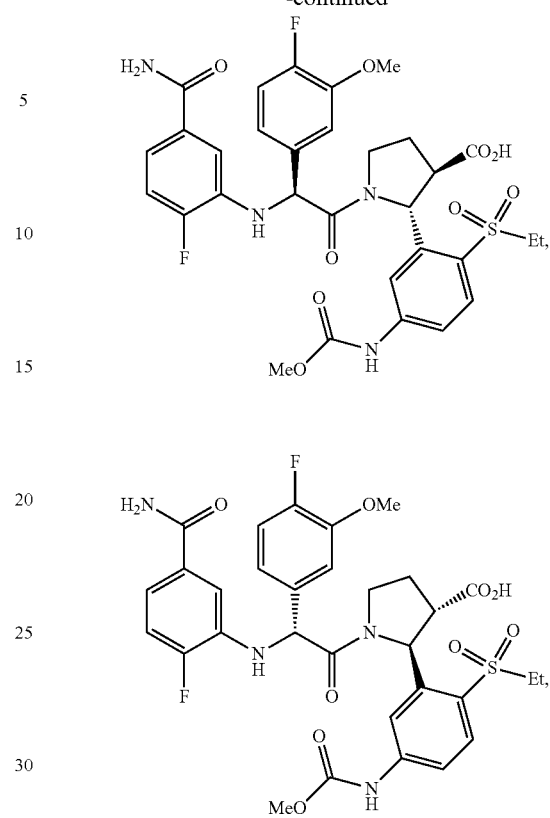
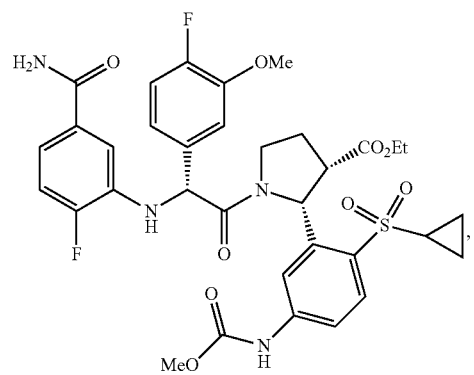
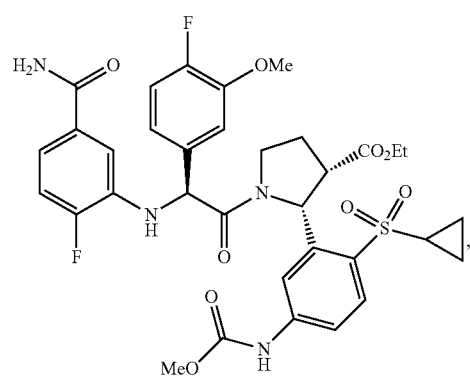

193
194
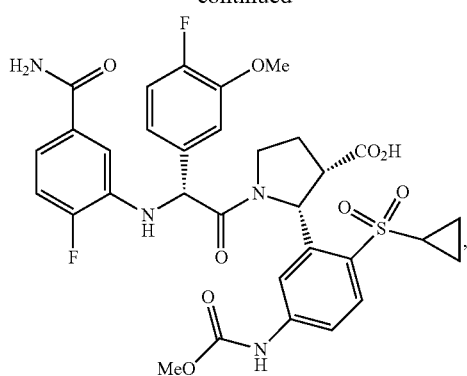
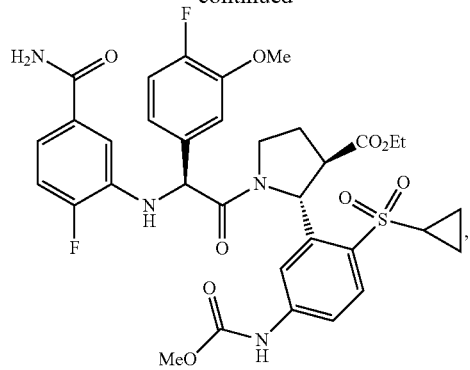
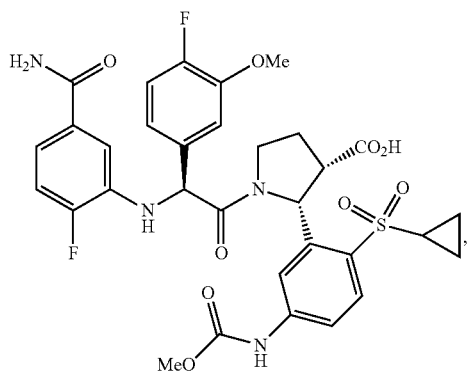
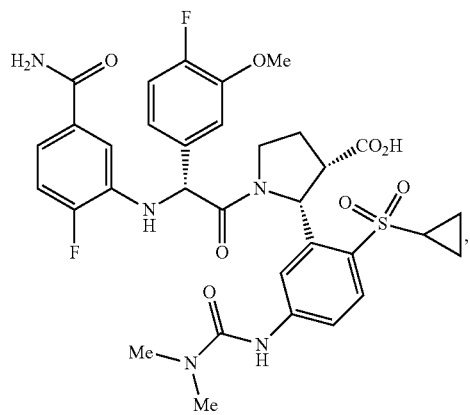
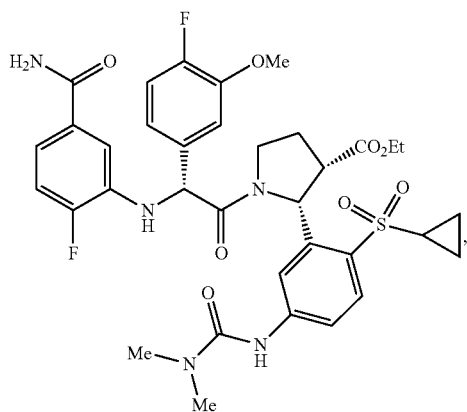
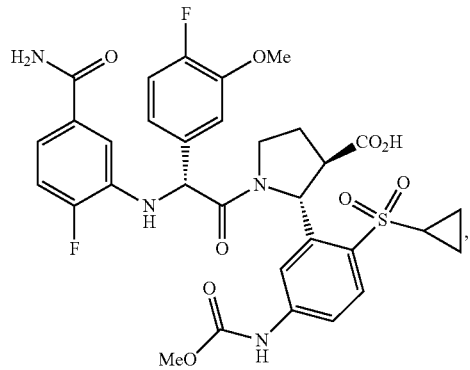
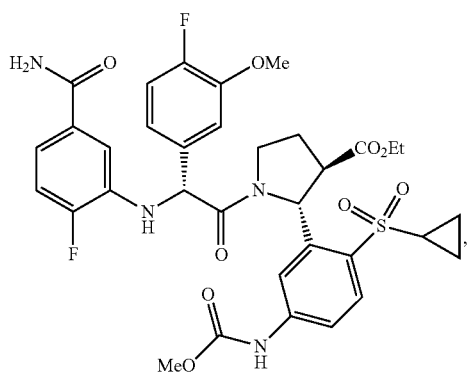
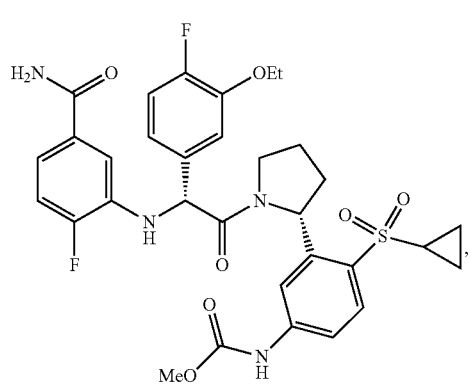

195
-continued
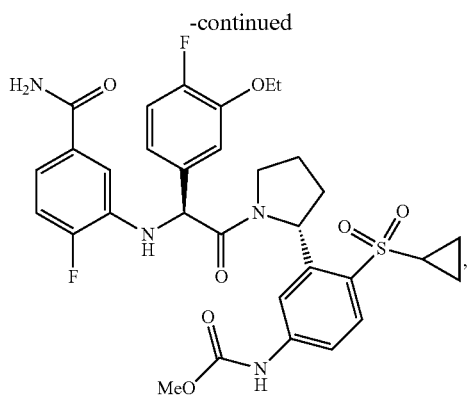
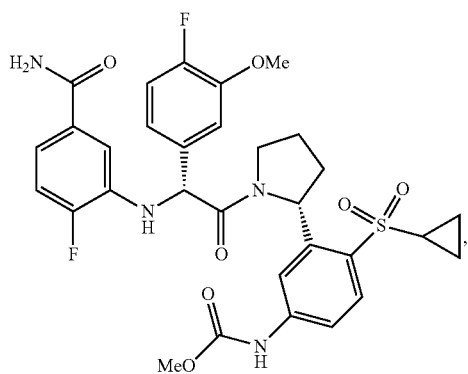
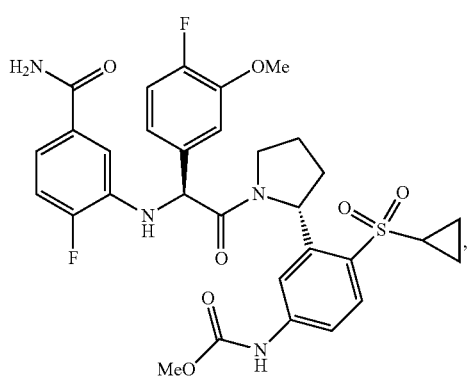
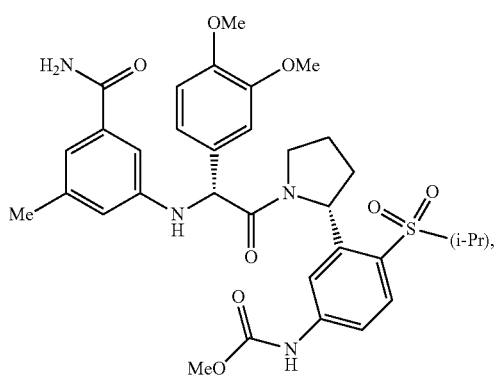
196
-continued
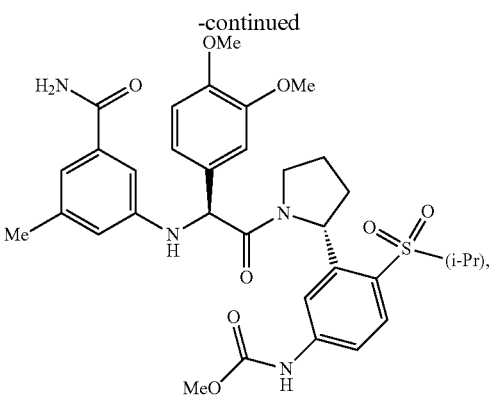
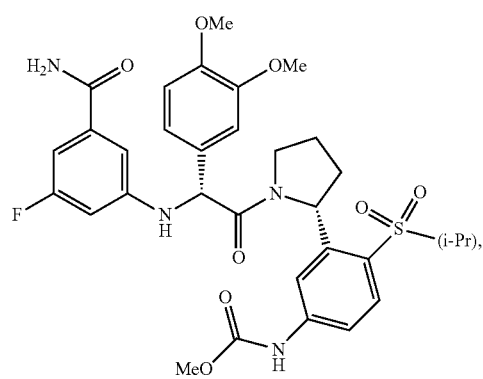
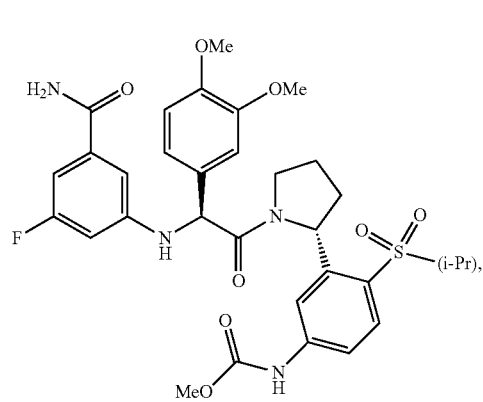
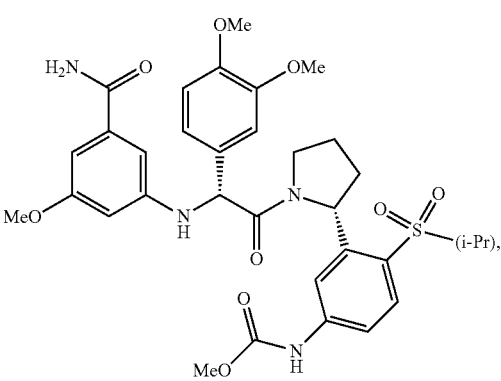

197

-continued

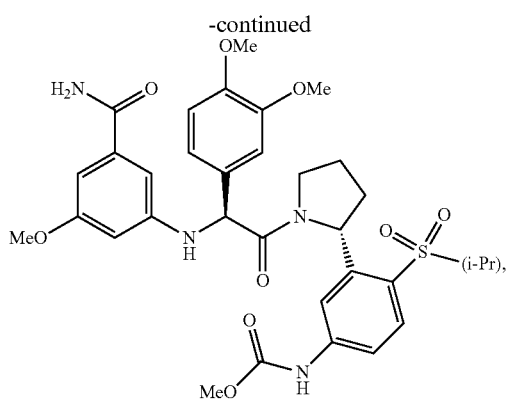

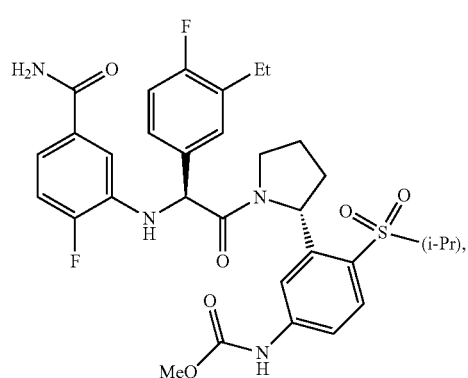

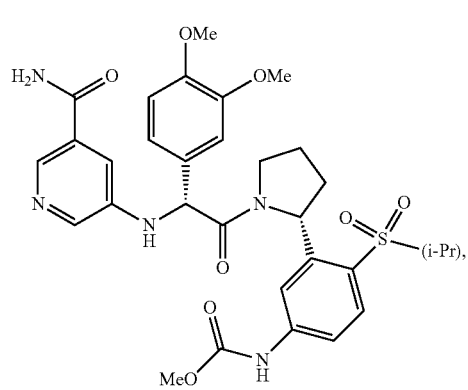

198

-continued

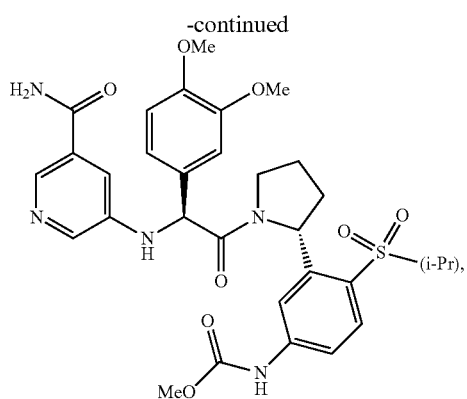

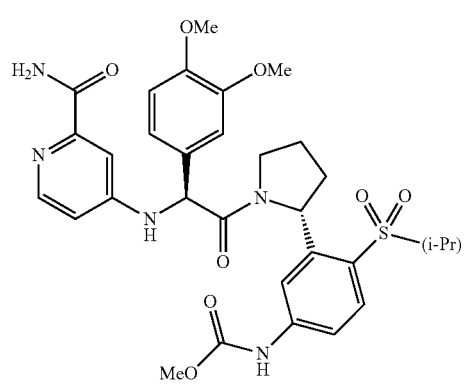

and or pharmaceutically acceptable salts thereof.

13. A pharmaceutical composition, comprising: a pharmaceutically acceptable carrier and a compound of claim 1 or stereoisomers, tautomers, pharmaceutically acceptable salts thereof.

14. A pharmaceutical composition, comprising: a pharmaceutically acceptable carrier and a compound of claim 3 or stereoisomers, tautomers, or pharmaceutically acceptable salts thereof.

15. A pharmaceutical composition, comprising: a pharmaceutically acceptable carrier and a compound of claim 5 or stereoisomers, tautomers, or pharmaceutically acceptable salts thereof.

16. A pharmaceutical composition, comprising: a pharmaceutically acceptable carrier and a compound of claim 11 or stereoisomers, tautomers, or pharmaceutically acceptable salts thereof.

17. A pharmaceutical composition, comprising: a pharmaceutically acceptable carrier and a compound of claim 12 or stereoisomers, tautomers, or pharmaceutically acceptable salts thereof.

* * * * *

UNITED STATES PATENT AND TRADEMARK OFFICE
CERTIFICATE OF CORRECTION

PATENT NO. : 8,222,453 B2
APPLICATION NO. : 12/303571
DATED : July 17, 2012
INVENTOR(S) : Eldon Scott Priestley and Xiaojun Zhang It is certified that error appears in the above-identified patent and that said Letters Patent is hereby corrected as shown below:

Column 167, Claim 3
Line 29, "$OR^g$," should read -- $OR^a$, --; and
Line 30, "–$C(O)R^g$," should read -- –$C(O)R^a$, --.

Column 170, Claim 4
Line 37, "-$SO_{2-5}$" should read -- -$SO_2$-, --;
Line 41, "$(CH_2)_r$–," should read -- $(CH_2)_n$ --; and
Line 42, "$(CH_2)_r$-phenyl" should read -- $(CH_2)_n$-phenyl --.

Column 191, Claim 12
Lines 1-66, four structures should be deleted.

Column 197, Claim 12

Lines 19-32, " 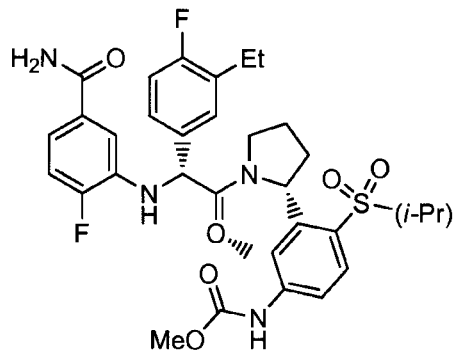 " should read

Signed and Sealed this
Sixteenth Day of April, 2013

Teresa Stanek Rea
*Acting Director of the United States Patent and Trademark Office*

CERTIFICATE OF CORRECTION (continued)
U.S. Pat. No. 8,222,453 B2

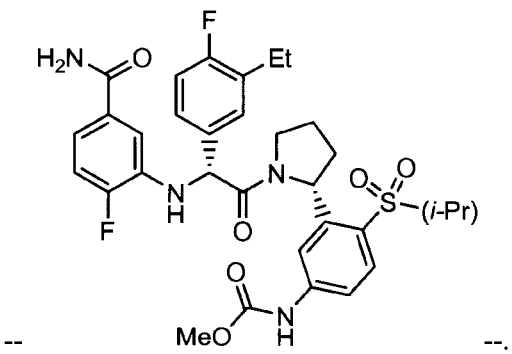

Column 198, Claim 12
Line 66, after "tautomers," delete "or".

Column 199, Claim 15
Line 3, after "tautomers," delete "or"; and

Column 199, Claim 16
Line 7, after "tautomers," delete "or".

Column 200, Claim 17
Line 3, after "tautomers," delete "or".